(12) United States Patent
Nassar et al.

(10) Patent No.: US 12,268,680 B2
(45) Date of Patent: *Apr. 8, 2025

(54) COMPOSITIONS AND METHODS FOR TREATING CANCER

(71) Applicant: Children's Hospital Medical Center, Cincinnati, OH (US)

(72) Inventors: Nicolas Nassar, Cincinnati, OH (US); William Seibel, Liberty Township, OH (US); Anjelika Gasilina, Bethesda, MD (US); Jose Cancelas, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/080,041

(22) Filed: Dec. 13, 2022

(65) Prior Publication Data

US 2023/0129271 A1  Apr. 27, 2023

Related U.S. Application Data

(63) Continuation of application No. 16/864,961, filed on May 1, 2020, now Pat. No. 11,564,913.

(60) Provisional application No. 62/842,839, filed on May 3, 2019.

(51) Int. Cl.
*A61K 31/444* (2006.01)
*A61K 31/53* (2006.01)
*A61P 35/02* (2006.01)

(52) U.S. Cl.
CPC ............ *A61K 31/444* (2013.01); *A61K 31/53* (2013.01); *A61P 35/02* (2018.01)

(58) Field of Classification Search
CPC ........ A61K 31/444; A61K 31/53; A61P 35/02
See application file for complete search history.

(56) References Cited

U.S. PATENT DOCUMENTS

| | | |
|---|---|---|
| 2002/0095039 A1 | 7/2002 | Cupps et al. |
| 2002/0107196 A1 | 8/2002 | Gupta |
| 2013/0345268 A1 | 12/2013 | Ratner et al. |

FOREIGN PATENT DOCUMENTS

| | | |
|---|---|---|
| CN | 102264720 A | 11/2011 |
| CN | 104586832 A | 5/2015 |
| WO | WO 00/66112 A1 | 11/2000 |
| WO | WO 2011/058139 A1 | 5/2011 |
| WO | WO 2016/077793 A1 | 5/2016 |

OTHER PUBLICATIONS

Doyle et al., Selective binding and oligomerization of murine granulocyte colony-stimulating factor receptor by a low mol. weight nonpeptidyl ligand. J. or Biological Chemistry, vol. 278(11), pp. 9426-9434 (Year: 2003).*
Aguilar, H., et al., "VAV3 mediates resistance to breast cancer endocrine therapy," Breast Cancer Res, 2014, 16:R53, 16 pgs.
Anastassiadis, T., et al., "Comprehensive assay of kinase catalytic activity reveals features of kinase inhibitor selectivity," Nat Biotechnol, 2012, 29(11):1039-1045, 19 pgs.
Aoki, Y., et al., "Recent advances in RASopathies" J Hum Genet, 2016, 61:33-39, 7 pgs.
Araki, M., et al., "Solution Structure of the State 1 Conformer of GTP-bound H-Ras Protein and Distinct Dynamic Properties between the State 1 and State 2 Conformers," J Biol Chem, 2011, 286(45):39644-39653, 10 pgs.
Arrigoni, E. et al. "Concise Review: Chronic Myeloid Leukemia: Stem Cell Niche and Response to Pharmacologic Treatment," Stem Cells Transl Med, 2018, 7:305-314, 10 pgs.
Azam, M., et al., "Mechanisms of Autoinhibition and STI-571/ Imatinib Resistance Revealed by Mutagenesis of BCR-ABL," Cell, 2003, 112:831-843, 13 pgs.
Bar-Sagi, D., et al., "Ras and Rho GTPases: A Family Reunion," Cell, 2000, 103(2):227-238, 12 pgs.
Bassermann, F., et al., "Association of Bcr-Abl with the Proto-oncogene Vav Is Implicated in Activation of the Rac-1 Pathway," J Biol Chem, 2002, 277(14):12437-12445, 9 pgs.
Basu, T.N., et al. "Aberrant regulation of ras proteins in malignant tumour cells from type 1 neurofibromatosis patients," Nature, 1992, 356:713-715, 3 pgs.
Bavetsias, V., et al., "Optimization of Imidazo[4,5-b]pyridine-Based Kinase Inhibitors: Identification of a Dual FLT3/Aurora Kinase Inhibitor as an Orally Bioavailable Preclinical Development Candidate for the Treatment of Acute Myeloid Leukemia," J Med Chem, 2012, 55:8721-8734, 14 pgs.
Berridge, M.V., et al., "Tetrazolium dyes as tools in cell biology: New insights into their cellular reduction," Biotechnol Annu Rev, 2005, 11:127-152, 26 pgs.
Biesiada, J., et al., "Survey of public domain software for docking simulations and virtual screening," Hum Genomics, 2011, 5(5):497-505, 9 pgs.
Biswas, M., et al., "MBD3/NuRD loss participates with KDM6A program to promote DOCK5/8 expression and Rac GTPase activation in human acute myeloid leukemia," FASEB J, 2019, 33:5268-5286, 19 pgs.
Bixby, D., et al., "Mechanisms of resistance to tyrosine kinase inhibitors in chronic myeloid leukemia and recent therapeutic strategies to overcome resistance," Hematology, 2009, 461-476, 16 pgs.
Boriack-Sjodin, P.A., et al., "The structural basis of the activation of Ras by Sos," Nature, 1998, 394:337-343, 7 pgs.
Bos, J.L., "ras Oncogenes in Human Cancer: A Review," Cancer Res, 1989, 49:4682-4689, 8 pgs.

(Continued)

*Primary Examiner* — Barbara P Badio
(74) *Attorney, Agent, or Firm* — Frost Brown Todd LLP; Nicole M. Tepe

(57) ABSTRACT

A small molecule compound IODVA1 has been found to have cellular inhibitory activity against several transformed cell lines including Ras-driven cells. IODVA1 decreases cell-cell and cell-extra cellular matrix interactions and reduces growth of Ras-driven tumors. Applicants also synthesized compound NIRA2 and showed in vitro and in vivo efficacy and potency against models of Ph+(BCR-ABL1) B-ALL and of colon adenocarcinoma xenografts.

7 Claims, 48 Drawing Sheets

(56) References Cited

OTHER PUBLICATIONS

Bos, J.L., et al., "GEFs and GAPs: Critical Elements in the Control of Small G Proteins," Cell, 2007, 129:865-877, 13 pgs.

Bourgoin, S., et al., "Low Molecular Weight GTP-binding Proteins in HL-60 Granulocytes. Assessment of the Role of ARF and of a 50-kDa Cytosolic Protein in Phospholipase D Activation," J Biol Chem, 1995, 270(7):3172-3178, 7 pgs.

Bustelo, X.R., "RHO GTPases in cancer: known facts, open questions, and therapeutic challenges," Biochem Soc Trans, 2018, 46:741-760, 20 pgs.

Cardama, G.A., et al., "Relevance of small GTPase Rac1 pathway in drug and radio-resistance mechanisms: Opportunities in cancer therapeutics," Crit Rev Oncol/Hematol, 2018, 124:29-36, 8 pgs.

Cardarella, S., et al., "The Impact of Genomic Changes on Treatment of Lung Cancer," Am J Respir Crit Care Med, 2013, 188(7):770-775, 6 pgs.

Chang, K.H., et al., "Vav3 collaborates with p190-BCR-ABL in lymphoid progenitor leukemogenesis, proliferation, and survival," Blood, 2012, 120(4):800-811, 12 pgs.

Chardin, P., et al., "Human Sos1: A Guanine Nucleotide Exchange Factor for Ras That Binds to GRB2," Science, 1993, 260:1338-1343, 6 pgs.

Chatterjee, S.S., et al., "SMARCB1 Deficiency Integrates Epigenetic Signals to Oncogenic Gene Expression Program Maintenance in Human Acute Myeloid Leukemia," Mol Cancer Res, 2018, 16(5):791-804, 14 pgs.

Chen, X., et al., "Vav3 oncogene is upregulated and a poor prognostic factor in breast cancer patients," Oncol Lett, 2015, 9:2143-2148, 6 pgs.

Cheng, T., et al., "Structure-Based Virtual Screening for Drug Discovery: a Problem—Centric Review," AAPS J, 2012, 14(1):133-141, 9 pgs.

Cilloni, D., et al., "Molecular Pathways: BCR-ABL," Clin Cancer Res, 2012, 18:930-937, 8 pgs.

Citterio, C., et al., "The Rho Exchange Factors Vav2 and Vav3 Control a Lung Metastasis-Specific Transcriptional Program in Breast Cancer Cells," Sci Signal, 2012, 5(244):ra71, 16 pgs.

Coleman, M.L., et al., "RAS and RHO GTPases in G1-Phase Cell-Cycle Regulation," Nat Rev Mol Cell Biol, 2004, 5:355-366, 12 pgs.

Condeelis, J., et al., "The Great Escape: When Cancer Cells Hijack the Genes for Chemotaxis and Motility," Annu Rev Cell Dev Biol, 2005, 21:695-718, 27 pgs.

Corsello, S.M., et al., "The Drug Repurposing Hub: a next-generation drug library and information resource," Nat Med, 2017, 23(4):405-408, 11 pgs.

Cox, A.D., et al., "Drugging the undruggable RAS: mission possible?" Nat Rev Drug Discov, 2014, 13(11):828-851, 47 pgs.

De Melo, M., et al., "Phosphorylated Extracellular Signal-Regulated Kinases Are Significantly Increased in Malignant Mesothelioma," J Histochem Cytochem, 2006, 54(8):855-861, 7 pgs.

Declue, J.E., et al., "Abnormal Regulation of Mammalian p21$^{ras}$ Contributes to Malignant Tumor Growth in von Recklinghausen (type 1) Neurofibromatosis," Cell, 1992, 69:265-273, 9 pgs.

Denizot, F., et al., "Rapid colorimetric assay for cell growth and survival: Modifications to the tetrazolium dye procedure giving improved sensitivity and reliability," J Immunol Methods, 1986, 89:271-277, 7 pgs.

Downward, J., "Targeting RAS Signalling Pathways in Cancer Therapy," Nat Rev Cancer, 2003, 3:11-22, 12 pgs.

Doyle, M.L., et al., "Selective Binding and Oligomerization of Murine Granulocyte Colony-stimulating Factor Receptor by a Low Molecular Weight, Nonpeptidyl Ligand," J Biol Chem, 2003, 278(11):9426-9434, 9 pgs.

Espina, C., et al., "A Critical Role for Rac1 in Tumor Progression of Human Colorectal Adenocarcinoma Cells," Am J Pathol, 2008, 172(1):156-166, 11 pgs.

Etienne-Mannerville, S., et al., "Rho GTPases in cell biology," Nature, 2002, 420:629-635, 7 pgs.

Euhus, D.M., et al., "Tumor Measurement in the Nude Mouse," Journal of Surgical Oncology, 1986, 31:229-234, 4 pgs.

Evelyn, C.R., et al., "Combined Rational Design and a High Throughput Screening Platform for Identifying Chemical Inhibitors of a Ras-activating Enzyme," J Biol Chem, 2015, 290(20):12879-12898, 20 pgs.

Evelyn, C.R., et al., "Rational design of small molecule inhibitors targeting the Ras GEF, SOS1," Chem Biol, 2014, 21(12):1618-1628, 23 pgs.

Fife, C.M., et al., "Movers and shakers: cell cytoskeleton in cancer metastasis," Br J Pharmacol, 2014, 171:5507-5523, 17 pgs.

Ford, B., et al., "Structure of the G60A Mutant of Ras: Implications for the Dominant Negative Effect," J Biol Chem, 2005, 280(27):25697-25705, 9 pgs.

Ford, B.A., et al., "Characterization of a Ras mutant with identical GDP-and GTP-bound structures," Biochemistry, 2009, 48(48):11449-11457, 21 pgs.

Foty, R., "A Simple Hanging Drop Cell Culture Protocol for Generation of 3D Spheroids," JoVE, 2011, 51, 4 pgs.

Fujikawa, K., et al., "Vav1/2/3-null Mice Define an Essential Role for Vav Family Proteins in Lymphocyte Development and Activation but a Differential Requirement in MAPK Signaling in T and B Cells," J Exp Med, 2003, 198(10):1595-1608, 14 pgs.

Gasilina, A., et al., "IODVA1, a guanidinobenzimidazole derivative, targets Rac activity and Ras-drive cancer models," PLoS ONE, Mar. 2020, 15(3):e0229801, 28 pgs.

Gennaro, A.R., (ed.), Remington: The Science and Practice of Pharmacy, 19$^{th}$ Ed., 1995, Mack Publishing Company, Easton, Pennsylvania, 6 pgs. (Table of Contents Only).

Gennaro, A.R., (ed.), Remington: The Science and Practice of Pharmacy, 20$^{th}$ Ed., 2000, Lippincott Williams & Wilkins, Philadelphia, Pennsylvania, 5 pgs. (Table of Contents Only).

Gennaro, A.R., (ed.), Remington's Pharmaceutical Sciences, 18$^{th}$ Ed., 1990, Mack Publishing Company, Easton, Pennsylvania, 8 pgs. (Table of Contents Only).

Geyer, M., et al., "Conformational Transitions in p21$^{ras}$ and in Its Complexes with the Effector Protein Raf-RBD and the GTPase Activating Protein GAP," Biochemistry, 1996, 35:10308-10320, 13 pgs.

Gorre, M.E., et al., "Clinical Resistance to STI-571 Cancer Therapy Caused by BCR-ABL Gene Mutation or Amplification," Science, 2001, 293:876-880, 5 pgs.

Green, J., et al., "Design, Synthesis, and Structure-Activity Relationships of Pyridine-Based Rho Kinase (ROCK) Inhibitors," J Med Chem, 2015, 58:5028-5037, 10 pgs.

Gutjar, P., "Design and synthesis of anti cancer agents that inhibit cysteine proteases, limit oxidative stress or terminate proliferation of BCR-ABL expressing cells," Dissertation submitted to the Graduate School of the University of Cincinnati in Partial Fulfillment of the Requirements for the Degree of Doctor of Philosophy (Ph.D.) in the Department of Chemistry, Jul. 2018, 20 pgs.

Hall, A., "Small GTP-Binding Proteins and the Regulation of the Actin Cytoskeleton," Annu Rev Cell Biol, 1994, 10:31-54, 25 pgs.

Hamilton, A., et al., "Chronic myeloid leukemia stem cells are not dependent on Bcr-Abl kinase activity for their survival," Blood, 2012, 119(6):1501-1510, 10 pgs.

Harnois, T., et al., "Differential interaction and activation of Rho family GTPases by p210$^{bcr-abl}$ and p190$^{bcr-abl}$" Oncogene, 2003, 22:6445-6454, 10 pgs.

Hollestelle, A., et al., "Phosphatidylinositol-3-OH Kinase or RAS Pathway Mutations in Human Breast Cancer Cell Lines," Mol Cancer Res, 2007, 5(2):195-201, 7 pgs.

Huey, R., et al., "A Semiempirical Free Energy Force Field with Charge-Based Desolvation," J Comput Chem, 2007, 28:1145-1152, 8 pgs.

Hwang, M.C., et al., "The Differential Effects of the Gly-60 to Ala Mutation on the Interaction of H-Ras p21 with Different Downstream Targets," J Biol Chem, 1996, 271(14):8196-8202, 7 pgs.

Irwin, J.J., et al., "ZINC—A free Database of Commercially Available Compounds for Virtual Screening," J Chem Inf Model, 2005, 45(1):177-182, 11 pgs.

(56) References Cited

OTHER PUBLICATIONS

Irwin, J.J., et al., "ZINC: A Free Tool to Discover Chemistry for Biology," J Chem Inf Model, 2012, 52:1757-1768, 12 pgs.
Jabbour, E. et al., "Characteristics and outcomes of patients with chronic myeloid leukemia and T315I mutation following failure of imatinib mesylate therapy," Blood, 2008, 112:53-55, 3 pgs.
Jabbour, E., et al., "Frequency and clinical significance of BCR-ABL mutations in patients with chronic myeloid leukemia treated with imatinib mesylate," Leukemia, 2006, 20:1767-1773, 7 pgs.
Jaffe, A.B., et al., "Rho GTPases: Biochemistry and Biology," Annu Rev Cell Dev Biol, 2005, 21:247-269, 26 pgs.
Janes, M.R., et al., "Targeting KRAS Mutant Cancers with a Covalent G12C-Specific Inhibitor," Cell, 2018, 172:578-589, 30 pgs.
Jerabek-Willemsen, M., et al., "Molecular Interaction Studies Using Microscale Thermophoresis," Assay Drug Dev Technol, 2011, 9(4):342-353, 12 pgs.
Kiosses, W.B., et al., "Rac recruits high-affinity integrin αvβ3 to lamellipodia in endothelial cell migration," Nat Cell Biol, 2001, 3:316-320, 5 pgs.
Kissil, J.L., et al. "Requirement for Rac1 in a K-ras induced Lung Cancer in the Mouse," Cancer Res, 2007, 67(17): 8089-8094, 6 pgs.
Kristelly, R., "Preliminary structure analysis of the DH/PH domains of leukemia-associated RhoGEF," Acta Crystallogr D Biol Crystallogr, 2003, D59:1859-1862, 4 pgs.
Lavecchia, A., et al., "Virtual Screening Strategies in Drug Discovery: A Critical Review," Current Medicinal Chemistry, 2013, 20:2839-2860, 22 pgs.
Lee, K., et al., "Vav3 oncogene activates estrogen receptor and its overexpression may be involved in human breast cancer," BMC Cancer, 2008, 8:158, 13 pgs.
Lee, L.H., et al., "Real-time genomic profiling of histiocytoses identifies early-kinase domain BRAF alterations while improving treatment outcomes," JCI Insight, 2017, 2(3):e89473, 11 pgs.
Lee, S.H., et al., "Regulation of Actin Cytoskeleton Dynamics in Cells," Mol Cells, 2010, 29(4):311-325, 26 pgs.
Levine, A.J., et al., "The Control of the Metabolic Switch in Cancers by Oncogenes and Tumor Suppressor Genes," Science, 2010, 330:1340-1344, 6 pgs.
Li, Y., et al., "Somatic Mutations in the Neurofibromatosis 1 Gene in Human Tumors," Cell, 1992, 69:275-281, 7 pgs.
Lipinski, C.A., et al., "Experimental and computational approaches to estimate solubility and permeability in drug discovery and development settings," Advanced Drug Delivery Reviews, 2001, 46:3-26, 24 pgs.
Loirand, G., et al., "The role of Rho protein signaling in hypertension," Nat Rev Cardiol, 2010, 7:637-647, 11 pgs.
Lorenzo-Martin, L.F., et al., "Vav proteins maintain epithelial traits in breast cancer cells using miR-200c-dependent and independent mechanisms," Oncogene, 2019, 38:209-227, 19 pgs.
Lounnas, V., et al., "Current Progress in Structure-Based Rational Drug Design Marks a New Mindset in Drug Discovery," Comput Struct Biotechnol J, 2013, 5(6):e201302011, 14 pgs.
Loveland, B.E., et al., "Validation of the MTT Dye Assay for Enumeration of Cells in Proliferative and Antiproliferative Assays," Biochem Int, 1992, 27(3):501-510, 6 pgs.
Lugo, T.G., et al., "Tyrosine Kinase Activity and Transformation Potency of bcr-abl Oncogene Products," Science, 1990, 247:1079-1082, 4 pgs.
Lyons, R., et al., "The RAC specific guanine nucleotide exchange factor Asef functions downstream from TEL-AML1 to promote leukaemic transformation," Leuk Res, 2010, 34:109-115, 7 pgs.
Mack, N.A., et al., "The diverse roles of Rac signaling in tumorigenesis," Cell Cycle, 2011, 10(10):1571-1581, 11 pgs.
McCormick, F., "K-Ras protein as a drug target," J Mol Med, 2016, 94:253-258, 6 pgs.
Milojkovic, D., et al., "Mechanisms of Resistance to Imatinib and Second-Generation Tyrosine Inhibitors in Chronic Myeloid Leukemia," Clin Cancer Res, 2009, 15(24):7519-7527, 9 pgs.
Minden, A., et al., "Selective Activation of the JNK Signaling Cascade and c-Jun Transcriptional Activity by the Small GTPases Rac and Cdc42Hs," Cell, 1995, 81:1147-1157, 11 pgs.
Mizukawa, B., et al., "Inhibition of Rac GTPase signaling and downstream prosurvival Bcl-2 proteins as combination targeted therapy in MLL-AF9 leukemia," Blood, 2011, 118(19):5235-5245, 11 pgs.
Morris, G.M., et al., "Automated Docking Using a Lamarckian Genetic Algorithm and an Empirical Binding Free Energy Function," J Computational Chemistry, 1998, 19(14):1639-1662, 24 pgs.
Morris, G.M., et al., "AutoDock4 and AutoDockTools4: Automated Docking with Selective Receptor Flexibility," J Comput Chem, 2009, 30(16):2785-2791, 12 pgs.
Mulloy, J.C., et al., "Rho GTPases in hematopoiesis and hemopathies," Blood, 2010, 115(5):936-947, 12 pgs.
Newey, S.E., et al., "Rho GTPases, Dendritic Structure, and Mental Retardation," J Neurobiol, 2005, 64:58-74, 17 pgs.
Nicolini, F.E., et al., "Mutation status and clinical outcome of 89 imatinib mesylate-resistant chronic myelogenous leukemia patients: a retrospective analysis from the French intergroup of CML (Fi(φ)-LMC Group)," Leukemia, 2006, 20:1061-1066, 6 pgs.
Nieborowska-Skorska, M., et al., "Rac2-MRC-cIII-generated ROS cause genomic instability in chronic myeloid leukemia stem cells and primitive progenitors," Blood, 2012, 119(18):4253-4563, 11 pgs.
Nishimura, T., et al., "Reaction of Guanidines with a-Diketones, Syntheses of 4,5-Disubstituted-2-aminoimidazoles and 2.6-Unsymmetrically Substituted Imidazo[4,5-d]imidazoles," J Org Chem, 1979, 44(5):818-824, 7 pgs.
Nouri, K., et al., "IQGAP1 Interaction with RHO Family Proteins Revisited: Kinetic and Equilibrium Evidence for Multiple Distinct Binding Sites," J Biol Chem, 2016, 291(51):26364-26376, 13 pgs.
Olson, M.F., et al., "The actin cytoskeleton in cancer cell motility," Clin Exp Metastasis, 2009, 26:273-287, 15 pgs.
Ostrem, J.M.L., et al., "Direct small-molecule inhibitors of KRAS: from structural insights to mechanism-based design," Nat Rev Drug Discov, 2006, 15:771-785, 15 pgs.
Pai, E.F., et al., "Structure of the guanine-nucleotide-binding domain of the Ha-ras oncogene product p21 in the triphosphate conformation," Nature, 1989, 341:209-214, 6 pgs.
Porter, A.P., et al., "Deregulation of Rho GTPases in cancer," Small GTPases, 2016, 7(3):123-138, 16 pgs.
PubChem, Compound Summary, 5-(4-Chlorophenyl)-3-[(E)-2-(4-chlorophenyl)-2-phenylethneyl]-5-phenyloxolan-2-one, PubChem CID: 6514822, Created May 3, 2006, Modified Jun. 13, 2020, 8 pgs.
PubChem, Substance Record, NSC-124205, PubChem SID: 417201, Deposited Mar. 26, 2005, Modified: Dec. 19, 2011, 8 pgs.
Qu, Y., et al., "Antitumor activity of selective MEK1/2 inhibitor AZD6244 in combination with PI3K/mTOR inhibitor BEZ235 in gefitinib-resistant NSCLC xenograft models," J Exp Clin Cancer Res, 2014, 33:52, 10 pgs.
Quevedo, C.E., et al., "Small molecule inhibitors of RAS-effector protein interactions derived using an intracellular antibody fragment," Nature Communications, 2018, 9:3169, 12 pgs.
Qui, R.G., et al., "An essential role for Rac in Ras transformation," Nature, 1995, 374:457-459, 3 pgs.
Rauen, K.A., "The RASopathies," Annu Rev Genomics Hum Genet, 2013, 14:355-369, 20 pgs.
Reuther, G.W., et al., "Leukemia-associated Rho Guanine Nucleotide Exchange Factor, a Dbl Family Protein Found Mutated in Leukemia, Causes Transformation by Activation of RhoA," J Biol Chem, 2001, 276(29):27145-27151, 7 pgs.
Ridley, A.J., "Rho GTPase signalling in cell migration," Curr Opin Cell Biol, 2015, 36:103-112, 10 pgs.
Ridley, A.J., et al., "The Small GTP-Binding Protein rac Regulates Growth Factor-Induced Membrane Ruffling," Cell, 1992, 70:401-410, 10 pgs.
Ridley, A.J., et al., "The Small GTP-Binding Protein rho Regulates the Assembly of Focal Adhesions and Actin Stress Fibers in Response to Growth Factors," Cell, 1992, 70(3):389-399, 11 pg.
Roberts, A.E., et al., "Germline gain-of-function mutations in SOS1 cause Noonan syndrome," Nat Genet, 2007, 39(1):70-74, 5 pgs.

(56) References Cited

OTHER PUBLICATIONS

Rojas, J.M., et al., "Mammalian Son of Sevenless Guanine Nucleotide Exchange Factors: Old Concepts and New Perspectives," Genes & Cancer, 2011, 2(3):298-305, 8 pgs.
Rolfo, C., et al., "Novel therapeutic strategies for patients with NSCLC that do not respond to treatment with EGFR inhibitors," Cancer Treat Rev, 2014, 40:990-1004, 15 pgs.
Rouard, H., et al., "Vav and SLP-76 recruitment by cross-linking of FcγRIIal in promyelocytic HL-60 cells," Immunol Lett, 1999, 68:347-353, 7 pgs.
Saci, A., et al., "Rac1 Regulates the Activity of mTORC1 and mTORC2 and Controls Cellular Size," Mol Cell, 2011, 42(1):50-61, 22 pgs.
Sahai, E., et al., "RHO-GTPases and Cancer," Nat Rev Cancer, 2002, 2:133-142, 11 pgs.
Sahai, E., "Mechanisms of cancer cell invasion," Curr Opin Genet Dev, 2005, 15:87-96, 10 pgs.
Sahay, S., et al., "The RhoGEF domain of p210 Bcr-Abl activates RhoA and is required for transformation," Oncogene, 2008, 27(14):2064-2071, 17 pgs.
Schopel, M., et al., "Bisphenol A Binds to Ras Proteins and Competes with Guanine Nucleotide Exchange: Implications for GTPase-Selective Antagonists," J Med Chem, 2013, 56:9664-9672, 9 pgs.
Sengupta, A., et al., "Rac2 GTPase deficiency depletes BCR-ABL[+] leukemic stem cells and progenitors in vivo," Blood, 2010, 116(1):81-84, 4 pgs.
Shima, F., et al., "Structural Basis for Conformational Dynamics of GTP-bound Ras Protein," J Biol Chem, 2010, 285(29):22696-22705, 10 pgs.
Shima, F., et al., "In silico discovery of small-molecule Ras inhibitors that display antitumor activity by blocking the Ras-effector interaction," PNAS USA, 2013, 110(20):8182-8187, 6 pgs.
Siegel, R., et al. "Cancer Statistics, 2013," CA Cancer J Clin, 2013, 63:11-30, 20 pgs.
Simanshu, D.K., et al., "RAS Proteins and Their Regulators in Human Disease," Cell, 2017, 170(1):17-33, 34 pgs.
Skorski, T., et al., "BCR/ABL-mediated leukemogenesis requires the activity of the small GTP-binding protein Rac," PNAS USA, 1998, 95:11858-11862, 5 pgs.
Somervaille, T.C., et al., "Identification and characterization of leukemia stem cells in murine MLL-AF9 acute myeloid leukemia," Cancer Cell, 2006, 10:257-268, 12 pgs.
Spencer-Smith, R., et al., "Direct inhibition of RAS: Quest for the Holy Grail?" Semin Cancer Biol, 2019, 54:138-148, 25 pgs.
Spiegel, J., et al., "Small-Molecule Modulation of Ras Signaling," Nature Chemical Biology, 2014, 10:613-622, 10 pgs.
Spoerner, M., et al., "Dynamic properties of the Ras switch I region and its importance for binding to effectors," PNAS USA, 2001, 98(9):4944-4949, 6 pgs.
Spoerner, M., et al., "Conformational States of Human Rat Sarcoma (Ras) Protein Complexed with Its Natural Ligand GTP and Their Role for Effector Interaction and GTP Hydrolysis," J Biol Chem, 2010, 285(51):39768-39778, 11 pgs.
Spoerner, M., et al., "Slow conformational dynamics of the guanine nucleotide-binding protein Ras complexed with the GTP analogue GTPγS," The FEBS Journal, 2007, 274:1419-1433, 15 pgs.
Steffen, A., et al., "Rac function is crucial for cell migration but is not required for spreading and focal adhesion formation," J Cell Sci, 2013, 126:4572-4588, 17 pgs.
Stephen, A.G., et al., "Dragging Ras Back in the Ring," Cancer Cell, 2014, 25:272-281, 10 pgs.
Studier, F.W., "Protein production by auto-induction in high density shaking cultures," Protein Expr Purif, 2005, 41:207-234, 28 pgs.
Sun, Q., et al., "Discovery of Small Molecules that Bind to K-Ras and Inhibit Sos-Mediated Activation," Angew Chem Int Ed, 2012, 51:6140-6143, 4 pgs.
Sundaresan, M., et al., "Regulation of reactive-oxygen-species generation in fibroblasts by Rac1," Biochem J, 1996, 318(Pt 2):379-382, 4 pgs.
Sung, Y.J., et al., "Mutagenesis of the H-ras p21 at Glycine-60 Residue Disrupts GTP-Induced Conformational Change," Biochemistry, 1995, 34:3470-3477, 8 pgs.
Sung, Y.J., et al., "The Dominant Negative Effects of H-Ras Harboring a Gly to Ala Mutation at Position 60," J Biol Chem, 1996, 271(48):30537-30543, 7 pgs.
Tajan, M., et al., "The RASopathy Family: Consequences of Germline Activation of the RAS/MAPK Pathway," Endocr Rev, 2018, 39:676-700, 25 pgs.
Tartaglia, M., et al., "Gain-of-function SOS1 mutations cause a distinctive form of Noonan syndrome," Nat Genet, 2007, 39(1):75-79, 6 pgs.
Tartaglia, M., et al., "Noonan syndrome and clinically related disorders," Best Pract Res Clin Endocrinol Metab, 2011, 25(1):161-179, 25 pgs.
Thomas, E.K., et al., "Rac guanosine Triphosphatases Represent Integrating Molecular Therapeutic Targets for BCR-ABL-Induced Myeloproliferative Disease," Cancer Cell, 2007, 12:467-478, 12 pgs.
Thomas, E.K., et al., "Rac GTPases as key regulators of p210-BCR-ABL-dependent leukemogenesis," Leukemia, 2008, 22(5):898-904, 14 pgs.
Tidyman, W.E., et al., "The RASopathies: Developmental syndromes of Ras/MAPK pathway dysregulation," Curr Opin Genet Dev, 2009, 19(3):230-236, 11 pgs.
Tomayko, M.M., et al., "Determination of subcutaneous tumor size in athymic (nude) mice," Cancer Chemotherapy and Pharmacology, 1989, 24:148-154, 7 pgs.
Trovo-Marqui, A.B., et al., "Neurofibromin: a general outlook," Clin Genet, 2006, 70:1-13, 13 pgs.
Vetter, I.R., et al., "The Guanine Nucleotide-Binding Switch in Three Dimensions," Science, 2001, 294:1299-1304, 6 pgs.
Vicent, S., et al., "ERK1/2 is activated in non-small-cell lung cancer and associated with advanced tumours," Br J Cancer, 2004, 90:1047-1052, 6 pgs.
Vigil, D., et al., "Ras superfamily GEFs and GAPs: validated and tractable targets for cancer therapy?" Nat Rev Cancer, 2010, 10(12):842-857, 32 pgs.
Wang, Z., et al., "Rac1 is crucial for Ras-dependent skin tumor formation by controlling Pak1-Mek-Erk hyperactivation and hyperproliferation in vivo," Oncogene, 2010, 29(23):3362-3373, 12 pgs.
Wei, J., et al., "Microenvironment Determines Lineage Fate in a Human Model of MLL-AF9 Leukemia," Cancer Cell, 2008, 13(6):483-495, 26 pgs.
Welsch, M.E., et al., "Multivalent small-molecule pan-RAS inhibitors," Cell, 2017, 168(5):878-889, 53 pgs.
Williams, D.A., et al., "Dominant negative mutation of the hematopoietic-specific Rho GTPase, Rac2, is associated with a human phagocyte immunodeficiency," Blood, 2000, 96:1646-1654, 9 pgs.
Wittinghofer, A., et al., "How Ras-related proteins talk to their effectors," Trends in Biochemical Sciences, 1996, 21:488-491, 4 pgs.
Woods, K.W., et al., "Synthesis and SAR of indazole-pyridine based protein kinase B/Akt inhibitors," Bioorganic & Medicinal Chemistry, 2006, 14:6832-6846, 15 pgs.
Xing, L., et al., "Scaffold mining of kinase hinge binders in crystal structure database," J Comput Aided Mol Des, 2014, 28:13-23, 11 pgs.
Yamaguchi, H., et al., "Regulation of the actin cytoskeleton in cancer cell migration and invasion," Biochim Biophys Acta, 2007, 1773(5):642-652, 20 pgs.
Yamaguchi, H., et al., "Cell migration in tumors," Current Opinion in Cell Biology, 2005, 17:559-564, 6 pgs.
Yoshizawa, A., et al., "Overexpression of Phospho-eIF4E is Associated with Survival through AKT Pathway in Non-Small Cell Lung Cancer," Clin Cancer Res, 2010, 16(1):240-248, 20 pgs.
Zandvakili, I., et al., "Rho GTPases: Anti-or Pro-neoplastic Targets?" Oncogene, 2017, 36(23):3213-3222, 24 pgs.
Zhang, S.C., et al., "Liposome Reconstitution and Modulation of Recombinant Prenylated Human Rac1 by GEFs, GDI1 and Pak1," PLoS One, 2014, 9(7):e102425, 11 pgs.

(56) References Cited

OTHER PUBLICATIONS

Zhu, Y. et al., "Neurofibromin, a Tumor Suppressor in the Nervous System," Exp Cell Res, 2001, 264:19-28, 10 pgs.

Zhuang, H., et al., "Progress of clinical research on targeted therapy combined with thoracic radiotherapy for non-small-cell lung cancer," Drug Des Devel Ther, 2014, 8:667-675, 9 pgs.

Canadian Office Action dated Nov. 29, 2023 for Application No. CA 3,138,876, 4 pgs.

Chinese Office Action, Notification of the First Office Action and Preliminary Search Report dated Jun. 29, 2023 for Application No. CN 2020800478233, 11 pgs.

European Supplementary Search Report and Written Opinion dated Nov. 23, 2022 for Application No. EP 20802505.6, 9 pgs.

Indian Examination Report dated Nov. 8, 2023 for Application No. IN 202117050783, 7 pgs.

International Search Report and Written Opinion dated Sep. 4, 2020 for Application No. PCT/US2020/031298, 21 pgs.

Chen, Yuxiang, ed., *Molecular Pharmaceutics*, Hunan Normal University Press, Changsha, Hunan, China, Jan. 31, 2010, pp. 2-5, [English & Chinese language versions included.], 13 pgs.

McKim, A.S., et al., "Dimethyl Sulfoxide USP, PhEur in Approved Pharmaceutical Products and Medical Devices," Pharmaceutical Technology, 2008, 32(5), 7 pgs.

Sydykov, B., et al., "Storage stability of liposomes stored at elevated subzero temperatures in DMSO/sucrose mixtures," Plos One, 2018, 13(7):e0199867, 16 pgs.

Van Eerdenbrugh, B., et al., "Characterization of physico-chemical properties and pharmaceutical performance of sucrose co-freeze-dried solid nanoparticulate powders of the anti-HIV agent loviride prepared by media milling," Int J Pharma, 2007, 338(Issues 1-3):198-206, 9 pgs.

\* cited by examiner

COMPOSITIONS AND METHODS FOR TREATING CANCER

CROSS REFERENCE TO RELATED APPLICATIONS

The present application hereby claims the benefit of the provisional patent application of the same title, Ser. No. 62/842,839, filed on May 3, 2019, the disclosure of which is herein incorporated by reference in its entirety.

STATEMENT REGARDING FEDERALLY-SPONSORED RESEARCH

This invention was made with government support under CA115611 awarded by the National Institutes of Health. The government has certain rights in the invention.

BACKGROUND

Cancer is a serious public health problem in the United States and other developed countries. Currently, one in four deaths in the United States is due to cancer. However, many cancers are not responsive to existing treatments, or are only minimally responsive, such that existing therapies are not effective. In addition, appearance of resistance mechanisms to current therapies and relapse continue to be a major impediment in the clinic. The leading therapies for cancer are currently surgery, radiation, targeted and immunotherapies, and chemotherapy. Chemotherapeutic approaches such as antitumor antibiotics, alkylating agents, nitrosourea compounds, vinca alkaloids, steroid hormones, and anti-metabolites form the bulk of therapies available to oncologists. They have undesirable side effects because they don't distinguish between healthy and cancerous tissue. Despite advances in the field of cancer treatment, cancer remains a major health problem.

Thus, there is an urgent need in the art for compositions and methods for treatment of cancer. The present disclosure seeks to address this need in the art.

BRIEF DESCRIPTION OF THE DRAWINGS

Those of skill in the art will understand that the drawings, described below, are for illustrative purposes only. The drawings are not intended to limit the scope of the present teachings in any way.

DETAILED DESCRIPTION

Definitions

Figure 1:
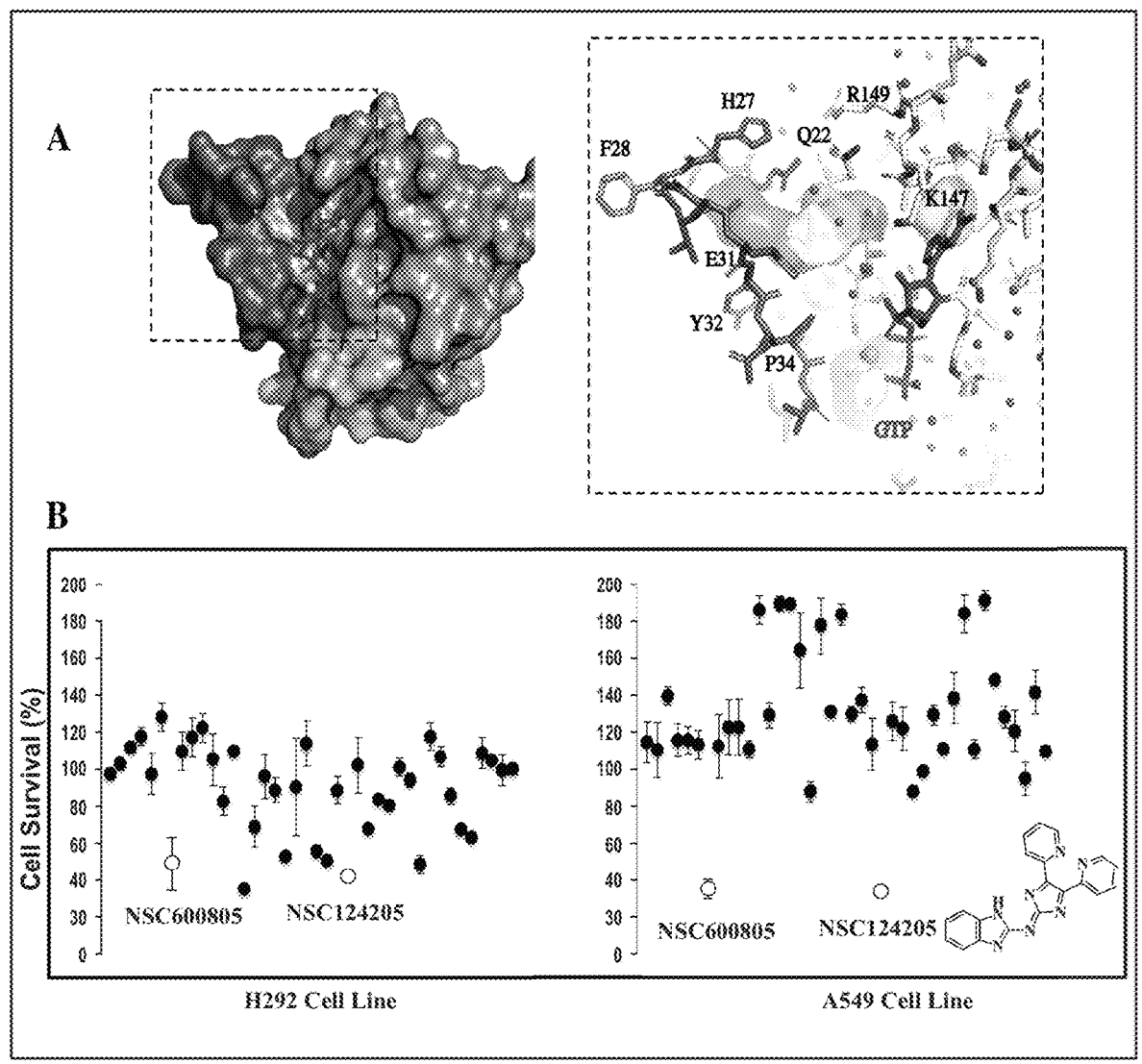
FIG. 1. Identification of NSC124205. (A) Surface representation (left) of the RasG60A in the GTP-bound form (PDB ID 1XCM) with the nucleotide in red ball-and-stick and the $Mg^{2+}$-ion as a green ball. Switch 1 region is in maroon and switch II in salmon pink. Zoom in on the surface used in the docking experiments (right). Water molecules are shown as red balls. Figure prepared with the program PyMol. (B) NSC600805 and NSC124205 inhibit H292 and A549 cell growth. H292 and A549 lung adenocarcinoma cells were plated at 10,000 cells in 24-well plates and treated in triplicates with vehicle control or each of the 40 top scoring NCI compounds at 10 µM. Cell proliferation was determined by the MTS assay and plotted at the 4-day time point relative to vehicle control.

Unless otherwise noted, terms are to be understood according to conventional usage by those of ordinary skill in the relevant art. In case of conflict, the present document, including definitions, will control. Preferred methods and materials are described below, although methods and materials similar or equivalent to those described herein may be used in practice or testing of the present invention. All publications, patent applications, patents and other references mentioned herein are incorporated by reference in their entirety. The materials, methods, and examples disclosed herein are illustrative only and not intended to be limiting.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" may mean within 1 or more than 1 standard deviation, per the practice in the art. Alternatively, "about" may mean a range of up to 20%, or up to 10%, or up to 5%, or up to 1% of a given value. Alternatively, particularly with respect to biological systems or processes, the term may mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "effective amount" means the amount of one or more active components that is sufficient to show a desired effect. This includes both therapeutic and prophylactic effects. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "individual," "host," "subject," and "patient" are used interchangeably to refer to an animal that is the object of treatment, observation and/or experiment. Generally, the term refers to a human patient, but the methods and compositions may be equally applicable to non-human subjects such as other mammals. In some embodiments, the terms refer to humans. In further embodiments, the terms may refer to children.

The terms "pharmaceutically acceptable salts" or "a pharmaceutically acceptable salt thereof" refer to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts; salts of free acids and bases; inorganic salts, e.g., sulfate, hydrochloride, and hydrobromide; and other salts which are currently in widespread pharmaceutical use and are listed in sources well known to those of skill in the art, such as The Merck Index. Any suitable constituent can be selected to make a salt of an active drug discussed herein, provided that it is non-toxic and does not substantially interfere with the desired activity. In addition to salts, pharmaceutically acceptable precursors and derivatives of the compounds can be employed. Pharmaceutically acceptable amides, lower alkyl esters, and protected derivatives of the disclosed actives can also be suitable for use in the compositions and methods disclosed herein. A salt of a compound of this disclosure may be formed between an acid and a basic group of the compound, such as an amino functional group, or a base and an acidic group of the compound, such as a carboxyl functional group. According to another embodiment, the compound is a pharmaceutically acceptable acid addition salt. Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The terms "treat," "treating" or "treatment," as used herein, refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

The term "carrier" applied to pharmaceutical compositions of the disclosure refers to a diluent, excipient, or vehicle with which an active compound is administered. Such pharmaceutical carriers can be sterile liquids, such as water, saline solutions, aqueous dextrose solutions, aqueous glycerol solutions, and oils, including those of petroleum, animal, vegetable, or synthetic origin, such as peanut oil, soybean oil, mineral oil, sesame oil and the like. Suitable pharmaceutical carriers are described in "Remington's Pharmaceutical Sciences" (any edition).

The term "compound," as used herein, is also intended to include any salts, solvates, or hydrates thereof.

The term "alkyl" includes straight, branched chain, or cyclic alkyl groups, such as, but not limited to, methyl, ethyl, propyl, butyl, trifluoromethyl, and tetradecyl.

The term "alkoxy" includes straight, branched chain, or cyclic alkoxy groups, such as, but not limited to, methoxy, ethoxy, propoxy, butoxy, 2-methoxyethoxy, sec-butoxy, hexyloxy, and 2-ethylhexyloxy, tetradecyloxy groups.

The term "aryl" encompasses monocyclic and polycyclic aryl groups which contain only carbons on the first ring. The term "monocyclic aryl" refers to phenyl (where the ring only contains carbons), and the term "polycyclic aryl" refers to napthyl and anthracenyl, to phenyl rings having at least a second ring fused thereto, and to napthyl rings having a third ring fused thereto. In the case of a polycyclic aryl consisting of a phenyl ring having a second or third ring fused thereto, or a napthyl ring having a third ring fused thereto, the additional rings may be aromatic or non-aromatic carbocyclic or heterocyclic rings, provided that in such cases the point of attachment will be to the carbocyclic aromatic ring. For example, a subset of this aryl group is a polycyclic aryl group wherein the second ring is a "heteroaryl" which contains carbon atoms and at least one heteroatom selected from the group consisting of O, N, and S (provided that 0 and S cannot be adjacent to each other in the same ring). Alternatively, a ring carbon atom of the second and/or third further rings may be replaced with a carbonyl [—C(=O) group] (e.g., when such rings are non-aromatic). "Substituted aryl" refers to an aryl group substituted by one or more substituents, preferably 1 to 4 substituents (more preferably 1 or 2), at any point of attachment of any ring, selected from alkyl, substituted alkyl, and the substituents recited above for substituted alkyl groups.

Accordingly, examples of aryl groups that are of interest in forming compounds of the invention include:

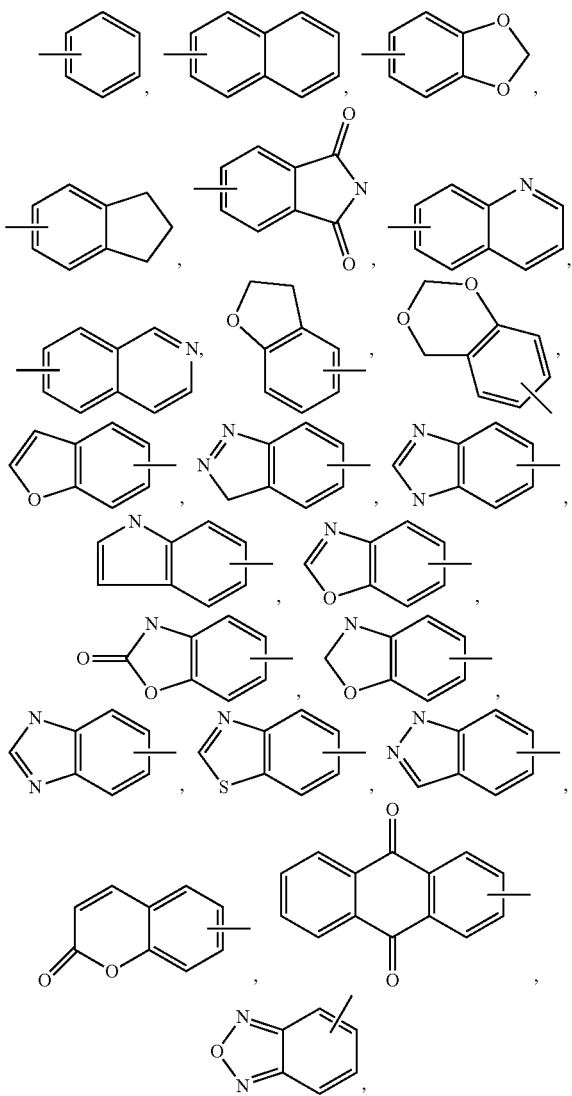

and, additionally, similar structures.

The terms "heterocycle", "heterocyclic" and "heterocyclo" refer to fully saturated, partially unsaturated, or fully unsaturated, including aromatic (i.e., "heteroaryl") cyclic groups (for example, 3 to 7 membered monocyclic, 7 to 11 membered bicyclic, or 10 to 16 membered tricyclic ring systems) which have at least one heteroatom in at least one carbon atom-containing ring. Thus, the term "heteroaryl" is a subset of heterocyclo groups. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized, provided sulfur and oxygen are not adjacent to each other in the ring. (The term "heteroarylium" refers to a heteroaryl group bearing a quaternary nitrogen atom and thus a positive charge.) Additionally, one or more (preferably one) carbon ring atoms of the heterocyclo ring may, as valence allows, be replaced with carbonyl group, i.e., —C(=O)—. The heterocyclic group may be attached to the remainder of the molecule at any heteroatom or carbon atom of the ring or ring system.

Exemplary monocyclic heterocyclic groups include those selected from the group consisting of ethylene oxide, azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include those selected from the group consisting of indolyl, isoindolyl, benzothiazolyl, benzodioxolyl, benzoxazolyl, benzoxadiazolyl, benzothienyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydrobenzodioxinyl, dihydrodioxidobenzothiophenyl, dihydroisoindolyl, dihydroindolyl, dihydroquinolinyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrolinyl, dibenzofuranyl, acridinyl, phenanthridinyl, xanthenyl and the like.

The term "heterocyclene" refers to bivalent heterocycle groups as defined above.

"Substituted heterocycle", "substituted heterocyclic" and "substituted heterocyclo" (such as "substituted heteroaryl") refer to heterocycle, heterocyclic or heterocyclo groups substituted with one or more substituents, preferably 1 to 4 substituents, at any available point of attachment, wherein the substituents are selected from those recited above for substituted cycloalkyl groups.

The term "group" is used, it is intended to encompass not only the substituent's unsubstituted form, but also its form further substituted with any substituent group or groups as herein mentioned, so long as the substituent does not destroy properties necessary for utility. Suitably, a substituent group may be halogen or may be bonded to the remainder of the molecule by an atom of carbon, nitrogen, oxygen, or sulfur.

In one aspect, a composition that may be used according to the disclosed methods may comprise a compound having the following structure:

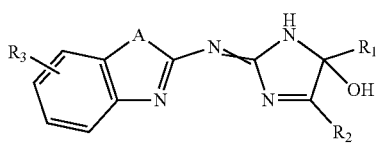

(referred to herein as "Compound 1," or "an IODVA1 compound") and a pharmaceutically acceptable carrier;
  wherein A=NH, NRB, S, O, C=C, N=C, C=N
  wherein R1, R2 are independently substituted or unsubstituted aryl or heteroaryl rings
  wherein R3=singly or multiply substituted as H, D, Halo, CN, C1-C4 Alkyl, C1-C4

Alkoxy, C1-C4 Alkylsulfonyl, C1-C4 Alkyl amino, or C1-C4 mercapto wherein R8=H, M;

and all tautomers thereof.

In one aspect, the compound may have the structure

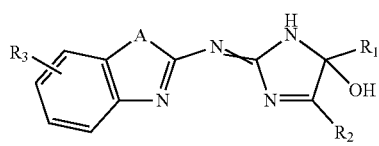

wherein A=NH, S wherein R1, R2 are independently substituted or unsubstituted phenyl, pyridyl, furanyl, pyrimidinyl, triazinyl, or diazinyl rings wherein R3=singly or multiply substituted as H, D, Halo, CN, OH, OMe, OEt, SMe, SEt, SO2Me, NHMe, NMe2, Me, Et, or Pr;

and all tautomers thereof.

In one aspect, the compound may have the structure

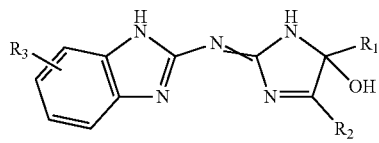

and wherein R1, R2 are independently substituted or unsubstituted phenyl, pyridyl, furanyl, pyrimidinyl rings wherein R3=singly or multiply substituted as H, D, Halo, CN, OH, OMe, OEt, SMe, SEt, SO2Me, NHMe, NMe2, Me, Et, or Pr, and all tautomers thereof.

In one aspect, the compound may have the structure

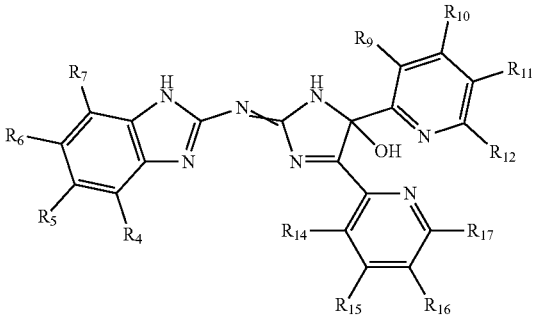

wherein R4-R17 are independently selected from H, D, Halo, CN, OH, OMe, OEt, SMe, SEt, SO2Me, NHMe, NMe2, Me, Et, or Pr, and all tautomers thereof.

In one aspect, the compound may have the structure

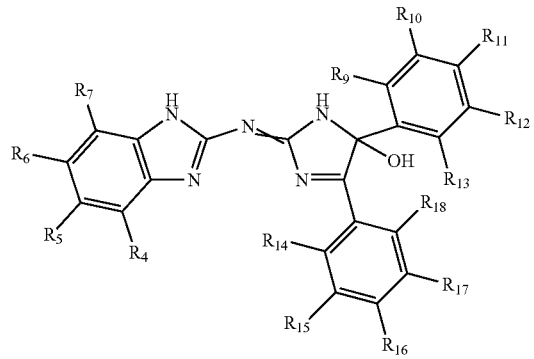

wherein R4-R17 are independently selected from H, D, Halo, CN, OH, OMe, OEt, SMe, SEt, SO2Me, NHMe, NMe2, Me, Et, or Pr, and all tautomers thereof.

In one aspect, the compound may have the structure

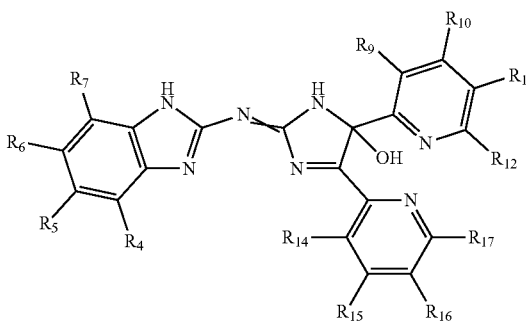

wherein R4-R7 are independently selected from H, D, F, Cl, CN, OH, OMe, SMe, Me, or Et;

wherein R9-R17 are independently selected from H, D, F, Cl, CN, OH, OMe, SO2Me, NHMe, NMe2, Me, or Et;

and all tautomers thereof.

In one aspect, the compound may have the structure

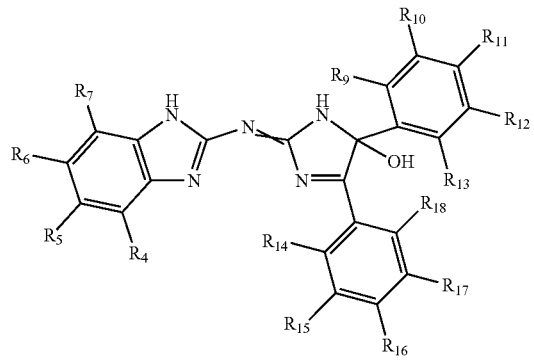

wherein R4-R7 are independently selected from H, D, F, Cl, CN, OH, OMe, SMe, Me, or Et;

wherein R9-R17 are independently selected from H, D, F, Cl, CN, OH, OMe, SO2Me, NHMe, NMe2, Me, or Et, and all tautomers thereof.

In one aspect, the compound may have the structure

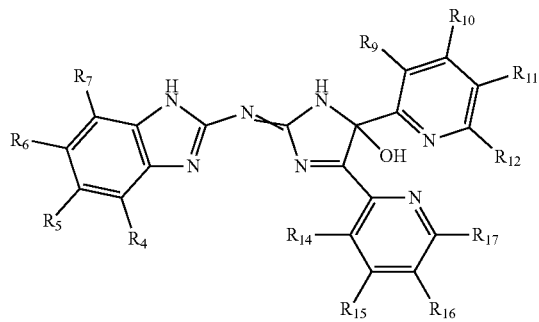

wherein R4-R7 are independently selected from H, D, F, OH, OMe, Me;
wherein R9-R17 are independently selected from H, D, F, Cl, CN, OH, OMe, SO2Me, NHMe, NMe2, Me, or Et,
and all tautomers thereof.

In one aspect, the compound may have the structure

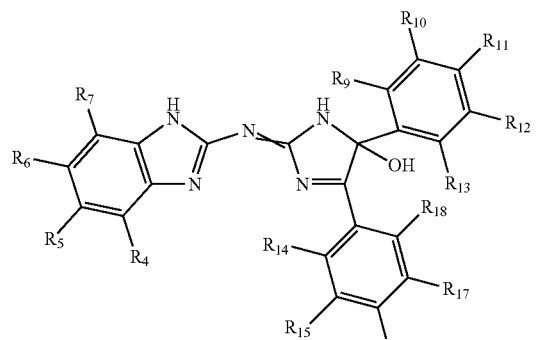

wherein R5, R6 are independently selected from H, D, F, Cl, OH, OMe, or Me;
wherein R9-R17 are independently selected from H, D, F, Cl, OH, OMe, or Me;
wherein each ring bears ≤2 non-H substituents;
and all tautomers thereof.

In one aspect, the compound may have the structure

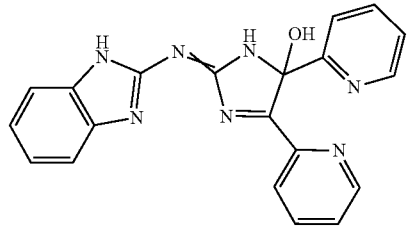 [SMILES: OC1(c2ccccn2)NC(=Nc2nc3ccccc3[nH]2)N=C1c1ccccn1]

and all tautomers thereof.

In one aspect, the compound may have the structure

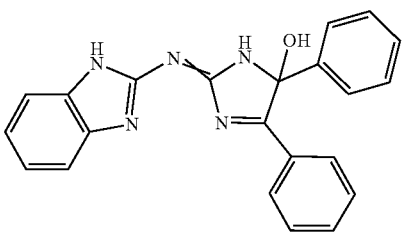 [SMILES: OC1(c2ccccc2)NC(=Nc2nc3ccccc3[nH]2)N=C1c1ccccc1]

and all tautomers thereof.

In one aspect, a composition comprising a compound having the structure (1c)

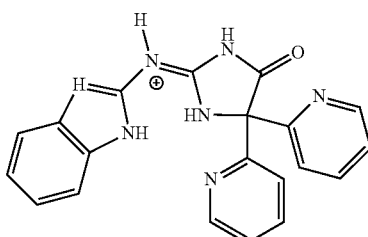

and a pharmaceutically acceptable carrier is disclosed.

In one aspect, the compound may have the structure

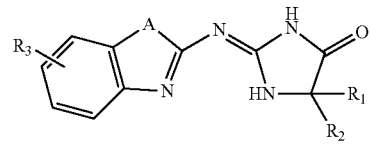

wherein A is selected from NH, NRB, S, O, C═C, N═C, C═N; wherein R1, R2 are independently substituted or unsubstituted* aryl or heteroaryl rings; wherein R3 is singly or multiply substituted as H, D, Halo, CN, C1-C4 Alkyl, C1-C4 Alkoxy, C1-C4 Alkylsulfonyl, C1-C4 Alkyl amino, or C1-C4 mercapto; wherein R8 is H or Me; and all tautomers thereof.

In one aspect, the compound may have the structure

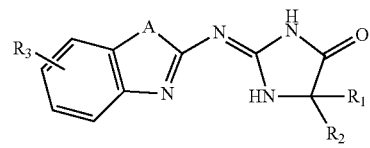

wherein A is NH or S; wherein R1, R2 are independently substituted or unsubstituted phenyl, pyridyl, furanyl, pyrimidinyl, triazinyl, or diazinyl rings; wherein R3 is singly or multiply substituted as H, D, Halo, CN, OH, OMe, OEt, SMe, SEt, SO2Me, NHMe, NMe2, Me, Et, or Pr; and all tautomers thereof.

In one aspect, the compound may have the structure

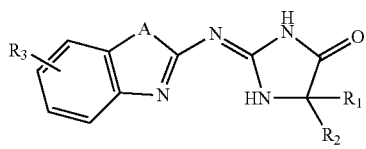

wherein R1, R2 are independently substituted or unsubstituted phenyl, pyridyl, furanyl, pyrimidinyl rings; wherein R3 is singly or multiply substituted as H, D, Halo, CN, OH, OMe, OEt, SMe, SEt, SO2Me, NHMe, NMe2, Me, Et, or Pr; and all tautomers thereof.

In one aspect, the compound may have the structure

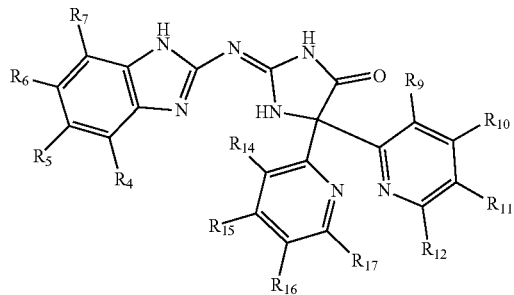

wherein R4-R17 are each independently selected from H, D, Halo, CN, OH, OMe, OEt, SMe, SEt, SO2Me, NHMe, NMe2, Me, Et, or Pr; and all tautomers thereof.

In one aspect, the compound may have the structure

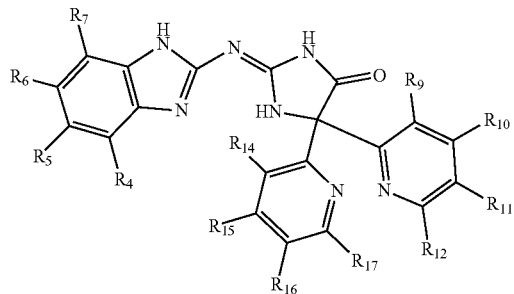

wherein R4-R17 are each independently selected from H, D, Halo, CN, OH, OMe, OEt, SMe, SEt, SO2Me, NHMe, NMe2, Me, Et, or P; and all tautomers thereof.

In one aspect, the compound may have the structure

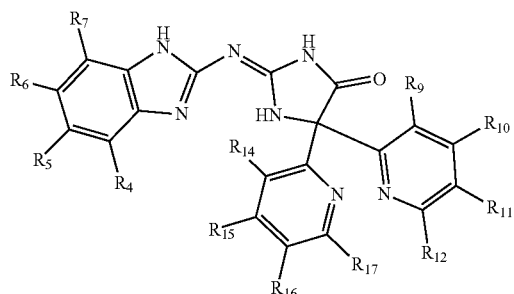

wherein R4-R7 are each independently selected from H, D, F, Cl, CN, OH, OMe, SMe, Me, or Et; wherein R9-R17 are each independently selected from H, D, F, Cl, CN, OH, OMe, SO2Me, NHMe, NMe2, Me, or Et; and all tautomers thereof.

In one aspect, the compound may have the structure

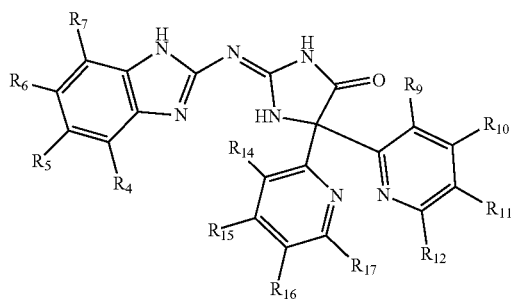

wherein R4-R7=H, D, F, Cl, CN, OH, OMe, SMe, Me, or Et; wherein R9-R17=H, D, F, Cl, CN, OH, OMe, SO2Me, NHMe, NMe2, Me, or Et, and all tautomers thereof.

In one aspect, the compound may have the structure

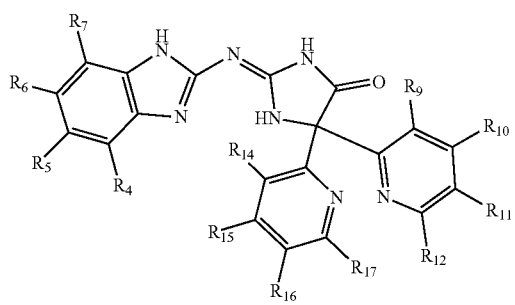

wherein R4-R7=Independently H, D, F, OH, OMe, Me; wherein R9-R17 may be independently selected from H, D, F, Cl, CN, OH, OMe, SO2Me, NHMe, NMe2, Me, or Et, and all tautomers thereof.

In one aspect, the compound may have the structure

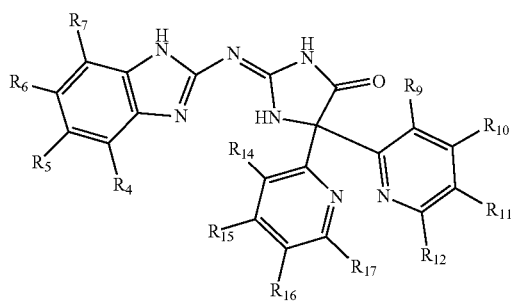

wherein R4-R7=Independently H, D, F, Cl, OH, OMe, or Me; wherein R9-R12 and R14-R17 may be independently selected from H, D, F, Cl, OH, OMe, or Me. Each ring bearing ≤2 non-H substituents; and all tautomers thereof.

In one aspect, a composition comprising

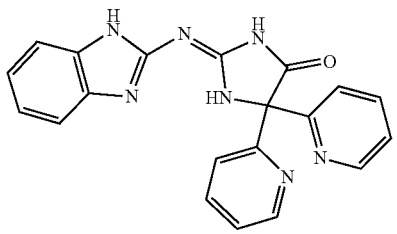 [SMILES: O=C1N/C(=N/c2nc3ccccc3[nH]2)NC1(c1ccccn1)c1ccccn1]

and all tautomers thereof, and a pharmaceutically acceptable carrier is disclosed.

In one aspect, a composition comprising

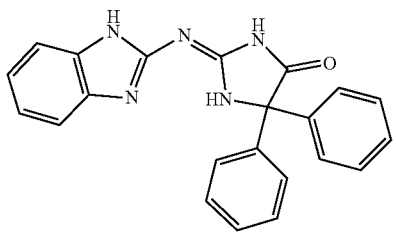 [SMILES: O=C1N/C(=N/c2nc3ccccc3[nH]2)NC1(c1ccccc1)c1ccccc1]

and all tautomers thereof, and a pharmaceutically acceptable carrier, is disclosed.

In one aspect, composition comprising what is herein referred to as the NIRA2 class of compounds, is disclosed. The composition may comprise a compound having the structure:

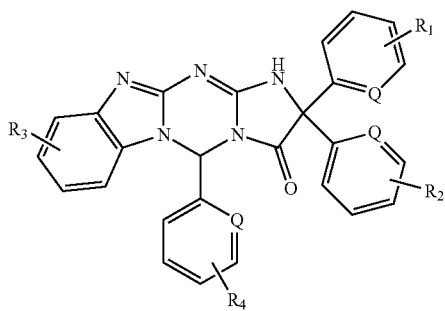

wherein R1, R2, and R4 are independently selected from H, D, Halo, CN, OH, OMe, OEt, SMe, SEt, SO2Me, NHMe, NMe2, Me, Et, or Pr, and all tautomers thereof, wherein R3 is singly or multiply substituted as H, D, Halo, CN, C1-C4 alkyl, C1-C4 alkoxy, C1-C4 alkylsufonyl; C1-C4 akylamino, or C1-C4 mercapto; wherein A is selected from NH, NRB, S, O, C═C, N═C, C═N, wherein R8 is H or Me, wherein each Q is independently selected from N, C, and S; and a pharmaceutically acceptable carrier.

In one aspect, the compound may have the structure

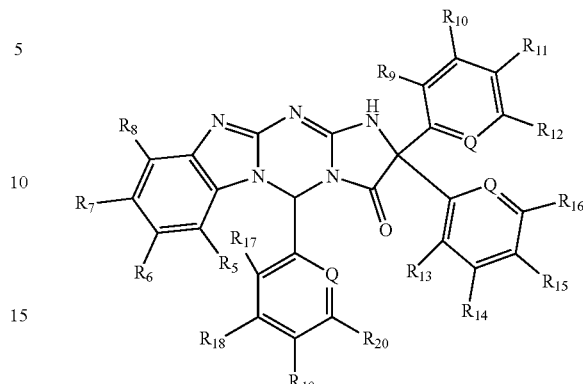

wherein R5-R20 are independently selected from H, D, Halo, CN, OH, OMe, OEt, SMe, SEt, SO2Me, NMe2, Me, Et, or Pr, wherein each Q is independently selected from N, C, and S, and all tautomers thereof; and a pharmaceutically acceptable carrier.

In one aspect, the compound may have the structure

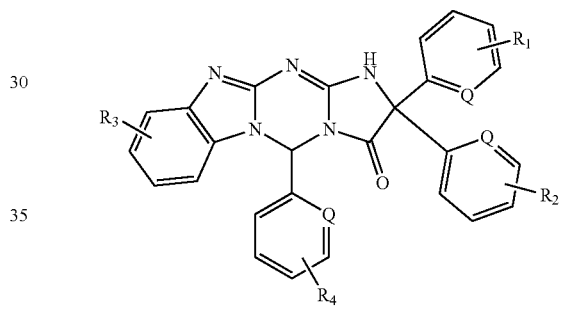

wherein R1, R2, and R4 are independently selected from H, D, Halo, CN, OH, OMe, OEt, SMe, SEt, SO2Me, NHMe, NMe2, Me, Et, or Pr, and all tautomers thereof; wherein R3 is singly or multiply substituted as H, D, Halo, CN, C1-C4 alkyl; C1-C4 alkoxy; C1-C4 alkysulfonyl; C1-C4 akylamino; or C1-C4 mercapto; wherein A is selected from NH, NR8, S, O, C═C, N═C, C═N, wherein R8 is H or Me, wherein each Q is independently selected from N, C, and S; and a pharmaceutically acceptable carrier.

In one aspect, the compound may have the structure

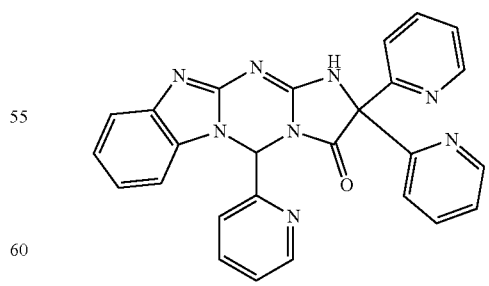

("NIRA2")

or a pharmaceutically acceptable salt thereof and a pharmaceutically acceptable carrier. In one aspect, the compound may have the structure

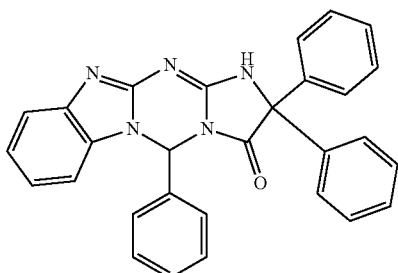

or a pharmaceutically acceptable salt thereof and a pharmaceutically acceptable carrier.

In one aspect, any of the aforementioned compositions may be free of, or substantially free of one or both of the following compounds:

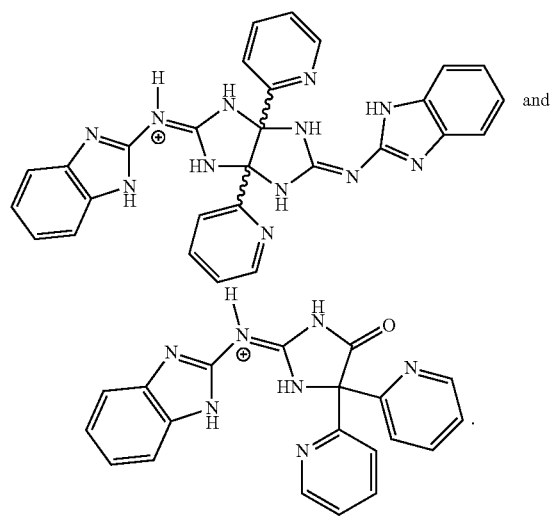

In one aspect, a composition comprising

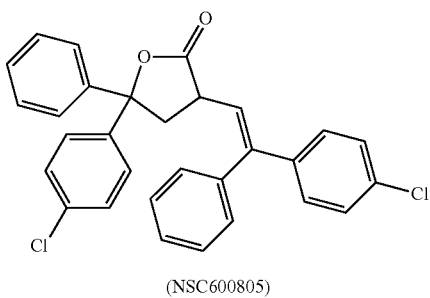 [SMILES: O=C1OC(c2ccccc2)(c2ccc(Cl)cc2)CC1/C=C(\c1ccccc1)c1ccc(Cl)cc1]

(NSC600805)

and a pharmaceutically
  acceptable carrier is disclosed.

In one aspect, a method of treating cancer in an individual in need thereof, is disclosed. The method may comprise the step of administering to said individual a compound or composition as disclosed herein.

In one aspect, the cancer may be a solid tumor. The treating step may effect a decrease in tumor volume.

In one aspect, the treating step may effect a decrease in cancer cell proliferation. In one aspect, the treating step may affect an increase in cancer cell death.

In one aspect, the cancer may be selected from a leukemia, preferably ALL, AML, or MLL, chemotherapy-resistant leukemia, immunotherapy-resistant leukemia, relapsed leukemia, and other targeted-therapy resistant leukemias. In one aspect, the cancer may be selected from adenocarcinoma, breast cancer. In one aspect, the cancer may be one in which Vav3 is overexpressed, such as prostate cancer, ovarian cancer, endometrial cancer, thyroid cancer, lung cancer, particularly non-small cell lung cancer, colorectal cancer, pancreatic cancer, and cervical cancer. In one aspect, the cancer may be a Ras-driven cancer, including RASopathies, for example, NF1 or MPNST. In one aspect, the cancer is any cancer that overexpresses Vav3.

In a further aspect, a method of treating a cancer based on the status of Vav3 expression is disclosed. In this aspect, the method may comprise the step of determining the level of Vav3 in a biopsy obtained from a cancer in an individual; and administering a composition as described herein to said individual where said level of Vav3 is elevated as compared to a control.

Pharmaceutical Compositions

The compositions may be administered in oral dosage forms such as tablets, capsules (each of which includes sustained release or timed-release formulations), pills, powders, granules, elixirs, tinctures, suspensions, syrups, and emulsions. They may also be administered in intravenous (bolus or infusion), intraperitoneal, subcutaneous, intralesional, or intramuscular forms all utilizing dosage forms well known to those of ordinary skill in the pharmaceutical arts. The compositions may be administered by intranasal route via topical use of suitable intranasal vehicles, or via a transdermal route, for example using conventional transdermal skin patches. A dosage protocol for administration using a transdermal delivery system may be continuous rather than intermittent throughout the dosage regimen.

In one aspect, pharmaceutical compositions are isotonic with the blood or other body fluid of the recipient. The isotonicity of the compositions may be attained using sodium tartrate, propylene glycol or other inorganic or organic solutes. An example includes sodium chloride. Buffering agents may be employed, such as acetic acid and salts, citric acid and salts, boric acid and salts, and phosphoric acid and salts. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Viscosity of the pharmaceutical compositions may be maintained at the selected level using a pharmaceutically acceptable thickening agent. Methylcellulose is useful because it is readily and economically available and is easy to work with. Other suitable thickening agents include, for example, xanthan gum, carboxymethyl cellulose, hydroxypropyl cellulose, carbomer, and the like. In some embodiments, the concentration of the thickener will depend upon the thickening agent selected. An amount may be used that will achieve the selected viscosity. Viscous compositions are normally prepared from solutions by the addition of such thickening agents.

A pharmaceutically acceptable preservative may be employed to increase the shelf life of the pharmaceutical compositions. Benzyl alcohol may be suitable, although a variety of preservatives including, for example, parabens, thimerosal, chlorobutanol, or benzalkonium chloride may also be employed. A suitable concentration of the preservative is typically from about 0.02% to about 2% based on the total weight of the composition, although larger or smaller amounts may be desirable depending upon the agent selected. Reducing agents, as described above, may be advantageously used to maintain good shelf life of the formulation.

In one aspect, active agents provided herein may be in admixture with a suitable carrier, diluent, or excipient such as sterile water, physiological saline, glucose, or the like, and may contain auxiliary substances such as wetting or emulsifying agents, pH buffering agents, gelling or viscosity enhancing additives, preservatives, flavoring agents, colors, and the like, depending upon the route of administration and the preparation desired. See, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively). Such preparations may include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. The presence of such additional components may influence the physical state, solubility, stability, rate of in vivo release, and rate of in vivo clearance, and are thus chosen according to the intended application, such that the characteristics of the carrier are tailored to the selected route of administration.

For oral administration, the pharmaceutical compositions may be provided as a tablet, aqueous or oil suspension, dispersible powder or granule, emulsion, hard or soft capsule, syrup or elixir. Compositions intended for oral use may be prepared according to any method known in the art for the manufacture of pharmaceutical compositions and may include one or more of the following agents: sweeteners, flavoring agents, coloring agents and preservatives. Aqueous suspensions may contain the active ingredient in admixture with excipients suitable for the manufacture of aqueous suspensions.

Formulations for oral use may also be provided as hard gelatin capsules, wherein the active ingredient(s) are mixed with an inert solid diluent, such as calcium carbonate, calcium phosphate, or kaolin, or as soft gelatin capsules. In soft capsules, the active agents may be dissolved or suspended in suitable liquids, such as water or an oil medium, such as peanut oil, olive oil, fatty oils, liquid paraffin, or liquid polyethylene glycols. Stabilizers and microspheres formulated for oral administration may also be used. Capsules may include push-fit capsules made of gelatin, as well as soft, sealed capsules made of gelatin and a plasticizer, such as glycerol or sorbitol. The push-fit capsules may contain the active ingredient in admixture with fillers such as lactose, binders such as starches, and/or lubrimayts such as talc or magnesium stearate and, optionally, stabilizers.

Tablets may be uncoated or coated by known methods to delay disintegration and absorption in the gastrointestinal tract and thereby provide a sustained action over a longer period of time. For example, a time delay material such as glyceryl monostearate may be used. When administered in solid form, such as tablet form, the solid form typically comprises from about 0.001 wt. % or less to about 50 wt. % or more of active ingredient(s), for example, from about 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1 wt. % to about 2, 3, 4, 5, 6, 7, 8, 9, 10, 15, 20, 25, 30, 35, 40, or 45 wt. %.

Tablets may contain the active ingredients in admixture with non-toxic pharmaceutically acceptable excipients including inert materials. For example, a tablet may be prepared by compression or molding, optionally, with one or more additional ingredients. Compressed tablets may be prepared by compressing in a suitable machine the active ingredients in a free-flowing form such as powder or granules, optionally mixed with a binder, lubricant, inert diluent, surface active or dispersing agent. Molded tablets may be made by molding, in a suitable machine, a mixture of the powdered active agent moistened with an inert liquid diluent.

In some embodiments, each tablet or capsule contains from about 1 mg or less to about 1,000 mg or more of an active agent provided herein, for example, from about 10, 20, 30, 40, 50, 60, 70, 80, 90, or 100 mg to about 150, 200, 250, 300, 350, 400, 450, 500, 550, 600, 650, 700, 750, 800, or 900 mg. In some embodiments, tablets or capsules are provided in a range of dosages to permit divided dosages to be administered. A dosage appropriate to the patient and the number of doses to be administered daily may thus be conveniently selected. In certain embodiments two or more of the therapeutic agents may be incorporated to be administered into a single tablet or other dosage form (e.g., in a combination therapy); however, in other embodiments the therapeutic agents may be provided in separate dosage forms.

Suitable inert materials include diluents, such as carbohydrates, mannitol, lactose, anhydrous lactose, cellulose, sucrose, modified dextrans, starch, and the like, or inorganic salts such as calcium triphosphate, calcium phosphate, sodium phosphate, calcium carbonate, sodium carbonate, magnesium carbonate, and sodium chloride. Disintegrants or granulating agents may be included in the formulation, for example, starches such as corn starch, alginic acid, sodium starch glycolate, Amberlite, sodium carboxymethylcellulose, ultramylopectin, sodium alginate, gelatin, orange peel, acid carboxymethyl cellulose, natural sponge and bentonite, insoluble cationic exchange resins, powdered gums such as agar, karaya, or alginic acid or salts thereof.

Binders may be used to form a hard tablet. Binders include materials from natural products such as acacia, starch and gelatin, methyl cellulose, ethyl cellulose, carboxymethyl cellulose, polyvinyl pyrrolidone, hydroxypropylmethyl cellulose, and the like.

Lubricants, such as stearic acid or magnesium or calcium salts thereof, polytetrafluoroethylene, liquid paraffin, vegetable oils and waxes, sodium lauryl sulfate, magnesium lauryl sulfate, polyethylene glycol, starch, talc, pyrogenic silica, hydrated silicoaluminate, and the like, may be included in tablet formulations.

Surfactants may also be employed, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose.

Controlled release formulations may be employed wherein the active agent or analog(s) thereof is incorporated into an inert matrix that permits release by either diffusion or leaching mechanisms. Slowly degenerating matrices may also be incorporated into the formulation. Other delivery systems may include timed release, delayed release, or sustained release delivery systems.

Coatings may be used, for example, nonenteric materials such as methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols, or enteric materials such as phthalic acid esters. Dyestuffs or pigments may be added for identification or to characterize different combinations of active agent doses.

When administered orally in liquid form, a liquid carrier such as water, petroleum, oils of animal or plant origin such as peanut oil, mineral oil, soybean oil, or sesame oil, or synthetic oils may be added to the active ingredient(s). Physiological saline solution, dextrose, or other saccharide solution, or glycols such as ethylene glycol, propylene glycol, or polyethylene glycol are also suitable liquid carriers. The pharmaceutical compositions may also be in the form of oil-in-water emulsions. The oily phase may be a vegetable oil, such as olive or arachis oil, a mineral oil such as liquid paraffin, or a mixture thereof. Suitable emulsifying agents include naturally occurring gums such as gum acacia, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions may also contain sweetening and flavoring agents.

Pulmonary delivery of the active agent may also be employed. The active agent may be delivered to the lungs while inhaling and traverses across the lung epithelial lining to the blood stream. A wide range of mechanical devices designed for pulmonary delivery of therapeutic products may be employed, including but not limited to nebulizers, metered dose inhalers, and powder inhalers, all of which are familiar to those skilled in the art. These devices employ formulations suitable for the dispensing of active agent. Typically, each formulation is specific to the type of device employed and may involve the use of an appropriate propellant material, in addition to diluents, adjuvants, and/or carriers useful in therapy. The active ingredients may be prepared for pulmonary delivery in particulate form with an average particle size of from 0.1 um or less to 10 um or more, for example, from about 0.2, 0.3, 0.4, 0.5, 0.6, 0.7, 0.8, or 0.9 um to about 1.0, 1.5, 2.0, 2.5, 3.0, 3.5, 4.0, 4.5, 5.0, 5.5, 6.0, 6.5, 7.0, 7.5, 8.0, 8.5, 9.0, or 9.5 um. Pharmaceutically acceptable carriers for pulmonary delivery of active agent include carbohydrates such as trehalose, mannitol, xylitol, sucrose, lactose, and sorbitol. Other ingredients for use in formulations may include DPPC, DOPE, DSPC, and DOPC. Natural or synthetic surfactants may be used, including polyethylene glycol and dextrans, such as cyclodextran. Bile salts and other related enhancers, as well as cellulose and cellulose derivatives, and amino acids may also be used. Liposomes, microcapsules, microspheres, inclusion complexes, and other types of carriers may also be employed.

Pharmaceutical formulations suitable for use with a nebulizer, either jet or ultrasonic, typically comprise the active agent dissolved or suspended in water at a concentration of about 0.01 or less to 100 mg or more of active agent per mL of solution, for example, from about 0.1, 1, 2, 3, 4, 5, 6, 7, 8, 9, or 10 mg to about 15, 20, 25, 30, 35, 40, 45, 50, 55, 60, 65, 70, 75, 80, 85, or 90 mg per mL of solution. The formulation may also include a buffer and a simple sugar (e.g., for protein stabilization and regulation of osmotic pressure). The nebulizer formulation may also contain a surfactant, to reduce or prevent surface induced aggregation of the active agent caused by atomization of the solution in forming the aerosol.

Formulations for use with a metered-dose inhaler device generally comprise a finely divided powder containing the active ingredients suspended in a propellant with the aid of a surfactant. The propellant may include conventional propellants, such as chlorofluorocarbons, hydrochlorofluorocarbons, hydrofluorocarbons, and hydrocarbons. Example propellants include trichlorofluoromethane, dichlorodifluoromethane, dichlorotetrafluoroethanol, 1,1,1,2-tetrafluoroethane, and combinations thereof. Suitable surfactants include sorbitan trioleate, soya lecithin, and oleic acid.

Formulations for dispensing from a powder inhaler device typically comprise a finely divided dry powder containing active agent, optionally including a bulking agent, such as lactose, sorbitol, sucrose, mannitol, trehalose, or xylitol in an amount that facilitates dispersal of the powder from the device, typically from about 1 wt. % or less to 99 wt. % or more of the formulation, for example, from about 5, 10, 15, 20, 25, 30, 35, 40, 45, or 50 wt. % to about 55, 60, 65, 70, 75, 80, 85, or 90 wt. % of the formulation.

In some embodiments, an active agent provided herein may be administered by intravenous, parenteral, or other injection, in the form of a pyrogen-free, parenterally acceptable aqueous solution or oleaginous suspension. Suspensions may be formulated according to methods well known in the art using suitable dispersing or wetting agents and suspending agents. The preparation of acceptable aqueous solutions with suitable pH, isotonicity, stability, and the like, is within the skill in the art. In some embodiments, a pharmaceutical composition for injection may include an isotonic vehicle such as 1,3-butanediol, water, isotonic sodium chloride solution, Ringer's solution, dextrose solution, dextrose and sodium chloride solution, lactated Ringer's solution, or other vehicles as are known in the art. In addition, sterile fixed oils may be employed conventionally as a solvent or suspending medium. For this purpose, any bland fixed oil may be employed including synthetic mono or diglycerides. In addition, fatty acids such as oleic acid may likewise be used in the formation of injectable preparations. The pharmaceutical compositions may also contain stabilizers, preservatives, buffers, antioxidants, or other additives known to those of skill in the art.

The duration of the injection may be adjusted depending upon various factors, and may comprise a single injection administered over the course of a few seconds or less, to 0.5, 0.1, 0.25, 0.5, 0.75, 1, 2, 3, 4, 5, 6, 7, 8, 9, 10, 11, 12, 13, 14, 15, 16, 17, 18, 19, 20, 21, 22, 23, or 24 hours or more of continuous intravenous administration.

Dosage

In one aspect, an agent disclosed herein may be present in an amount of from about 0.5% to about 95%, or from about 1% to about 90%, or from about 2% to about 85%, or from about 3% to about 80%, or from about 4%, about 75%, or from about 5% to about 70%, or from about 6%, about 65%, or from about 7% to about 60%, or from about 8% to about 55%, or from about 9% to about 50%, or from about 10% to about 40%, by weight of the composition.

In one aspect, the compounds may be administered at the rate of 100 μg to 1000 mg per day per kg of body weight. Orally, the compounds may be suitably administered at the rate of about 100, 150, 200, 250, 300, 350, 400, 450, or 500 μg to about 1, 5, 10, 25, 50, 75, 100, 200, 300, 400, 500, 600, 700, 800, 900, 1000 mg per day per kg of body weight. The required dose can be administered in one or more portions. For oral administration, suitable forms are, for example, tablets, gel, aerosols, pills, dragees, syrups, suspensions, emulsions, solutions, powders and granules; one method of administration includes using a suitable form containing from 1 mg to about 500 mg of active substance. In one aspect, administration may comprise using a suitable form containing from about 1, 2, 5, 10, 25, or 50 mg to about 100, 200, 300, 400, 500 mg of active substance.

A dosage regimen will vary depending upon known factors such as the pharmacodynamic and pharmacokinetic characteristics of the agents and their mode and route of administration; the species, age, sex, health, medical condition, and weight of the patient, the nature and extent of the symptoms, the kind of concurrent treatment, the frequency of treatment, the route of administration, the renal and hepatic function of the patient, and the desired effect. The effective amount of a drug required to prevent, counter, or arrest progression of a symptom or effect of a muscle contracture can be readily determined by an ordinarily skilled physician. In one aspect, active agents provided herein may be administered in a dosage form selected from intravenous or subcutaneous unit dosage form, oral, parenteral, intravenous, and subcutaneous. In some embodiments, active agents provided herein may be formulated into liquid preparations for, e.g., oral administration. Suitable forms include suspensions, syrups, elixirs, and the like. In some embodiments, unit dosage forms for oral administration include tablets and capsules. Unit dosage forms configured for administration once a day; however, in certain embodiments it may be desirable to configure the unit dosage form for administration twice a day, or more.

In some embodiments, active agents provided herein may additionally employ adjunct components conventionally found in pharmaceutical compositions in their art-established fashion and at their art-established levels. Thus, for example, the compositions may contain additional compatible pharmaceutically active materials for combination therapy or may contain materials useful in physically formulating various dosage forms, such as excipients, dyes, thickening agents, stabilizers, preservatives or antioxidants.

In some embodiments, the active agents provided herein may be provided to an administering physician or other health care professional in the form of a kit. The kit is a package which houses a container which contains the active agent(s) in a suitable pharmaceutical composition, and instructions for administering the pharmaceutical composition to a subject. The kit may optionally also contain one or more additional therapeutic agents currently employed for treating a disease state as described herein. For example, a kit containing one or more compositions comprising active agents provided herein in combination with one or more additional active agents may be provided, or separate pharmaceutical compositions containing an active agent as provided herein and additional therapeutic agents may be provided. The kit may also contain separate doses of an active agent provided herein for serial or sequential administration. The kit may optionally contain one or more diagnostic tools and instructions for use. The kit may contain suitable delivery devices, e.g., syringes, and the like, along with instructions for administering the active agent(s) and any other therapeutic agent. The kit may optionally contain instructions for storage, reconstitution (if applicable), and administration of any or all therapeutic agents included. The kits may include a plurality of containers reflecting the number of administrations to be given to a subject.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus may be considered to constitute examples of modes for its practice. However, those of skill in the art should, in light of the present disclosure, appreciate that many changes may be made in the specific embodiments that are disclosed and still obtain a like or similar result without departing from the spirit and scope of the invention.

Ras is a target in several human cancers and in a set of genetic diseases termed RASopathies (Aoki et al., 2016; McCormick, 2016; Simanshu et al., 2017; Tidyman and Rauen, 2009b). Applicants targeted the GTP-bound form of the G60A point mutant previously described by the applicants (Ford et al., 2005). Targeting the RasG60A structure by virtual screening was justified as follows. First, a potential binding site cleft situated between the switch 1 and the triphosphate nucleotide, albeit small, can be identified in this structure. This cleft results from the adoption of the switch 1 region in the GTP- but not GDP-bound structure of this mutant. This conformation is different from wild-type Ras, but similar to nucleotide-free Ras in complex with the guanine nucleotide exchange factor Sos (Boriack-Sjodin et al., 1998), which applicants terms 'the open conformation' of Ras. Switch 1 corresponds to residues 24-40 and is responsible for GTP-/$Mg^{2+}$-coordination and binding to effectors and regulators (Pai et al., 1989; Vetter and Wittinghofer, 2001; Wittinghofer and Nassar, 1996). Second, this mutation severely attenuates the binding of Ras to its effector, Raf kinase, in vitro (Ford et al., 2005) and reverts the transforming ability of constitutively active Ras in cells (Hwang et al., 1996; Sung et al., 1995; Sung et al., 1996). Third, it was previously shown using solution $^{31}$P-NMR spectroscopy that GTP-bound Ras adopts two conformations in equilibrium (Geyer et al., 1996; Spoerner et al., 2010; Spoerner et al., 2007): one is capable of effector binding and therefore signaling, while the other is non-signaling and is mimicked by the G60A and T35S mutants (Araki et al., 2011; Shima et al., 2010; Spoerner et al., 2001). Taken together, it is believed that a small molecule that keeps Ras in the open conformation may inhibit its signaling. A similar approach has previously led to the discovery of the anti-Ras 'Kobe' compounds (Shima et al., 2013).

Combined data from virtual screening, cell growth and colony formation assays, and chemical synthesis and analysis identified a small molecule termed IODVA1, with cellular inhibitory activity against several transformed cell lines including Ras-driven cells. Applicants showed that IODVA1 targets Rac activation and signaling. Applicants have demonstrated that IODVA 1 has in vivo activity against human MDA-MB-231 triple negative breast cancer (TNBC) and H2122 non-small cell lung cancer (NSCLC) cell lines in xenograft mouse tumor models.

Results

Docking. Using the Autodock program (Huey et al., 2007; Morris et al., 1998; Morris et al., 2009), Applicants performed virtual screening for small molecules that could potentially fit into the identified Ras binding interface pocket. The pocket is lined by Ile21, Gln22, switch 1 residues Gln25-Pro34, Lys147 and Arg149 and the GTP-ribose (FIG. 1A). Approximately 118,500 compounds from the NCI/DTP Open Chemical Repository were used to identify potential binders. Applicants designed a grid box incorporating the Ras pocket for docking of compounds and searched for the ones with lowest possible binding energy. Autodock returned predicted binding poses grouped in binding clusters with a root mean square deviation (rmsd) tolerance of less than 1 Å between poses of the cluster. The results were evaluated by ranking various complexes toward the predicted binding energy. Cluster analysis was subsequently accomplished on the basis of rmsd values with respect to the starting ligand geometry. The docked conformation with the most favorable binding free energy and the more populated cluster was selected as the best result. For each cluster, the estimated free energy of binding in kcal/mol was obtained and an estimated inhibition constant (Ki) at 298.15 K was derived. Compounds were sorted according to their Ki. Forty compounds with the highest Ki were requested and obtained when available from the NCI Developmental Therapeutics Program (NCI/DTP, http://dtp.nci.nih.gov). Compounds were dissolved in DMSO as 10 mM stock solutions when possible or lower when poorly soluble.

Cellular & Biochemical Phenotypic Screening Assays. To assess the effect on proliferation, the 40 hit compounds were tested in cellular assays. Hits at 10 µM were screened against the human lung mucoepidermoid carcinoma cell line H292 and the human lung adenocarcinoma cell line A549 using the MTS cell proliferation assay (Berridge et al., 2005; Denizot and Lang, 1986; Loveland et al., 1992). These two epithelial cell lines were selected because H292 encodes wild-type RAS ($RAS^{WT}$) while A549 encodes $KRAS^{G12V}$ mutation with the expectation that compounds that differentiate between these two cell lines should be specific for oncogenic vs. $RAS^{WT}$. FIG. 1B shows that except for NSC600805 and NSC124205, which significantly decreased proliferation of A549 cells compared to vehicle control, most compounds had little to no effect on this cell line (mean relative proliferation=127.7% and STDEV=36.0%); some compounds almost doubled its rate of proliferation. The averaged proliferation rate of A549 cells by NSC600805 and NSC124205 relative to DMSO vehicle control was 34.4% and 32.9% corresponding to a z-score of 2.60 and 2.63, respectively. When tested on H292 cells, a few compounds from the tested set (mean compounds relative proliferation=88.3% and STDEV=24.1%) decreased its proliferation by 40% or more but our attempts at identifying one compound that had anti-proliferative effects on A549 but not or less on H292 cells failed. Relative to vehicle control, NSC600805 and NSC124205 rate of proliferation of H292 cells was 49.4% and 41.6% corresponding to a z-score of 1.61 and 1.94, respectively (FIG. 1B).

While NSC124205 at 5 µM inhibited the growth of yeast strains containing single mutations in the rad50, mec2, and bub3 genes and doubly mutant sgs1+mgt1, cln2+rad14, and mlh1+rad18 strains at better than 80% compared to untreated controls. The results of the NCI screen are consistent with those shown here.

Figure 2:
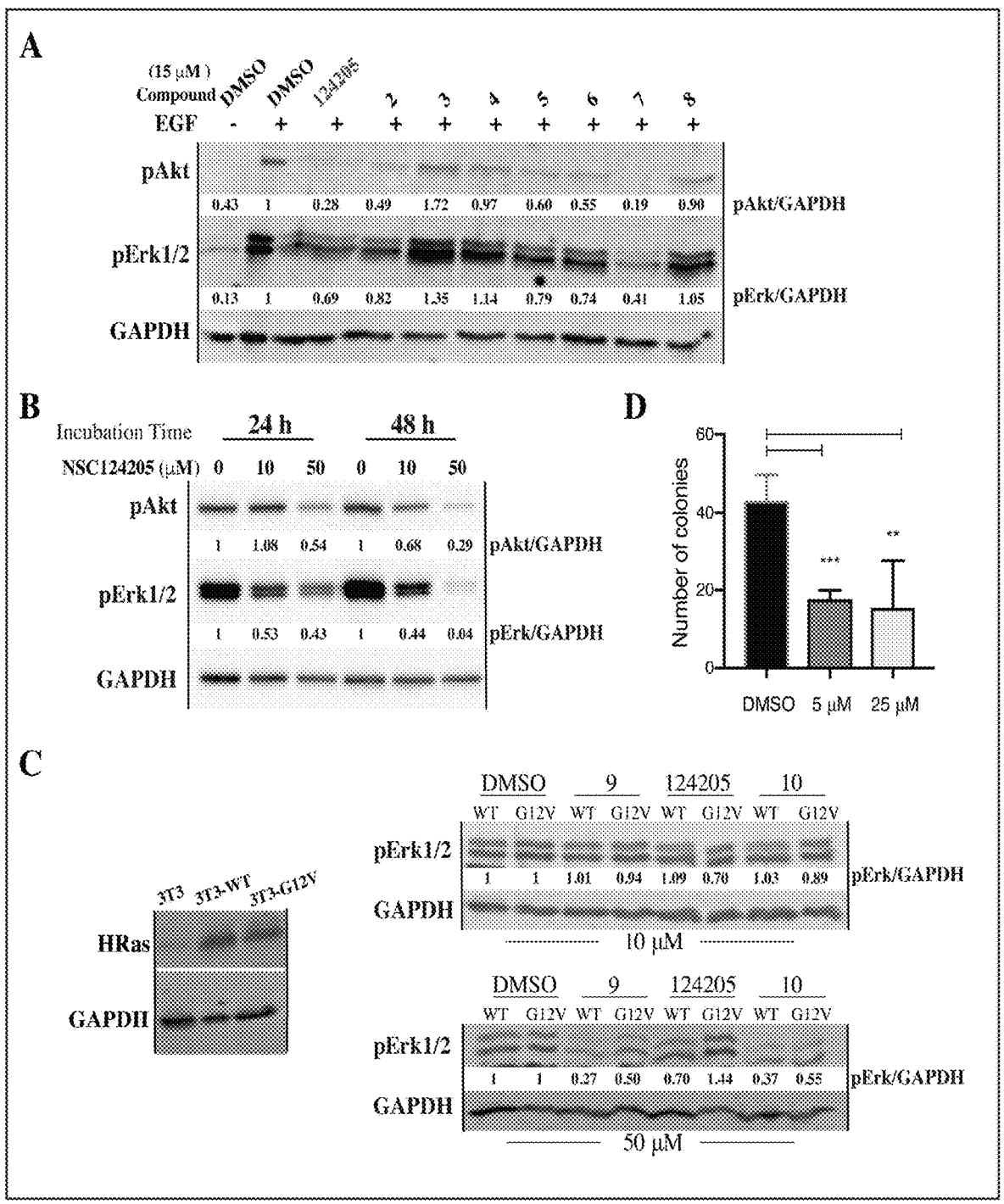
FIG. 2: Biochemical validation of NSC124205. (A) NSC124205 decreases acute AKT and ERK activation in NIH-3T3 cells. NIH-3T3 cells were starved for 24 h, incubated with DMSO vehicle control or the indicated NCI compounds at 15 µM for 1 h, EGF stimulated to 5 min, and lysed with sample buffer. Lysates (30 µg) were resolved on 12% SDS-PAGE, transferred, and blotted for pAKT and pERK1/2. GAPDH was used as loading control. (B)NSC124205 decreases chronic levels of pAKT and pERK in Ras-activated cells. ST8814 cells were grown in RPMI medium 1640 supplemented with 10% FBS in the presence of indicated concentrations of NSC124205 for 24 or 48 h. Levels of pAKT and pERK were revealed by immunoblotting and quantified in reference to GAPDH levels. (C)NSC124205 has no effect on ERK activation in cells expressing $Ras^{G12V}$. NIH-3T3 cells were stably transduced with full-length wild-type or G12V H-Ras. Cells were lysed in RIPA supplemented with protease and phosphatase inhibitors. Lysates (30 µg) were resolved on 12% SDS-PAGE, transferred, and blotted for HRas and GAPDH. 3T3 cells were serum starved for 24 h, incubated with 10 or 50 µM of the listed compounds for 2 h, EGF/serum activated for 5 min, lysed, normalized, separated by the SDS-PAGE, and blotted for pERK. (D) Effects of NSC124205 on colony formation ability of $HRAS^{G12V}$ expressing NIH-3T3 cells. Soft-agar colony formation assays were done with the 3T3 cells expressing $HRAS^{G12V}$ in the presence of NSC124205 at 5 and 25 µM. The data represent means±standard errors of three experiments performed in quadruplicates. The statistical significance of the difference between control and treated cultures was calculated by Student's t-test. NCI compounds 2 to 10 are from a different arm of our drug discovery project.

Biochemistry of NSC124205. Applicants tested the ability of NSC124205 and 7 other compounds to acutely decrease ERK and AKT phosphorylation in 3T3 cells. Cells were serum starved for 24 h, incubated with the DMSO vehicle control or with the compounds at 15 µM for 1 h, EGF stimulated for 5 min, and change in ERK- and AKT-phosphorylation was checked by immunoblotting. FIG. 2A shows a significant decrease in both pERK and pAKT by NSC124205. To confirm that this decrease is not cell specific, Applicants tested the effect of NSC124205 on the NF1-associated malignant peripheral nerve sheath tumors (MPNST) cell line ST8814, which is characterized by active wild-type Ras (Basu et al., 1992; Mahller et al., 2006). ST8814 were grown in RPMI medium supplemented with 10% FBS for 24 and 48 h in the presence or absence of NSC124205 at 10 and 50 µM and levels of pAKT and pERK were quantified by immunoblotting. FIG. 2B shows that following 24 h incubation, NSC124205 at 10 and 50 µM decreases levels of pERK by at least 50%. Decrease in pERK remains unchanged at 48 h for the 10 µM dose and increases substantially for the 50 µM dose. pAKT level decreases in a time and dose dependent way. Taken together, the cellular and biochemical data show that NSC124205 decreases proliferation of Ras-driven cell transformation and decreases ERK-phosphorylation albeit at high concentration.

To probe the effect of NSC124205 on oncogenic Ras signaling, Applicants generated NIH-3T3 cells overexpressing wild-type or dominant active $HRAS^{G12V}$ (FIG. 2C) and tested the ability of the compounds at interfering with acute ERK activation in these cells. Cells were serum starved for 24 h, incubated with 10 µM or 50 µM of NSC124205 and two other compounds for 2 h, and EGF/serum activated for 5 min. Cells were lysed, normalized, and cell lysates separated by the SDS-PAGE and blotted for pERK. There was no decrease in pERK in a NSC124205 dose-dependent manner in $RAS^{WT}$ or $RAS^{G12V}$ expressing cells (FIG. 2C). Therefore, the mechanism of action of NSC124205 is not dependent upon Ras activating mutations.

Inhibition of Anchorage-independent Growth. NSC124205 was screened for its ability to inhibit proliferation of the $HRAS^{G12V}$ overexpressing 3T3 cells using the soft agar colony formation assay at concentrations of 5 and 25 µM. As shown in FIG. 2D, both NSC124205 concentrations decreased colony formation of the 3T3 cells by 60% with no significant difference between the two concentrations.

Figure 3:
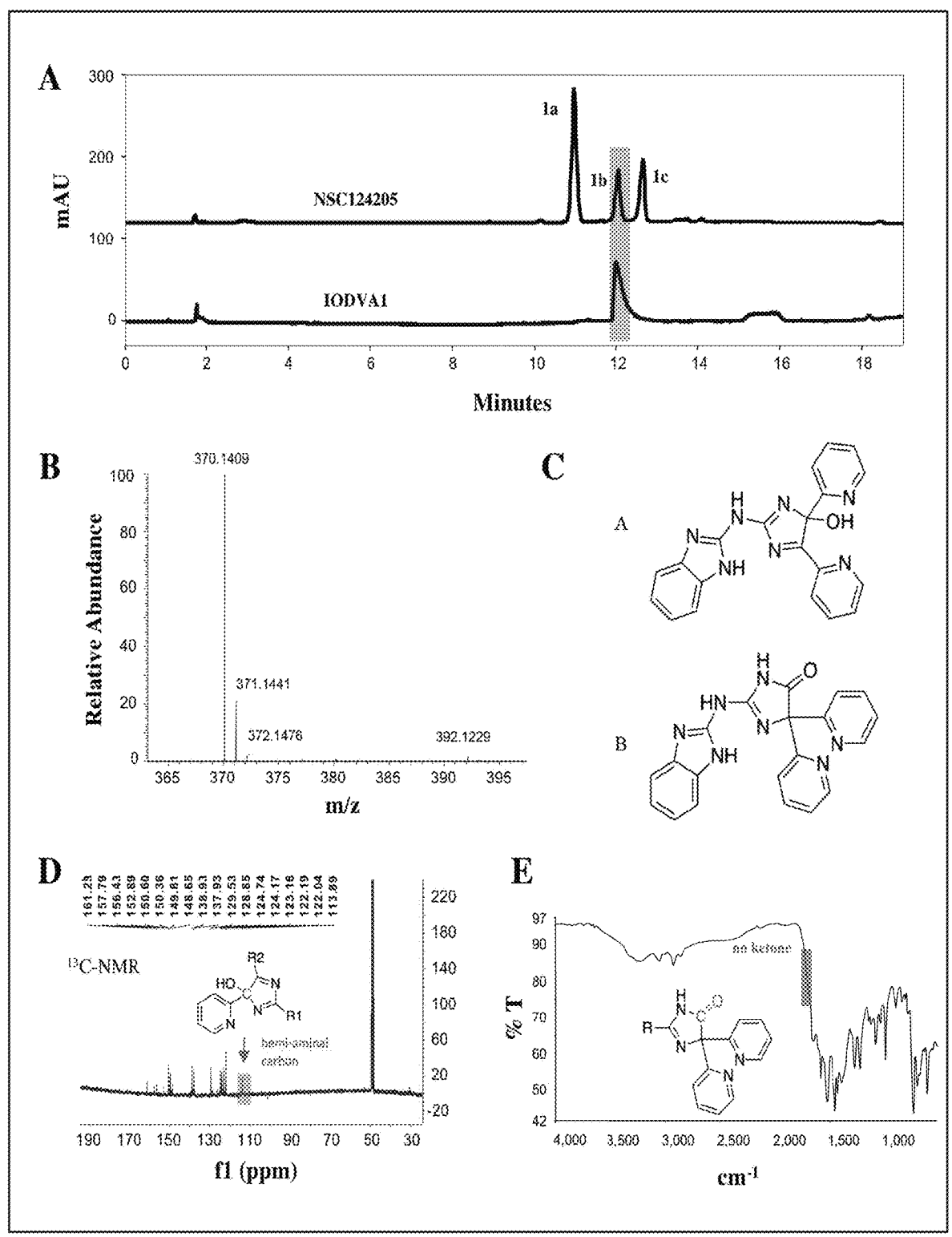
FIG. 3. Chemical Analysis of NSC124205. Chemical Analysis of NSC124205. (A) NSC124205 is a mixture of compounds. 20 µL of a 1 mM NSC124205 solution was loaded on a C18 column washed with buffer A (95% water, 5% acetonitrile, 0.1% formic acid) and a linear gradient was applied over 20 min with buffer B (95% acetonitrile, 5% water, 0.1% formic acid). Three peaks 1a-1c eluted at 11.6 min, 12.8 min, and 13.4 min, respectively (upper chart). Under identical conditions, IODVA1 elutes as a single peak at 12.8 min. (B) Mass spectroscopy electrospray ionization (ESI) spectrum of IODVA1. (C) Proposed structures for IODVA1 with m/z of 370.1409 [M+H]+ following (Nishimura & Kitajima 1979) reported reaction of guanidine derivatives with a-diketones. (D) $^{13}$C-NMR of synthesized IODVA1 in methanol-d4. The peak corresponding to the C with the hydroxyl group is boxed. (E) IR-spectrum of IODVA1. The expected stretching in the carbonyl region is boxed. (F) Electrospray ionization spectrum of the 3 peaks at 11.6, 12.8, and 13.4 minutes, respectively. Structure of each component is shown. (G) MS-MS fragmentation of the 370.1409 peak of IODVA1. (H) $^1$H NMR of synthesized IODVA1 in methanol-d4. (I) Proposed mechanism of the reaction between 2-guanidinobenzimidazole and α-pyridoin resulting in structures A and B, NSC124205, and other products.
Figure 3:
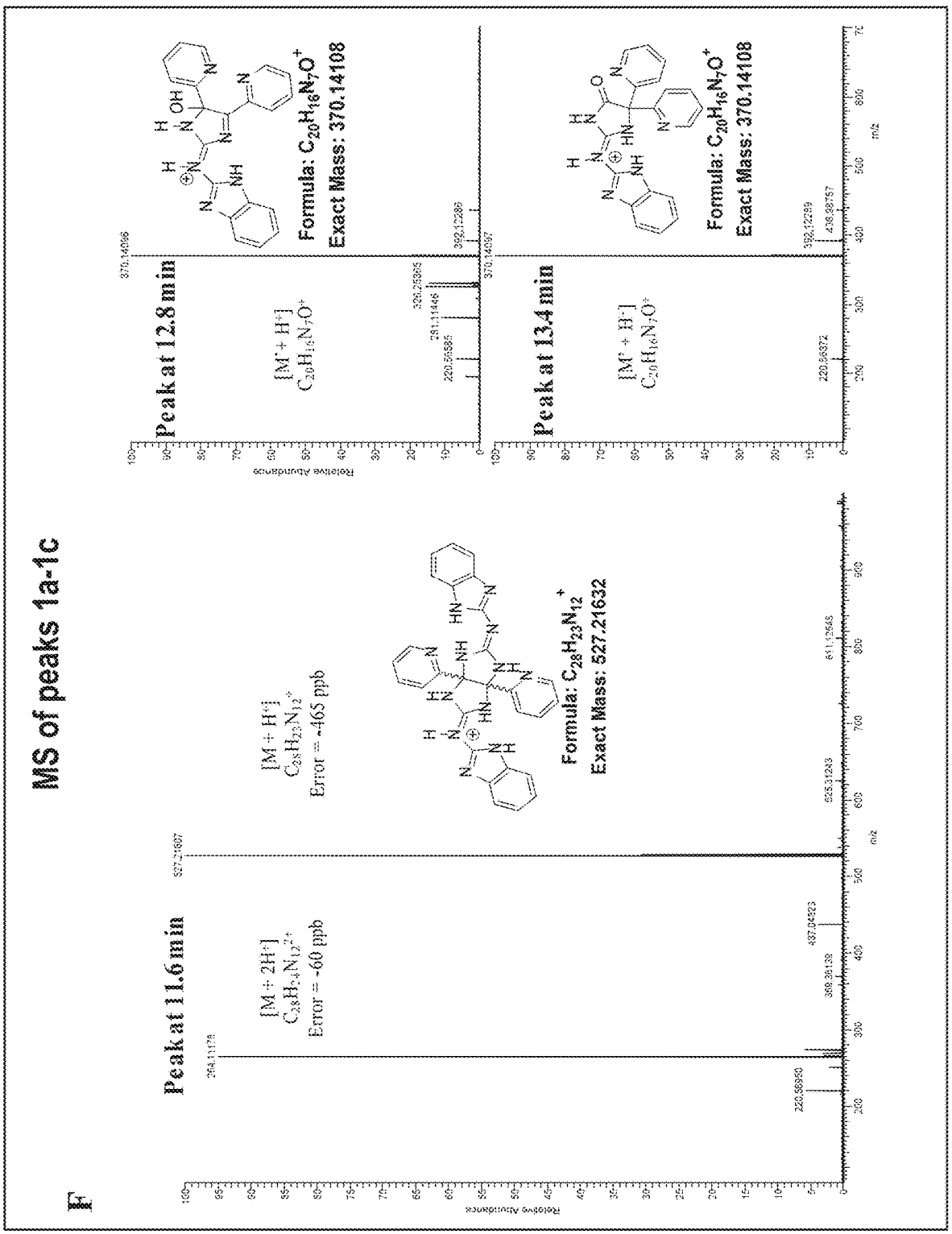
Figure 3:
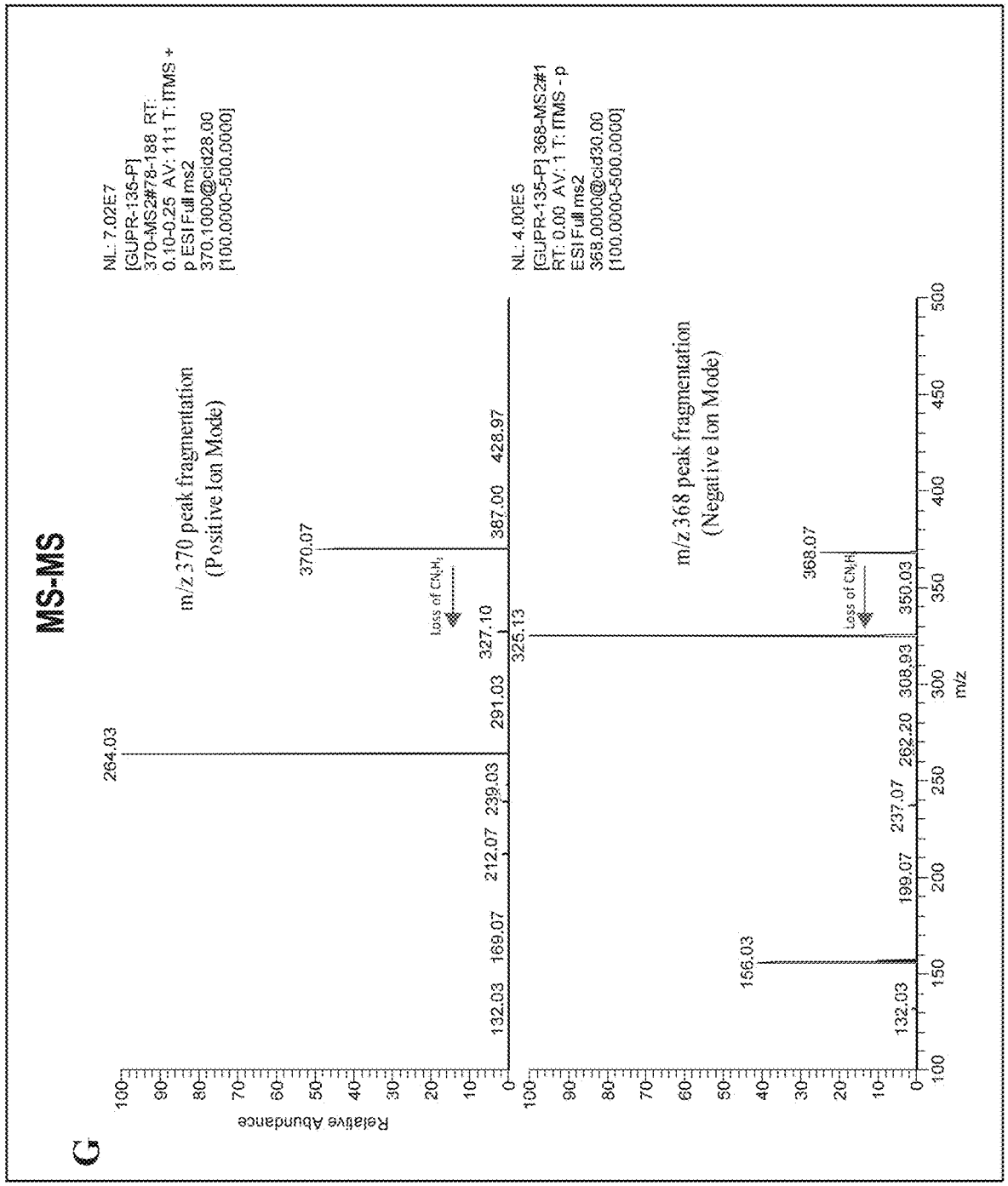
Figure 3:
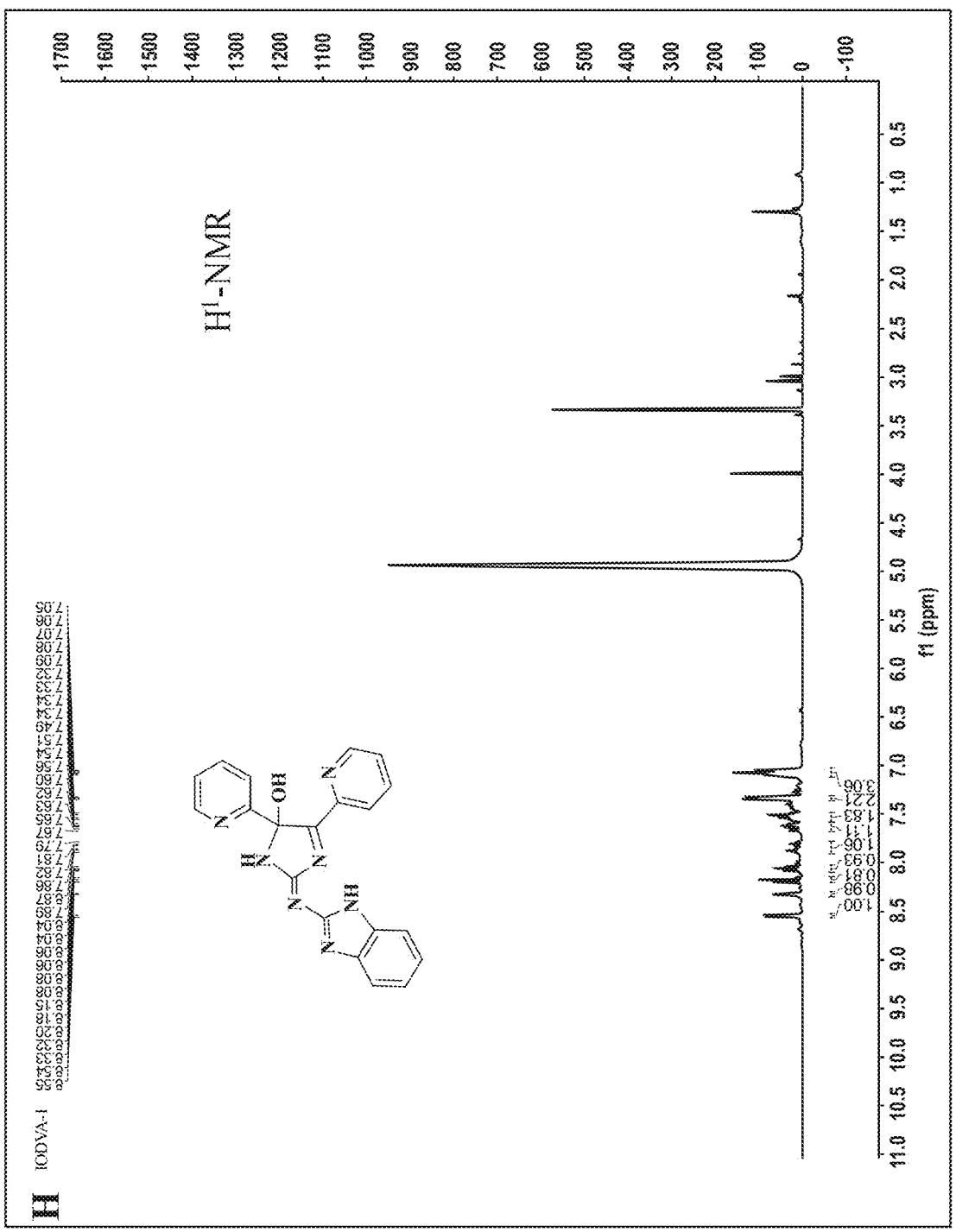
Figure 3:
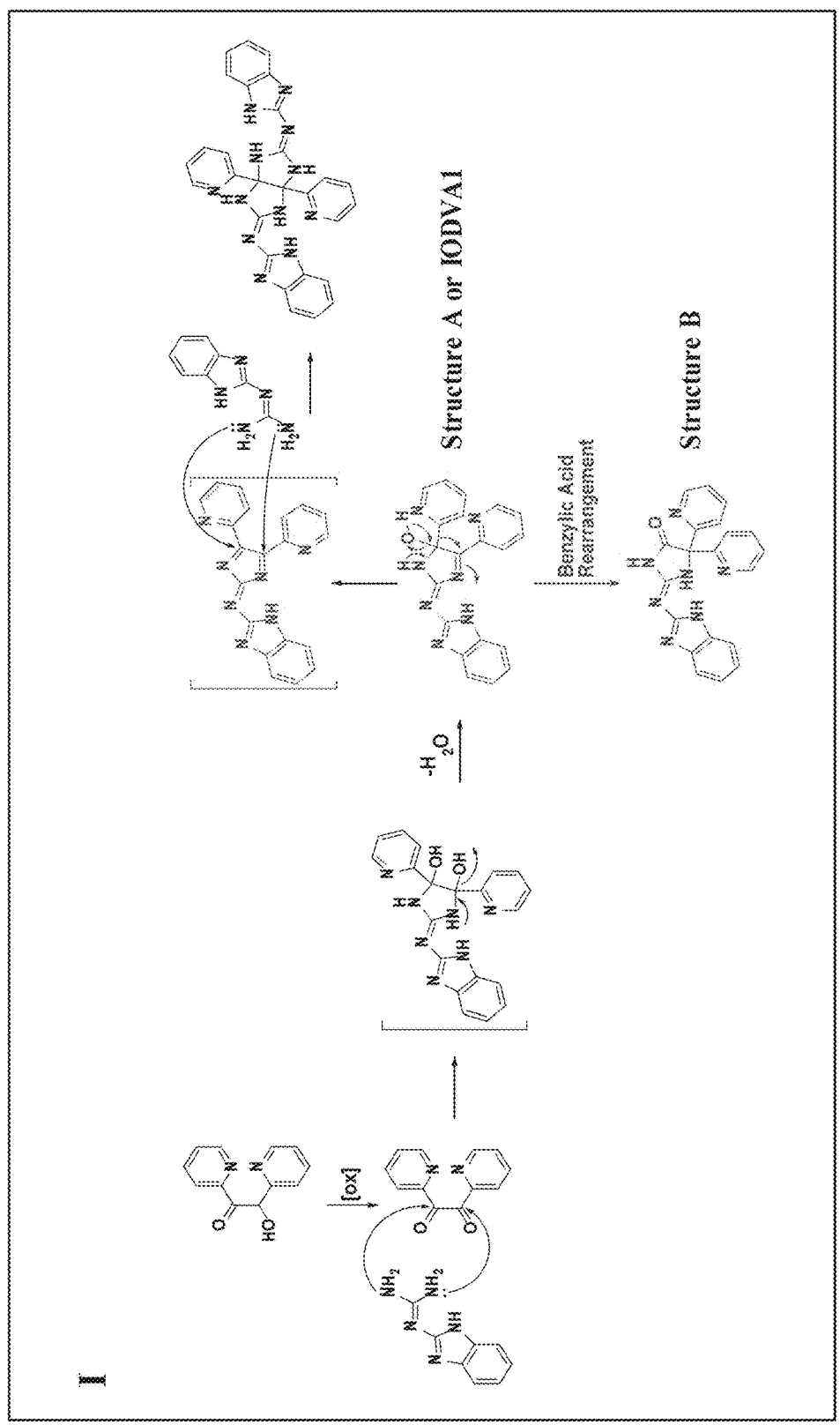

Chemical Synthesis of IODVA1. Before entering in vivo studies, Applicants checked compound NSC124205's identity and purity. Applicants tested a freshly made DMSO solution of NSC124205 obtained from the NCI by high-performance liquid chromatography-mass spectroscopy (HPLC/MS). As shown in FIG. 3A, the HPLC profile of the NSC124205 solution is consistent with a mixture of at least three constituents that absorb at 210 nm and elute at 11.6 min, 12.8 min, and 13.4 min in approximately 2:1:1 ratio, respectively. Inspection of the UV profile of each peak indicated that peaks at 12.8 min and 13.4 min had a similar absorbance profile with maxima close to 250 nm and 300 nm. The mixture was analyzed by LCMS using the same column and conditions (FIG. 3F). The first band at 11.6 min (peak 1a) has a mass-to-charge ratio m/z 264.11178 [M+2H$^+$] and 527.21607 [M+H$^+$] and an elemental composition of $C_{28}H_{23}N_{12}^+$, which equates to an exact mass of 527.21632 Da. This band likely corresponds to two guanidinobenzimidazole additions (FIGS. 3F & 3I). This is in line with the observation that its spectrum lacks red-shifted absorbance maxima due to lack of the extended aromatic system. The other two bands at 12.8 and 13.4 min have the same m/z 370.14096 [M'] and elemental composition, $C_{20}H_{16}N_7O^+$, which equates to an exact mass of 370.14108 Da. The minor peaks at m/z 392.12286 correspond to [M'+Na$^+$]. Both bands possessed similar absorbance spectra suggesting similar structural basis and possible tautomers. Neither peak gives a mass corresponding to the structure of NSC124205 reported on the PubChem website (FIG. 1B) which has a calculated mass of 352.1305 Da. The mass difference of 18 Da suggests the presence of additional (O+2×H) in the structure of NSC124205.

Applicants focused on the structure shown in FIG. 1B and reported on the PubChem site. Applicants synthesized a compound, hereafter IODVA1, according to scheme 1, having the following structure:

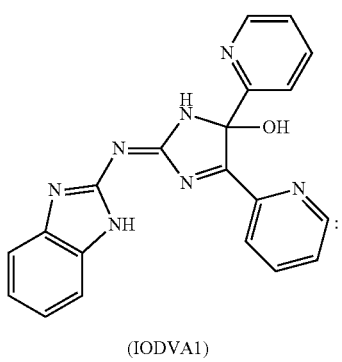

(IODVA1)

The synthesis is derived from analogous molecules in the literature. 2-guanidinobenzimidazole and α-pyridoin were heated in presence of acetic acid at 90° C. HPLC analysis of the synthesized compound shows that a single band is observed at 12.8 min corresponding to peak 1b observed in the NSC124205 sample (FIGS. 3A & 3F). The UV-profile of the synthesized compound also matches with peak 1b of the provided sample. The MS analysis of the synthesized molecule shows a mass of 370.1409 [M+H$^+$] and the MS-MS data suggests that the additional 18 Da in mass we saw in NCI sample is covalently bonded to the molecule (FIG. 3G). Two molecules possessing the same exact mass as the synthesized one can be generated from the synthetic route (FIGS. 3C & 3F). Molecule (A) is the result of the cyclo-condensation of 2-guanidinobenzimidazole and 2-2'-pyridil. Molecule (B) is the result of the pinacol-like rearrangement of (A). The H$^1$-NMR analysis (FIG. 3G) shows 13 protons in the aromatic region consistent with structure (A) with no evidence of symmetry that would suggest structure (B). This is also confirmed by C$^{13}$-NMR and infrared (IR) spectroscopy analyses that showed no peaks around 170-190 ppm nor stretching at around 1680 cm$^{-1}$, respectively, characteristic of a carbonyl group (FIGS. 3D & 3E). The spectroscopic data are thus consistent with IODVA1, the synthesized molecule, being structure (A).

Analysis of IODVA1 shows that it has some favorable drug-like properties despite the large nitrogen content and aromatic character. Applicants performed several calculations to predict the drugability of IODVA1. Calculations show that the target molecule is non-planar, reasonably soluble in aqueous phase with a log P of 3.25, has one hydrogen-bond donor and four hydrogen-bond acceptors. Because of these chemical properties, IODVA1 follows the Lipinski's rule of 5.

Figure 4:
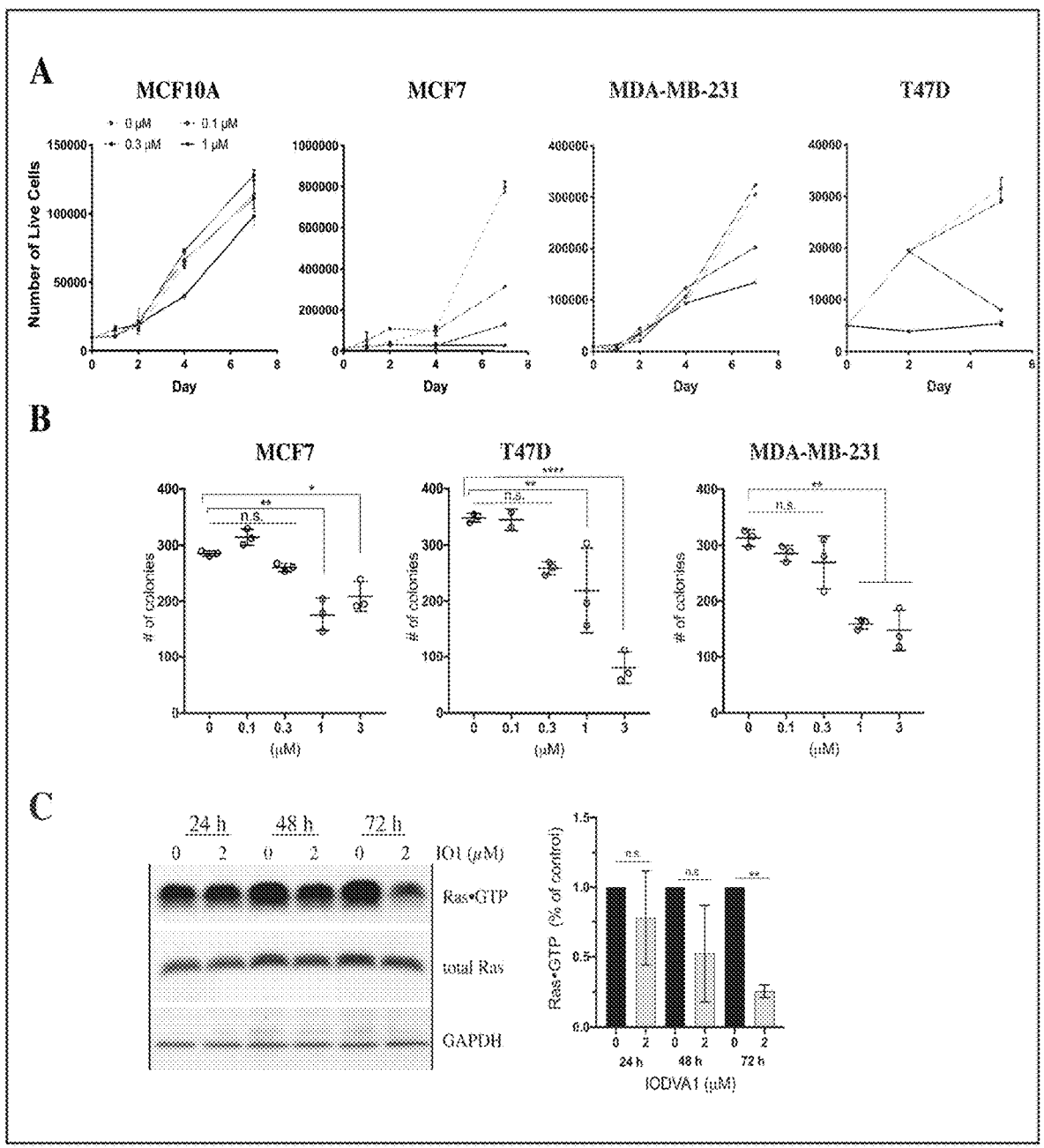
FIG. 4. IODVA1 inhibits proliferation of cancer model cells. (A) IODVA1 is a potent cell proliferation inhibitor. MCF10A, MCF7, MDA-MB-231, and T47D cells were grown in the presence of the indicated IODVA1 concentrations and counted for 4 or up to 7 days. Each dot and bar is the mean±stdev respectively, of 3 independent experiments, with 2 technical replicates in each experiment. (B) Number of colonies made by MCF7, T47D, and MDA-MB-231 cells at the indicated IODVA1 concentrations. Results shown are mean±stdev of 2 independent experiments with 4 technical replicates each. (C) IODVA1 deactivates Ras at late incubation times. Total Ras immunoprecipitated with GST-RafRBD from ST8814 cells treated with 0 or 2 µM IODVA1 at the indicated times demonstrate that IODVA1 decreases Ras activation post 48 h treatment. Quantification summary of 2 independent experiments is presented in the graph. n.s.—not significant, *—p<0.05, —p<0.01, **—p<0.0001. (D) IODVA1 inhibits proliferation of ST8814 cells. ST8814 cells were grown in the presence of the indicated IODVA1 concentrations and counted daily for 4 days. Each dot and bar is the mean and standard deviation respectively, of 3 independent experiments.
Figure 4:
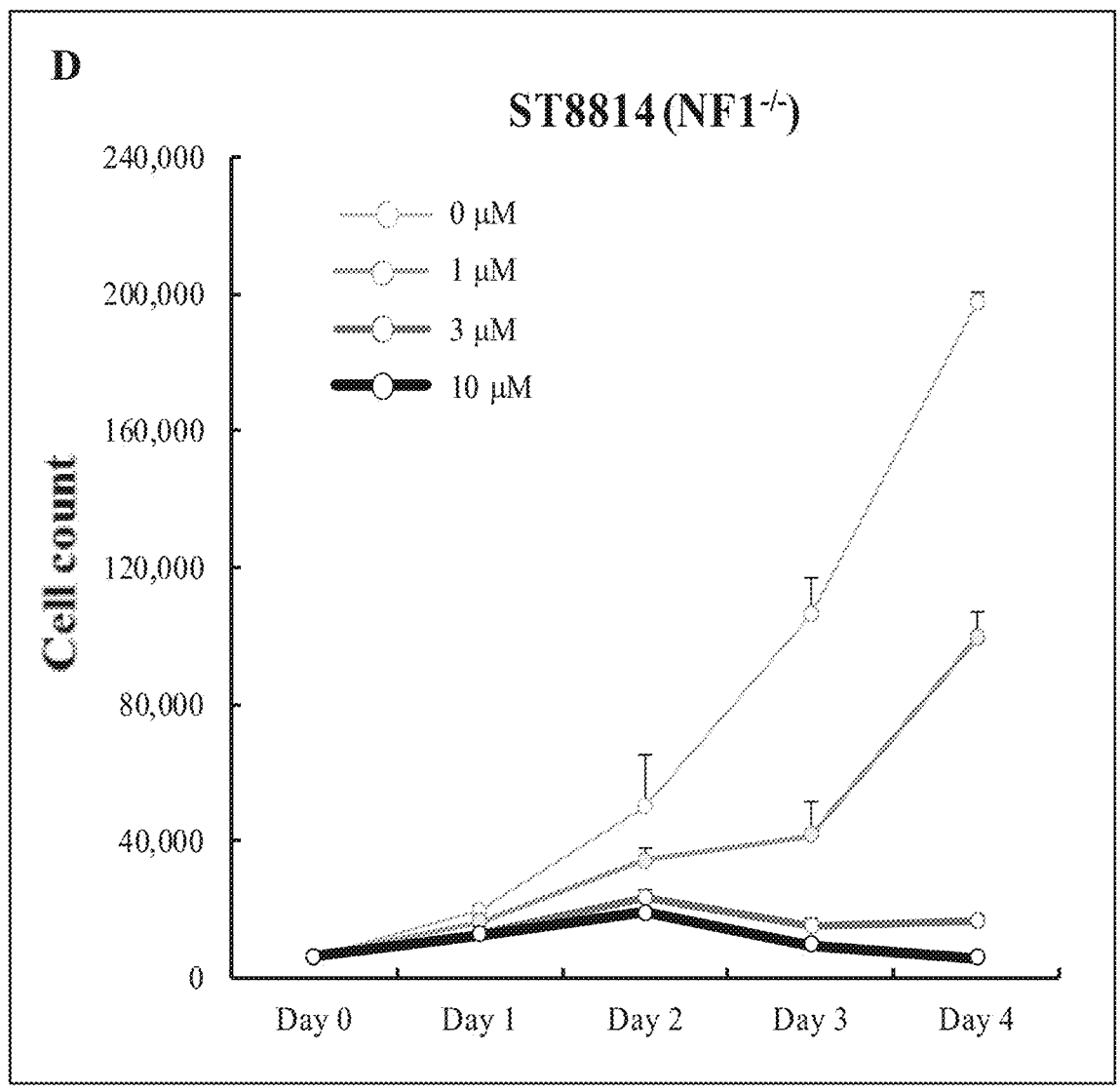

Effects of IODVA1 on proliferation of cells harboring activated Ras. Applicants tested IODVA1's ability to inhibit the proliferation of cells harboring activated Ras and therefore its ability to recapitulate the compound obtained from the NCI. Applicants chose the NF1-associated malignant peripheral nerve sheath tumors (MPNST) cell line ST8814, which is characterized by active wild-type Ras (Basu et al., 1992; Mahller et al., 2006) and the triple negative breast cancer cell line MDA-MB-231 carrying the oncogenic KRAS$^{G13D}$ mutation (Hollestelle et al., 2007). In addition, applicants used the non-transformed mammary epithelial cell line MCF10A (RAS$^{WT}$ immortalized by a spontaneous t(3;9)(3p13;9p22) translocation that deletes the CDKN2A gene, also known as p16) and the non-invasive estrogen receptor (ER) and progesterone receptor (PR) positive RAS$^{WT}$ breast cancer cell line MCF7 (wild-type p53) and T47D (mutant p53). Cells were grown in growth media containing IODVA1 at concentrations between 0.1 and 10 μM or vehicle control and cell number was counted using the trypan blue exclusion method. FIG. 4D shows that increasing concentration of IODVA1 inhibits ST8814 cell proliferation with 50% growth inhibitory concentration (GI50) at day 4 of 1 μM. Similar results were observed with MCF7, MDA-MB-231, and T47D cells with estimated GI50s≤1 μM (FIG. 4A). Appreciable decrease in proliferation of non-transformed MCF10A cells was not observed. IODVA1 significantly decreases number of colonies of the breast cancer cells in soft agar at 1 and 3 μM consistent with the cell proliferation results (FIG. 4B).

IODVA1 and Ras Activation. To check if IODVA1 inhibits Ras activation in cells, applicants determined the levels of active-GTP-bound-Ras in ST88-14 cells treated with IODVA1 (2 μM) or vehicle control at various time points. GST-RafRBD bound glutathione-beads were incubated with ST8814 cell lysates, thoroughly washed, and the protein complex separated on SDS-PAGE. Levels of GTP-bound pan-RAS proteins bound to RafRBD were determined by immunoblotting. As shown in FIG. 4C, levels of active Ras between IODVA1 and vehicle control treated cells were similar after 24 h treatment. However, the decrease in active Ras levels is seen after 48 h drug treatment and is very noticeable at the 72 h time point. Without intending to be limited by theory, because the levels of active Ras require at least 48 h to decrease, it may be that IODVA1 does not bind Ras and that its mechanism of action is Ras-independent.

Figure 5:
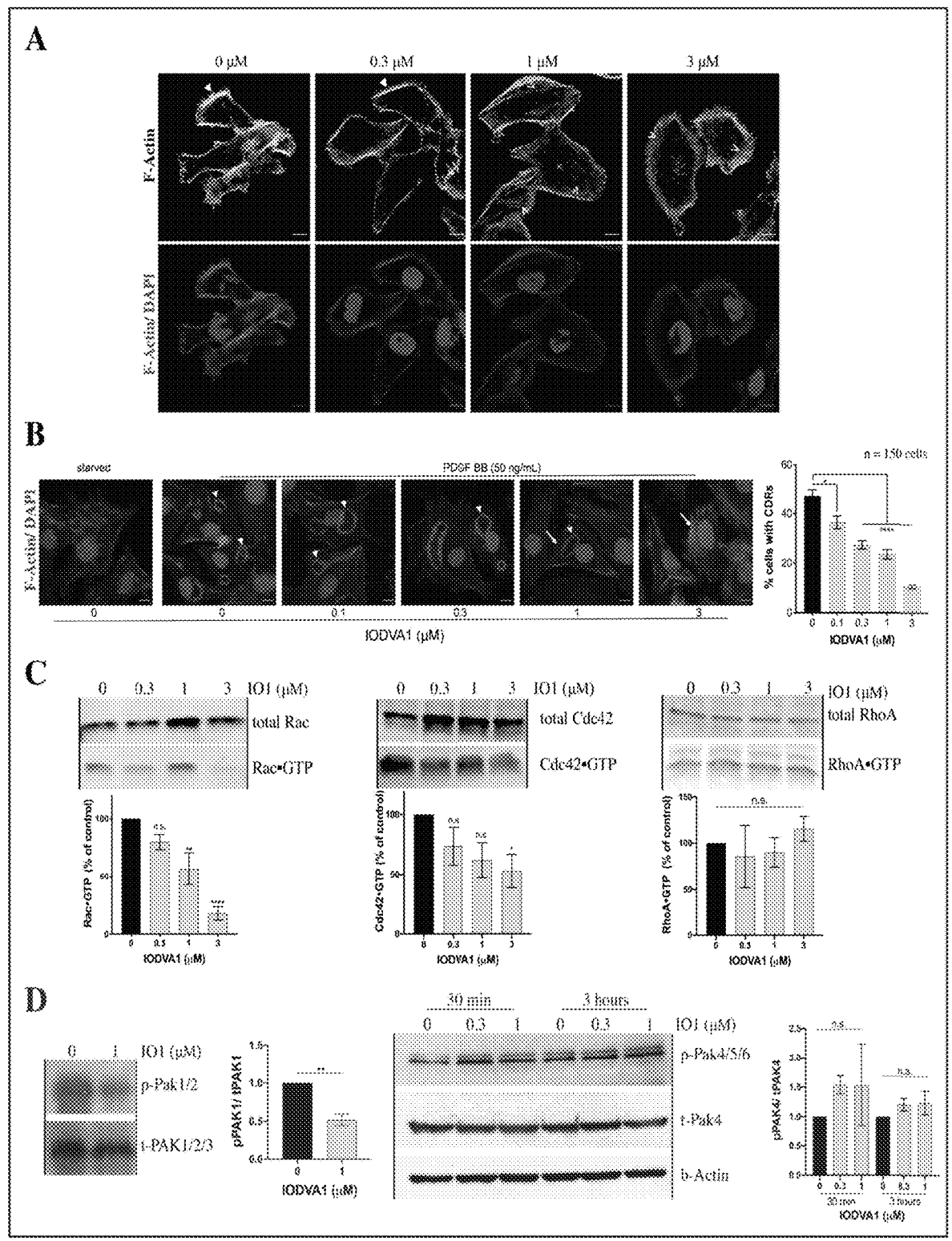
FIG. 5: Cytoskeletal changes induced by IODVA1 treatment. IODVA1 inhibits lamellipodia and circular dorsal ruffle (CDR) formation in MDA-MB-231 cells and decreases Rac activation. (A) IODVA1 inhibits EGF-induced lamellipodia formation in MDA-MB-231 cells. MDA-MB-231 cells were plated on fibronectin-coated coverslips, serum starved for 4 h, incubated with the indicated concentrations of IODVA1 for 1 h, then EGF (50 ng/mL) stimulated, fixed and stained with Phalloidin Alexa Fluor 594 (F-Actin, pseudocolored red) and DAPI (nuclei, pseudocolored blue). Representative images show lamellipodia formation and enrichment of actin staining at the leading edge (white closed arrowheads) at 0 and 0.3 μM concentrations and lack of lamellipodia with rounded cell morphology at 1 and 3 μM. Note equally distributed phalloidin staining with presence of stress fibers in the cell body of the 1 and 3 μM treated-cells (white open arrowheads) indicative of stationary cells. Scale bar=10 μm. Results are representative of three independent experiments. (B) IODVA1 inhibits PDGF-induced CDR formation in 3T3 fibroblasts. NIH-3T3 cells were plated on fibronectin-coated coverslips, serum starved for 4 h, incubated with the indicated concentrations of IODVA1 for 1 h, then PDGF (50 ng/mL) stimulated, fixed and stained with Phalloidin Alexa Fluor 594 (F-Actin, pseudocolored magenta) and DAPI (nuclei, pseudocolored blue). Closed white arrowheads indicate circular dorsal ruffles, arrows indicate lack of elongated morphology typical in stimulated fibroblasts. The percentage of cells with CDRs was counted as the number of cells with CDRs normalized to the total number of cells in the field. Around 150 cells were counted per condition per experiment. Cells with multiple CDRs were counted only once. Results are representative of three independent experiments. Scale bar=10 μm. (C) MDA-MB-231 cells were incubated with IODVA1 (IO1) at the indicated concentrations for 1 h, lysed, and incubated with GST-PAK-GBD (binds active Rac and Cdc42) and GST-Rhotekin RBD (binds active RhoA). The protein complexes were resolved on SDS-PAGE and immunoblotted with pan-Rac, Cdc42 or RhoA antibodies. Levels of active Rac (RacGTP, % of control), active Cdc42 (Cdc42GTP, % of control) and active RhoA (RhoAGTP, % of control) were quantified using ImageJ and ImageLab and show combined data as mean±s.e.m. from at least 3 independent experiments. (D) Left panel—MDA-MB-231 cells were incubated with IODVA1 (IO1, 1 μM) for 30 min, lysed, and immunoblotted for pPAK1(T423)/pPAK2(T402). Lysates were loaded in two replicates. Results shown are mean±s.e.m. of two independent experiments. Right panel—MDA-MB-231 cells were incubated with IODVA1 (IO1, 0.3 and 1 μM) for 30 min or 3 hours, lysed and immunoblotted for pPAK4(S474)/pPAK5(S602)/PAK6 (S560). Results shown are mean±s.e.m. of two independent experiments. n.s.—not significant, *—p<0.05, —p<0.01, **—p<0.0001. (E) MDA-MB-231 cells were EGF activated for 10 min, washed, treated with DMSO vehicle control or IODVA1 3 μM for 30 min, fixed, and stained for F-actin and nuclei (N=3). Arrows point to lamellipodia structures. Images were taken at 100×. Scale bar=10 μm.
Figure 5:
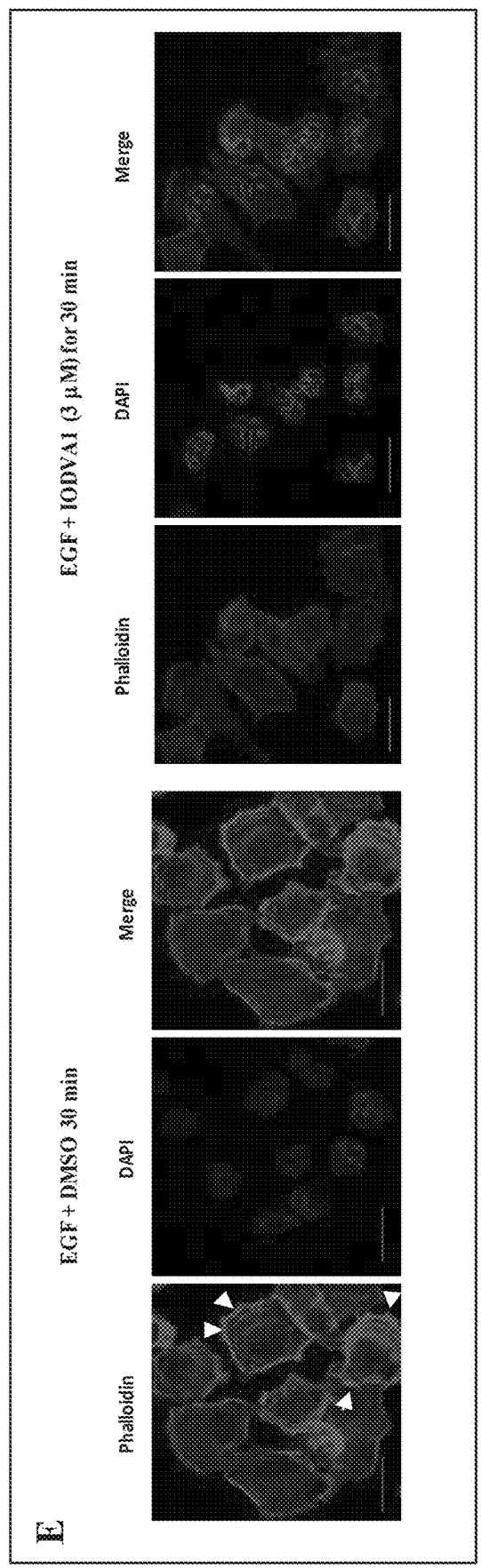

IODVA1 interferes with lamellipodia and circular dorsal ruffle formation. Progression of cancer invasion and metastasis requires the aberrant activation of cell migration, which is driven by the reorganization of the actin cytoskeleton (Condeelis et al., 2005; Sahai, 2005; Yamaguchi and Condeelis, 2007; Yamaguchi et al., 2005). A major trait of Ras-transformed cells is a reorganized actin cytoskeleton, which leads to poor adhesion, increased motility, invasiveness, and contact-independent growth. To check the effect of IODVA1 on overall actin cytoskeleton structures, MDA-MB-231 cells were serum starved for 4 h, treated with IODVA1 (0-3 μM) for 1 h, then stimulated cells with EGF for 30 min, which induces lamellipodia formation. FIG. 5A shows that, in comparison to the vehicle-treated cells (0 μM), lamellipodia formation and enrichment of cortical filamentous actin are inhibited with IODVA1 treatment. Cells treated with 1 and 3 μM IODVA1 had more prominent stress fibers and rounded cell shape (open arrow heads). In a parallel experiment, actin cytoskeleton structures of cells stimulated by EGF were examined, followed by wash out and subsequent treatment with IODVA1 or vehicle control. FIG. 5E shows that overall filamentous actin staining is qualitatively reduced within 30 min of IODVA1 (3 μM) treatment.

Lamellipodium formation and membrane ruffling in response to growth factor stimulation is characteristic of Rac activation (Ridley and Hall, 1992; Ridley et al., 1992). Based on the observation that IODVA1 treatment impedes formation of lamellipodia, applicants evaluated the action of IODVA1 on another Rac-mediated actin structure—circular dorsal ruffles (CDRs) (Steffen et al., 2013). CDRs are enclosed, dynamic, ring-shaped structures that erect vertically and appear on the dorsal surface of cells and Rac activity is required for their formation. 3T3 fibroblasts were starved for 4 h, treated with IODVA1 (0-3 μM) for 1 h, and stimulated with PDGF for 10 min. FIG. 5B shows that CDR formation is inhibited with IODVA1 treatment. Cells treated with 1 and 3 µM IODVA1 had intact stress fibers, exhibited "starfish" or triangular cell shape and were devoid of protrusions.

IODVA1 inhibits Rac-activation. To confirm that IODVA1 interferes with Rac activation, applicants checked the levels of active Rac and its downstream effector PAK1/2. MDA-MB-231 cells were incubated with IODVA1 (0-3 µM) for 1 h and levels of GTP-bound active Rac were measured by GST-PAK-GBD pull-downs and quantified (FIG. 5C). IODVA1 significantly decreases levels of active Rac in a dose-dependent manner, levels of the related active Cdc42 GTPase are also decreased but only at the highest IODVA1 concentration. Levels of active RhoA were not affected by IODVA1 (FIG. 5C) and no effect on stress fiber arrangement was observed. Similarly, MDA-MB-231 cells incubated with IODVA1 (1 µM) for 30 min experience a 50% decrease in levels of pPAK1/2(T423/T402). Levels of pPAK4/5/6 however, did not change even following 3 h incubation; PAK4/5/6 are primarily Cdc42 specific (FIG. 5D). Taken together, these data suggest that at low concentrations, IODVA1 inhibits Rac activation and downstream signaling leading to inhibition of lamellipodia and CDR formation.

Figure 6:
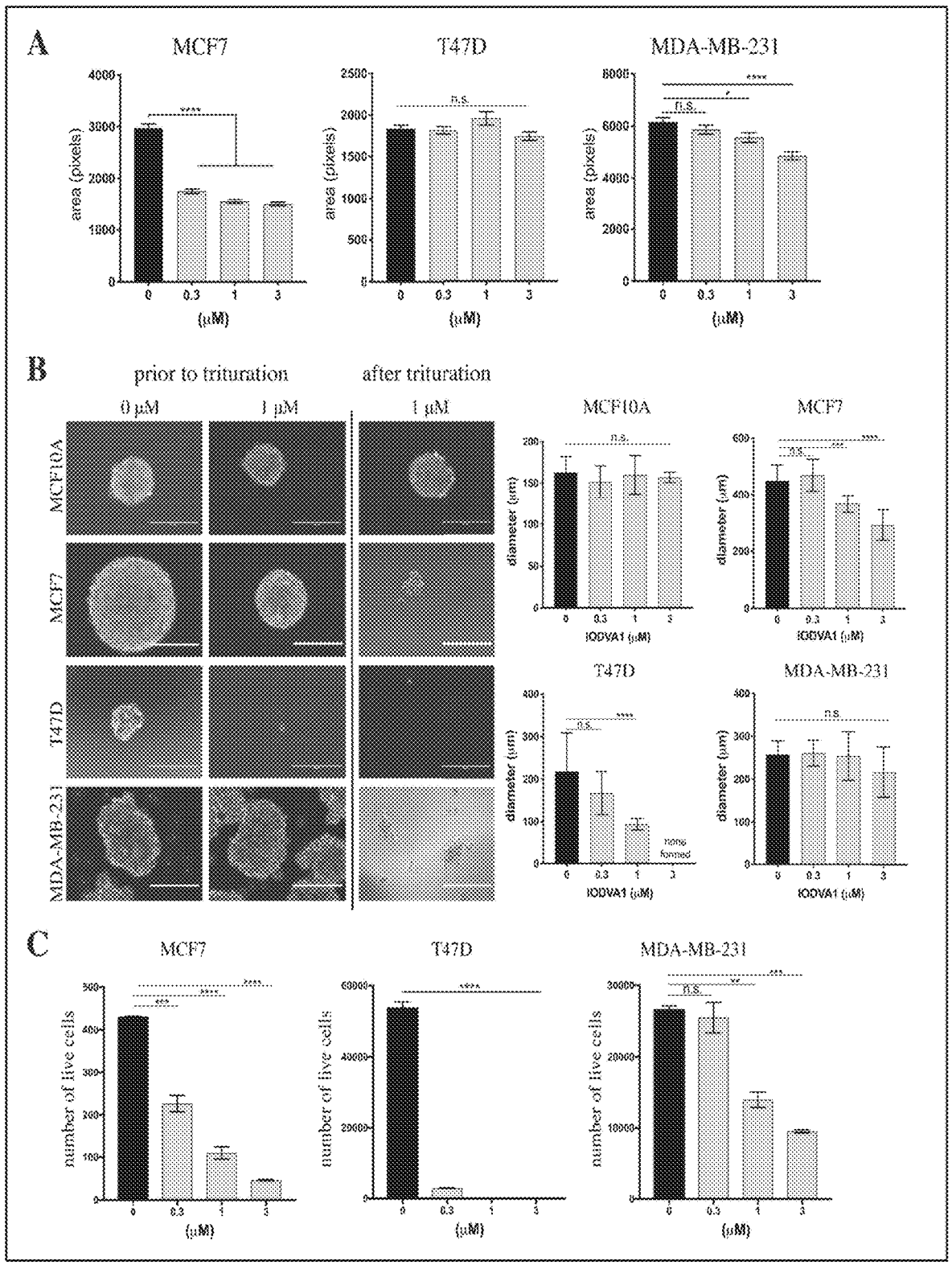
FIG. 6: IODVA1 inhibits cell-substratum and cell-cell interactions. (A) IODVA1 impedes spreading of MCF7 and MDA-MB-231 cells on fibronectin. MCF7, T47D, and MDA-MB-231 cells were incubated on fibronectin coated coverslips for 10 min, then further incubated with the indicated concentrations of IODVA1 for 30 min in serum-free media, fixed and observed by bright field microscopy. Areas of single cells were calculated from 6 random fields (no less than 300 cells total per treatment group). Results shown are mean±s.e.m. of a single experiment and are representative of three independent experiments. (B) Effects of IODVA1 treatment on spheroid formation in MCF10A, MCF7, T47D, and MDA-MB-231 cells. Left panel—representative bright field images of hanging drop cultures of MCF10A, MCF7, T47D, and MDA-MB-231 cells grown in the absence (0 μM) and presence of IODVA1 (1 μM) prior to and post mechanical pipetting (trituration). Scale bar=200 μm. Right panel, changes in spheroid/aggregate size due to IODVA1 treatment indicated by the diameter of the spheroids. Results shown are mean±stdev, N=15. (C) IODVA1 treatment reduces proliferation capacity in adhesion-free environment. MCF7, T47D, and MDA-MB-231 cells were grown in complete media in the presence of IODVA1 or vehicle control in ultra-low attachment plates for 5 days. Aggregates and spheroids were dissociated with accutase and trituration, and the number of live cells was determined by trypan blue exclusion. Results shown are combined mean±stdev of two independent experiments. n.s.—not significant, *—p<0.05, —p<0.01, *—p<0.001, ****—p<0.0001.

IODVA1 may decrease cell-ECM and cell-cell interactions. Applicants assessed if IODVA1 interferes with cell spreading on the extracellular matrix, an event that is also governed by the rearrangement of the actin cytoskeleton. MCF7, T47D, or MDA-MB-231 cells were plated on fibronectin coated coverslips for 10 min, incubated for additional 30 min in the presence of 0-3 µM IODVA1, fixed and examined by bright field microscopy. FIG. 6A shows that exposure to IODVA1 interferes with spreading of MCF7 at 0.3 µM and with MDA-MB-231 at 1 µM, as indicated by the decrease in cell area. No changes in the area in T47D cells were detected, although more rounded cells in the presence of IODVA1 were observed. These results indicate that cells treated with IODVA1 fail to initiate and/or maintain actin reorganization needed for cell spreading and leading-edge formation upon contact with the extracellular matrix and mitogen stimulation, respectively.

In vitro 3D assays, such as spheroid formation, serve as an intermediate between 2D (monolayer) cellular assays and in vivo animal models. Spheroid formation is mediated by matrix development and remodeling and changes in the cytoskeleton and cell-cell contacts and adhesion. To evaluate the effect of IODVA1 on spheroid formation, single cell suspension were plated in complete media containing vehicle control or IODVA1 at 0.1-3 µM range using the hanging drop and ultra-low attachment (ULA) methods (Foty R. 2011).

In the hanging drop method, spheroids were mixed with the indicated concentrations of IODVA1 in complete media and spheroids were allowed to form in 25 µL hanging drops on the lid of a 10-cm dish. After 96 h, spheroids were transferred into a 10-cm dish using a wide-barrel pipet tip and imaged before and after trituration using bright field microscopy. FIG. 6B shows that IODVA1-treated MCF7 cells formed smaller spheroids at 1 µM. Mechanical disruption by pipetting resulted in complete dissociation of the spheroids at 1 µM IODVA1. T47D cells treated with 1 µM IODVA1 failed to form packed spheroids, but rather remained as cell aggregates. MDA-MB-231, which form loose aggregates, rather than tight spheroids, were not affected by IODVA1 treatment, but disassembled into smaller aggregates after trituration. No effect was observed in IODVA1-treated MCF10A cells.

For the spheroid formation in the ultra-low attachment plates, MCF7, T47D, and MDA-MB-231 (5,000 cells) were incubated in complete media with IODVA1 at 0-3 µM for 5 days. Aggregates and spheroids were dissociated with Accutase and live cells were counted using trypan blue exclusion. Treatment with IODVA1 significantly decreased the number of live cells in a spheroid (FIG. 6C). These results indicate that IODVA1 is effective at inhibiting sphere formation in a 3D-culture system probably through inhibition of proliferation.

Figure 7:
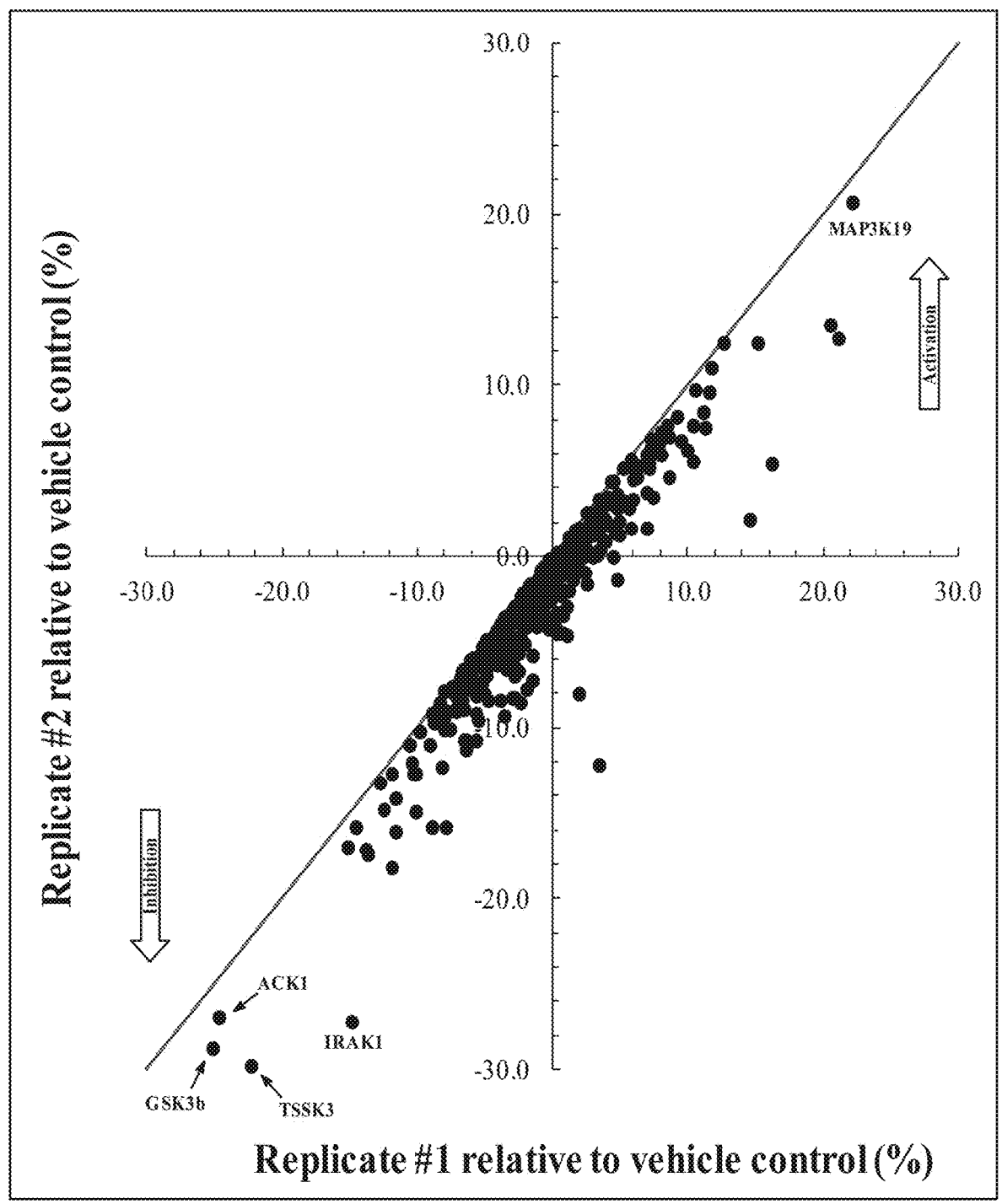
FIG. 7: IODVA1 Kinome Inhibitory Activity. The activity of 369 kinases was tested twice in the presence of 0.5 μM IODVA1. Plotted is the remaining activity of replicate 1 vs 2 expressed as % of vehicle control set at 0%) for each kinase. Kinases whose activities were decreased or increased by more than 3σ from mean are indicated in red and green, respectively

IODVA1 Kinase Inhibitory Activity. IODVA1 has two pyridine groups attached to a central imidazole group. Pyridine is among the most common scaffolds found in kinase inhibitors (Xing et al., 2014) and is found in several potent inhibitors of FLT3, Aurora, ROCK, AKT, and other kinases (Bavetsias et al., 2012; Green et al., 2015; Woods et al., 2006) suggesting that IODVA1 might have kinase inhibitory activity. To test this hypothesis, applicants evaluated the potential of IODVA1 to interfere with the ability of 369 recombinant wild-type kinases to hydrolyze ATP. Each kinase was tested twice at one single IODVA1 concentration of 0.5 µM and data were averaged and compared to vehicle DMSO control. A plot of the replicates compared to vehicle control set at 100% is shown in FIG. 7. Statistical analysis of the kinome data shows that IODVA1 is ineffective on 98.6% (364 out of 369) of the tested kinases in vitro. It shows a decrease in activity (by 22 to 27%) of ACK1, TSSK3/STK22C, GSK3b, and IRAK1 and an increase in activity (21%) of YSK4/MAP3K19 at better than 3 standard deviations (>3σ). However, the inhibition and stimulation effects are modest and higher IODVA1 concentrations are needed to inhibit or stimulate the aforementioned kinases to a level of 50%. Thus, IODVA1 is not a kinase inhibitor and the cellular effects previously observed cannot be explained by kinase inhibition or stimulation given that the cellular GI50s of IODVA1 (0.5 to 1 µM) are similar to the concentration used for the kinase assays.

Figure 8:
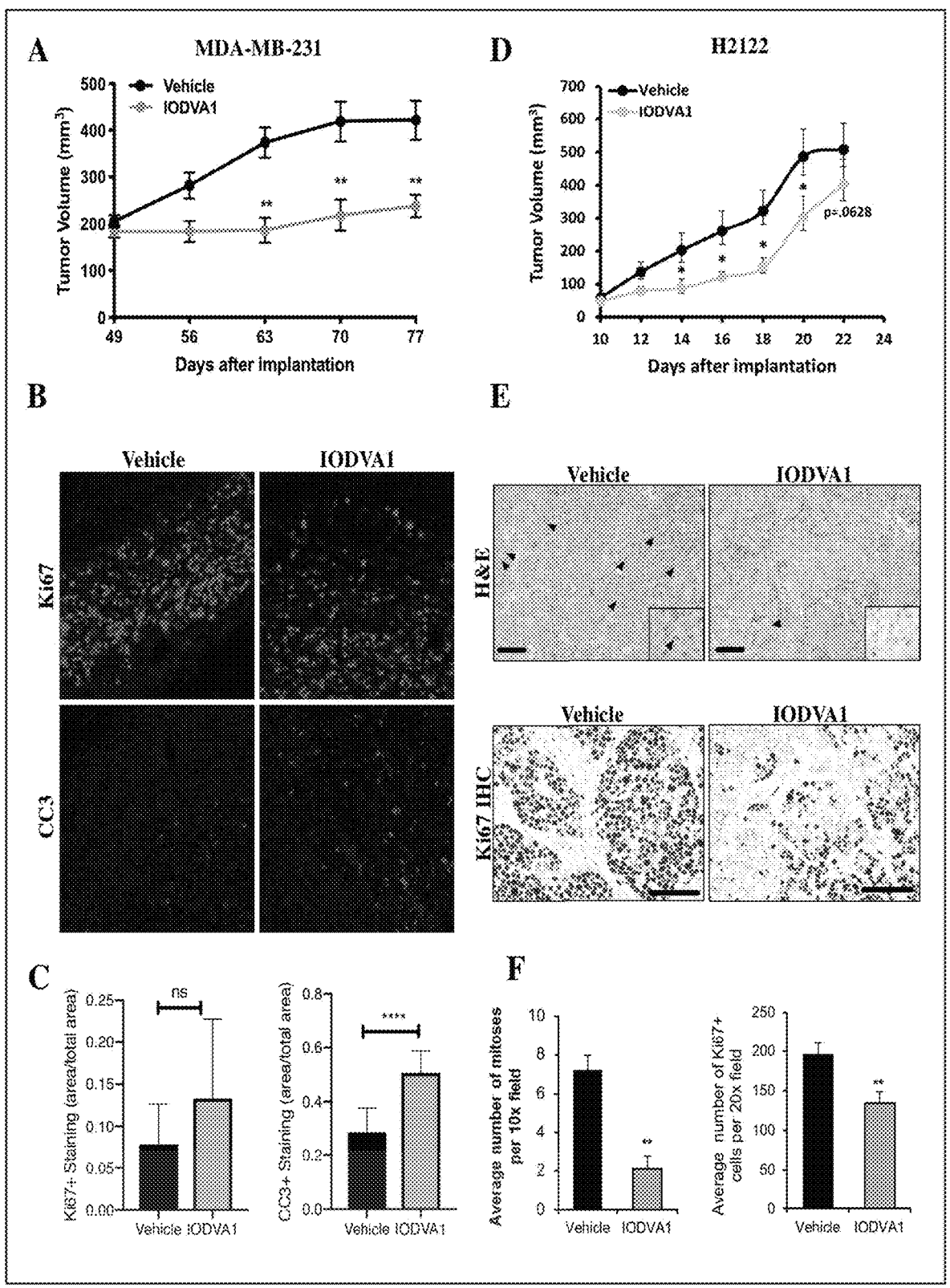
FIG. 8: IODVA1 inhibits tumor growth of human breast and lung cancer xenografts. (A) Orthotopic xenografts of MDA-MB-231 triple negative breast cancer cells demonstrated decreased tumor growth with IODVA1 treatment. Animals began treatment with vehicle (N=6) or IODVA1 (N=5) when tumors reached 200 mm$^3$ in volume (day 49 post-injection) and received IODVA1 treatment three times per week for the next 28 days. (B) Tumors were also stained for Ki67 as a proliferation marker (top panel). IODVA1 treated tumors had a higher percentage of apoptotic cells compared to vehicle treated tumors as detected by cleaved caspase 3 immunofluorescence (CC3, lower panel). (C) Quantification of Ki67-positive and cleaved caspase 3-positive cells of tumors shown in (B). (D) Xenograft tumors of H2122 lung cancer cells demonstrated decreased tumor growth with IODVA1 treatment. Animals began treatment when tumors became detectable at 10 days post-injection (*, p<0.05). (E) H&E staining of representative H2122 tumors indicates that IODVA1 decreases the number of mitotic cells in the tumor (top, arrowheads). IODVA1 treated tumors also had fewer proliferating cells compared to control vehicle treated animals, as determined by immunohistochemical staining for Ki67 (bottom) and increased intratumoral fibrosis. Representative images were taken at 100× magnification, scale bar is 200 μm. (F) Quantification of Ki67+ cells in control and IODVA1 treated tumors shown in (E).

IODVA1 reduces tumor burden of solid tumors in vivo. To examine if the ability of IODVA1 to reduce oncogene-driven cell proliferation can be translated in vivo, applicants tested its efficacy on one breast cancer and one lung cancer xenograft mouse model. The breast cancer model utilizes the human triple negative breast cancer MDA-MB-231 cells. Cells were orthotopically injected into the right and left inguinal mammary glands of immunodeficient female mice. Tumor-bearing mice then received an intraperitoneal (IP) injection of 250 µL of 1 mM IODVA1 every other day, for an average dose of 3.5 mg/kg. Dosage regimen was not optimized, and it is expected that better results are obtained if IODVA1 dosage is increased. Four weeks post treatment a significant decrease of ≥50% of tumor volume compared to vehicle-treated control mice was observed (FIG. 8A-8C). While vehicle treated tumors doubled in volume, IODVA1-treated tumors failed to grow beyond the pre-treatment tumor size (FIG. 8A). Tumors were then excised, fixed and paraffin embedded, then stained via immunohistochemistry for a proliferation marker (Ki-67), an apoptosis marker (cleaved Caspase-3), and with DAPI (FIG. 8B). Comparison of Ki-67 stained tumors treated with vehicle control and with IODVA1 did not reveal a statistical change in cell proliferation. However, cleaved caspase-3 stained tumor sections showed significant increase in apoptosis for cells treated with IODVA1 compared to vehicle control (FIG. 8C). Thus, IODVA1 has the capacity to induce caspase activation, thereby limiting tumor growth, in vivo.

Figure 9:
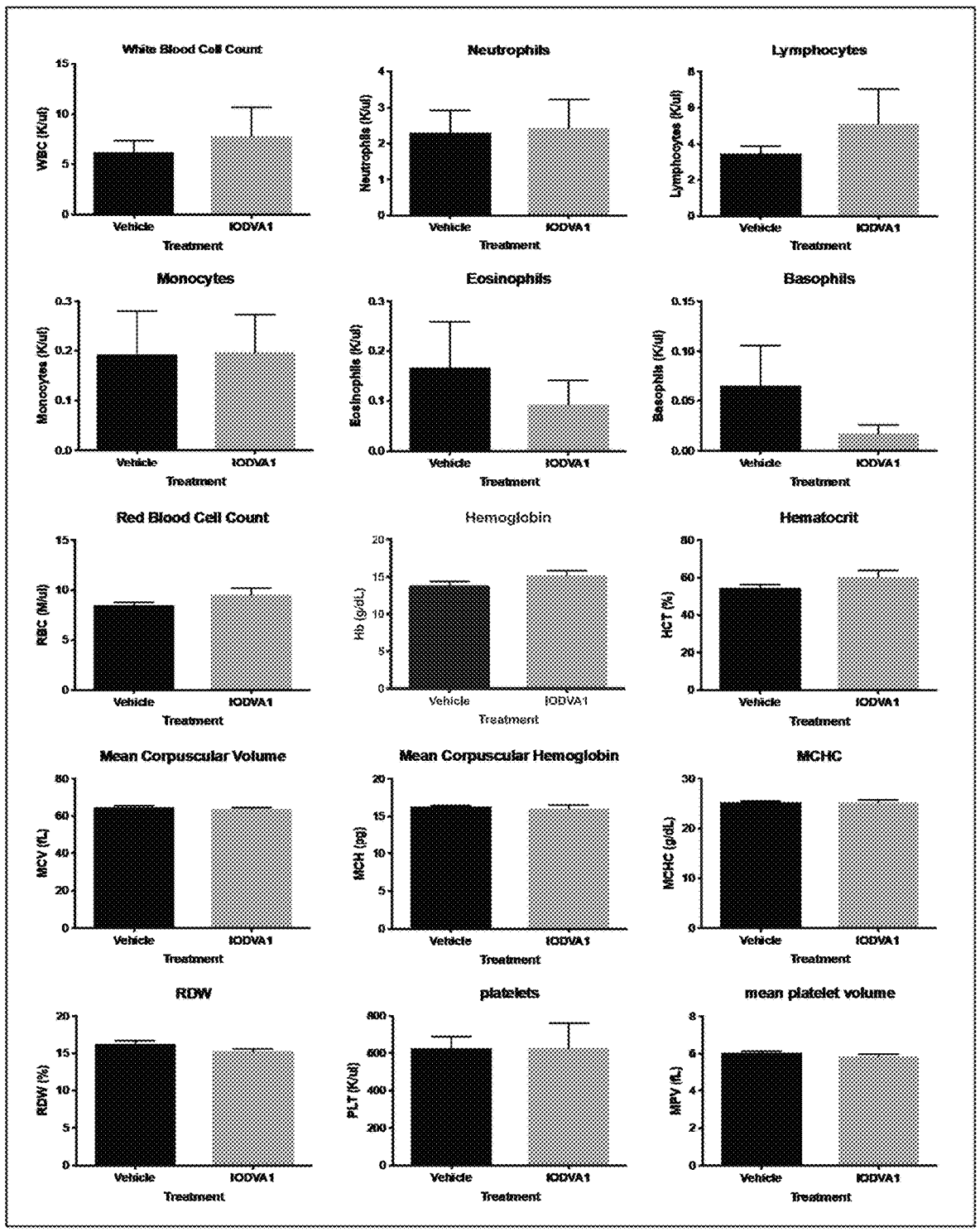
FIG. 9: Repeated doses of IODVA1 do not cause toxicity in the hematopoietic system. Peripheral blood collected after 12 doses of IODVA1 in tumor-bearing breast cancer xenograft animals were analyzed for blood counts with a Hemavet. No statistically significant changes in blood counts were detected between vehicle control and IODVA1 treated animals (N=4, mean, SEM).

At the end of the four-week treatment when mice were euthanized, peripheral blood was collected via cardiac puncture to check the effect of IODVA1 on white and red blood cells of treated mice for any sign of toxicity. There was no significant difference in WBC, neutrophils, lymphocytes, monocytes, RBC, hemoglobin, hematocrit, mean corpuscular volume, mean corpuscular hemoglobin, mean corpuscular hemoglobin volume (MCHV), red cell distribution width (RDW), platelets, and mean platelet volume between blood of drug- and vehicle-treated mice (FIG. 9).

The lung cancer mouse model was generated by injecting the lung cancer H2122 cells at the right and left flanks of NSG mice. These cells harbor the KRAS$^{G12C}$ mutation and form aggressive tumors. Mice were treated with IODVA1 or with vehicle control every other day for 14 days. Here also, a significant decrease in tumor volume was observed for mice treated with IODVA1 (FIG. 8D). Tumors were excised and sections were stained with hematoxylin and eosin (H&E) and for Ki67 proliferation marker (FIG. 8E).

Vehicle-treated H2122 tumors were dense with tumor cells with a high mitotic rate (arrows in FIG. 8E). IODVA1-treated H2122 tumors had a decreased frequency of mitotic cells and increased infiltration of stromal cells, indicative of a therapy-induced fibrotic response. Quantification of the Ki67-positive cells revealed significant decrease in number of Ki67-positive tumor cells in mice treated with IODVA1 (FIG. 8E), suggesting that IODVA1 negatively impacts cell proliferation in vivo.

Taken together, applicant's in vivo data suggest that IODVA1 is efficacious at treating solid tumors, including Ras-driven solid tumors, likely by increasing tumor cell apoptosis and decreasing cell proliferation. In addition, IODVA1 administration does not result in adverse effects on bone marrow function due to lack of biologically relevant peripheral blood count changes.

Ras is at the center of many protein-protein interactions that are key to proper cell signaling and normal physiology. Single point mutations or loss of an otherwise fine-tuned regulation lead to a decrease in its GTPase activity and are frequently found in cancer and in a class of diseases called RASopathies (Rauen, 2013; Stephen et al., 2014; Tajan et al., 2018; Tidyman and Rauen, 2009a). Despite decades long efforts in academia and private pharmaceutical companies, targeting Ras has been extremely challenging to translate to therapeutics. Excellent reviews discussing this topic and the various approaches taken to target Ras have been reported in the literature (Marin-Ramos et al., 2018; Ostrem and Shokat, 2016; Spencer-Smith and O'Bryan, 2017; Spiegel et al., 2014). High-resolution structures did not reveal a deep druggable cavity and there are no known Ras agonists or antagonists to provide a starting scaffold to build a chemical discovery process. Despite these difficulties, several low molecular weight chemicals have been reported to bind to Ras albeit with low affinity (Cox et al., 2014; Maurer et al., 2012; Quevedo et al., 2018; Shima et al., 2013; Spiegel et al., 2014; Sun et al., 2012). Inhibiting Ras-binding to its downstream effectors also has been challenging since Ras makes flat and large interfaces (~1,000-2,000 Å$^2$) with Raf kinase, PI-3 kinase, and RalGDS formed by the juxtaposition of β-strands from each partner protein. Because GTP-loading is such an essential step in Ras signaling, recent efforts are aiming at interfering with the GDP-GTP exchange by targeting the Ras/Sos interface (Evelyn et al., 2015; Evelyn et al., 2014; Maurer et al., 2012; Schopel et al., 2013; Spiegel et al., 2014; Sun et al., 2012). In general, it remains to be seen if these small molecules are efficient in in vivo models of oncogenic Ras, if their true mechanism of action is by directly inhibiting Ras, or if they represent a molecular scaffold on which more potent molecules can be derived. If the task seems insurmountable, recent reports suggest that it is not impossible. For example, the finding that compound 3144 binds to all Ras isoforms and displays anti-tumor activity in xenograft mouse cancer models is encouraging (Welsch et al., 2017). And so is the recent advance toward covalent in vivo inhibition of KRAS$^{G12C}$, a common mutation in lung adenocarcinoma (Janes et al., 2018).

In attempting to exploit a cavity identified in the crystal structure of the GTP-bound form of Ras$^{G60A}$ (Ford et al., 2005; Ford et al., 2009) and to target it by a small molecule that restraints the switch 1 loop from coordinating the Mg$^{2+}$-ion and adopting a signaling conformation, applicants were able to combine in silico screening with cell proliferation and colony formation assays, and identify NSC124205, an inhibitor of the proliferation of Ras-transformed cells at low micromolar concentration. However, HPLC/MS analysis showed that NSC124205 is a mixture of at least three components. Other investigators have reported a high percentage of commercially available chemicals that failed quality control by UPLC (Corsello et al., 2017). This prompted Applicants to identify the active ingredient in the NSC124205 mixture responsible for the antiproliferative activity. Following a simple synthesis scheme in an attempt to resynthesize NSC124205, applicants synthesized a novel small molecule with drug-like properties we termed IODVA1. HPLC and MS analysis indicate that IODVA1 corresponds to peak 1b of the NSC mixture. Given that peak 1c is a tautomer of 1b and given that peak 1a is inactive in cellular assays it is believed that IODVA1 is the active ingredient in NSC124205.

The high sensitivity of RAS$^{WT}$ expressing MCF7 and T47D cells and oncogenic Ras expressing MDA-MB-231 to IODVA1 suggest that IODVA1 targets a node used by Ras to regulate cell survival and cell spreading and movement including lamellipodia formation. One such node is the small GTPase Rac. The biochemical observations that IODVA1 decreases Rac activation and signaling, e.g. PAK1 activity (FIGS. 5C & 5D) suggest that IODVA1 targets Rac signaling. The cellular and in vivo data support this idea. For example, IODVA1's ability to inhibit formation of Rac-driven cellular actin suprastructures, including lamellipodia and CDRs (FIGS. 5A & 5B) and affect cell spreading and shape (FIG. 6A) within minutes of cell exposure, as well as cell-cell adhesion (FIGS. 6B & 6C), is consistent with IODVA1 targeting Rac activity. The role of Rac in regulating the organization of the actin cytoskeleton has long been recognized (Etienne-Mannerville & Hall, 2002; Hall A., 1994; Lee & Dominguez, 2010). The increase in in vivo cleaved caspase-3 and decrease in proliferation in the MDA-MB-231 and H2122 xenograft tumors, respectively indicate that IODVA1 targets a node required by Ras to regulates cell survival and proliferation such as Rac. The role of Rac in regulating Ras-driven tumorigenesis in vivo has been reported in various mouse models (Mack et al., 2011; Kissil et al., 2007; Espina et al., 2008; Malliri et al., 2002; Wang et al., 2010; Bar-Sagi & Hall, 2000). IODVA1 seems to be specific to Rac as it affects Cdc42 but only at high concentrations and has no effect on Rho. This specificity is consistent with the inability of IODVA1 to decrease levels of pPAK4/5/6 downstream of Cdc42 or remodel stress fibers downstream of Rho.

In conclusion, applicants identified a di-pyridine guanidinobenzimidazole derivative with in vitro and in vivo activity against cell lines xenograft models of cancer. IODVA1 significantly reduces the proliferation of a variety of cancer model cells with diverse genetic lesions and it does so at a low micromolar concentration. The in vivo data show that it inhibits tumor growth by increasing apoptosis and/or decreasing proliferation of cancer cells. The cellular studies and studies of peripheral blood from mice treated with IODVA1 for four weeks (12 doses) revealed no apparent toxicity and suggest that IODVA1 may be specific to transformed cells. Applicant's cellular and in vivo data are consistent with IODVA1 targeting Rac signaling.

Experimental Procedures

Plasmids, Cell Lines, and Reagents. MDA-MB-231, MCF7, T47D, MCF10A and HEK239T cells were obtained from ATCC and have since been verified by DNA Diagnostics Center (Fairfield, OH) during the course of these studies. NIH-3T3 fibroblasts were a kind gift from Dr. Susanne I. Wells, ST8814 cells were a kind gift from Dr. Nancy Ratner, A549 and H292 cells were a kind gift from Dr. Jeffrey Whitsett. MDA-MB-231 cells were maintained in Improved MEM media (Invitrogen) supplemented with 10% FBS, 1% penicillin/streptomycin, and 1% amphotericin B. MCF10A were maintained in DMEM/F12 (Invitrogen) supplemented with 5% horse serum, 20 ng/mL EGF, 0.5 mg/mL hydrocortisone, 100 ng/mL cholera toxin and 10 μg/mL insulin. MCF7 and T47D were maintained in DMEM, supplemented with 10% FBS and 10 μg/mL insulin. HEK293T and NIH/3T3 cells were maintained with DMEM supplemented with 10% FBS and 1% penicillin/streptomycin. ST8814, A549, and H292 cells were grown in RPMI supplemented with 10% FBS. Cells were treated with the indicated concentrations of compounds. Control cells were treated with equal volumes of diluent only. The following antibodies were used—GAPDH (GeneTex GTX627408, 1:5000), pERK1/2 T202/Y204 (CST 4370, 1:2000), total ERK1/2 (CST 4696, 1:2000), pAKT 5473 (CST 9271, 1:1000), pPAK1 T423/pPAK2 T402 (CST 2601S, 1:1000), PAK1/2/3 (CST 2604, 1:2000), PAK1 (CST 2602, 1:1000), pPAK4 5474/pPAK5 S602/pPAK6 5560 (CST 3241, 1:1000), PAK4 (CST 62690, 1:1000), anti-mouse Eu (Molecular Devices R8205), anti-rabbit Eu (Molecular Devices R8204), anti-mouse-HRP (CST 7076, 1:5000), and anti-rabbit-HRP (CST 7074, 1:5000), Ki67 (Abcam, IHC 1:100), cleaved caspase 3 (Asp175, CST 9661, IHC 1:100), goat anti-rabbit Alexa Fluor 568 (Abcam, IF 1:500). Fluorescent phalloidins and DAPI were from Invitrogen.

Computational Virtual Screening. Virtual Screening was performed to identify candidate molecules that would stabilize the open conformation of Ras by targeting the cleft situated between the switch 1 and the triphosphate nucleotide in the crystal structure of HRasG60A (PDB ID: 1XCM) (FIG. 1A) for which position 60 was restituted to Gly. The docking simulations for the virtual screening were performed using rigid body docking, as implemented in AutoDock ver. 4.2 (Morris et al., 2009), in conjunction with the Cincinnati Children's Hospital Medical Center (CCHMC) Protein Informatics Core' computational pipelines on a Linux cluster with upwards of 512 CPUs. Polyview-3D (polyview.cchmc.org) was used to analyze the protein structures and guide the choice of simulation boxes.

A subset of 118,500 drug-like synthetic compounds from the NCI/DTP Open Chemical Repository (http://dtp.cancer.gov) was used for virtual screening. These compounds were derived from the NCI Plated 2007 deposited in the Zinc library (http://zinc.docking.org/catalogs/ncip) by using chemoinformatic filters as described in (Irwin and Shoichet, 2005; Irwin et al., 2012; OpenEye Scientific Software). 3D-structures for the resulting subset of 118,500 compounds were downloaded from ZINC. Gesteiger partial charges were used for both the Ras and chemical compounds. Screening was performed in three stages, using increasingly stringent parameters and gradually more extensive sampling. The latter was achieved by increasing the number of energy evaluations (from $2\times10^5$ to $1\times10^7$), Genetic Algorithm runs (from 20 to 50) and population size (from 75 to 150), as previously discussed (Biesiada et al., 2011) After initial fast screening, 30,000 top candidates with the highest estimated binding affinities were retained, and subsequently re-scored using improved sampling in the refinement stage. 3,000 top hits were then re-scored using extensive sampling and assessed further to select candidates for experimental validation.

These candidate compounds were ranked based on their estimated binding affinities and entropy of clustering of docking poses in multiple runs of docking simulations resulting in a set of 299 NCI library hits that had entropy of docking poses below 0.2 and predicted median binding constants of less than 10 μM. These top hits were subsequently clustered based on their chemical similarity using Chemmine (chemmine.ucr.edu) to further select candidates for experimental validation, while avoiding over-representation of some classes of chemicals, and to visually analyze candidate compounds.

From this joint set, a subset of 40 compounds representing different clusters of chemicals were selected for experimental screening based upon assessment of drug-like properties, similarity to classes of compounds often identified in virtual screening as false positives, and availability of compounds from the NCI/DTP Open Chemical Repository (dtp.cancer.gov).

MTS assays. The colorimetric CellTiter 96 AQueous One Solution Cell Proliferation Assay (MTS, Promega) was used to determine the number of viable cells and evaluate effect of compounds on cell proliferation. Measurements were made as per supplier's protocol. Assays were performed by adding 10 μL of MTS reagent directly to the culture wells followed by 1 h incubation at 37° C. The amount of formazan obtained at the end of incubation was measured by absorbance at 490 nm in a 96-well plate reader (Molecular Devices; Sunnyvale, CA). Each 96-well plate had a set of four wells containing medium only and a set of four wells containing cells treated with DMSO vehicle control. Background absorbance was first evaluated from the set of wells containing medium only, averaged, and subtracted from each well. Background corrected absorbance readings were then normalized to and expressed as a relative percentage of the plate averaged DMSO vehicle control. Each experiment was repeated twice per cell line and order of compound arrangement in plates was randomized in different experiments.

Chemical Synthesis. All chemicals, reagents and solvents were purchased from Sigma-Aldrich, Ark Pharm Inc., and Fisher Scientific. Indicated reaction temperatures refer to those of the reaction bath, while room temperature (RT) is noted as 25° C. Analytical thin layer chromatography (TLC) was performed with glass backed silica plates (20×20 cm, pH=5, MF254). Visualization was accomplished using a 254 nm UV lamp. $^1$H- and $^{13}$C-NMR spectra were recorded on a Bruker Avance 400 MHz spectrometer using solutions of samples in methanol-d6. Chemical shifts are reported in ppm with tetramethylsilane as standard. Data are reported as follows: chemical shift, number of protons, multiplicity (s=singlet, d=doublet, dd=doublet of doublet, t=triplet, q=quartet, b=broad, m=multiplet). All compounds were characterized by $^1$H-NMR, $^{13}$C-NMR and high resolution mass spectroscopy (HRMS).

Scheme 1: Synthesis of IODVA1

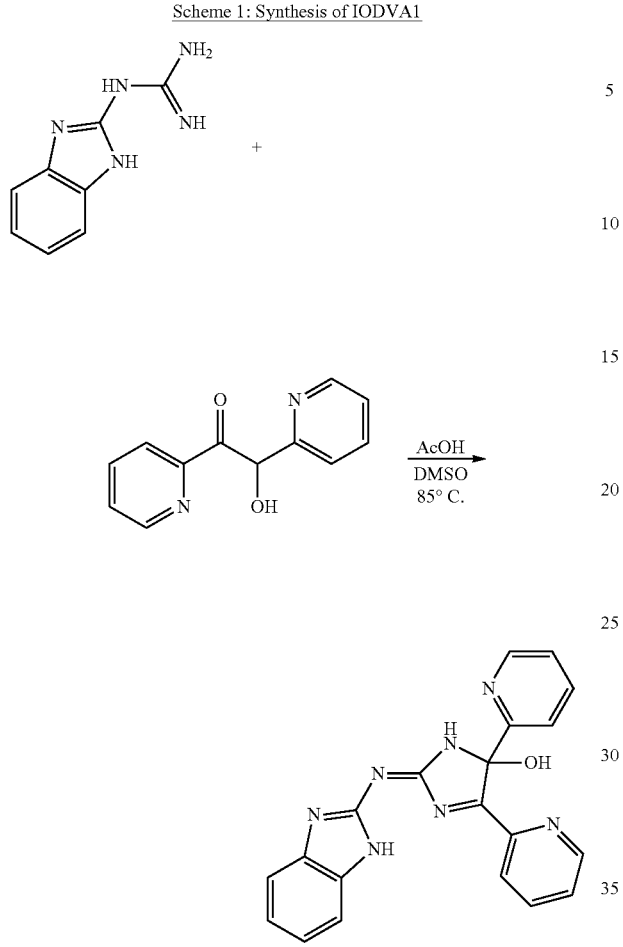

(Z)-2-((1H-benzo[d]imidazol-2-yl)imino)-4,5-di(pyridin-2-yl)-2,5-dihydro-1H-imidazol-5-ol (IODVA1)

2-guanidinobenzimidazole (500 mg, 2.86 mmol) and α-pyridoin (1.22 g, 5.72 mmol) were dissolved in N—N-dimethylformamide (5 mL). After the addition of glacial acetic acid (0.2 ml, 3.4 mmol), the reaction was stirred at 85° C. for 48 h. The reaction was cooled then quenched with water, the pH was neutralized, and the aqueous solution was extracted three times with ethyl acetate. The organic layers were combined and washed with water and brine then dried over $Na_2SO_4$ and filtered using filter paper. Silica (2 g) was added before concentrating the solution under reduced pressure. The solid was loaded onto a column then purified with flash chromatography using 1:10 methanol:methylene chloride gradient. The targeted fractions (Rf=0.5) were collected and reduced under pressure to yield 111 mg (0.30 mmol, 11%) of the desired product as a brown-gold solid.

$^1$H NMR (400 MHz, MeOD-d6): δ=7.07 (m, 3H), 7.33 (m, 2H), 7.51 (m, 2H), 7.63 (m, 1H), 7.85 (m, 1H), 8.05 (m, 1H), 8.19 (m, 1H), 8.33 (m, 1H), 8.53 (d, 1H).

$^{13}$C NMR (400 MHz, MeOD-d6): δ=113.89, 122.04, 122.19, 123.16, 124.17, 124.74, 128.85, 129.53, 137.93, 138.93, 148.65, 149.81, 150.36, 150.60, 152.89, 156.43, 157.79, 161.23.

HRMS-ESI: [M+H]$^+$ ($C_{20}H_{16}N_7O$): calculated: m/z=370.1411. Found: m/z=370.1409

Synthesis of NIRA2:

2-((1H-benzo[d]imidazol-2-yl)imino)-5,5-di(pyridin-2-yl)imidazolidin-4-one and 2,2,5-tri(pyridine-2-yl)-1,2-dihydrobenzo[4,5]imidazo[1,2-a]imidazo[2,1-d][1,3,5]triazin-3(5H)-one (NIRA2)

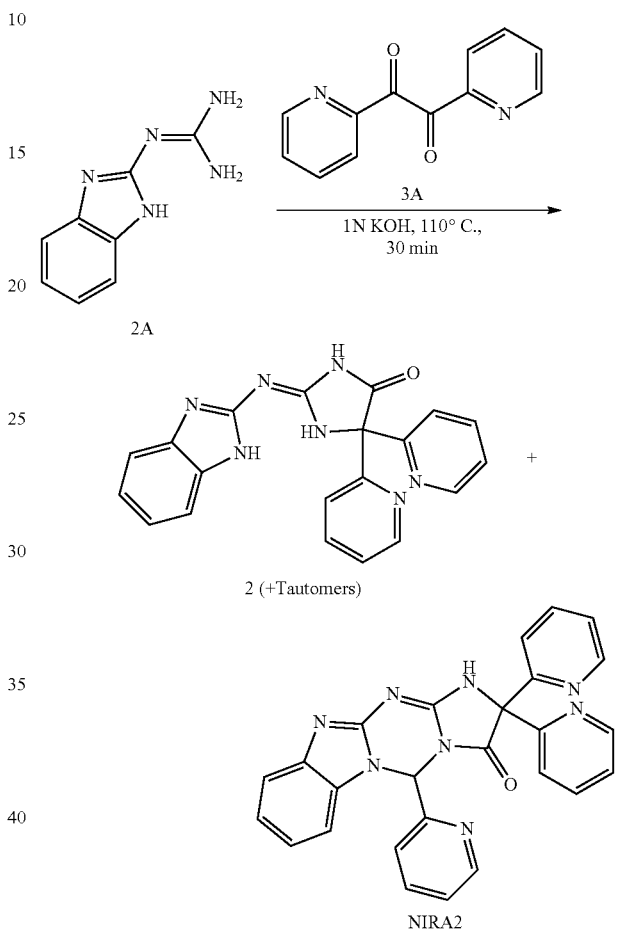

1,2-di(pyridin-2-yl)ethane-1,2-dione (5 g, 23.6 mmol) and 2-(1H-benzo[d]imidazol-2-yl)guanidine (5.37 g, 30.6 mmol) in DMSO (80 mL) was heated to 110° C. 1 M KOH solution in water (28.3 mL) was added dropwise and the mixture was kept at 110° C. for 30 min. The mixture was poured into water (300 mL) and acidified with 1 N HCl solution to pH=6. The mixture was extracted with EtOAc (3×100 mL). The combined organic phase was dried with anhydrous sodium sulfate, filtered and concentrated in vacuum. The crude product was triturated with EtOH/DMF (5:1, 50 mL) and filtered to give 1 g of 2-((1H-benzo[d]imidazol-2-yl)imino)-5,5-di(pyridin-2-yl)imidazolidin-4-one as a light yellow solid and 0.72 g of 2,2,5-tri(pyridin-2-yl)-1,2-dihydrobenzo[4,5]imidazo[1,2-a]imidazo[2,1-d][1,3,5] triazin-3(5H)-one, which was further purified by reverse phase HPLC (column: Kromasil C18 (250*50 mm*10 um); mobile phase: [water (10 mM $NH_4HCO_3$)-ACN]; B %: 15%-40%, 10 min) to afford 2,2,5-tri(pyridin-2-yl)-1,2-dihydrobenzo[4,5]imidazo[1,2-a]imidazo[2,1-d][1,3,5]triazin-3(5H)-one (NIRA2) (100 mg, 1% yield). LCMS: m/z found 459.1 [M+H]$^+$ 2,2,5-tri(pyridin-2-yl)-1,2-dihydrobenzo[4,5]imidazo[1,2-a]imidazo[2,1-d][1,3,5]triazin-3(5H)-one (NIRA2_P1) and 2,2,5-tri(pyridin-2-yl)-1,2-dihydrobenzo[4,5]imidazo[1,2-a]imidazo[2,1-d][1,3,5]triazin-3(5H)-one (NIRA2_P2)

MS: m/z found 459.2 [M+H]+; HPLC: Rt: 1.757 min; SFC: Rt=1.893 min on OJ column; ¹H NMR (400 MHz, MeOD): δ 8.62 (d, J=4.8 Hz, 1H), 8.50 (d, J=4.8 Hz, 1H), 8.42 (d, J=4.8 Hz, 1H), 7.87-7.84 (m, 4H), 7.52-7.41 (m, 5H), 7.36-7.28 (m, 2H), 7.20 (d, J=8.0 Hz, 1H), 7.10 (t, J=7.6 Hz, 1H), 7.03 (t, J=7.6 Hz, 1H).

Alternate synthetic route for NIRA2:

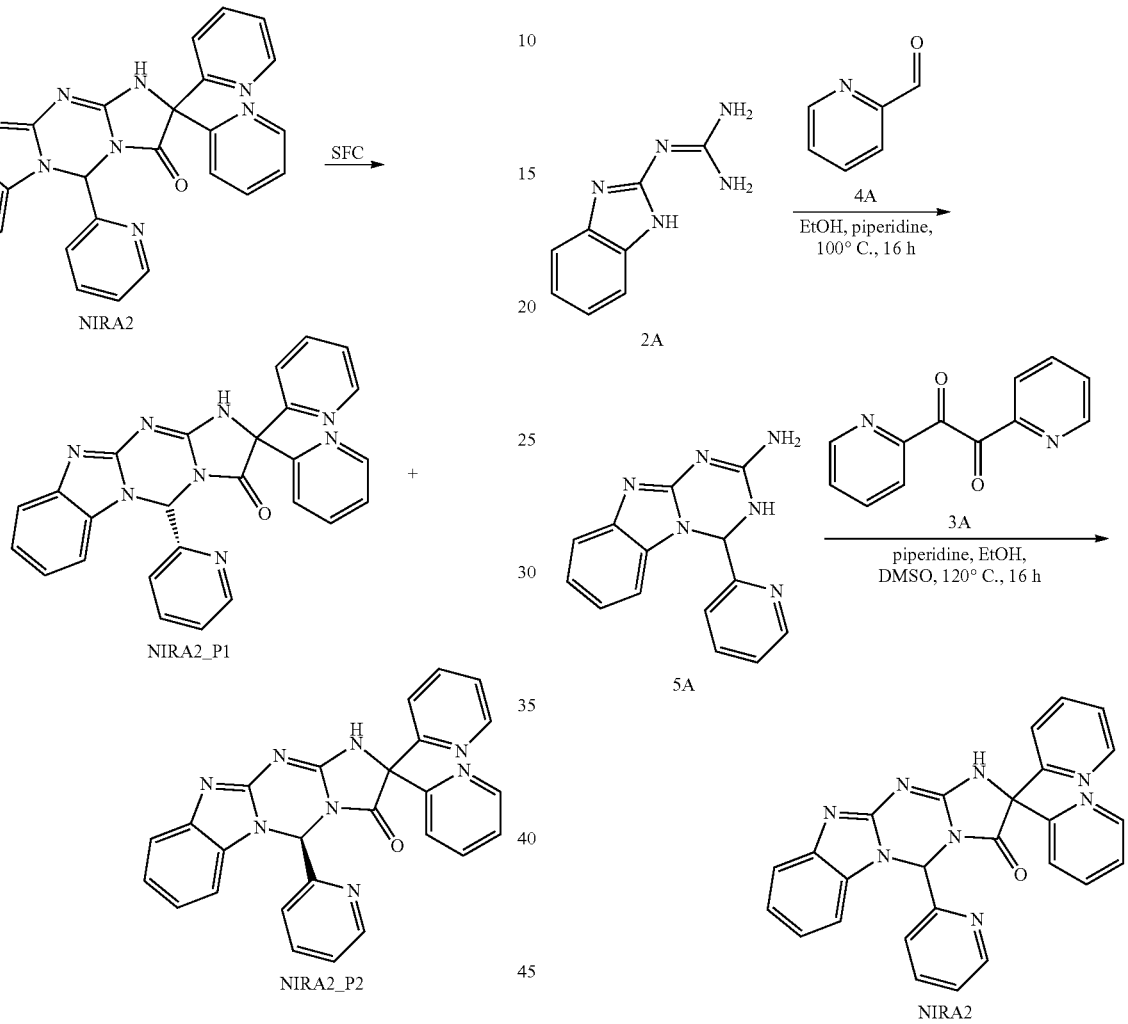

100 mg of the mixture of enantiomers was separated by SFC (column: DAICEL CHIRALCEL OJ (250 mm*30 mm, 10 μm); mobile phase: [0.1% NH₃H₂O IPA]; B %: 43%-43%, min) to give 22,25,25-tris(2-pyridyl)-29,30,31,32,33-pentazatetracyclohexadeca-(8),1(9), 16,21(29),24(31)-pentaen-23-one (NIRA2_P1) (faster eluting enantiomer, 35.75 mg, 36% yield) as white solid and 22,25,25-tris(2-pyridyl)-29,30,31,32,33-pentazatetracyclohexadeca-(8),1(9),16,21(29),24(31)-pentaen-23-one (NIRA2_P2) (slower eluting enantiomer, 37.01 mg, 37% yield) as white solid.

2,2,5-tri(pyridin-2-yl)-1,2-dihydrobenzo[4,5]imidazo[1,2-a]imidazo[2,1-d][1,3,5]triazin-3(5H)-one (NIRA2_P1): MS: m/z found 459.2 [M+H]+; HPLC: Rt: 1.751 min; SFC: Rt=1.734 on OJ column; ¹H NMR (400 MHz, MeOD): δ 8.62 (d, J=4.8 Hz, 1H), 8.50 (d, J=4.8 Hz, 1H), 8.42 (d, J=4.8 Hz, 1H), 7.86-7.84 (m, 4H), 7.51-7.41 (m, 5H), 7.36-7.28 (m, 2H), 7.20 (d, J=8.0 Hz, 1H), 7.10 (t, J=7.6 Hz, 1H), 7.03 (t, J=7.6 Hz, 1H)

2,2,5-tri(pyridin-2-yl)-1,2-dihydrobenzo[4,5]imidazo[1,2-a]imidazo[2,1-d][1,3,5]triazin-3(5H)-one (NIRA2_P2):

4-(pyridin-2-yl)-3,4-dihydrobenzo[4,5]imidazo[1,2-a][1,3,5]triazin-2-amine

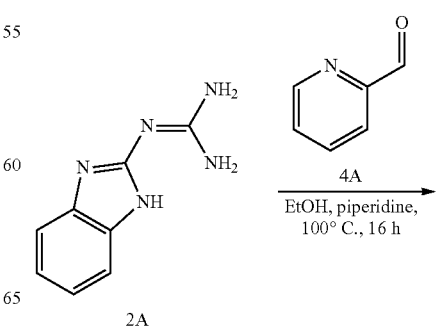

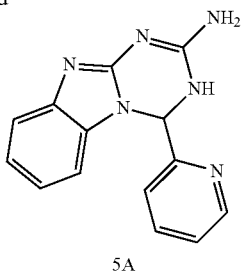

5A

To a mixture of 2-(1H-benzo[d]imidazol-2-yl)guanidine (2 g, 11.4 mmol) and pyridine-2-carbaldehyde (1.83 g, 17.1 mmol) in EtOH (40 mL) was added piperidine (0.8 mL, 7.99 mmol) under $N_2$. The mixture was stirred at 100° C. for 16 hours. The resulting white solid was collected by filtration and washed with EtOH (30 mL), dried in vacuo to give 4-(pyridin-2-yl)-3,4-dihydrobenzo[4,5]imidazo[1,2-a][1,3,5]triazin-2-amine (2.7 g, 89% yield) as a white solid. $^1$H NMR (400 MHz, DMSO-d6): δ 8.56 (d, J=4.4 Hz, 1H), 8.09 (s, 1H), 7.82 (t, J=7.0 Hz, 1H), 7.38-7.35 (m, 1H), 7.25-7.22 (m, 2H), 6.95-6.88 (m, 2H), 6.83-6.77 (m, 2H), 6.44 (brs, 2H).

2,2,5-tri(pyridine-2-yl)-1,2-dihydrobenzo[4,5]imidazo[1,2-a]imidazo[2,1-d][1,3,5]triazin-3(5H)-one (NIRA2)

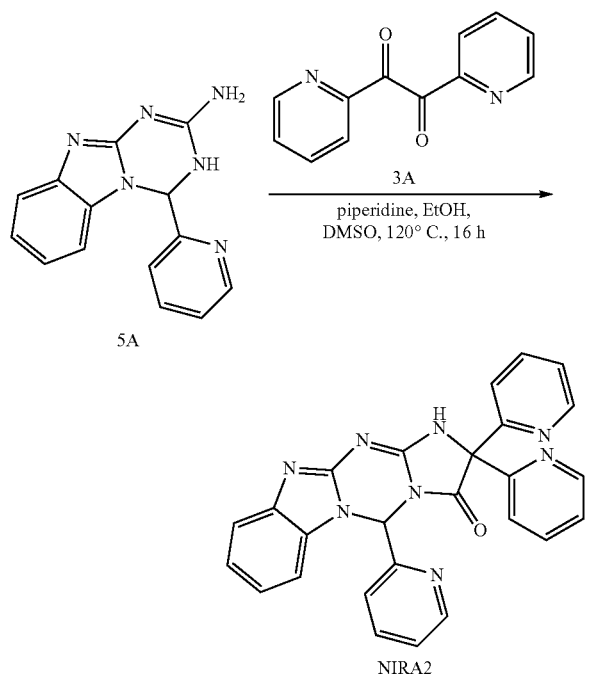

To a mixture of 4-(pyridin-2-yl)-3,4-dihydrobenzo[4,5]imidazo[1,2-a][1,3,5]triazin-2-amine (200 mg, 0.76 mmol) and 1,2-bis(2-pyridyl)ethane-1,2-dione (210 mg, 0.99 mmol) in EtOH (2 mL) and DMSO (4 mL) piperidine (38.81 mg, 0.46 mmol) was added under $N_2$. The mixture was stirred at 120° C. for 16 hours. The mixture was quenched with water (40 mL) and extracted with EtOAc (3×20 mL). The combined organic layers were dried over anhydrous sodium sulfate, filtered and concentrated under reduced pressure. The crude was purified by trituration with EtOAc (30 mL), filtered, yellow solid was dried in vacuo to give 2,2,5-tri(pyridine-2-yl)-1,2-dihydrobenzo[4,5]imidazo[1,2-a]imidazo[2,1-d][1,3,5]triazin-3(5H)-one (80 mg, 23% yield) as yellow solid. $^1$H NMR (400 MHz, DMSO_d6): δ10.43 (brs, 1H), 8.59 (d, J=4.0 Hz, 1H), 8.49 (d, J=4.0 Hz, 1H), 8.38 (d, J=4.0 Hz, 1H), 7.88-7.83 (m, 4H), 7.66 (s, 1H), 7.42-7.31 (m, 7H), 7.00-6.95 (m, 2H).

Immunoblotting. Cells were lysed in RIPA buffer, supplemented with 1% SDS, protease (Sigma P8340) and phosphatase inhibitors (Roche 04906845001). Lysates were separated on 12%, 15% or 4-20% SDS-PAGE and transferred onto PVDF membrane (Bio-Rad TurboBlot). Membranes were blocked in 5% BSA in TBS-T (0.05%) and incubated overnight with primary antibodies. Blots were washed, probed with the appropriate secondary antibodies and processed with ECL (film or Bio-Rad chemiluminescent system) or imaged on the SpectraMax i3 platform with ScanLater module (Molecular Devices).

Retrovirus production and transduction. pBabe puro HRas$^{G12V}$ plasmid was from Addgene (#9051). HRas$^{WT}$ was made by reverting G12V to G using site-directed mutagenesis. Plasmids were verified by Sanger Sequencing (CCHMC DNA Core). Retroviral supernatants were produced by transfecting HEK293T cells with pBabe-puro plasmids with pCL-Eco in 1:1 ratio using Calcium Phosphate method (Trono Lab). Supernatants were harvested 24 and 48 h post-transfection and filtered. NIH/3T3 cells were transduced overnight in the presence of polybrene (10 μg/mL) and selected with puromycin (3 μg/mL). Retroviral production and manipulation were performed in BSL-2 facilities.

Anchorage-independent growth assays. Bottom agar layer was prepared by mixing 2× complete DMEM with 1% Noble agar (BD) in a 12-well plate for a final concentration of 0.5% and allowed to solidify. For the top agarose layer for each well, 2,500 cells in 2× compete DMEM were resuspended in 0.6% low-melting agarose (IBI Scientific) and layered over the bottom agar layer. The next day, 100 μL of complete growth media containing test compounds was overlaid the upper layer to prevent desiccation. Media was refreshed twice weekly. After 21 days, colonies were stained with 0.1% p-iodonitro tetrazolium violet (Sigma-Aldrich), imaged using an EVOS microscope (Life Technologies), and counted.

Spheroid formation assay. Spheroids were formed by the hanging drop method or using ultra-low attachment (ULA) plates (Corning). For the hanging drop assay, cells were trypsinized, resuspended at 25,000 cells/mL in complete media containing vehicle (DMSO), or the indicated concentrations of IODVA1, and plated in 25 μL drops on an inverted lid of a 10-cm dish. The dish was filled with 7 mL PBS, the lid replaced and incubated for 3-5 days. For mechanical testing of spheroid compaction, spheroids were first imaged on EVOS microscope, repeatedly pipetted 7-9 times, then imaged again to assess spheroid disruption. For the ULA-based spheroid formation, 5,000 cells were resuspended in 500 μL of complete media containing vehicle (DMSO) or the indicated concentrations of IODVA1 and plated in 24-well ULA plates (Corning). Spheroid formation was monitored daily and imaged using EVOS microscope (Life Technologies). For assessment of attachment-free proliferation, the contents of the well were transferred into an Eppendorf tube, centrifuged at 100×g for 5 min, dissociated into a single cell suspension using trituration and Accutase (Invitrogen) treatment at room temperature and counted using trypan blue exclusion.

Active GTPase binding assays: Levels of active Ras, Rac, Cdc42 and RhoA were determined using the Active Ras Pull-Down and Detection Kit, Active Rac Pull-Down and Detection Kit (Thermo Scientific) and RhoA/Rac1/Cdc4 Pull-down Activation Assay Combo Biochem Kit (Cytoskeleton). Cells were cultured and treated as indicated and lysed in buffer provided by the manufacturer. Clarified whole cell lysates were incubated with recombinant GST-Raf1-RBD (for active Ras) (amino acids 1-149) and glutathione beads (both supplied by the manufacturer), GST-Rhotekin-RBD (for active RhoA), GST-PAK-GBD (for active Rac and Cdc42) for 1 h at 4° C., washed and the resulting complexes eluted from the resin by boiling in 2×SDS sample buffer. Proteins were resolved by SDS-PAGE, transferred to nitrocellulose and the level of active GTPase relative to input lysate were determined by immunoblotting analysis using the anti-Ras, anti-Rac, anti-Cdc42, or anti-RhoA antibody supplied by the manufacturer.

Kinase Assay: The Reaction Biology (reactionbiology.com) HotSPot miniaturized radioisotope filter binding assay platform was used to measure the activity of 369 wild-type kinases in presence of a single IODVA1 dose (Anastassiadis et al., 2011). In brief, for each reaction, kinase and substrate were mixed in a buffer containing 20 mM HEPES (pH 7.5), 10 mM $MgCl_2$, 1 mM EGTA, 0.02% Brij35, 0.02 mg/ml BSA, 0.1 mM $Na_3VO_4$, 2 mM DTT, and 1% DMSO. IODVA1 was then added to a final concentration of 0.5 μM to each reaction mixture. After 20 min incubation at room temperature, reaction was initiated by adding ATP (Sigma-Aldrich) and [γ-$^{32}$P]-ATP (PerkinElmer, specific activity of 10 Ci/L). Reactions were incubated for 2 h at room temperature and spotted onto P81 ion exchange cellulose chromatography paper (Whatman). Filter paper was washed in 0.75% phosphoric acid to remove excess ATP. The percent remaining kinase activity relative to a vehicle-containing (DMSO) kinase reaction was calculated for each kinase/IODVA1 pair. Each kinase inhibition assay was done in duplicates and averaged. Data were processed and analyzed in Excel.

Immunofluorescent analysis of Actin cytoskeleton: MDA-MB-231 cells were seeded at a density of 2×10$^4$ cells per chamber in an 8-chamber glass slide with or without EGF (5 ng/ml) for 10 min. After treatment with 1 uM IODVA1, cells were fixed in 4% paraformaldehyde, permeabilized in 0.2% TritonX-100, then stained with phalloidin conjugated to Alexa Fluor568 (1:100) and ProLong Gold with DAPI (both Life Technologies, Thermo-Fisher). Staining was visualized with a Nikon MR confocal microscope.

Immunofluorescence and microscopy: For assessment of lamellipodia initiation and maturation, assays were performed in two ways. 1) MDA-MB-231 were plated on fibronectin-coated coverslips in serum-free media for 4 h, followed by 1 h incubation with IODVA1 (0-3 μM) in serum-free media. Cells were then EGF stimulated (50 ng/mL) for 30 min to induce lamellipodia formation. Cells were fixed in 4% paraformaldehyde, permeabilized in 0.2% Triton-X 100 and stained with Phalloidin Alexa Fluor 568 or 594 and mounted in ProLong Gold DAPI (Life Technologies). 2) MDA-MB-231 cells were seeded at a density of 2×10$^4$ cells per chamber in an 8-chamber glass slide with or without EGF (5 ng/ml) for 10 min. After treatment with 1 μM IODVA1, cells were fixed and processed as in 1). Staining was visualized with a Nikon MR confocal microscope. 10-random fields were imaged and analyzed for lamellipodia formation. For assessment of circular dorsal ruffle formation, NIH-3T3 cells were processed as in (Steffen et al., 2013). Briefly, cells (4×10$^4$) were plated on fibronectin-coated coverslips, serum-starved for 4 hours and treated with IODVA1 (0-3 μM) in serum-free media for 1 hour. Ruffling was induced with PDGF BB (50 ng/mL, Peprotech) for 10 min. Cells were fixed in 4% paraformaldehyde and processed for immunofluorescence microscopy as above. Around 150 cells were counted per treatment group per experiment. For assessment of stress fibers, cells were plated on fibronectin-coated coverslips for 4 hours in serum-free media, incubated with IODVA1 (0-3 μM) for 1 h, fixed and processed with fluorescent phalloidin as before.

For cell spreading, MDA-MB-231, MCF7 and T47D were seeded on fibronectin-coated coverslips in serum-free media. After 10 min, IODVA1 (0-3 μM) was added in serum-free media. After 30 min (40 min total), cells were fixed in 4% paraformaldehyde and imaged using bright field microscopy (EVOS, Life Technologies). Six random fields were imaged under 20× objective and cell area of individual cells were quantified to assess the degree of spreading (ImageJ). Over 300 cells were counted per treatment group per experiment.

In vivo analysis using MDA-MB-231 xenograft mouse model: For xenograft studies, 1×10$^6$ MDA-MB-231 cells were suspended in PBS and injected into each inguinal mammary fat pad of nulliparous, 10-week old female athymic nude mice. Tumors were measured weekly with digital calipers and volume was calculated as $[(\pi/6) \times L \times W^2]$ (Euhus et al., 1986; Tomayko and Reynolds, 1989). Treatment began eight weeks post-injection, when tumors reached 200 mm$^3$. Mice received intraperitoneal injections of 250 uL of diluent (5% DMSO in PBS) or 1 mM of compound IODVA1 three times weekly for 4 weeks, for an average drug dose of 3.5 mg/kg. At necropsy, the mice were weighed and the tumors were excised, measured, weighed, fixed in 4% paraformaldehyde, and embedded in paraffin. Peripheral blood was collected by cardiac puncture and analyzed with a Hemavet (Drew Scientific, Miami Lakes, FL, USA) for complete blood counts. Usage and handling of mice were performed with the approval of the Cincinnati Children's Institutional Animal Care and Use Committee. All mice were housed in specific pathogen free housing with ad libitum access to food and water.

Histology: Tissues were fixed in 4% paraformaldehyde then paraffin embedded tissues were cut into 5 μm sections. Tissues were stained with either hematoxylin and eosin (H&E) or by immunofluorescence. Tissue sections were subjected to sodium citrate antigen retrieval, blocked with 10% normal goat serum, and incubated with antibodies to Ki67 (1:100, Abcam) or cleaved caspase 3 (Asp175, 1:100, Cell Signaling) then goat anti-rabbit:Alexa568 (1:500, Abcam). Tissues were counterstained with 4',6-diamidino-2-phenylindole (DAPI) and coverslipped with VectaShield HardSet (Vector Labs). Images were acquired by confocal microscopy (Nikon) and immunofluorescence analysis was performed using Image J.

In vivo analysis of H2122 xenograft Mouse Model. Human lung cancer cell line NCI-H2122 (ATCC) harboring biallelic KRAS$^{G12C}$ mutations were cultured in RPMI-1640 supplemented with 10% FBS. For injections, NCI-H2122 cells were trypsinized and suspended at a concentration of 2×10$^7$ cells/mL in 50% Matrigel (Corning). 100 μl of cell suspension was injected subcutaneously into 6-week old NOD. Cg-Prkdc$^{scid}$ Il2rg$^{tm1Wjl}$/SzJ (NSG) mice. Beginning 10 days post-xenograft, mice received intraperitoneal injections every other day for 14 days (7 injections total). A 200 mM IODVA1 stock solution in DMSO was freshly diluted 1:19 in DMSO then subsequently diluted 1:9 in PBS to achieve a 1 mM final concentration in 10% DMSO. Mice were injected with 250 µl of vehicle (10% DMSO) or IODVA1 (1 mM). Tumor size was measured using digital calipers and tumor volume estimated using the formula (length×width$^2$)/2. For immunostaining, paraffin-embedded sections were stained with Ki-67 antibody (clone SP6, ThermoFisher) at a dilution of 1:1,000. DAB stained slides were counterstained with nuclear-fast red stain. For quantification of Ki-67 positive cells, random fields were imaged at 200× magnification and quantified using Image J software. A minimum of 20 random fields were used for quantification. Scale bar=100 µm.

Notes: Vehicle treated mice had readily visible mitotic cells. IODVA1 had increased intratumoral fibrosis. Both vehicle and IODVA1 tumors had centralized necrosis, typical for subcutaneous tumors at that size.

Inhibition of Rac Activity

Rac GTPases (Rac1, Rac2, Rac3, and RhoG) are tightly regulated signaling switches that mediate inputs from various receptors and oncogenes to regulate growth, apoptosis, cell-cell and cell-matrix interactions in response to growth factors such as EGF, PDGF, and HGF. Regulation of the actin cytoskeleton, which plays a key role in cell shape, polarity, division, migration and metastasis, is a major function of Rac, as it promotes membrane ruffling and formation of lamellipodia and circular dorsal ruffles (Etienne-Manneville, 2002; Jaffe & Hall, 2005; Bustelo, 2018; Ridley & Hall, 2015; Ridley, 1992; Steffen, 2013). Rac also controls cell cycle progression and cell survival, integrin-mediated adhesion, and is required for Ras transformation (Coleman, 2004; Kiosses, 2001; Sundaresan, 1996; Mack, 2011; Qiu, 1995). Furthermore, Rac is pivotal in most aggressive types of leukemias (Thomas, 2007; Somervaille, 2006; Wei, 2008; Sengupta, 2010; Skorski, 1998; Mizukawa, 2011; Bassermann, 2002; Nieborowska-Skorska, 2012). Thus, Rac has been associated with pro-tumorigenic functions and linked to the development of cancer. Moreover, Rac is characteristic of resistance to chemo-, radio-, and targeted-therapies and associated with persistence of leukemic stem cell (Jaffe & Hall, 2005; Loirand, 2010; Mulloy, 2010; Newey, 2005; Sahai, 2002; Vigil, 2010; Porter, 2016; Zandvakili, 2017; Cardama, 2018).

Reducing Rac activity, specifically in cancer cells, is desirable and is an active area of research. However, no small molecule inhibitor of Rac signaling is in clinical use despite the many efforts. Rac activity is regulated by an intricate and well-orchestrated set of proteins comprised of guanine nucleotide exchange factors (GEFs), GTPase-activating proteins (GAPs), and guanine dissociation inhibitors (GDIs). RacGEFs activate Rac by exchanging the bound GDP to GTP to initiate signaling while GAPs deactivate Rac by increasing the rate of GTP hydrolysis to arrest signaling. GDIs extract Rac from membranes, thereby preventing it from signaling. When activated, Rac binds to and activates downstream effectors such as the p21-activated kinases (PAK1/2/3), which in turn activate pro-survival pathways and actin-regulating proteins. Rac regulators and effectors are themselves subject to tight regulation. For example, Vav proteins (Vav1, Vav2, and Vav3) are multi-domain tyrosine phosphorylation-dependent RacGEFs. Phosphorylation of specific tyrosine residues releases an N- and C-terminal autoinhibition mechanism allowing Rac to access the Dbl-homology (DH) domain necessary for the GTP-exchange reaction. Therefore, finding a small molecule inhibitor of Rac itself or its activator, such as the Vav proteins, will provide an effective strategy for treatment of malignancies with aberrant Rac signaling.

In this study, applicants reveal the mechanism of action (MoA) of IODVA1, a 2-guanidinobenzimidazole derivative identified as the active ingredient in NSC124205. Initial characterization of IODVA1 showed that it is not a kinase inhibitor but that it prevents lamellipodia and circular dorsal ruffle formation at low concentrations and within minutes of cell exposure. It also decreases cell-cell and cell-extra cellular matrix interactions and reduces growth of Ras-driven tumors. These properties and the specificity of IODVA1 to oncogene expressing cells hinted that it targets Rac activation. The Applicants used in vitro and in vivo leukemic models of the chimeric BCR-ABL1 oncoprotein B-cell acute lymphoblastic leukemia (Ph$^+$ B-ALL) to study the MoA of IODVA1. BCR-ABL1 B-ALL models are well-suited for this endeavor for several reasons. First, BCR-ABL B-ALL is a single-driver genetic model. Expression of BCR-ABL, which has constitutive kinase activity is sufficient to promote the growth advantage of leukemic cells. When expressed, BCR-ABL1 activates a variety of pathways including the Ras-mitogen-activated protein kinase (MAPK) leading to abnormal cell proliferation, the Janus-activated kinase (JAK)-STAT pathway leading to impaired transcriptional activity, and the phosphoinositide 3-kinase (PI-3K)/AKT pathway resulting in prolonged survival (Cilloni, 2012). In addition, expression of p190- or p210-BCR-ABL activates Rac signaling pathways to regulate leukemogenesis (Skorski, 1998; Thomas, 2008; Harnois, 2003; Sahay, 2008) and deleting Rac2 or the combination of Rac1 and Rac2, impairs myeloid leukemogenesis induced by p210-BCR-ABL expression in the hematopoietic stem and progenitor cell compartment (Thomas, 2007; Sengupta, 2010). Second, seemingly complex pathways activated by BCR-ABL all depend on the deregulated kinase activity of BCR-ABL (Lugo, 1990) and ABL1-tyrosine kinase inhibitors (ABL1-TKIs), e.g. imatinib, are used as first-line therapy. Thus, imatinib can be used as positive control to assess the efficacy of IODVA1. Third, despite their tremendous success in treating B-ALL in the clinic, appearance of mechanisms of TKI-dependent and -independent resistance limited their efficacy (Arrigoni, 2018; Hamilton, 2012). Thus, there is an unmet need for novel treatments of patients with TKI-resistant leukemia and treatments that prevent leukemic-cell persistence.

Here, the Applicants show that IODVA1 binds tightly and inhibits Vav3, consequently leading to the deactivation of Rac and of its downstream signaling and to the induction of apoptosis specifically in BCR-ABL expressing cells in vivo and in vitro. Further, the Applicants show that IODVA1 prolongates the survival of a mouse model of TKI-resistance and reduces its leukemic burden long after treatment was withdrawn. The Applicants also show that IODVA1 is effective in decreasing proliferation and survival of relapsed and de novo primary patient-derived cells. It is believed that IODVA1 is the first inhibitor of a RhoGEF with in vivo activity against xenograft mouse models of cancer. The Applicants findings have direct implications for overcoming TKI-resistance in the clinic and for treating cancers where Vav3 is a target, including Ras-driven cancers.

Results

Figure 10:
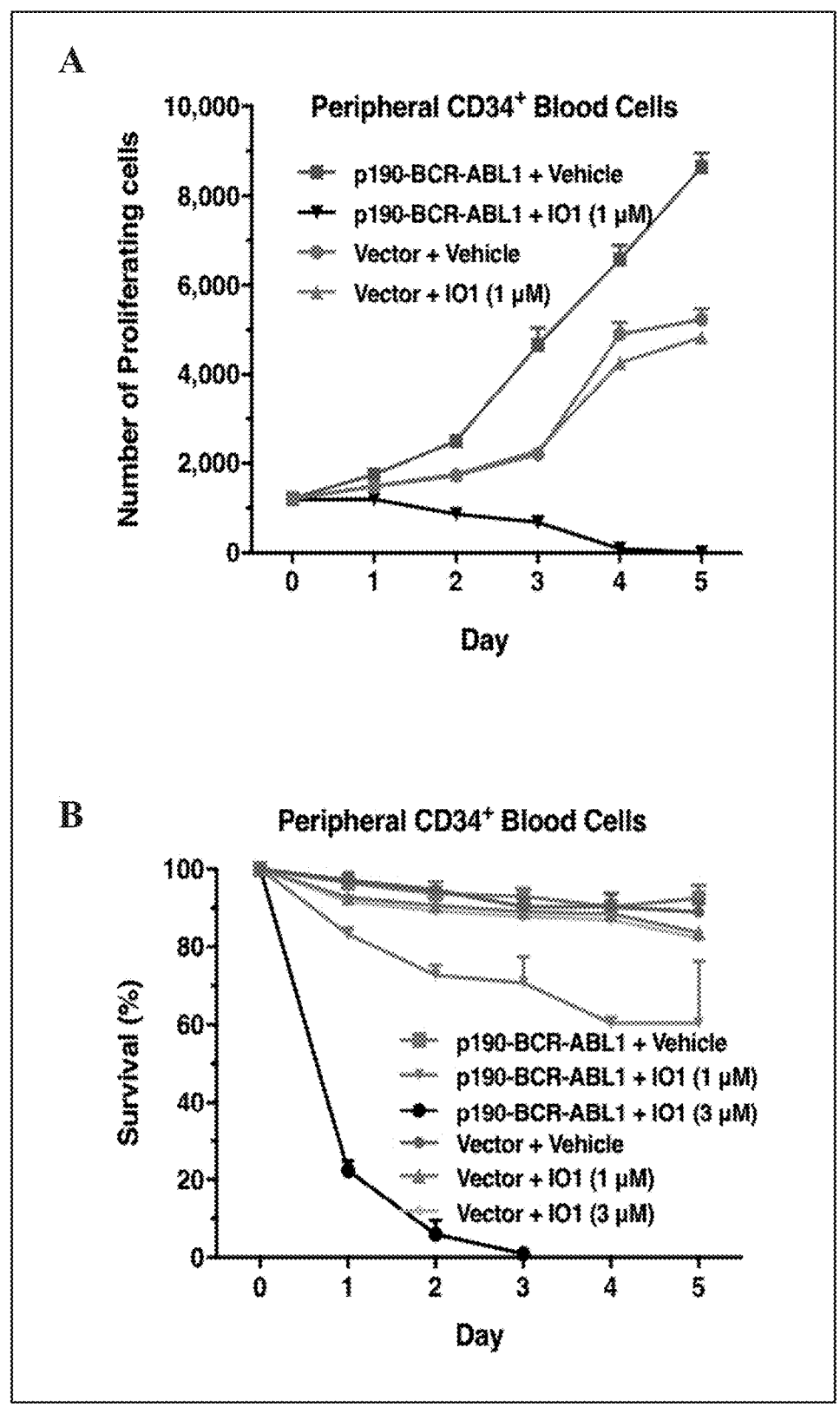
FIG. 10: IODVA1 inhibits the proliferation and survival of BCR-ABL expressing cells in vitro and in vivo and eradicates leukemia propagating cells in secondary transplants. (A) Human peripheral $CD34^+$ blood cells transduced with p190-BCR-ABL1 (grey line, squares, and black line, inverted triangles) or Mieg3 empty vector (lilac lines, circles and triangles) virus were co-cultured on OP-9 stromal cells and incubated with either vehicle or IODVA1 (IO1, 1 μM). Cell proliferation was assessed by flow cytometry. (B) Cells were transduced and cultured as in (A) but incubated with either vehicle or IODVA1 (IO1, 1 or 3 μM) and survival (%) was determined by trypan blue exclusion. (C) Kaplan-Meier plot showing survival of p190-BCR-ABL1 leukemic mice post-treatment with vehicle control, IODVA1 (IO1), imatinib (IM), or the combination at the indicated concentrations in the pump. LDBM cells were transduced with bicistronic p190-BCR-ABL1/EGFP retrovirus and transplanted into recipient mice. After initial assessment of leukemic burden, drugs were delivered in subcutaneously implanted osmotic pumps, each lasting two weeks. (D) Kaplan-Meier survival plot of secondary mice transplants with the $10^6$-cell dilution. Bone marrow cells from mice treated with vehicle, imatinib (IM), IODVA1 (IO1) or the combination at the indicated concentrations were transplanted into secondary recipients.
Figure 10:
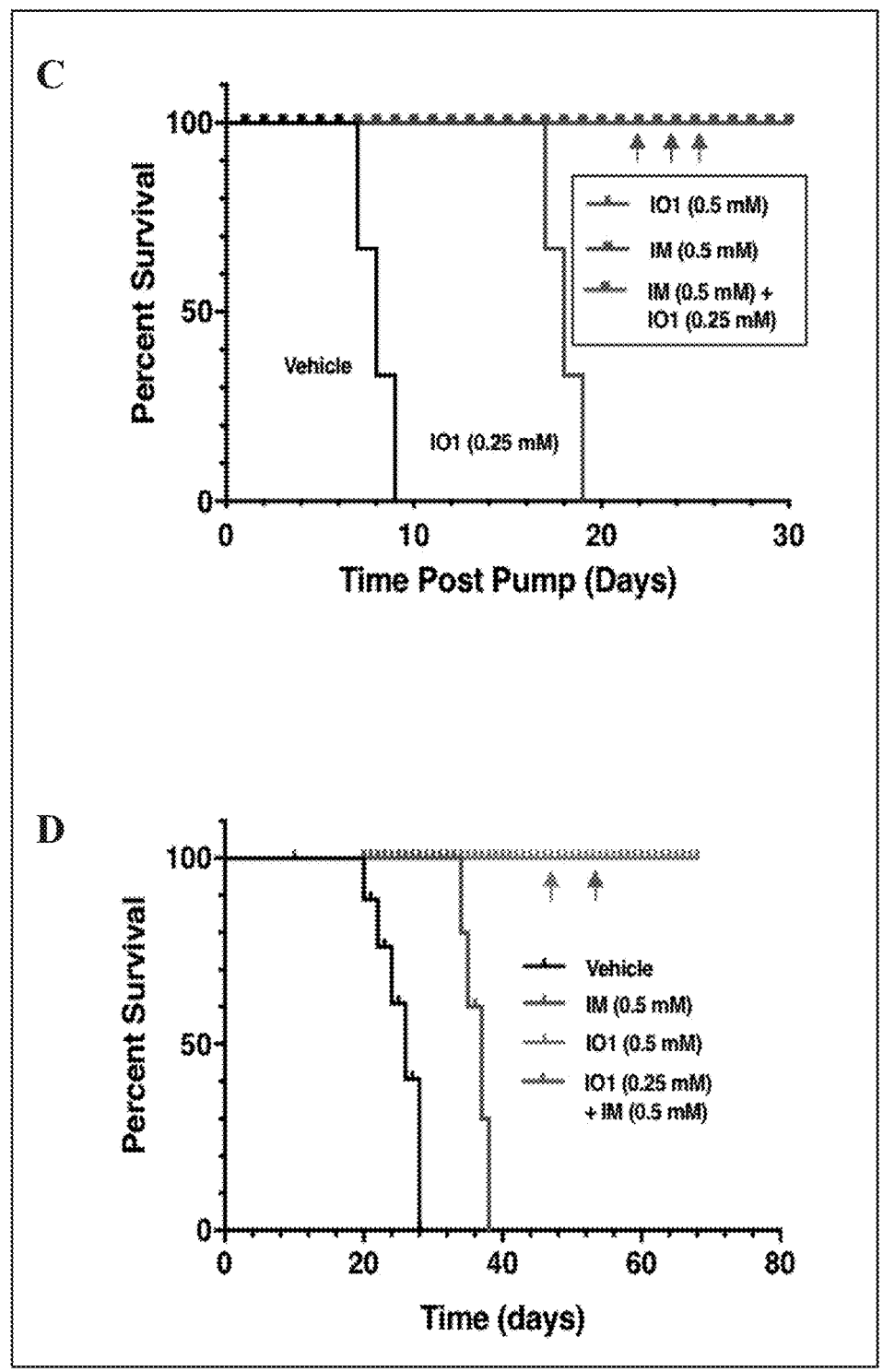

IODVA1 specifically targets BCR-ABL B-ALL cells in vitro. To confirm that IODVA1 is specific for oncogene-expressing cells, we tested its efficacy on the proliferation and survival of CD34$^+$ human peripheral blood mononuclear cells transduced with retroviral bicistronic p190-BCR-ABL or Mieg3 empty vector (Williams, 2000). As expected, expression of BCR-ABL increased cell proliferation (FIG. 10A). Treatment with IODVA1 (IO1, 1 µM) decreased proliferation of BCR-ABL-transformed cells, while proliferation of empty vector Mieg3 transduced cells was not affected. We then assessed survival of p190-BCR-ABL-transformed CD34$^+$ cells in the presence of IODVA1 by trypan blue exclusion. The survival of p190-BCR-ABL expressing cells decreased in a dose-dependent manner to 60±16% (SEM, N=3) at 1 µM on day 5 and to 1±0.2% (SEM, N=3) at 3 µM on day 3 (FIG. 10B). Survival of empty vector-expressing cells was not affected by IODVA1. IODVA1 irreversibly inhibits survival of p190- and p210-BCR-ABL1 but not empty vector (Mieg3)-expressing Ba/F3 cells with a half maximal effective concentration (EC50) of 380 nM, Nalm-1 cells with an EC50 of 680 nM, and inhibits the clonogenic ability of BCR-ABL1-transformed Ba/F3 cells in soft agar (FIG. 11A-11D). Together, these results indicate that IODVA1 specifically targets proliferation and survival of BCR-ABL1-transformed cells and are consistent with our previous report that IODVA1 is more specific to oncogene expressing cells (Gasilina et al., 2020).

Figure 11:
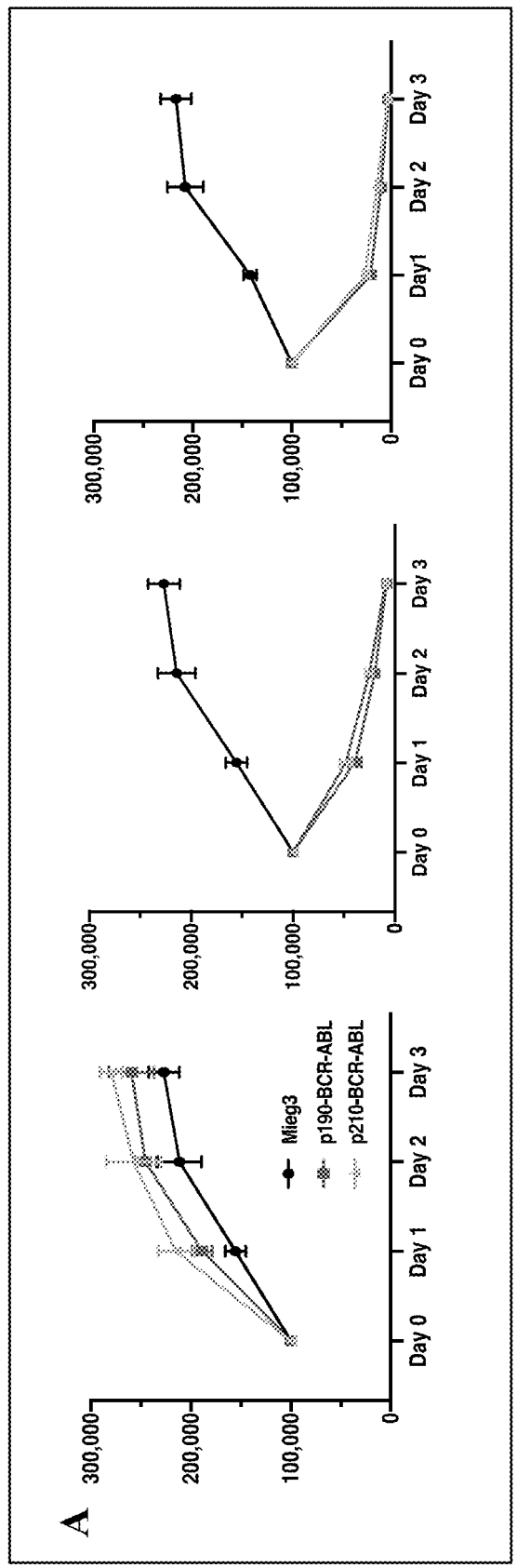
FIG. 11: IODVA1 inhibits the proliferation and survival of BCR-ABL1 expressing cells in vitro and in vivo and eradicates leukemia propagating cells in secondary transplants. (A) Leukemic Ba/F3 cells transduced with p190-BCR-ABL1 (grey squares), p210-BCR-ABL1 (light grey triangles), or Mieg3 empty vector (black circles) were grown in the presence of vehicle control or IODVA1 (IO1) at 1 and 3 μM and counted daily for 3 days using trypan blue exclusion. (B) IODVA1-dependent survival curves of empty vector (red circles) or p190-BCR-ABL1 (black circles) expressing Ba/F3 cells and of Nalm-1 cells. Fitting of the data was done in Prism version 8.4. (C) p190-BCR-ABL1 (grey line) or Mieg3 (black line) expressing Ba/F3 cells were allowed to grow for 1 day, treated with IODVA1 (IO1, 1 μM) for 1 day, and washed (black arrow). Cells were counted for 7 days using trypan blue exclusion. (D) Ba/F3 cells stably expressing p190-BCR-ABL1 were subjected to colony formation assay in soft agar (0.25% Noble Agar in RPMI/FBS/IL-3) in the presence of DMSO or IODVA1 (1 or 10 μM). Colonies were allowed to form for 10 days then stained with iodonitrotetrazolium (1 mg/mL). Data are representative of at least three independent experiments in triplicates. Note the smaller colony size in 1 μM IODVA1 treatment group. (E) Leukemic burden (%) of treated mice before treatment (left upper panel) and at the indicated treatment time was analyzed by flow cytometry of bone marrow aspirates as population containing $B220^+/CD43^+$ pro-B cells. (F) Count (%) of residual leukemic ($EGFP^+$-BCR-ABL1) cells in peripheral blood at weeks 3 and 5 for the secondary transplant mice from FIG. 1D. (G) Kaplan-Meier survival plot of secondary mice transplants with the $0.3\times10^6$ cell-dilution. (H) Count (%) of residual leukemic ($EGFP^+$-BCR-ABL1) cells in peripheral blood at weeks 3 and 5 for the secondary transplant mice from (G). (I & J) similar to G & H but with the $0.1\times10^6$ cell-dilution.
Figure 11:
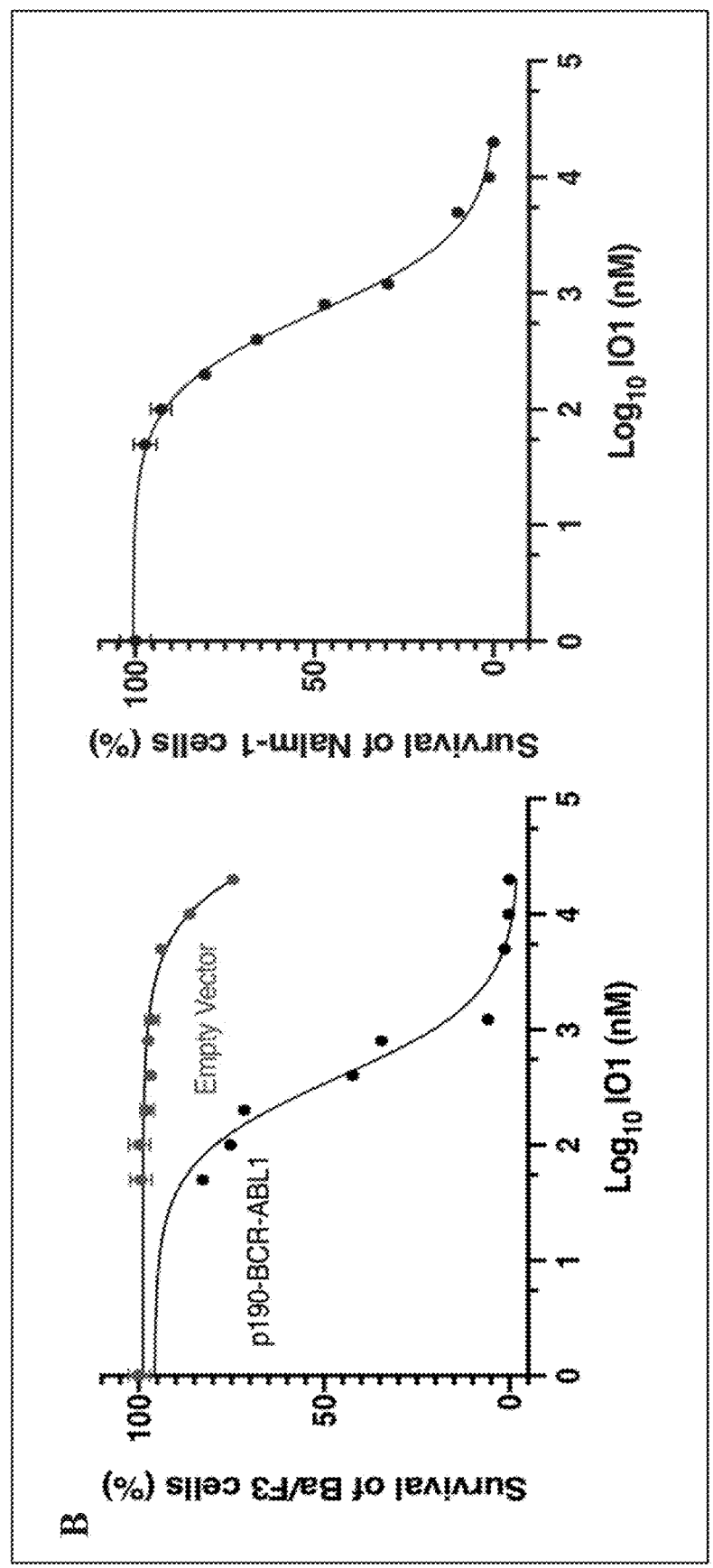
Figure 11:
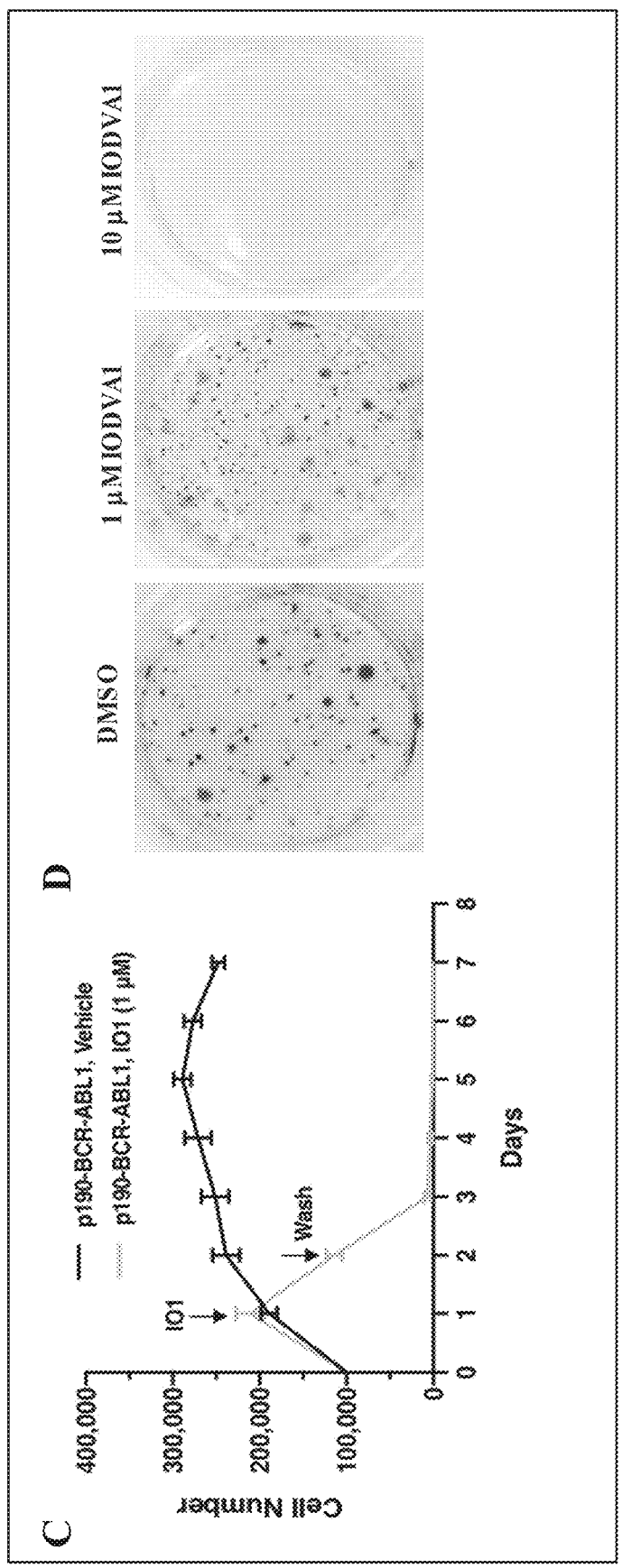
Figure 11:
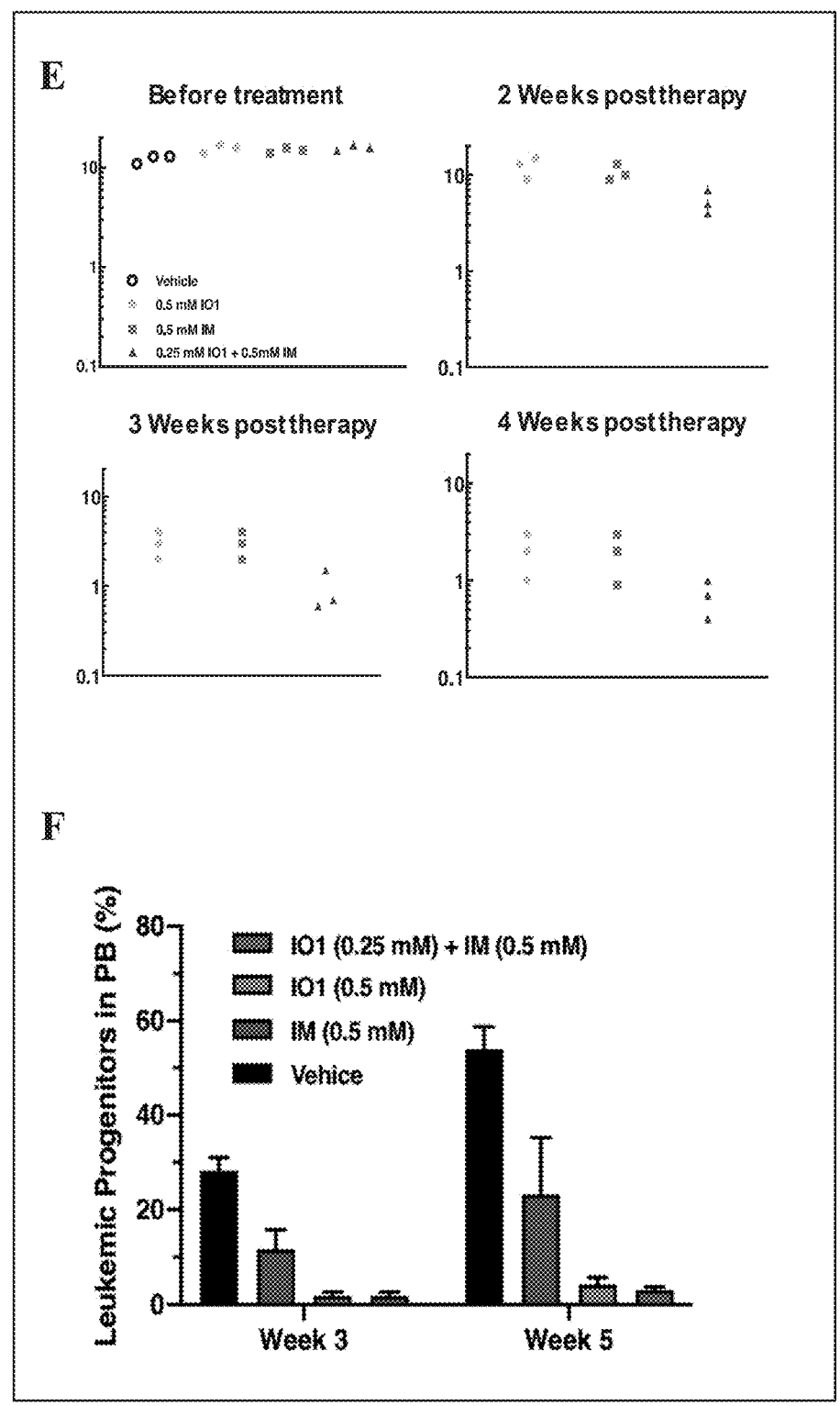
Figure 11:
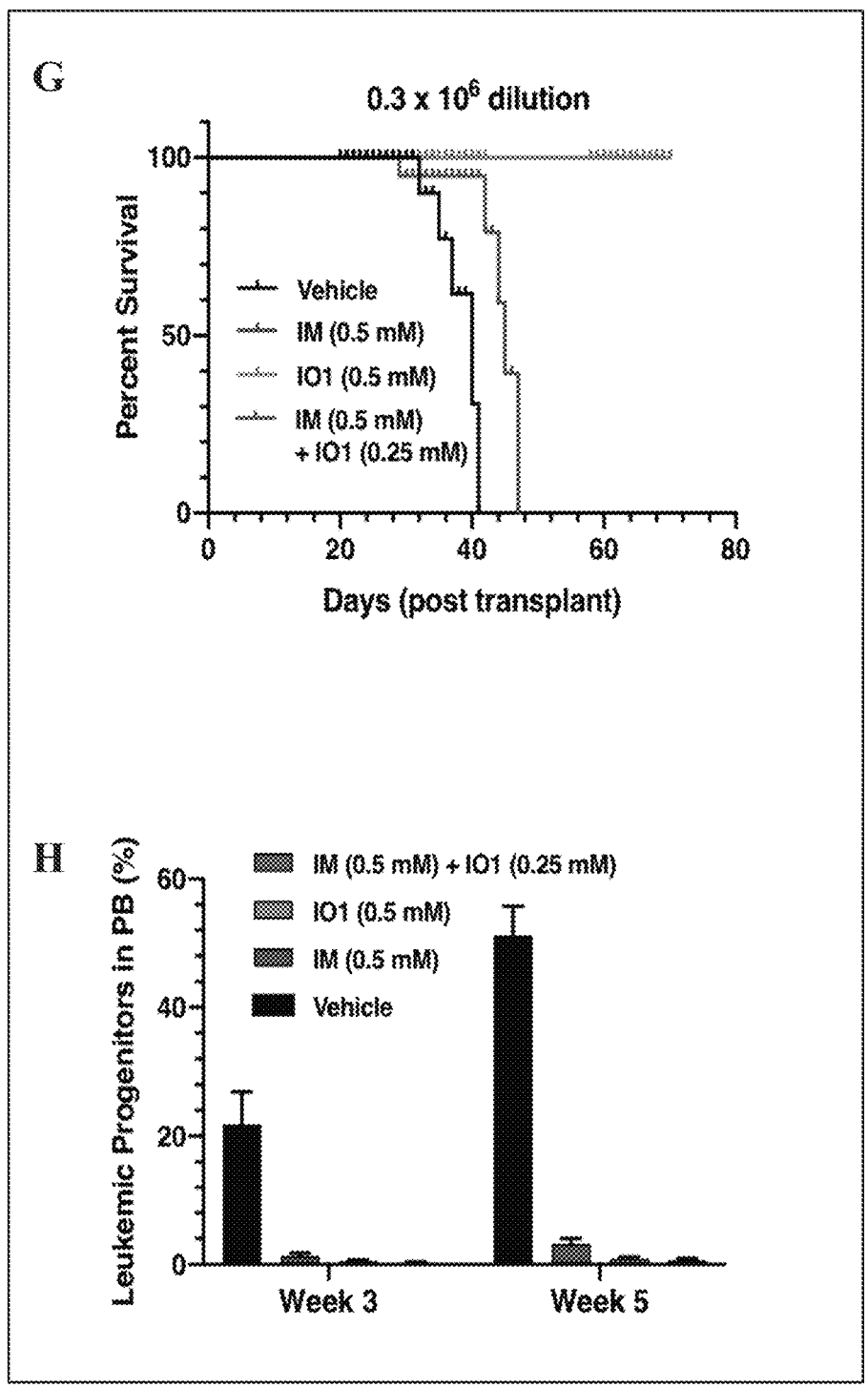
Figure 11:
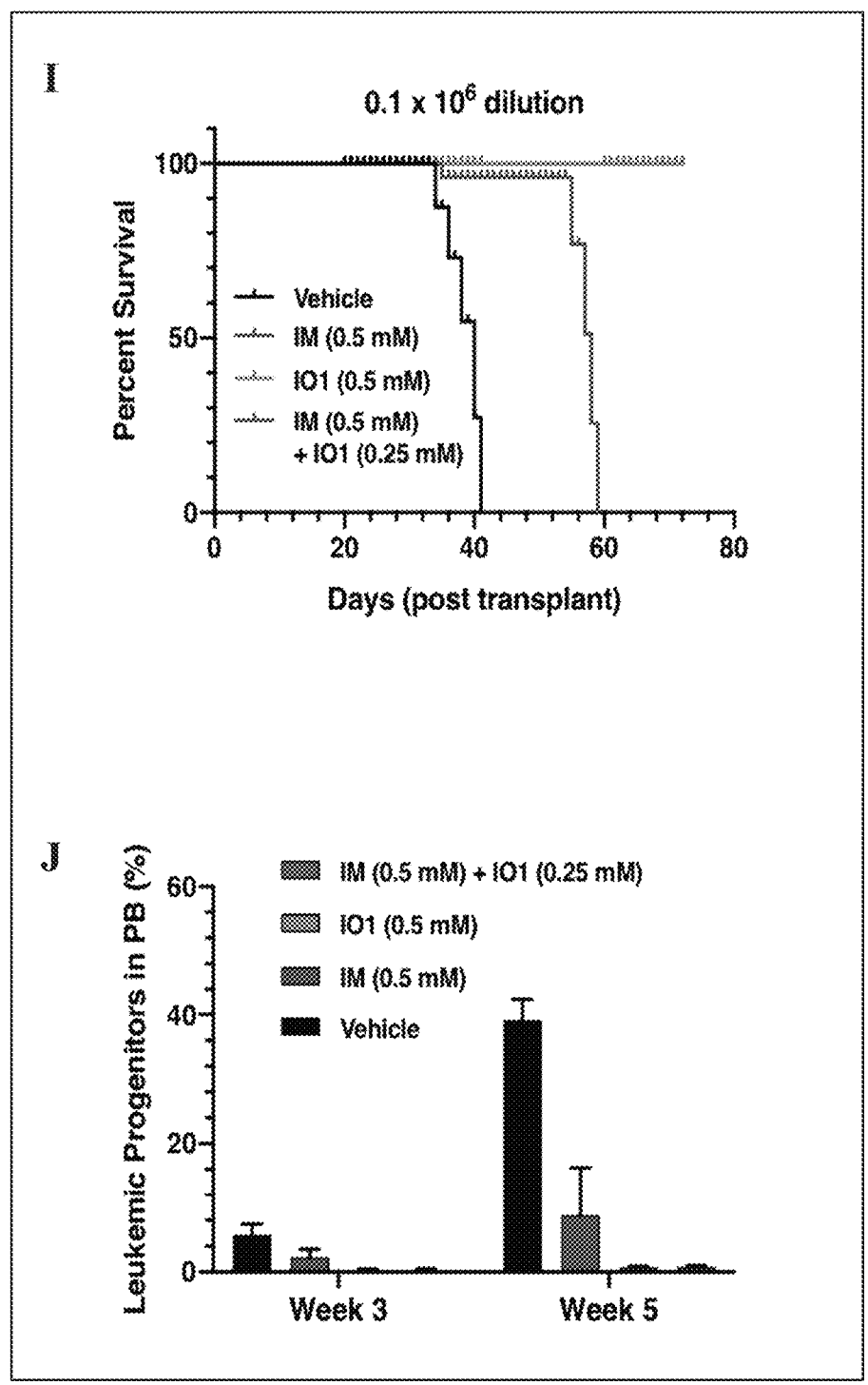

IODVA1 prevents leukemia-related death and significantly decreases the leukemia burden in a BCR-ABL-induced leukemic murine model. To test if IODVA1's potency on cells can be recapitulated in vivo, applicants probed its efficacy on a murine model of p190-BCR-ABL induced B-ALL and compared it to imatinib, an ABL1-TKI with well-characterized MoA in mouse models of Ph$^+$ B-ALL used as first-line therapy in Ph$^+$-induced malignancies in the clinic. C57Bl/6 mice were used as donors and/or recipients of transduction/transplantation model. Mouse low-density bone marrow (LDBM) cells were transduced with a MSCV-driven bicistronic retroviral vector (MSCV-IRES-EGFP) encoding p190-BCR-ABL. Transduced LDBM cells (1×10$^6$) were intravenously transplanted into lethally irradiated C57Bl/6 mice. Mice were bled post 23 days and GFP$^+$ cells were analyzed by flow cytometry. All mice had developed leukemia by day 28. Leukemic mice were stratified into 5 groups (7 mice per group) and administered either PBS control vehicle, 0.25 or 0.5 mM IODVA1, 0.5 mM imatinib, or the combination 0.25 mM IODVA1+0.5 mM imatinib. Vehicle control group had the same DMSO amount (0.1%) as the other groups. Drugs were administered subcutaneously in osmotic pumps for continuous slow release for 4 weeks. Mice survival plot shows that while the control group had died within 7 to 10 days post administration of the PBS vehicle, the low IODVA1 dose (0.25 mM) increased survival by an average of 10 days. Mice treated with imatinib or 0.5 mM IODVA1 or the combination were alive for the 4-week duration of the therapy (FIG. 10C). Significantly, IODVA1 decreased the residual p190-BCR-ABL expressing leukemic progenitor B-cells (EGFP$^+$/B220$^+$) from peripheral blood (PB) of treated mice (FIG. 11E).

IODVA1 eradicates leukemic propagating activity assessed by serial transplantation. Despite its significant clinical success, imatinib and, more generally, TKIs do not eliminate leukemic stem/progenitor cells in the bone marrow (BM), which can lead to residual disease, appearance of mechanisms of resistance, and ultimately relapse (Milojkovic, 2009; Bixby, 2009). To determine if IODVA1 eradicates progenitor B-cells with ability to propagate tumors as a functional surrogate of minimal residual disease capable of leukemia relapse, BM cells from vehicle-control and treated mice from FIG. 10C (without the 0.25 mM IODVA1-treated mice) were transplanted into lethally irradiated secondary C57BL/6 mice in a limiting dilution series of 1×10$^6$, 0.3× 10$^6$, and 0.1×10$^6$ cell doses and analyzed for leukemia development and survival in the absence of any additional therapy. Kaplan-Meier survival plots for the 10$^6$-cell dilution transplant indicate that administration of IODVA1 alone or in combination with imatinib resulted in survival of p190-BCR-ABL chimeric mice beyond the 70-day endpoint analysis (FIG. 10D). Mice transplanted with BM cells from primary recipient mice treated with imatinib alone died by day 40 post-transplantation. Analysis at week 5 post transplantation of the leukemic progenitor cells (EGFP$^+$/B220$^+$) from the peripheral blood of secondary transplanted mice (FIG. 11F) indicate that IODVA1 is superior to imatinib at eradicating leukemic cell burden. Poisson's distribution analysis of the lower cell dose transplantations (FIG. 11G-11J) indicates >10-fold depletion of tumor propagating activity in grafts from IODVA1- or IODVA1+imatinib-treated leukemic mice compared with leukemic mice treated with imatinib alone.

Figure 12:
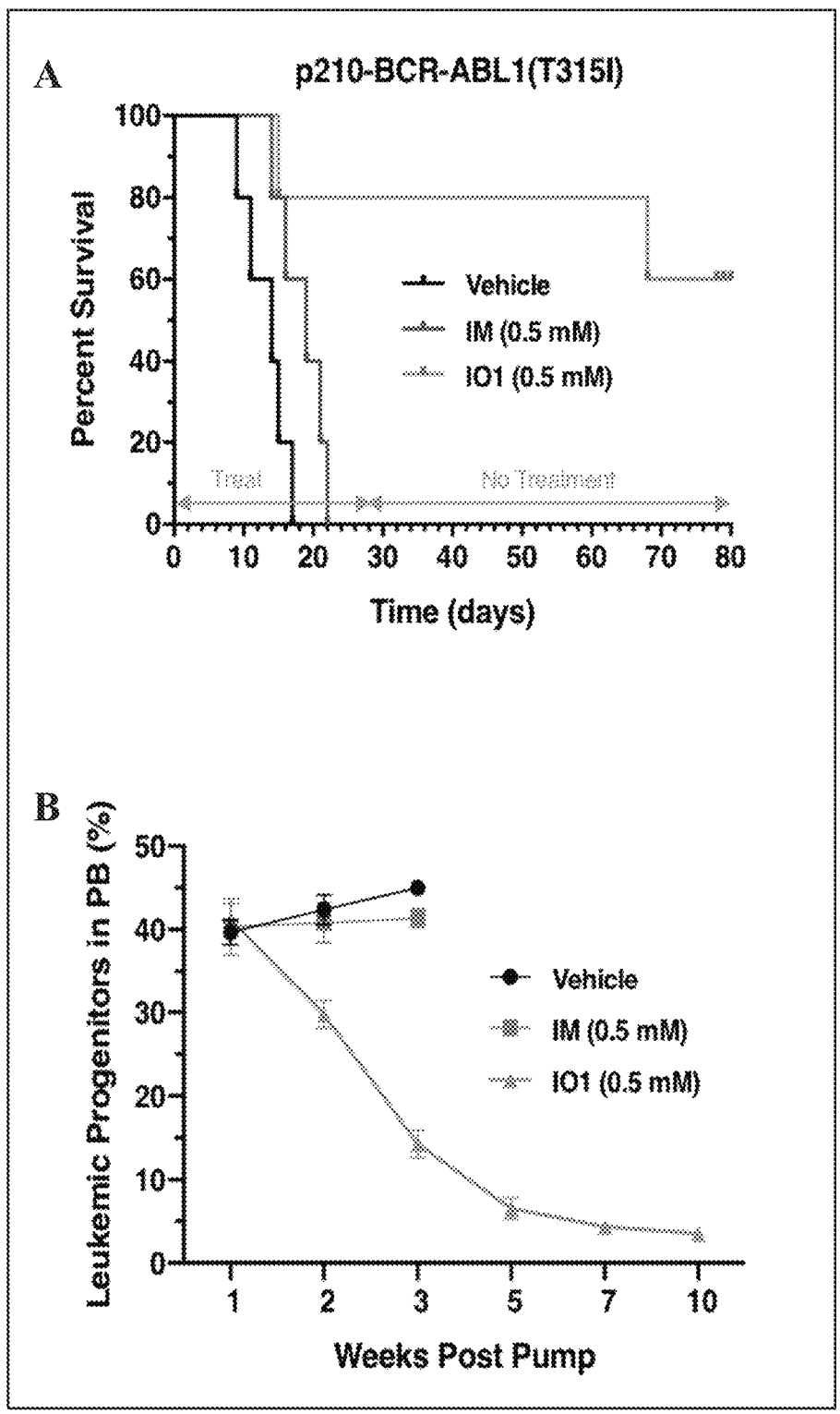
FIG. 12: IODVA1 but not imatinib increases the survival of a mouse model of TKI-resistant B-ALL. LDBM cells were transduced with TKI-resistant p210-BCR-ABL1 (T3150 (gatekeeper mutant) and transplanted into recipient mice as in FIG. 10. Pumps were surgically introduced into mice (N=5 per treatment group) and treatment lasted 28 days or two rounds of pumps. After 28 days, mice were monitored without any additional treatment. (A) Kaplan-Meier survival plot of imatinib-resistant mice. Pumps either carried vehicle control (black line), 0.5 mM imatinib (IM, grey line), or 0.5 mM IODVA1 (IO1, lilac line). (B) Flow cytometric analysis of leukemic progenitor ($EGFP^+$) B-cells in peripheral blood (PB) at the indicated week. Only IODVA1-treated mice remained alive for analysis at weeks 5, 7, and 10. (C) Pharmacodynamic assessment of leukemic progenitor cells (%) from the 2-week treated mice with vehicle control (black), imatinib (grey), or IODVA1 (lilac) using phospho-flow analysis of the indicated Rac-dependent and -independent effectors. * $p\leq0.05$, ** $p\leq0.01$.
Figure 12:
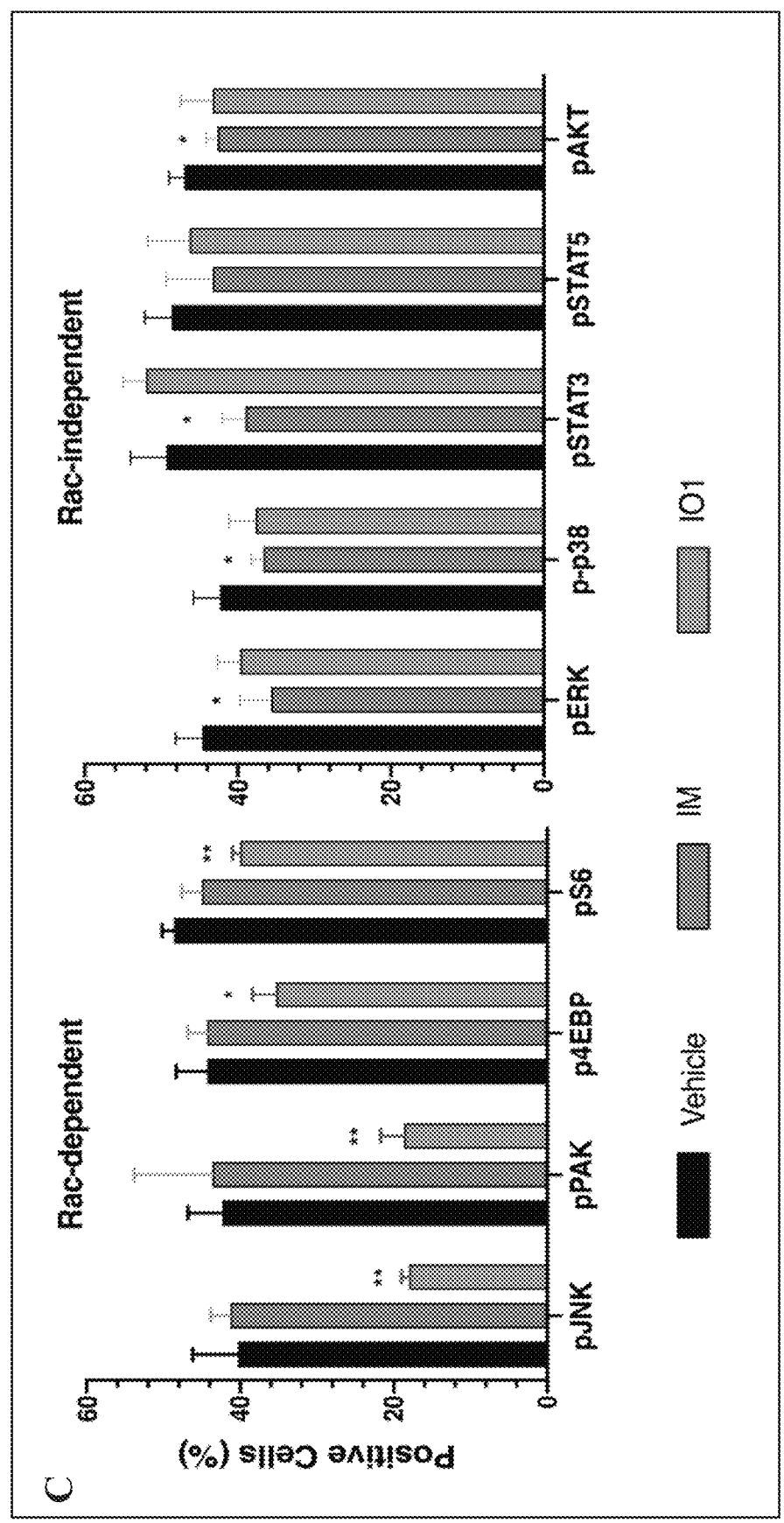

IODVA1 eradicates TKI-resistant BCR-ABL B-ALL. Because IODVA1 has no inhibitory activity against major wild-type kinases including ABL1 and SRC-like kinases, the anti-proliferative activity of IODVA1 towards in vitro and in vivo BCR-ABL B-ALL models and its ability to eradicate residual disease cannot be explained by ABL1 inhibition. To further test this idea, we evaluated the ability of IODVA1 to increase the survival of mice harboring p210-BCR-ABL (T315I). We chose this ABL1 mutant because it is one of the most frequent mutations arising in chronic myelogenous leukemia (CML) patients on imatinib therapy (Gorre, 2001; Azam, 2003; Jabbour, 2006; Nicolini, 2006; Jabbour, 2008). Mice were treated for 4 weeks with two rounds of pumps containing vehicle control, imatinib, or IODVA1. At the end of the 4-week treatment, surviving mice were kept in their cages without any additional treatment. As expected, p210 (T315I) mice did not respond to the TKI as all imatinib-treated mice died by day 22, before the end of the treatment (FIG. 12A). 80% of IODVA1-treated mice survived until day 65, 37 days post last treatment. 60% of IODVA1-treated mice survived till day 80, 52 days post last treatment (FIG. 12A). Counts of EGFP$^+$/B220$^+$ leukemic progenitor cells from the T315I-leukemic mice peripheral blood indicated that IODVA1 significantly decreased leukemic progenitor levels by 24% by week two, by 84% by week 5, and by 91% by week 10 (FIG. 12B).

To assess signaling pathways affected by IODVA1, EGFP$^+$/B220$^+$ LDBM cells were isolated from two-week treated p210(T315I) mice, stained with phospho-antibodies against the pro-proliferative Rac-dependent effectors JNK, PAK, 4EBP, and S6 and the Rac-independent effectors ERK1/2, STAT3, STAT5, p38, and AKT, and analyzed by flow cytometry. IODVA1 resulted in significant decreases in pJNK by 55% (p=0.0029), pPAK by 56% (p=0.0016), p4EBP by 20.3% (p=0.037), and pS6 by 17.8% (p=0.0012), respectively (FIG. 12C). Phosphorylation levels of p38, ERK, STAT3, STAT5, and AKT were not affected by IODVA1. Interestingly, imatinib had the opposite effect, it decreased the levels of pERK, pSTAT3, and pAKT but did not affect the phosphorylation levels of the Rac-dependent effectors. Taken together, IODVA1 not only overcomes TKI-resistance but also eliminates TKI-resistant leukemic stem/progenitor cells likely by acting on imatinib-independent growth signaling pathways that involve Rac effectors.

Figure 13:
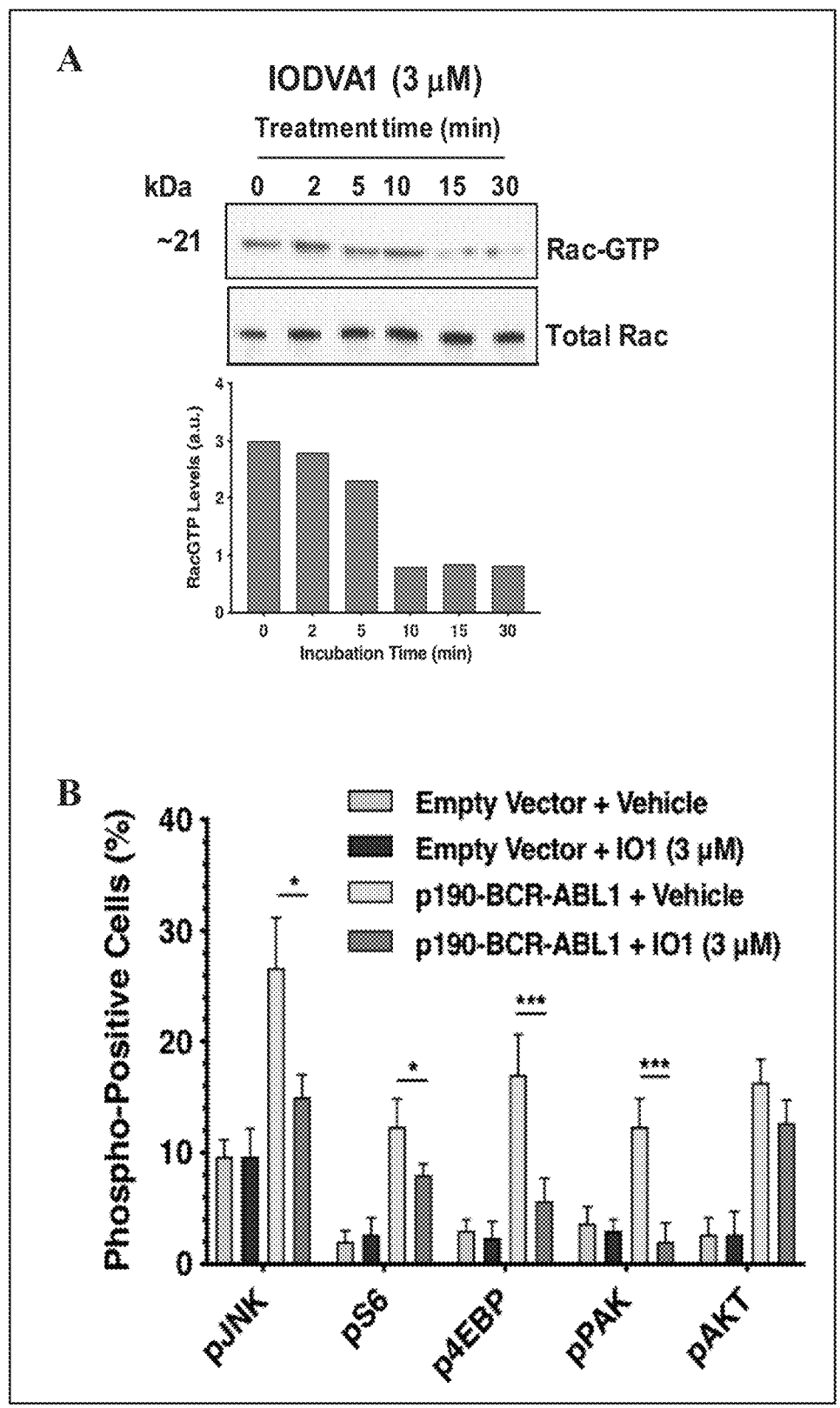
FIG. 13: IODVA1 decreases Rac activation and signaling. (A) Ba/F3 cells expressing p190-BCR-ABL1 were treated with IODVA1 (3 μM) as indicated and levels of active Rac (Rac-GTP) were assessed by pull-down using GST-PAK-GBD, followed by immunoblotting (upper panel) and densitometric quantification (lower panel). (B) Flow-cytometry analysis of pJNK, pS6, p4EBP, pPAK1, and pAKT of Ba/F3 cells expressing Mieg3 empty vector (light and dark blue) or p190-BCR-ABL1 (light and dark salmon) and treated with vehicle control or IODVA1 (3 μM) for 30 min. (C) Representative histogram data of the cell cycle analysis of Ba/F3 cells expressing p190-BCR-ABL and treated with vehicle control or IODVA1 (1, 3, and 10 μM) for 20 h. (D) Quantification of the average number of colonies of bone marrow wild-type (black) and $Rac1^{\Delta/\Delta}+Rac2^{-/-}$ (red) p190-BCR-ABL1 leukemic cells treated with vehicle control or IODVA1 (IO1, 1 μM). ns—not significant, * $p\leq0.05$,  $p\leq0.01$, * $p\leq0.001$. (E) As in FIG. 13A, but cells were incubated for a fixed amount of time (1 h) at the indicated IODVA1 concentrations. (F) Ba/F3 cells expressing p190-BCR-ABL1 were treated with IODVA1 (3 μM) and lysed at the indicated times. Cell lysates were separated on SDS-PAGE and immunoblotted for pPAK(T423), pBAD(S136), and BAD. (G) Ba/F3 cells expressing p190-BCR-ABL1 were treated with IODVA1 (3 μM) and levels of active Cdc42 (Cdc42-GTP) and Rho (Rho-GTP) were assessed by pull-down at the indicated times using GST-PAK-GBD and GST-Rhotekin respectively, followed by immunoblotting (left panel) and densitometric quantification (right panel). (H) Morphology of $GFP^+$ leukemic colonies (left panel). Western blot analysis of Rac1 and Rac2 protein expression in $Rac1^{\Delta/\Delta}+Rac2^{-/-}$ cells post poly-I:C injections (right panel). (I) Intrinsic (blue line) and p50GAP-stimulated GTP-hydrolysis reaction in the presence (red line) or absence (black line) of IODVA1. (J) Sedimentation assay of liposomal Rac1-GDP in the presence of IODVA1 (2 μM). Rac1 was visualized by immunoblotting from pellet (p) and soluble (s) fractions. (K) Stopped-flow measurement of GDI (10 μM) interaction with fluorescently-labeled Rac1 in the absence (black line) or presence (orange line) of IODVA1.
Figure 13:
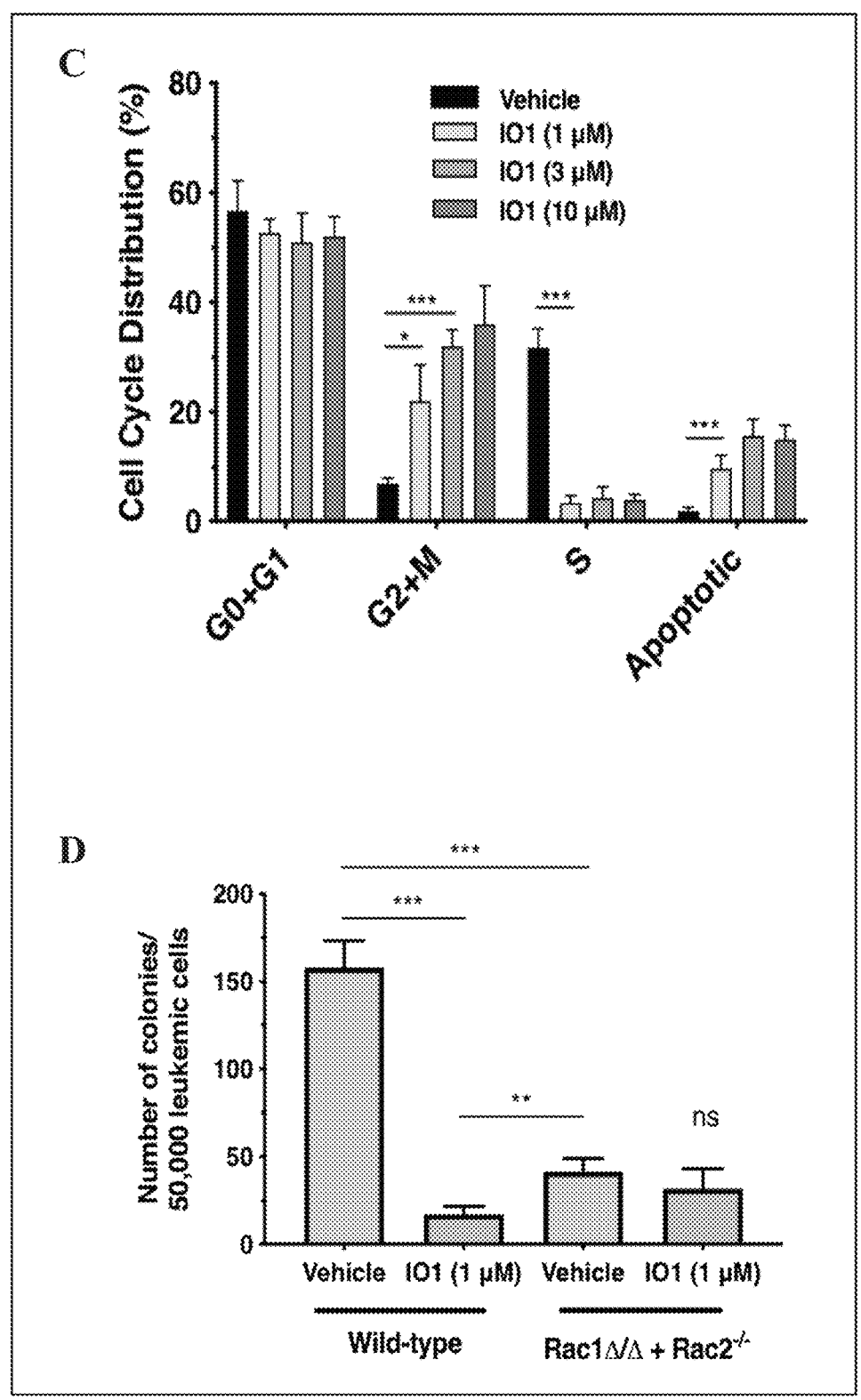
Figure 13:
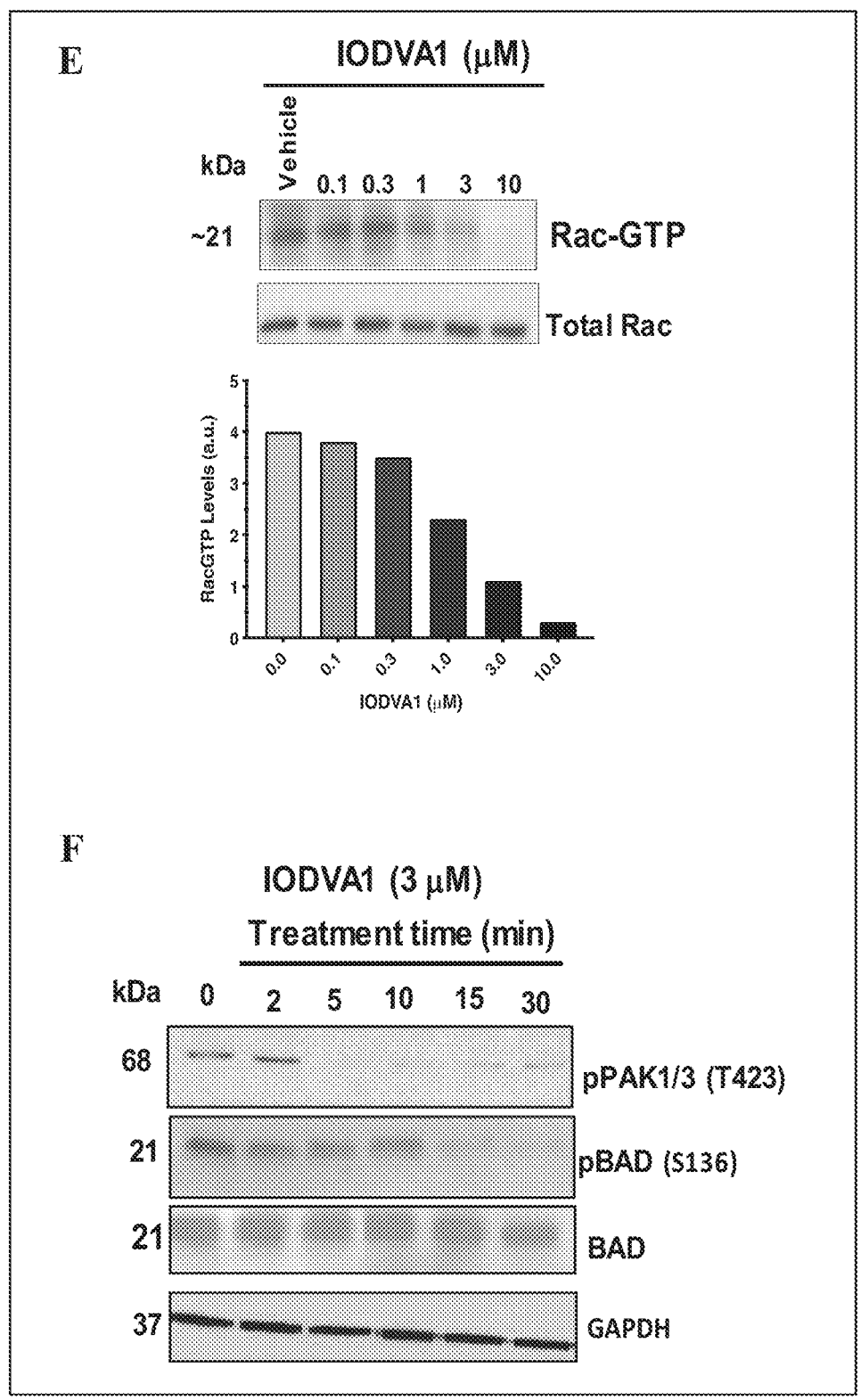
Figure 13:
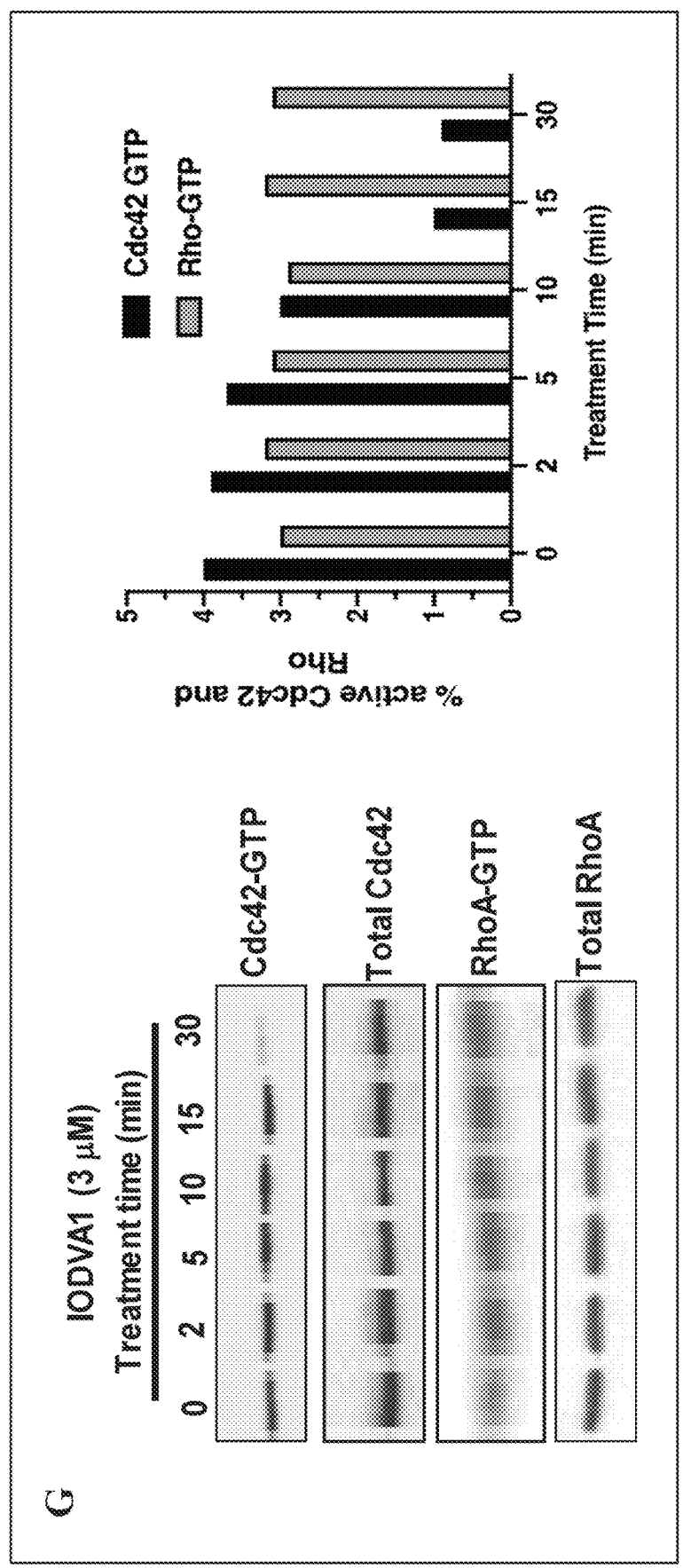
Figure 13:
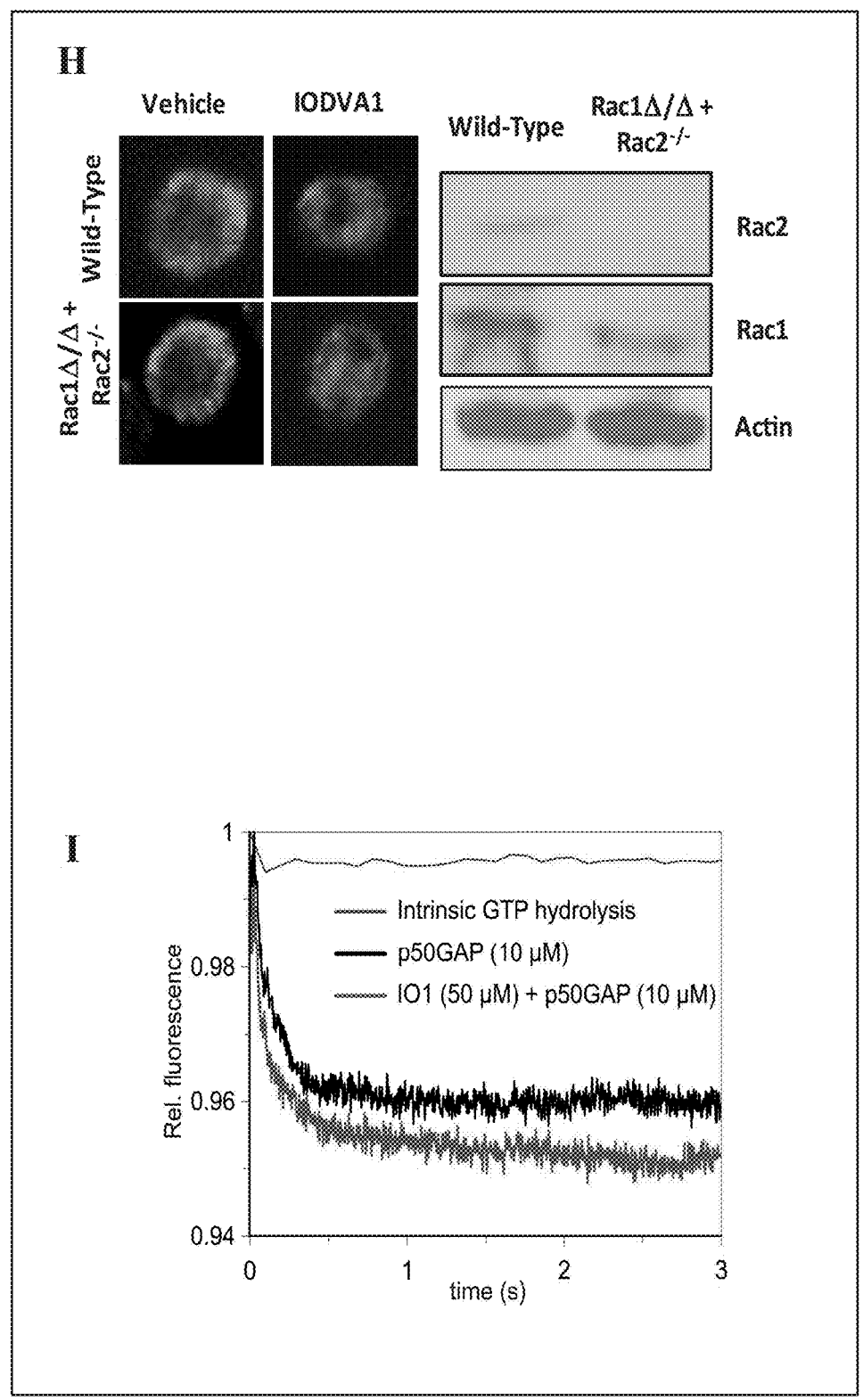
Figure 13:
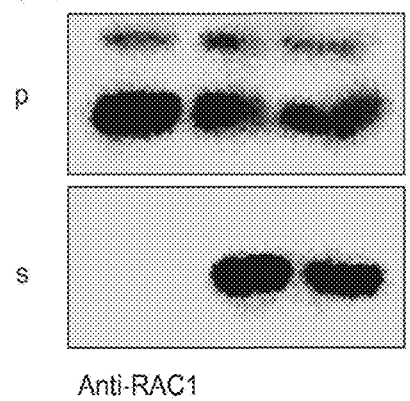
Figure 13:
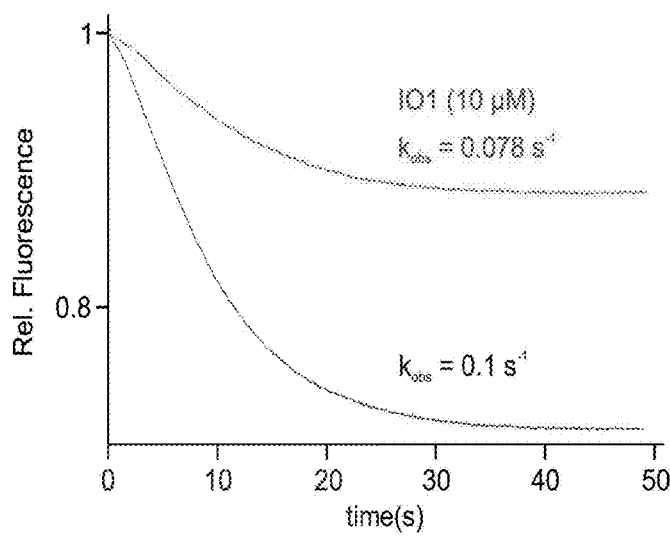

IODVA1 decreases Rac activity and downstream signaling. Having shown that IODVA1 prevents formation of F-actin suprastructures, such as lamellipodia and circular dorsal ruffles, within minutes of cell incubation (FIG. 5A-5B and Gasilina et al., 2020) we focused on Rac. Rac is a major regulator of lamellipodia formation and of JNK and TORC1 activities (Minden, 1995; Saci, 2011) and is required for circular dorsal ruffles formation and is also activated downstream of BCR-ABL. We thus tested if IODVA1 inhibits Rac activation and measured levels of Rac-GTP during treatment using PAK-GBD (GTPase-binding domain). A 70% decrease in the levels of active Rac occurs 10-15 minutes post incubation of p190-BCR-ABL transformed Ba/F3 cells with IODVA1 (3 μM, FIG. 13A). Interestingly, this 10-minute time point is consistent with the IODVA1-driven decrease in lamellipodia formation in MDA-MB-231 breast cancer cells (FIG. 5C). IODVA1 is specific to Rac (IC50=1 μM) and is less effective on Cdc42 and not on RhoA (FIG. 13G). Interestingly, rapid effect on and specificity to Rac by IODVA1 are consistent with the MDA-MB-231 breast cancer cells.

To test if the decrease in Rac activation is translated into a decrease in its downstream signaling in vitro as was observed with xenograft-derived TKI-resistant cells (FIG. 12C), we analyzed vehicle- and IODVA1-treated p190-BCR-ABL or empty vector expressing Ba/F3 cells by phospho-flow cytometry. Expression of BCR-ABL1 increases the phosphorylation levels of JNK, S6, 4EBP, PAK, and AKT by more than 2.5 times (FIG. 13B). IODVA1 decreases the phosphorylation levels of JNK by 1.8 (p=0.015), S6 by 1.5 (p=0.05), 4EBP by 3.0 (p=0.009), and PAK by 6.1 (p=0.004) fold, respectively. Importantly, IODVA1-induced decrease in the phosphorylation levels of effectors is specific to BCR-ABL1—but not empty vector-expressing cells. IODVA1 did not affect the phosphorylation levels of AKT regardless of the oncogene BCR-ABL status (FIG. 13B). The decrease in JNK, S6, and 4EBP activity in IODVA1-treated Ba/F3 cells mirrors the decrease observed in LDBM cells from IODVA1-treated p210-T315I mice in pharmacodynamics studies (FIG. 12C). Together, our in vitro and in vivo data are consistent with IODVA1 targeting activation of Rac and its downstream signaling.

Significantly, IODVA1 decreases Rac downstream pro-survival PAK and decreases inhibitory phosphorylation of pro-apoptotic BAD Ser136 activities within minutes of cell exposure (FIG. 13F). The decrease in PAK and BAD phosphorylation suggests that IODVA1 promotes reduction in survival and induction of apoptosis. To further test this hypothesis, we analyzed the cell cycle of murine p190-BCR-ABL leukemic progenitor cells (EGFP$^+$/B220$^{dim}$) incubated with vehicle control or IODVA1 (1-10 μM) for 20 h, followed by in vitro BrdU incorporation and flow cytometry analysis (FIG. 13C). IODVA1 did not affect the G0+G1 phase, it significantly affected the distribution of the G2+M, S, and apoptotic phases. It increased the percentage of cells in the G2+M phases from 7±1% (SD, N=3) in the presence of vehicle control to 22±6.6, 32±3, and 36±7% (SD, N=3) at 1, 3, and 10 μM, respectively. At 1 μM, it reduced the S-phase 8-fold (p=0.0002) and increased apoptosis by at least 5.3-times (p=0.007). Therefore, IODVA1 induces a G2/M arrest.

Rac-deficient cells do not respond to IODVA1. To confirm that IODVA1 targets Rac-dependent pathways, we assessed its effects in a Rac2-null background. Rac1$^{Δ/Δ}$+Rac2$^{-/-}$ murine leukemic cells show severe reduction in Rac1 expression and are deficient in Rac2 (FIG. 13H). Rac1$^{Δ/Δ}$+Rac2$^{-/-}$ or wild-type murine leukemic cells expressing p190-BCR-ABL (Thomas, 2008) were tested for clonogenic ability in the presence of IODVA1 (FIG. 13D). Rac1$^{Δ/Δ}$+Rac2$^{-/-}$ leukemic cells formed 3.8-times less colonies than wild-type leukemic cells (p=0.0003). IODVA1 did not alter the number of colonies formed by Rac1$^{Δ/Δ}$+Rac2$^{-/-}$ cells, suggesting these they are insensitive to IODVA1. Interestingly, Rac1$^{Δ/Δ}$+Rac2$^{-/-}$ leukemic cells treated with vehicle or IODVA1 formed 2.4-times more colonies than wild-type cells treated with IODVA1 (p=0.0091). Combined with the biochemical data, these data support the idea that IODVA1 targets Rac activity and thus, inhibits its downstream pro-survival signals, and induces a G2/M arrest that correlates with apoptosis.

Figure 14:
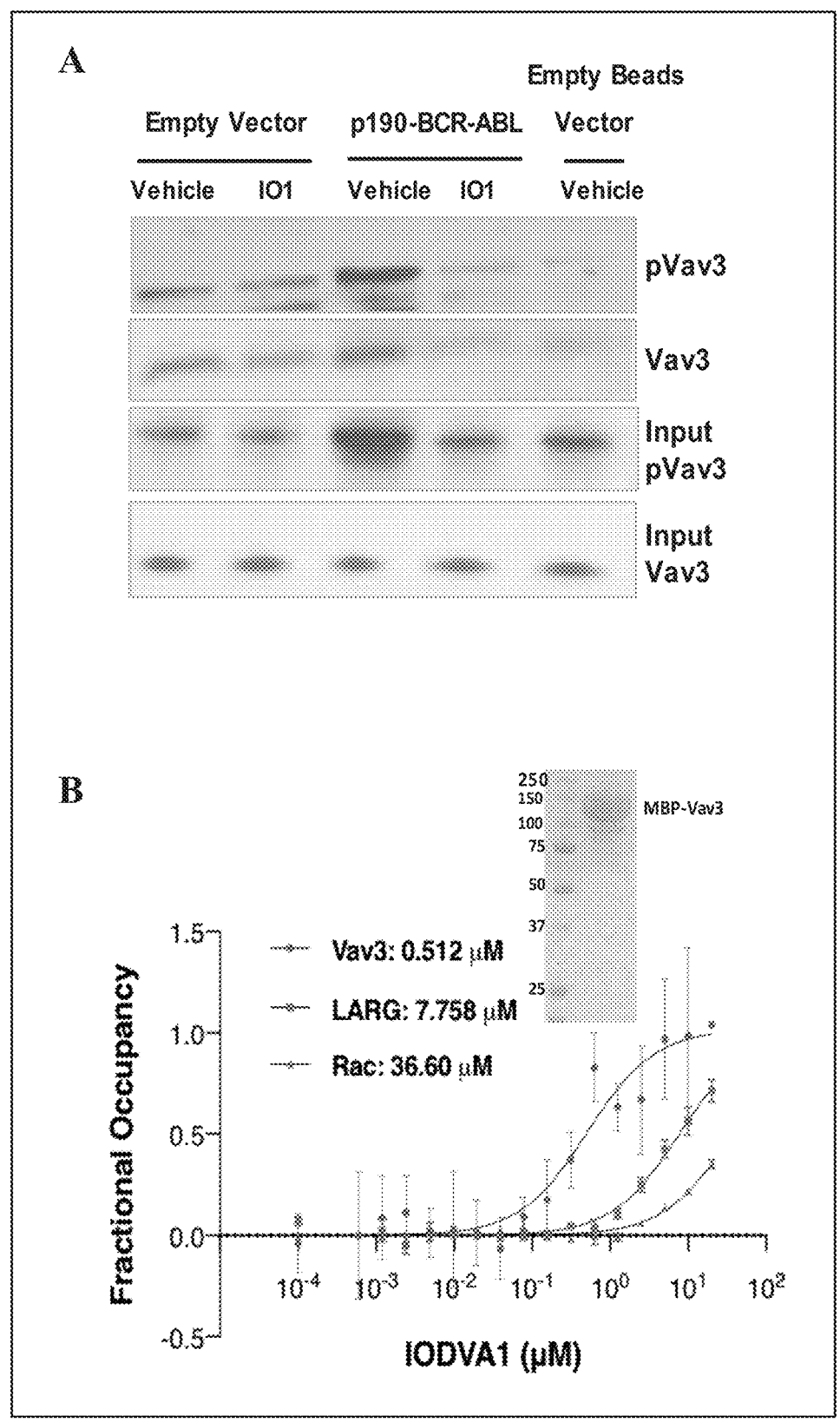
FIG. 14: IODVA1 targets Vav3 in vitro and in vivo. (A) Ba/F3 cells expressing empty vector Mieg3 or p190-BCR-ABL1 were treated with vehicle control or IODVA1 (IO1, 3 μM) for 30 min and incubated with GST-Rac and glutathione beads. Beads were washed and the protein complexes were separated on SDS-PAGE and immunoblotted for pVav3. Input Vav3 was used as control. (B) Binding affinity ($K_d$) between IODVA1 and Vav3 (green), LARG (brown), and RacGDP (blue). The microscale thermophoresis signal expressed as fractional occupancy was plotted against IODVA1 (0.1 nM-20 μM) and fitted to yield $K_d$. Error bars=SD; N=3. (C) Quantification of the average number of colonies made by bone marrow wild-type (black) and Vav3⁻/⁻ (lilac) p190-BCR-ABL1 leukemic cells treated with vehicle control or IODVA1 (IO1, 1 and 3 µM) (* p≤0.05;  p≤0.01; * p≤0.001; ns, not significant). (D) Representative histogram data of the cell cycle analysis of wild-type (black and grey bars) and Vav3⁻/⁻ (dark and light lilac) bone marrow cells expressing p190-BCR-ABL and treated with vehicle control or IODVA1 (IO1, 3 µM) for 20 h. (E) Quantification by densitometry of the pVav3 band from FIG. 14A. (F) Kaplan-Meier plot showing survival of wild-type or Vav3⁻/⁻ p190-BCR-ABL1 leukemic mice post-treatment with osmotic pumps implanted subcutaneously and carrying vehicle control or IODVA1 (IO1, 1 mM). (G) Count (% leukemic progenitors in peripheral blood) of residual leukemic (EGFP⁺-BCR-ABL1) cells at week 1 and 2 post-treatment for mice from (F). (H) Pharmacodynamic assessment of leukemic progenitor cells (%) from wild-type or Vav3-deficient mice with p190-BCR-ABL1 leukemia and treated with vehicle control (dark and light grey) or IODVA1 (IO1, dark and light lilac) following 2-week treatment using phospho-flow analysis of the indicated effectors (* p≤0.05; ** p≤0.01).
Figure 14:
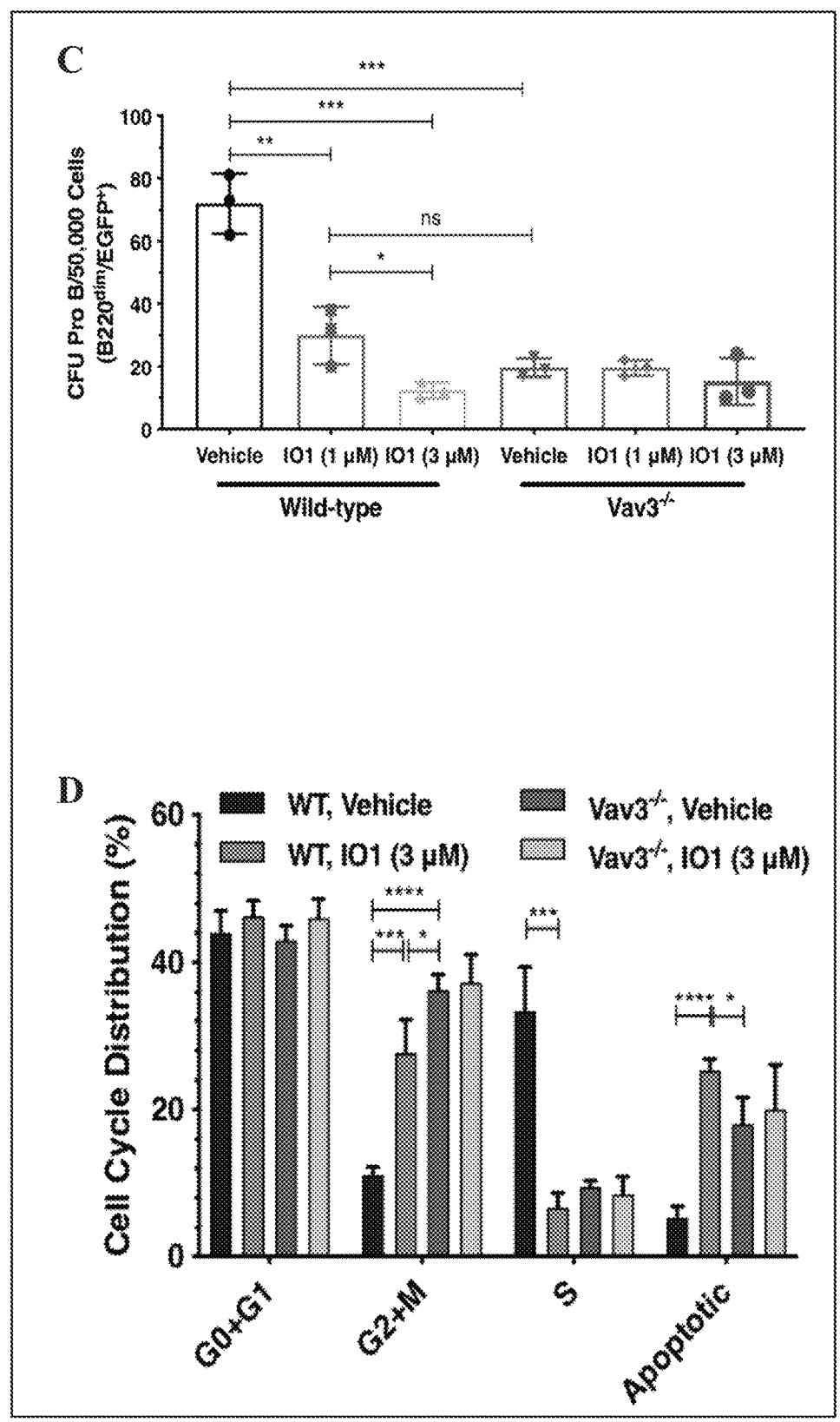
Figure 14:
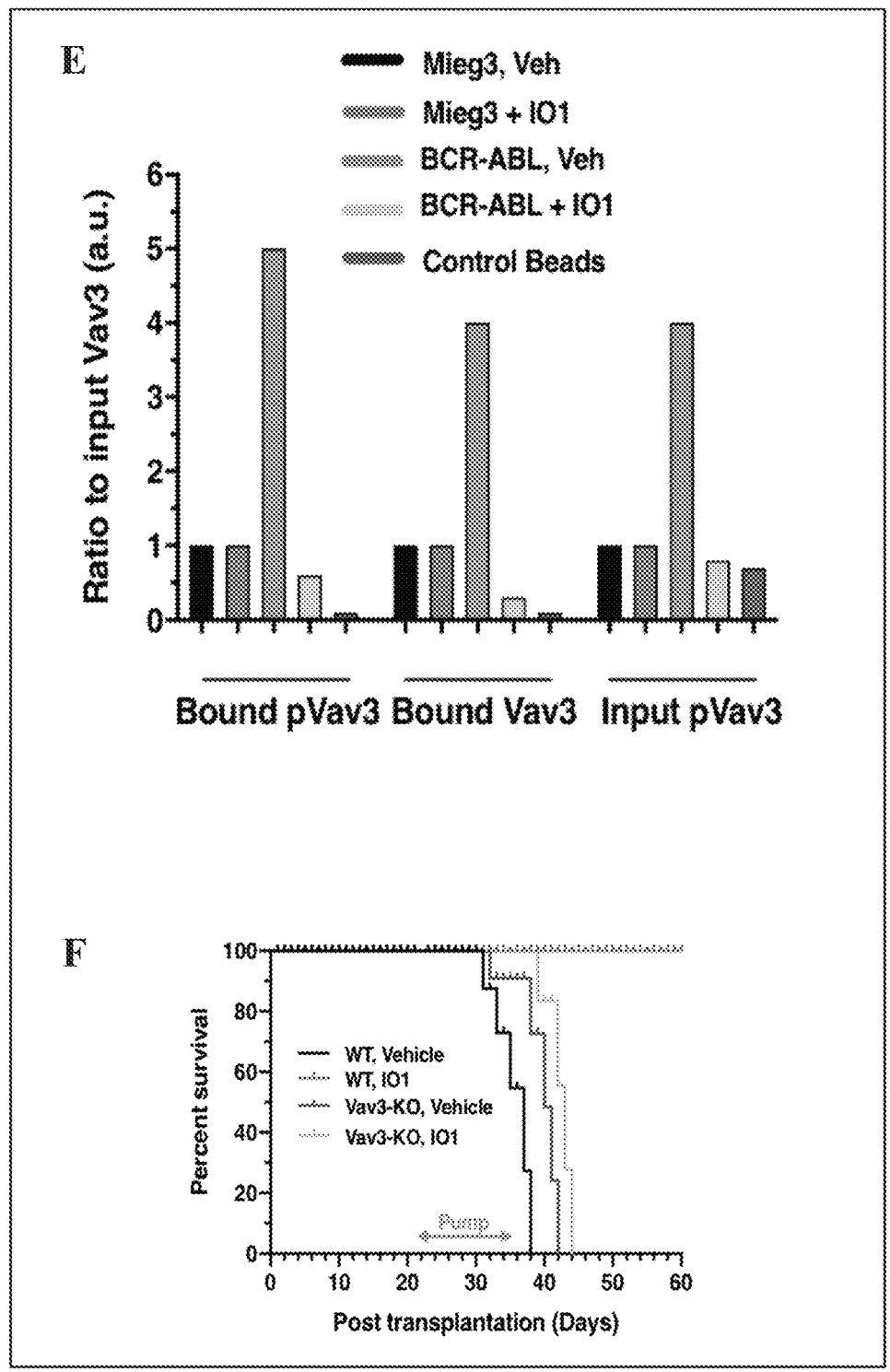
Figure 14:
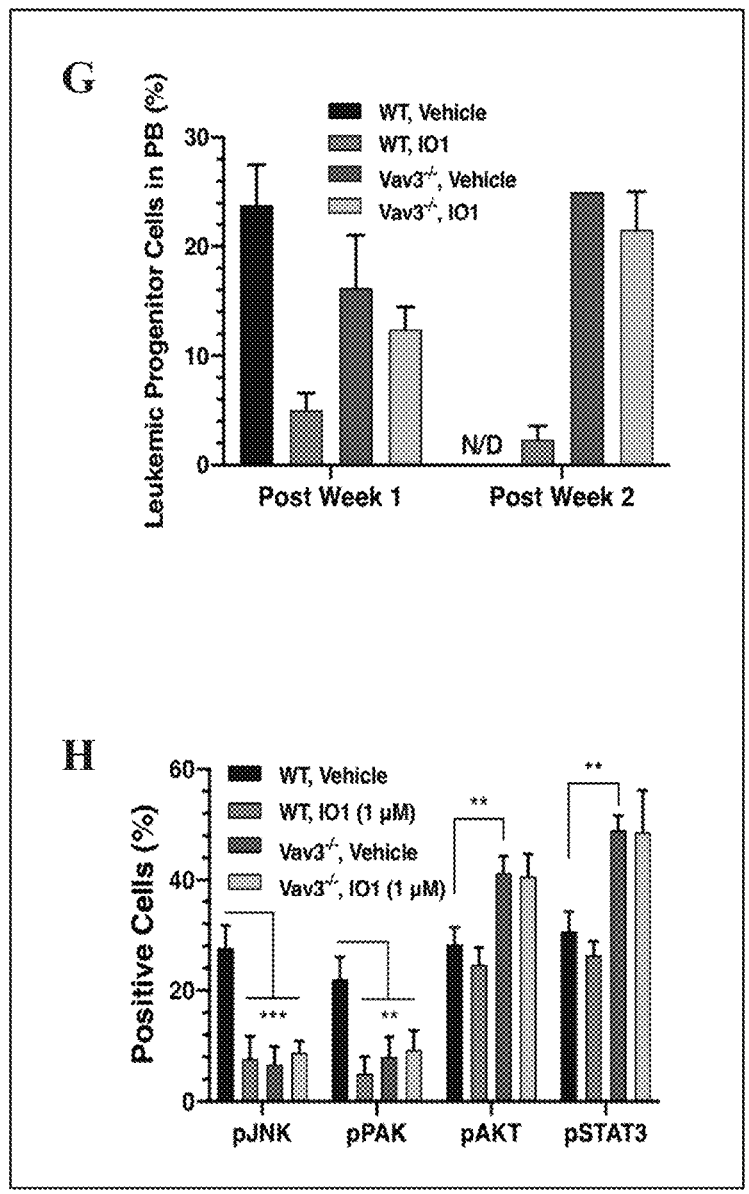

IODVA1 is an inhibitor of the RacGEF Vav3. Rac activity and signaling is regulated by GAPs, GDIs, and RacGEFs. We argued that the decrease in Rac activity might be caused by IODVA1 targeting one Rac regulator. Using biochemical assays, we show that IODVA1 does not stimulate the activity of the Rac negative regulators p50GAP and RhoGDI1 (FIG. 13I-12K). We next turned to GEFs and posited that IODVA1 inhibits one Rac-specific GEF leading to its inactivation. While several RacGEFs have been associated with leukemogenesis (Biswas, 2019; Chatterjee, 2018; Martin, 2013; Lyons, 2010; Reuther, 2001; Rouard, 1999; Bourgoin, 1995), Vav3 was shown to play an important role in leukemogenesis (Chang et al. 2012). We thus focused on Vav3 and tested if IODVA1 inhibits Vav3 binding to Rac. Ba/F3 cells expressing either p190-BCR-ABL or Mieg3 empty vector were incubated with IODVA1 (3 μM) or vehicle control for 30 min and subjected to GST-Rac pull-down. The pull-down protein complex was separated on SDS-PAGE and immunoblotted for pVav3 and Vav3 and quantified (FIGS. 14A & 14E). There was no significant change in Vav3 or pVav3 bound to Rac in empty vector expressing Ba/F3 cells treated with IODVA1 or vehicle control (FIG. 14A, lanes 1 & 2) suggesting that IODVA1 did not affect Vav3 binding to Rac in cells expressing the empty vector. Strong pVav3 and Vav3 bands appeared in cells expressing the p190-BCR-ABL oncogene and treated with vehicle (FIG. 14A, lane 3) implying strong binding between active Vav3 and Rac. Specifically, the 5-fold increase in the pVav3 intensity in Ba/F3 leukemic cells is consistent with similar observation that BCR-ABL increases Vav3 activation (Chang, 2012). The intensity of this band is decreased 8-times in cells treated with IODVA1 (FIG. 14A, lane 4) suggesting that IODVA1 inhibited Vav3 binding to Rac in BCR-ABL expressing cells. This inhibition is likely due to the overall decrease in pVav3 levels in IODVA1 treated cells (FIG. 14A, input pVav3 band, lanes 3 & 4). Taken together, our data suggest that IODVA1 interferes with Vav3 activation and binding to Rac thus preventing the activation of the latter.

IODVA1 binds to Vav3. The previous observation suggests that IODVA1 binds to Vav3. To test this hypothesis, we measured its binding affinity ($K_d$) to recombinant Vav3 and Rac1 using microscale thermophoresis (MST); the catalytic domain (DH/PH) of the RhoGEF LARG served as negative control. We used LARG for two reasons. First, we reasoned that if Rho-activation is not affected by IODVA1 (FIG. 13G), we should not detect any binding between LARG and IODVA1. Second, like Vav3, LARG contains a DH/PH domain responsible for the exchange activity such that any non-specific binding to this domain should be detected. The MST signal for Vav3 reaches saturation at 10 μM IODVA1 and beyond (FIG. 14B). The MST signal for Rac1 and LARG showed no saturation at the highest IODVA1 concentration tested. Fitting of the MST titration data shows that one molecule of IODVA1 binds to Vav3 with a $K_d$ of 512 nM. The best estimate for the $K_d$ for Rac and LARG is 35.5 and 7.7 μM, respectively. Thus, IODVA1 binds tightly and specifically to Vav3.

Vav3-deficient leukemic cells do not respond to IODVA1 in vitro and in vivo. To further validate Vav3 as a target of IODVA1, we studied the effects of IODVA1 on leukemic cells from the Vav3-KO (Vav3$^{-/-}$) mice we published previously (Thomas E K et al., 2007; Thomas E K et al, 2008; Bourgoin S. et al., 1995). We argued that if IODVA1 targets Vav3, then Vav3$^{-/-}$ cells should be insensitive to its action. Wild-type or Vav3$^{-/-}$ murine BM leukemic cells expressing p190-BCR-ABL (EGFP$^+$/B220$^+$) were tested in colony formation assay in the presence of IODVA1 (FIG. 14C). The number of colonies formed by leukemic cells expressing Vav3 decreased on average by 3- and 7-folds in the presence of 1 and 3 µM IODVA1, respectively. Vav3$^{-/-}$ cells on the other hand formed similar number of colonies when grown in the presence of vehicle control or IODVA1 suggesting they lost sensitivity to our drug. Interestingly, the difference in the number of colonies formed by Vav3$^{-/-}$ leukemic cells and by IODVA1-treated wild-type leukemic cells is not statistically significant (p=0.13). Similarly, cell cycle analysis shows that Vav3$^{-/-}$ cells expressing p190-BCR-ABL were not affected by IODVA1 (FIG. 14D). Taken together, our data suggest that while wild-type leukemic cells respond to IODVA1, Vav3$^{-/-}$ leukemic cells are irresponsive and mimic IODVA1-treated wild-type leukemic cells.

Figure 15:
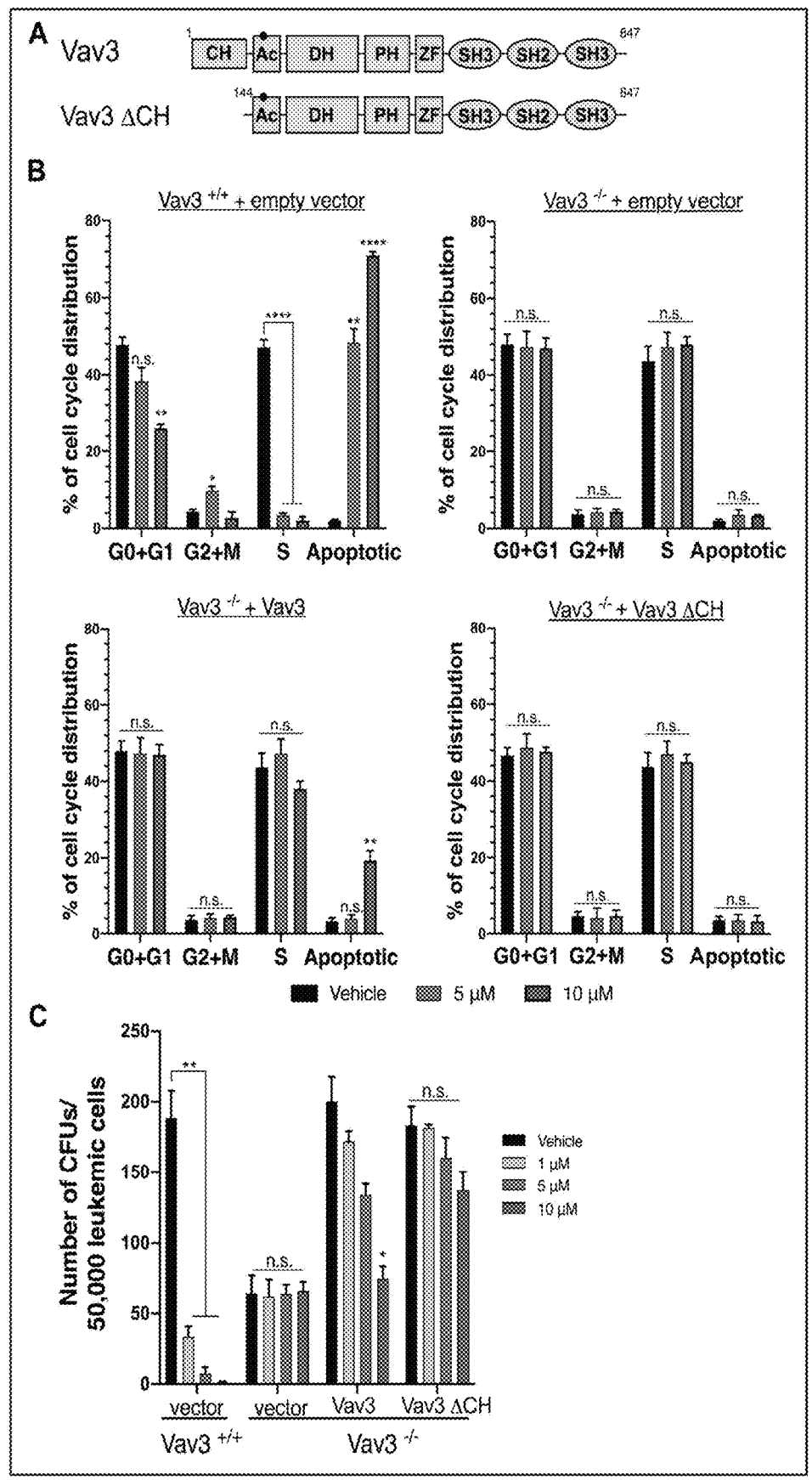
FIG. 15: Expression of transgenic Vav3 re-sensitizes Vav3-deficient cells to IODVA1. (A) Vav3 domain structure, calponin-homology (CH), acidic region (Ac), Dbl-homology (DH), pleckstrin-homology (PH), zinc finger (ZF), Src-homology 2 and 3 (SH2/SH3). (B) Representative histogram data of the cell cycle analysis of wild-type (Vav3⁺/⁺) and Vav3-deficient (Vav3⁻/⁻) p190-BCR-ABL1 leukemic bone marrow cells expressing empty vector, full-length Vav3 or ΔCH mutant and treated with vehicle control (black) or IODVA1 at 5 (red) or 10 µM (dark grey) for 18 h. (C) Quantification of the average number of colonies made by bone marrow wild-type and Vav3⁻/⁻ p190-BCR-ABL1 leukemic bone marrow cells expressing empty vector, full-length Vav3 or ΔCH mutant and treated with vehicle control (black) or IODVA1 at 1 (light salmon), 5 (red) and 10 µM (dark grey). *** p≤0.001.

Vav3 rescues IODVA1 sensitivity. Next, we reasoned that if IODVA1 targets Vav3, rescuing Vav3$^{-/-}$ leukemic cells by expressing exogenous Vav3 should re-sensitize those cells to IODVA1. We expressed full-length Vav3 or the dominant active ΔCH-mutant (FIG. 15A) in Vav3$^{-/-}$ p190-BCR-ABL1-transformed murine bone marrow leukemic cells and analyzed changes in cell cycle 18 h post-treatment with vehicle control or IODVA1 (FIG. 15B). Expressing full-length Vav3 but not the empty vector re-sensitized the Vav3$^{-/-}$ BM leukemic cells to IODVA1 as shown by a 5.8-fold increase in apoptosis (p=0.0005) and a 15% decrease (p=0.08) in cells in the S-phase at 10 µM. Expressing the ΔCH-mutant did not re-sensitize Vav3$^{-/-}$ leukemic cells to IODVA1 even at the highest concentration.

To test if the results of the previous rescue experiments hold in proliferation assays, we subjected the Vav3 full-length and ΔCH-mutant expressing Vav3$^{-/-}$ leukemic cells to colony formation assays in the presence of IODVA1 (1, 5, and 10 µM) or vehicle control (FIG. 15C). Re-introducing full-length or ΔCH Vav3 results in similar number of colonies as with wild-type BM leukemic cells (200 and 183 vs 188, respectively), a 3-fold increase from Vav3$^{-/-}$ leukemic cells expressing the empty vector (64 colonies). Importantly, Vav3$^{-/-}$ leukemic cells expressing Vav3 respond to IODVA1 in a dose dependent manner. At 10 µM IODVA1, the number of colonies made by Vav3$^{-/-}$ cells expressing full-length Vav3 is reduced by a third and becomes similar to that made by Vav3$^{-/-}$ expressing empty vector (75 vs 66 colonies). Interestingly, ΔCH expressing leukemic cells respond less to IODVA1.

Vav3$^{-/-}$ leukemia do not respond to IODVA1 in vivo. Next, we tested if the lack of response to IODVA1 by Vav3$^{-/-}$ cells holds in vivo. We transplanted wild-type or Vav3$^{-/-}$ LDBM cells transduced with p190-BCR-ABL retrovirus into lethally irradiated C57BL/6 mice, waited for the leukemia to develop, and treated the mice with either vehicle control or IODVA1 administered through osmotic pumps as before. Vav3$^{-/-}$ leukemic mice did not respond to IODVA1 supporting the hypothesis that Vav3 is IODVA1's target in vivo (FIG. 14F). Taken together, our data show that Vav3-deficient leukemia progenitor cells do not respond to IODVA1 in cellular and in vivo assays consistent with the idea that Vav3 is IODVA1's target in vivo and in vitro. The persistency of leukemia in vivo in Vav3$^{-/-}$ mice suggests that Vav3$^{-/-}$ BCR-ABL leukemia has evolved mechanisms of escape relying on Rac-independent pathways such as AKT and STAT3 signaling pathways (FIGS. 14G & 14H).

Figure 16:
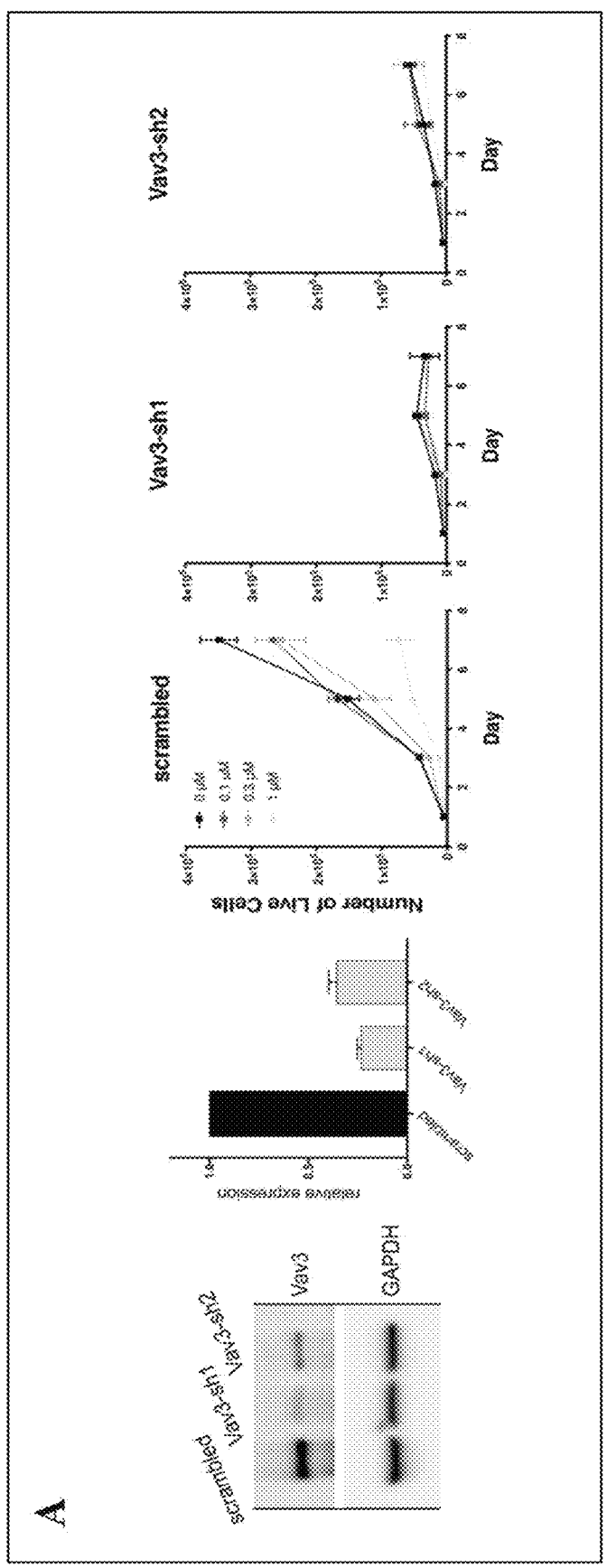
FIG. 16: IODVA1 decreases levels of pVav3 in in vitro and in vivo models of triple negative breast cancer. (A) Immunoblot and quantification of Vav3 protein in lysates of MDA-MB-231 triple negative breast cancer cells stably expressing scrambled or Vav3-targeting shRNAs. Viability of the MDA-MB-231 cells stably expressing shVav3 in the presence of IODVA1 (0-1 µM). Cells were grown in the presence of IODVA1 and counted by trypan blue exclusion at the indicated time points. (B) MDA-MB-231 cells were incubated with IODVA1 (3 µM) for 15 min and the levels of phosphorylated Vav3 (pY173) were assessed by immunoblotting. (C) Immunohistochemical staining of phosphorylated Vav3 in tissue derived from MDA-MB-231 xenografts treated with vehicle control or IODVA1.
Figure 16:
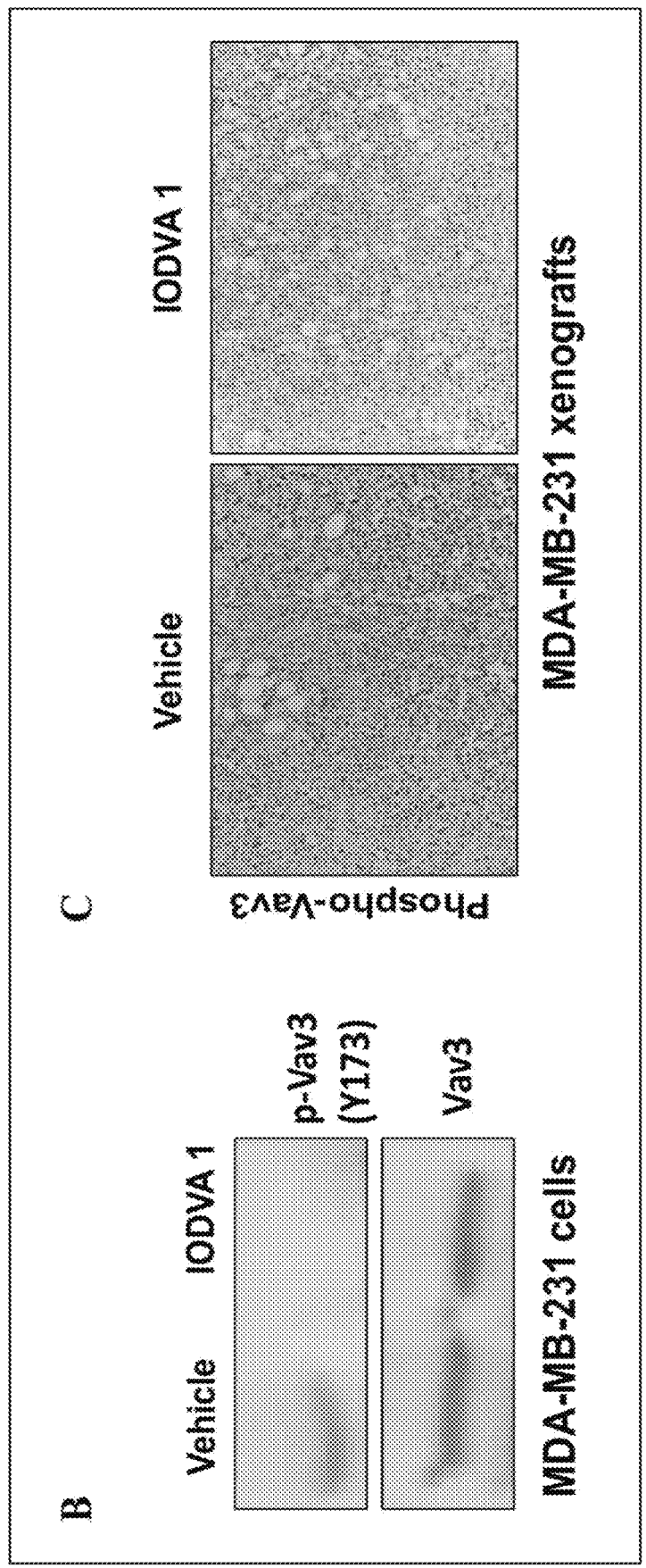

IODVA1 targets Vav3 in MDA-MB-231 cells and xenograft tumors. Next, we tested if IODVA1 is effective in another model of Vav3-dependent cancer. We chose MDA-MB-231 triple negative breast cancer cells because these cells express high endogenous levels of Vav3 (Chen, 2015) and because Vav3 is an acknowledged target in breast cancer (Chen, 2015; Lee, 2008; Aguilar, 2014; Citterio, 2012; Lorenzo-Martin. 2019). In addition, we have previously shown that these cells are sensitive to IODVA1 and that IODVA1 halts tumor growth and induces apoptosis in MDA-MB-231 xenograft mice (FIG. 8A-8C) and (Gasilina et al., 2020). First, we showed that reduction in Vav3 expression levels by targeting shRNA severely reduces proliferation of MDA-MB-231 cells. IODVA1 (0.1-1 µM) reduces, in a dose-dependent manner, the viability and proliferation of scrambled MDA-MB-231, it has no effect on the shVav3 expressing cells (FIG. 16A). Second, we incubated MDA-MB-231 cells with IODVA1 (3 µM) for 15 min and analyzed the levels of phosphorylated Vav3 (pY173) by immunoblotting. FIG. 16B shows that IODVA1 treatment results in a significant decrease in pY173 signal. Since phosphorylation of this Tyr173 is indicative of Vav3 activation, we conclude that IODVA1 inhibits Vav3 activity shortly after exposure.

To test if IODVA1 inhibits Vav3 in vivo, we took advantage of the MDA-MB-231 xenograft tumors we generated (FIG. 8A) and stained them by immunohistochemistry for pVav3. Comparison of pVav3 stained tumor sections treated with vehicle control and with IODVA1 shows significant decrease in pVav3 staining for tumors treated with IODVA1 than with vehicle control (FIG. 16C). Thus, IODVA1 also inhibits Vav3 in vitro and in vivo in solid tumor models and in a cell-independent manner.

Figure 17:
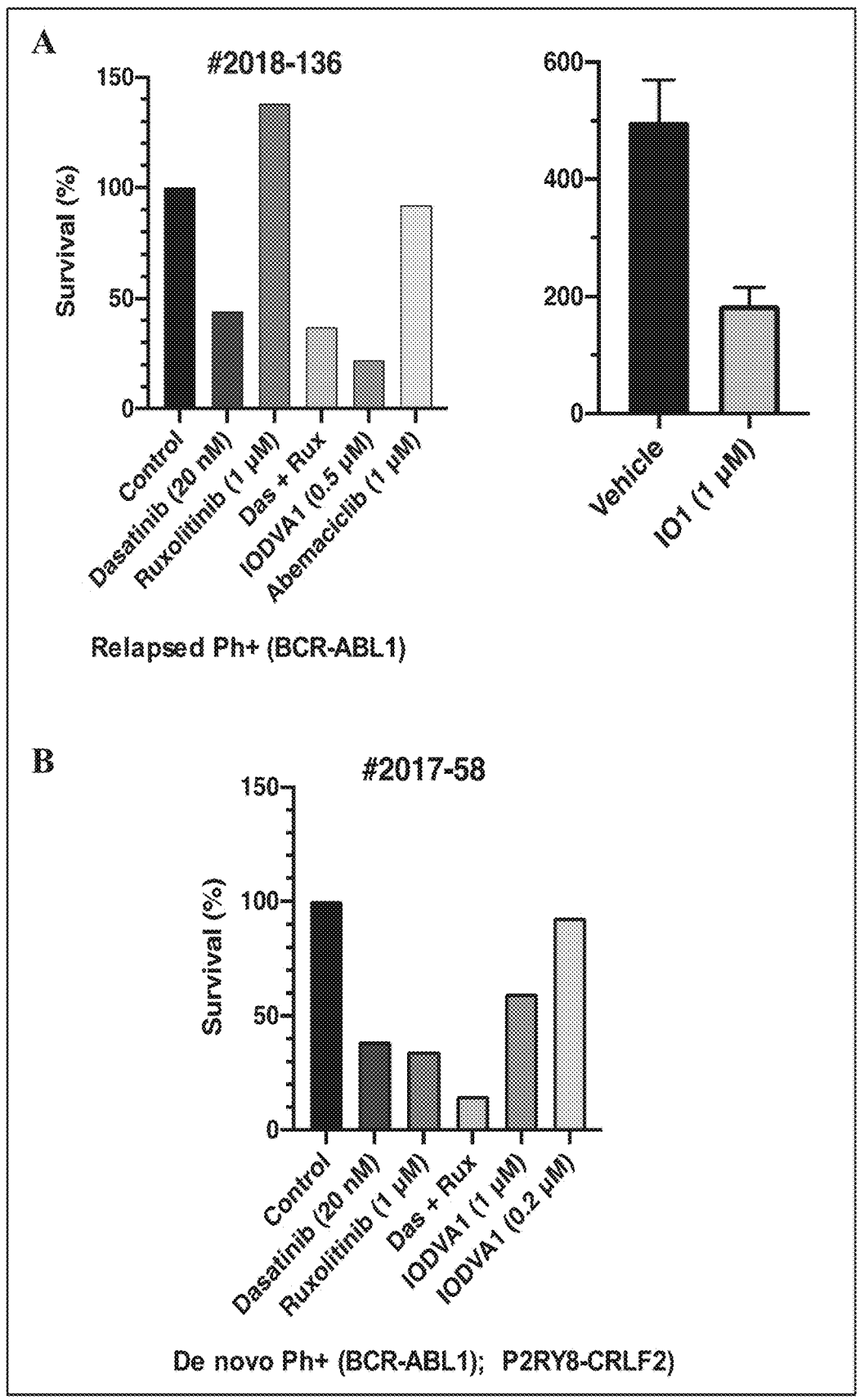
FIG. 17: IODVA1 reduces survival of cells derived from pediatric patients with relapsed and de novo Ph⁺ leukemia. Patient-derived xenograft (PDX) cells were co-cultured ex vivo on MS-5 or OP-9 stromal cells and treated with dasatinib (Das, ABL1-inhibitor), ruxolitinib (Rux, JAK-inhibitor), combination of dasatinib and ruxolitinib (Das+Rux), abemaciclib (CDK inhibitor), or IODVA1 and assessed for survival. (A) Representative survival and colony forming ability of IODVA1 (IO1)-treated cells from patient #2018-136. (B) Survival of treated cells from patient #2017-58 and (C) survival of treated cells from patient #2017-129 with BCR-ABL1(T315I) mutation. Note lack of toxicity of IODVA1 to normal stromal cells (black arrows) in the accompanying image.
Figure 17:
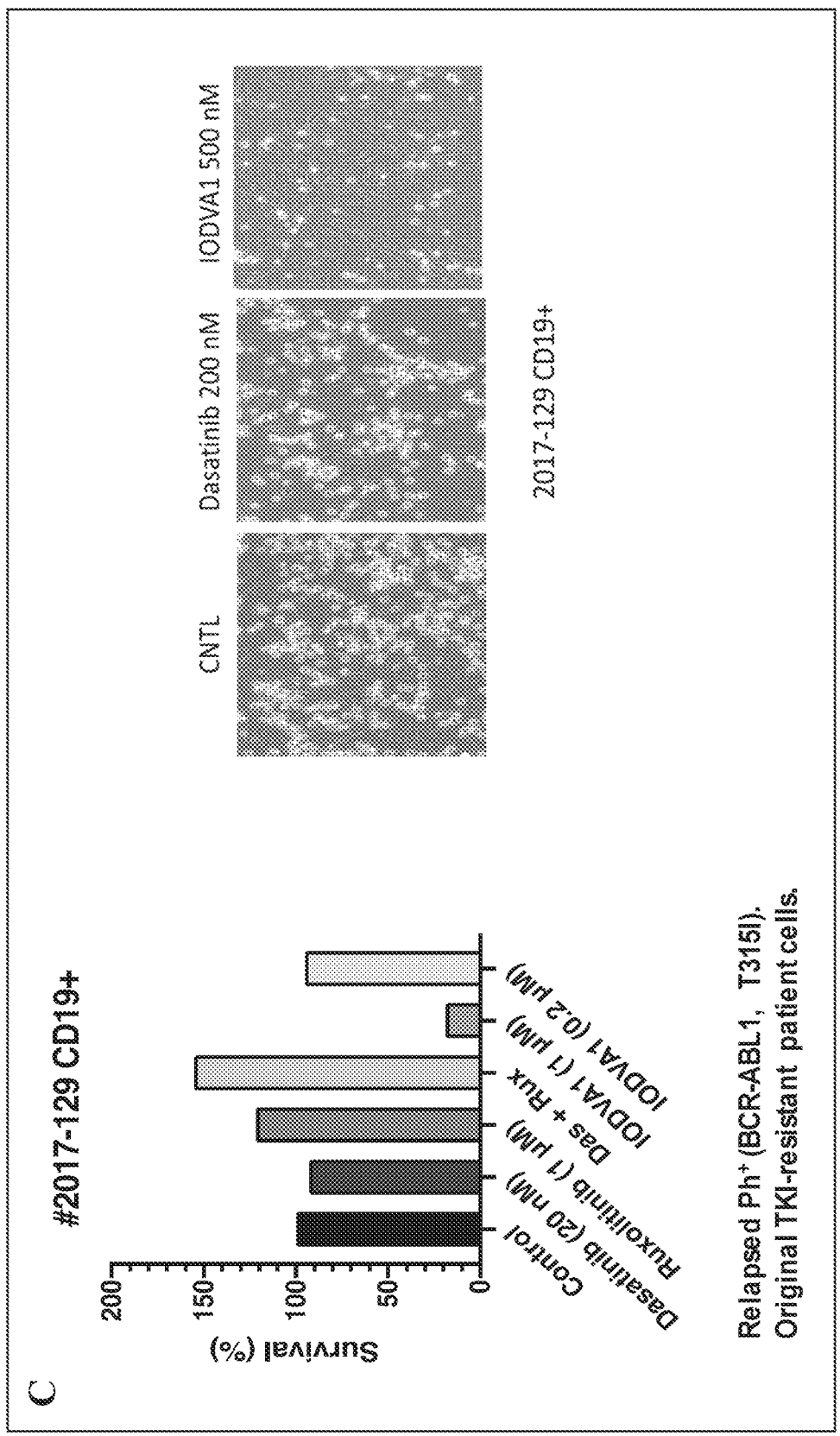

IODVA1 decreases survival of patient-derived leukemia cells. Consistent with our findings with peripheral CD34$^+$ BCR-ABL cells (FIG. 10A-10B), cells from PDX models representing pediatric Ph$^+$ B-ALL patients (Table 1) were found to be highly sensitive to IODVA1 ex vivo (FIG. 17).

Cells from relapsed patient #2018-136 with Ph$^+$ (BCR-ABL1) were treated with ABL-TKI dasatinib, JAK-inhibitor ruxolitinib, dasatinib and ruxolitinib combination (das+rux), CDK-inhibitor abemaciclib, and IODVA1. Dasatinib (20 nM) reduced the proliferation of #2018-136 cells by 56%; ruxolitinib or abemaciclib (1 µM) had no effect. The das+rux combination resulted in 63% decrease in proliferation, which is likely due to dasatinib's inhibitory action. IODVA1 (0.5 µM) reduced the proliferation of these cells by 78%. When tested in the colony formation assay, IODVA1 (1 µM) reduced the number of colonies by 60% (p=0.001) (FIG. 17).

Cells from patient #2017-58 with a dual Ph$^+$ (BCR-ABL1) and Ph-like (P2RY8-CRLF2) rearrangement were similarly treated. These cells clearly responded to dasatinib, ruxolitinib, and the combination. IODVA1 was not as potent as it decreased their proliferation by only 40% at 1 µM and had no effect at 0.2 µM (FIG. 17B). Original CD19$^+$ cells from patient #2017-129 with Ph$^+$ B-ALL (BCR-ABL1; T315I) who relapsed after initial treatment were treated with vehicle control, dasatinib, ruxolitinib, (das+rux), and IODVA1. As expected dasatinib, ruxolitinib, or the combination had no effect on proliferation of the CD19$^+$ cells (FIG. 17C, left panel). In contrast, IODVA1 at 1 µM but not at 0.2 µM reduced the CD19$^+$ B-ALL cell counts by 80%. Additionally, we confirmed that IODVA1 does not exert toxic effects to cells of normal stroma (FIG. 17C, right panel arrows). Thus, IODVA1 decreases the proliferation of Ph$^+$ B-ALL (BCR-ABL1) primary cells including cells expressing the TKI-resistant T315I mutant consistent with our findings that Ph$^+$ B-ALL (BCR-ABL1) model cells express high-levels of Vav3. The fact that #2017-58 cells did not respond to IODVA1 as well as the other two patient samples is probably due to the existence of other genetic mutations (e.g. P2RY8-CRLF2) that promote cell growth independently of Vav3.

Figure 18:
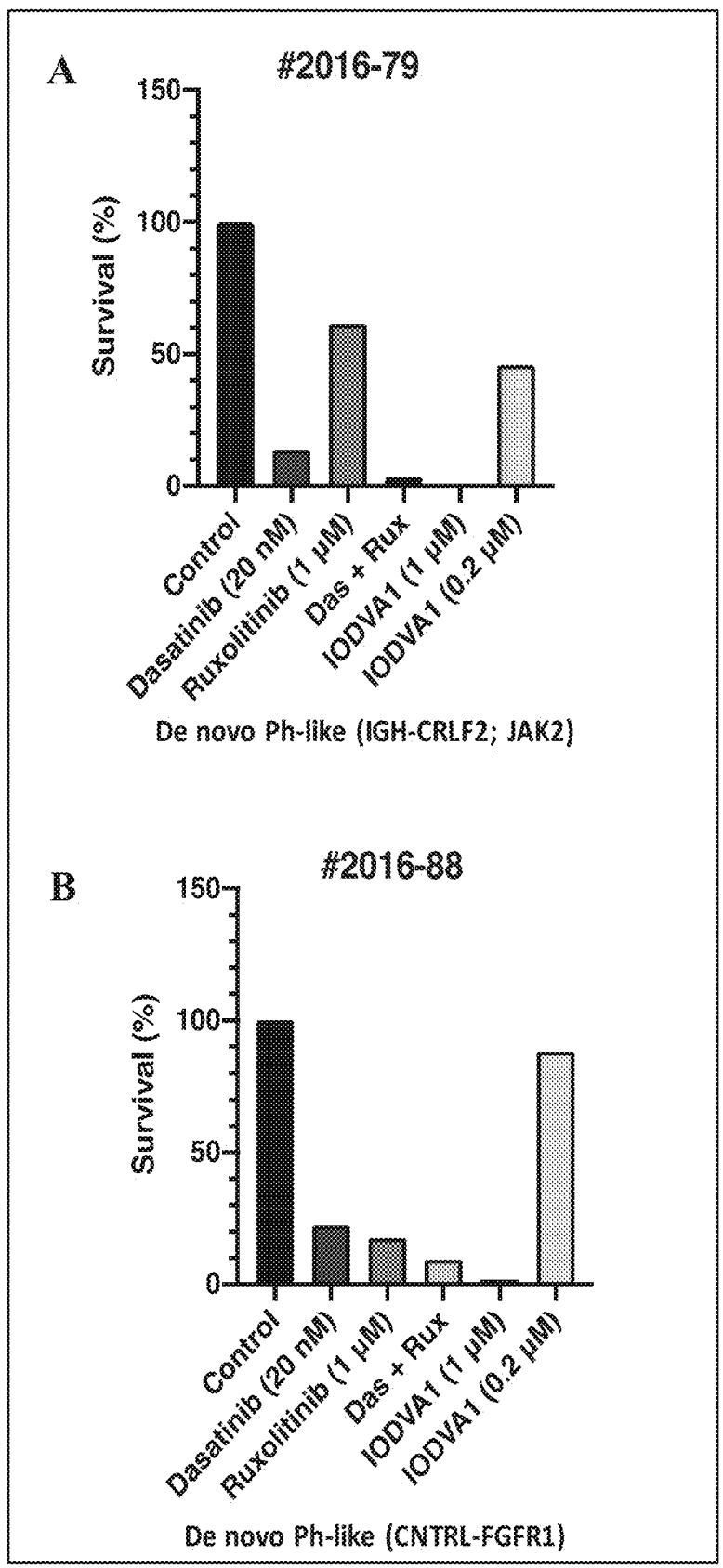
FIG. 18: IODVA1 reduces survival of leukemia cells derived from relapsed and de novo Ph-like and MLL pediatric patients. Patient derived xenograft (PDX) cells were co-cultured ex vivo on MS-5 or OP-9 stromal cells and treated with dasatinib (Das, ABL1-inhibitor), ruxolitinib (Rux, JAK-inhibitor), combination of dasarinib and ruxolitinib (Das+Rux), abemaciclib (CDK inhibitor), or IODVA1 and assessed for survival. (A) to (E) de novo Ph-like leukemia cells. (F) Leukemic cells from MLL/AF9 and relapsed MLL/AF1q patients (G-H).
Figure 18:
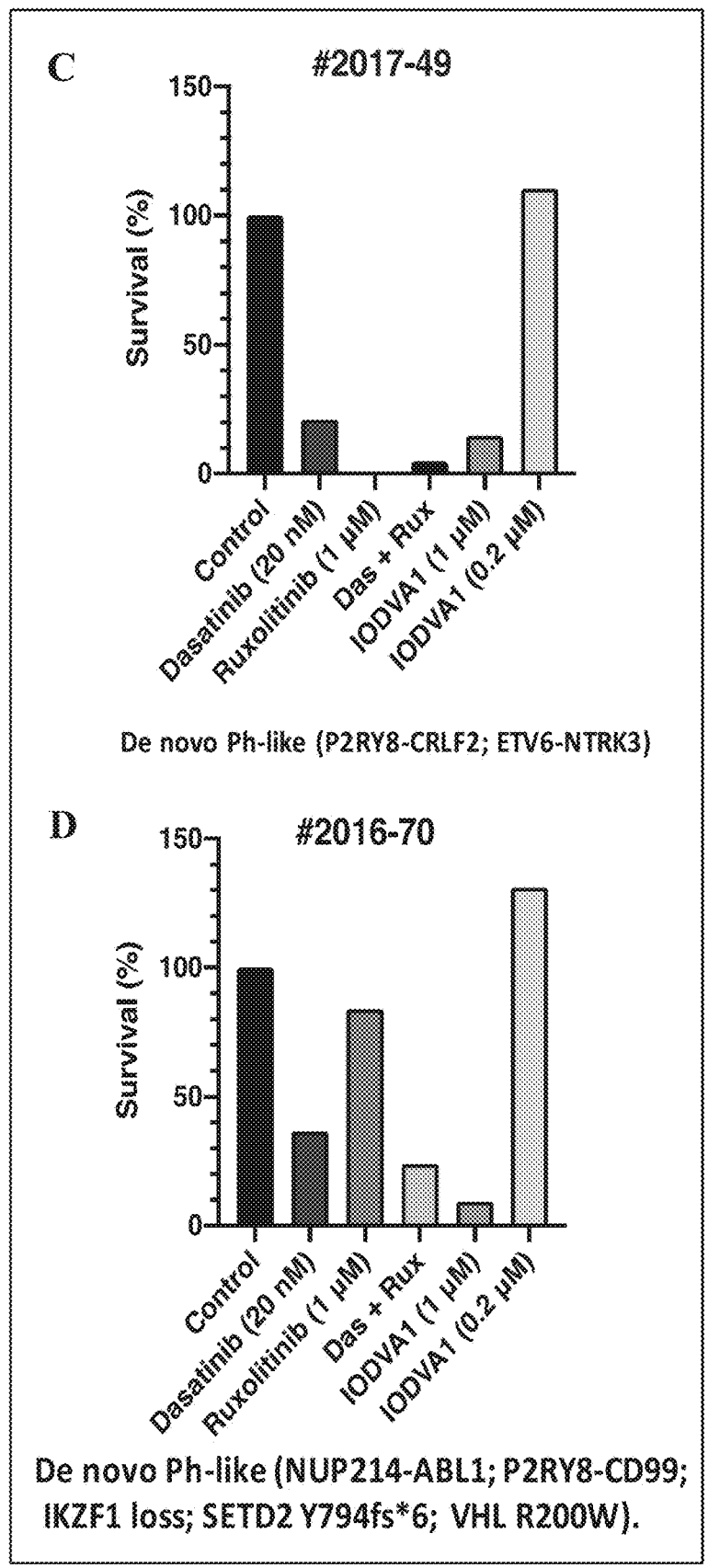
Figure 18:
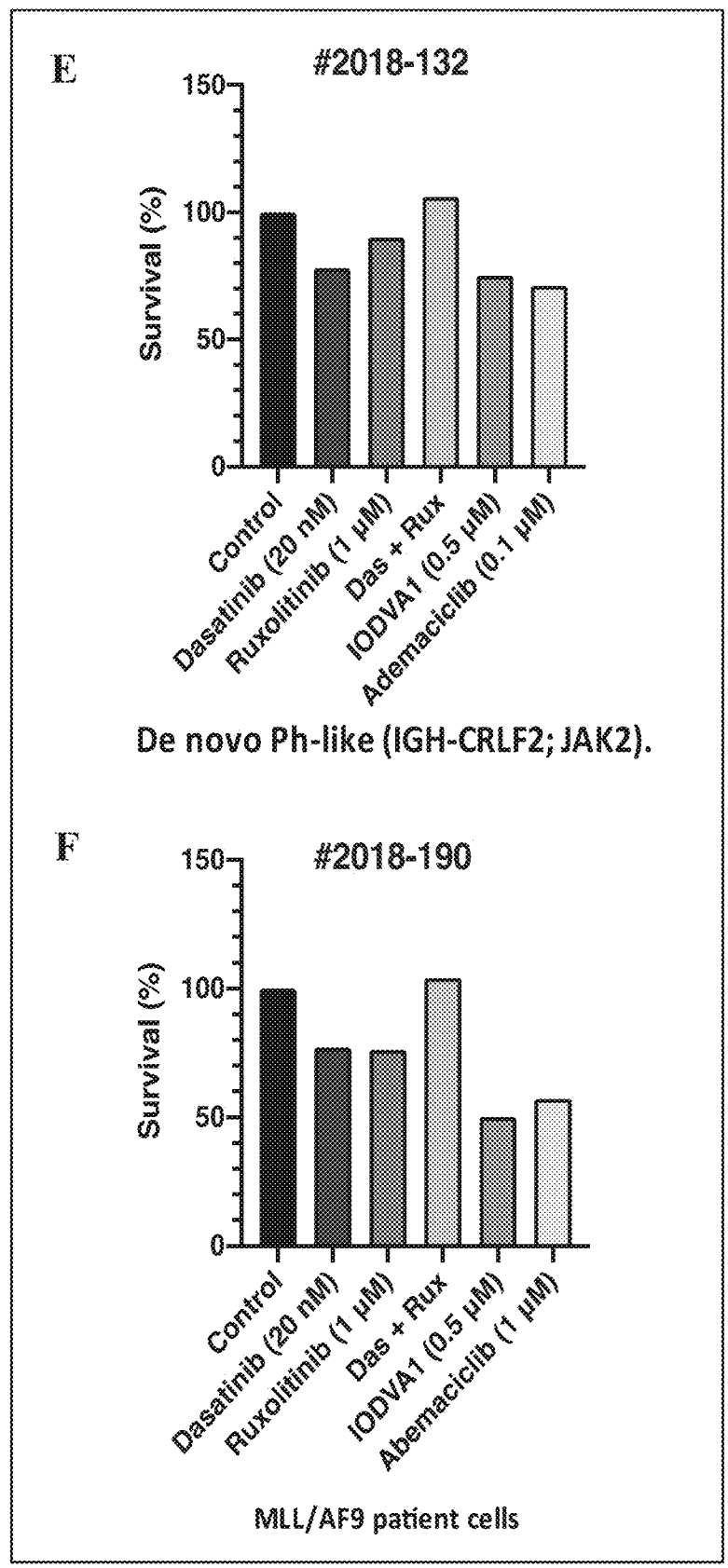
Figure 18:
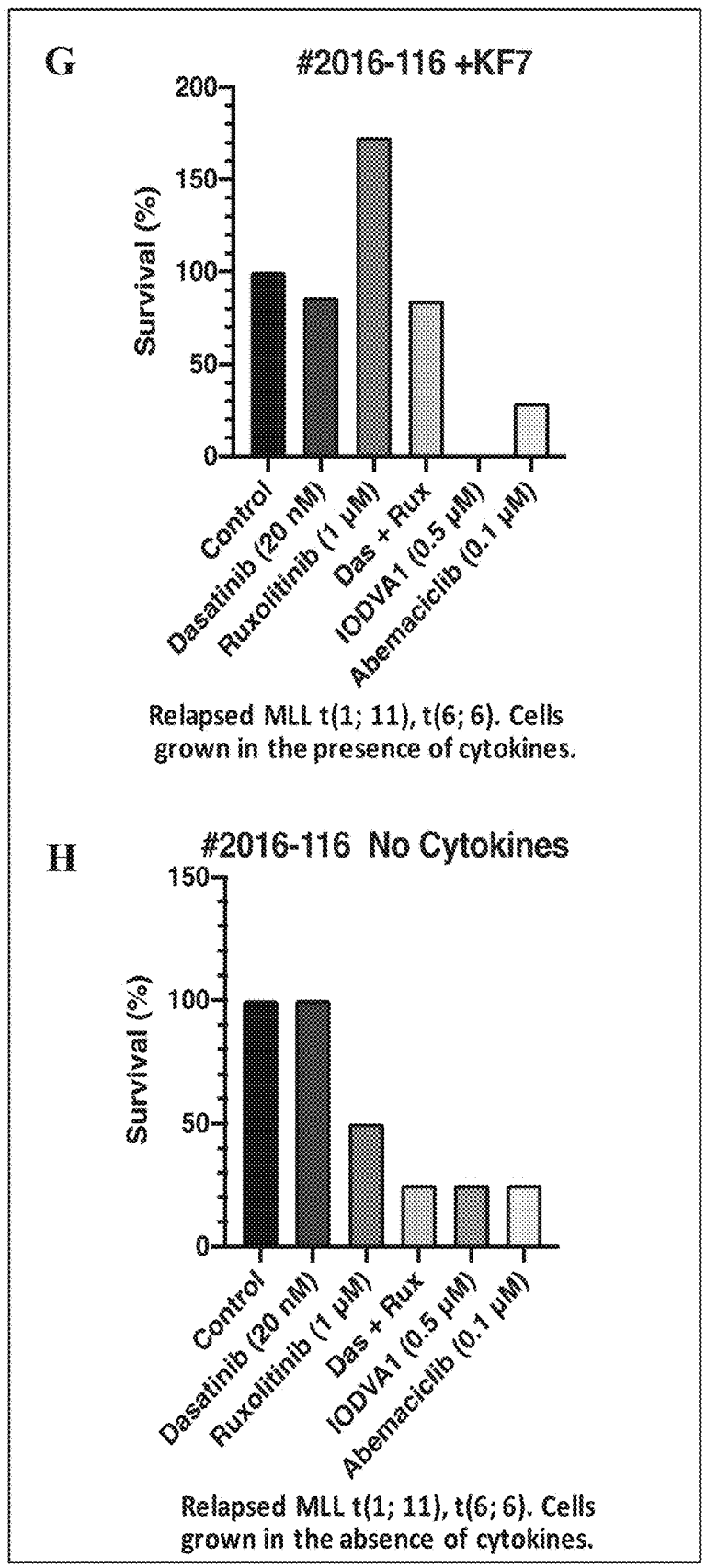

Our cohort of samples also contained numerous cases of Ph-like disease with a diverse series of genetic aberrations and a few cases of MLL-rearranged B-ALL. These patient cells generally responded positively to IODVA1 (FIG. 18).

In conclusion, we have shown that pharmacological inhibition of Vav3 by IODVA1 is an attractive therapeutic strategy to treat Ph$^+$ and TKI-resistant BCR-ABL B-ALL. This strategy should benefit other malignancies where Vav3 is a target, such as other leukemias, poor prognosis breast cancer, skin tumors, prostate cancer, gastric cancer, glioblastoma, or where it is highly expressed. We thus expect IODVA1 to have a broader therapeutic application. In addition, IODVA1 constitutes an exceptional tool to dissect the Vav3/Rac signaling axis. Broadly, RhoGEFs are multidomain proteins that are regulated by autoinhibition. Consequently, small molecules that stabilize the autoinhibited conformation of RhoGEFs and inhibit their activity could be developed into drugs to treat human cancers.

Plasmids, Cell Lines, and Reagents: Plasmid set for purification of fixed-arm carrier fusions pMalX (A-E) was a kind gift from Dr. Lars C. Pedersen (NIEHS), pET28b-N$_9$-MBP-mOrange plasmid was from Addgene (#29748), chaperone co-expression plasmid set was from TaKaRa (cat #3340). Primers were from Integrated DNA Technologies (IDT, Inc.). Primer and construct design was performed with NEBuilder Tool. Restriction enzymes, polymerases, cloning assembly kits and competent cells were from New England Biolabs and Invitrogen.

MDA-MB-231 cells were maintained in IMEM (Invitrogen) supplemented with 10% FBS, 1% penicillin/streptomycin, and 1% amphotericin B. Ba/F3 cells were cultured in RPMI (GIBCO) supplemented with 10% FBS and IL-3 (10 ng/ml). HEK293T cells were maintained with DMEM supplemented with 10% FBS and 1% penicillin/streptomycin. All cell lines were cultured at 37° C. in a 5% CO$_2$ humidified incubator. Cell viability was assessed by trypan blue exclusion assay as previously described. Cytokines were from Peprotech.

The following antibodies were used: GAPDH (#627408, GeneTex), pERK1/2 (#4370), pAKT (#9271 and #9018), c-Abl (#2862), Cdc42 (#2462), RhoA (#2117), pPAK1/2 (#2601S), pS6 (#4851S), PAK1 (#2602S), pBAD (#4366), and BAD (#9292), anti-mouse HRP (#7076), anti-rabbit HRP (#7074) were from Cell Signaling Technologies, pVav3 (Y173) (#ab109544) and total Vav3 (#ab203315) were from Abcam, pJNK (Alexa Fluor 647 conjugated, #562481), p-p38 (PE-conjugated, #612565), Rac2 (#610850), pStat3 (#55385), and pStat5 (Alexa Fluor 647 conjugated, #612599), and B220 APC-Cy7 antibody (#552094) were from BD Bioscience, anti-phosphotyrosine antibody was from Millipore Sigma (#05321), p4EBP1 (PE-conjugated, #12-9107-42) was from Thermofisher Scientific.

Lipids (Phosphatidylserine (PS), Phosphatidylcholine (PC), phosphatidylethanolamine (PE) and sphingomyelin (SM), and phosphatidylinositol 4,5-bisphosphate (PIP2) for membrane displacement assays were from Avanti Polar Lipids.

IODVA1 was synthesized from 2-guanidinobenzimidazole and purified as described and Gasilina et al., 2020. Imatinib (#SML1027) was from Millipore Sigma, dasatinib (#S1021), and ruxolitinib (#S1378) from Selleck.

Retroviral and Lentiviral Particle Production, Transduction and Transplantation of Transduced Leukemic cells: Production of lentivirus and retrovirus for stable transduction of murine and human cells were done as described previously (Lee et al., 2017). Scrambled and Vav3-specific shRNAs (Sigma-Aldrich MISSION shRNA) were obtained from Cincinnati Children's Lenti-shRNA Library Core. Retroviral and lentiviral vectors, viral transduction of cell lines and mouse LDBM, and transplantation of transduced leukemic cells were previously described (Chang et al., 2012).

For Vav3 rescue experiments, low density bone marrow cells from wild-type (Vav3$^{+/+}$) or Vav3$^{-/-}$ mice were transduced with bicistronic retroviral vector encoding p190 BCR-ABL1-IRES-YFP (yellow fluorescent protein) and YFP$^+$ cells were sorted 48 h post-transduction. Cells were then transduced with lentiviral particles encoding either empty vector, full-length Vav3 or ΔCHVav3 (pCDH1-MCS1-EF1-copGFP). Cells were sorted for GFP$^+$/YFP$^+$ and treated with IODVA1 at the indicated concentrations. Cell cycle was analyzed at 18 h post BrdU incorporation.

SDS-PAGE, Pull-down Assays and Immunoblotting: Exponentially growing (6×10$^6$) p190-BCR-ABL Ba/F3 cells were treated with either vehicle or IODVA1 at indicated concentrations and time points. Active GTPase pulldown was done according to the manufacturer's instructions using GST-PAK1-GBD or GST-Rhotekin (Thermofisher, #16118 and #16116). Protein complexes were separated on SDS-PAGE and immunoblotted with anti-Rac1, anti-Cdc42 and anti-RhoA antibodies.

For analysis of expression, cells were lysed in RIPA buffer, supplemented with phosphatase and protease inhibitors, separated on SDS-PAGE, transferred on PVDF or nitrocellulose membrane and blotted with appropriate primary and secondary antibodies, as described previously (Lee et al., 2017; Chang et al., 2012). Relative signals were normalized to the unstimulated conditions after normalization to the total protein amount. Quantification was performed using Li-COR Image Studio.

Cloning: Human Rac1 (GenBank accession n° NM_006908.4) was subcloned into pFastBacHTB vector (Invitrogen) and fused with an N-terminal His$_6$-tag.

For pMalX(E)-based expression, full-length Vav3 was amplified with primers overlapping NotI restriction site of pMalX(E) vector with N-terminal linkers AAAA, AAAASEF or AAAASEFGS linkers. The finalized construct encoded MBPX(E)-linker-Vav3. For His$_6$-MBP-N$_9$-TEV-Vav3 construct, full-length Vav3 cDNA with a stop codon at the end of the coding sequence was amplified by PCR with primers overlapping pET28a-MBP-N$_9$TEV-mOrange vector at the SspI site. The resulting construct encoded MBP-N$_9$-Vav3-His$_6$. All constructs were verified using Sanger sequencing using CCHCM DNA Core. To minimize aggregation and improve on quality of purified protein, the expression clones were tested with chaperone plasmids according to the manufacturer's protocol.

Protein Expression and Purification: For membrane displacement assays, full-length human Rac1 was purified from baculovirus. pFastBacHTB-Rac1 was transformed into DH10 cells and the resulting bacmid was used to generate baculovirus in Sf9 cells. Rac1 was produced in TNAO38 insect cells and purified using Ni-IMAC chromatography (Zhang et al, 2014).

For production of recombinant Vav3, plasmids were co-transformed with chaperone plasmid Gro7 groEL-groES in BL21 (DE3) or T7 Express. Cultures were grown in LB, supplemented with metal mix (Studier 2005). Protein was purified using Ni-IMAC chromatography, dialyzed and further purified using size-exclusion gel filtration (HiLoad Superdex 200 16/60). Fractions were analyzed by SDS-PAGE and protein fractions containing Vav3 were pooled, concentrated to ~10 mg/mL and flash frozen in liquid nitrogen. Final yields for MBP-N9-Vav3 and MBPXE-Vav3 were 5 mg and 20 mg per 6 L of culture, respectively.

Recombinant LARG (DH/PH) was purified as a MBP-fusion protein as described previously (Kristelly R. et al., 2003).

RhoGDI extracting prenylated Rac1 from liposomes: Displacement of prenylated-Rac1-GDP from synthetic liposomes by GST-RhoGDI1 in the presence and absence of IODVA1 was studied using liposome sedimentation assay as in Zhang et al., 2014. Briefly, liposomes were generated by using a defined composition of lipids (194 µg) containing 39% w/w phosphatidylethanolamine, 16% w/w phosphatidylcholine, 36% w/w phosphatidylserine, 4% sphingomyelin, and 5% w/w phosphatidylinositol 4,5-bisphosphate. Prenylated Rac1-GDP (1 µM) was added to liposomes suspended in protein buffer (20 mM Hepes, pH 7.4, 150 mM NaCl, 5 mM $MgCl_2$, 3 mM DTT) and incubated for 20 min on ice. GST-RHOGDI1 (2 µM) in the absence or presence of IODVA1 was added to the liposome/prenylated Rac1 and further incubated on ice for 30 min. The samples were then centrifuged at 20,000×g for 20 min at 4° C. Pellet and supernatant fractions were collected, separated on SDS-PAGE and immunoblotted for Rac1.

Microscale Thermophoresis (MST): Purified Vav3, LARG or Rac (1 µM) were incubated with the indicated concentrations of IODVA1 at room temperature for 30 min. Samples were loaded into Zero Background MST Premium Coated capillaries and binding events were measured on Monolith NT. LabelFree (NanoTemper Technologies). Binding data were analyzed using Thermophoresis or Thermophoresis with Temperature Jump analysis as described previously (Jerabek-Willemsen et al., 2011). Data were normalized using fraction-bound binding. The 95% confidence interval for $K_d$ values was 0.27 to 0.98 µM for Vav3, 5.9 to 10.37 µM for LARG, and 19.6 to 105.8 µM for Rac.

Stopped-flow spectrometry. GTPase assay and nucleotide exchange reaction were performed with a Hi-Tech Scientific (SF-61) stopped-flow instrument as described (Nouri et al., 2016). The excitation wavelengths were 543 nm and 362 nm for tamraGTP and mantGppNHp, respectively. For GTPase assay, equal volumes (600 µl) of 0.2 µM Rac1-tamraGTP and 10 µM of p50GAP were used. GTPase assay as well the protein-protein interaction were performed in presence of 5% DMSO.

Animals and in vivo Drug Administration: Vav3-deficient mice (Fujikawa et al., 2003) and Rac1$^{\Delta/\Delta}$+Rac2-deficient (Thomas et al., 2007) mice have been described previously. C57Bl/6 mice were commercially obtained (The Jackson Laboratory and Harlan Laboratories) and used as donors and/or recipients of transduction/transplantation models under a protocol approved by The Cincinnati Children's Hospital Medical Center Institutional Animal Care and Use Committee. For in vivo drug administration, Alzet implantable osmotic pumps (Model 2002, Durect) were used according to the manufacturer's protocol and implantation was done as described previously (Thomas et al., 2007).

Histology: Embedded tissues were cut into 4 µm sections then immunohistochemically stained using the Mouse on Mouse kit (MoM kit, Vector Laboratories). Tissue sections were subjected to sodium citrate antigen retrieval, pretreated with 0.3% hydrogen peroxide, blocked according to kit directions, and incubated with an antibody to phosphorylated Vav3 (1:200 dilution, Abcam) and HRP-conjugated anti-rabbit secondary (Vector Laboratories). Staining was completed with the DAB Peroxidase kit (Vector Laboratories) and counterstained with hematoxylin. Tissue sections were coverslipped with Cytoseal 60 and images acquired with a Nikon Eclipse Ci microscope.

CFU-proB assay: B-cell lineage colony-forming units (CFU-proB) were quantified post 9-day culture of leukemic BM cells or sorted for p190-BCR-ABL—expressing B-cell progenitors in M3134 methylcellulose (StemCell Technologies) supplemented with 30% FBS (for mouse B lymphoid colony forming cells; StemCell Technologies), 2 mM L-glutamine (Invitrogen), 1% penicillin-streptomycin (Invitrogen), 100 µM β-mercaptoethanol (Fisher-Scientific), 1% BSA (Sigma-Aldrich), 20 ng/mL of recombinant mouse IL-7 (PeproTech), and 100 ng/mL of recombinant mouse SCF (PeproTech).

Cell cycle analysis: Cell cycle was analyzed by using in vitro incorporation of 5-Bromo-2-deoxyuridine using Brdu Flow kit (BD Pharmingen, Cat #552598). Briefly, mice leukemic progenitors were incubated with 1 mM BrdU solution for 45 minutes, cells were further fixed and permeabilized. DNAse treatment was done according to the instructions and stained with anti BrdU and apoptosis was analyzed by 7-AAD staining through flow cytometry analysis.

Flow cytometry analysis: Red blood cells were removed from the peripheral blood samples using fixative-free lysis buffer (BD Pharm Lyse lysing buffer Cat #555899). After a single wash in PBS, cells were stained with anti-B220 APC-Cy7 antibody. Stained cells were washed once and analyzed by flow cytometry.

Primary PDX ex vivo drug treatments: Primary patient specimens were obtained from patients at CCHMC according to Institutional Review Board Approved protocols (#2008-0021 and #2008-0658). Samples were subjected to RBC lysis and the isolated WBCs were mixed with OKT3 anti-CD3 antibody to eliminate the potential for xenogenic Graft Versus Host Disease before injection into busulfan conditioned NSG or NRG mice[10]. Spleen preparations from mice successfully engrafted with B-ALL were co-cultured with MS-5 or OP9 stroma in MEMα media supplemented with 20% FBS and 10 ng/mL recombinant human SCF (Kit-L), Flt3L, and IL-7 (KF7). IODVA1 was added 24 h after initial seeding. Co-cultures were collected by trypsinization after 7 days and cell counts were performed with trypan blue. Flow cytometry was performed with mCD45-APC-Cy7 (BD), hCD45-FITC (BD), hCD19-VioBlue (Miltenyi Biotech), and 7-AAd (for viability) to determine percentage of human ALL in the cultures. Total absolute ALL cell numbers were determined by multiplying cell counts by percentage human ALL cells.

Figure 19:
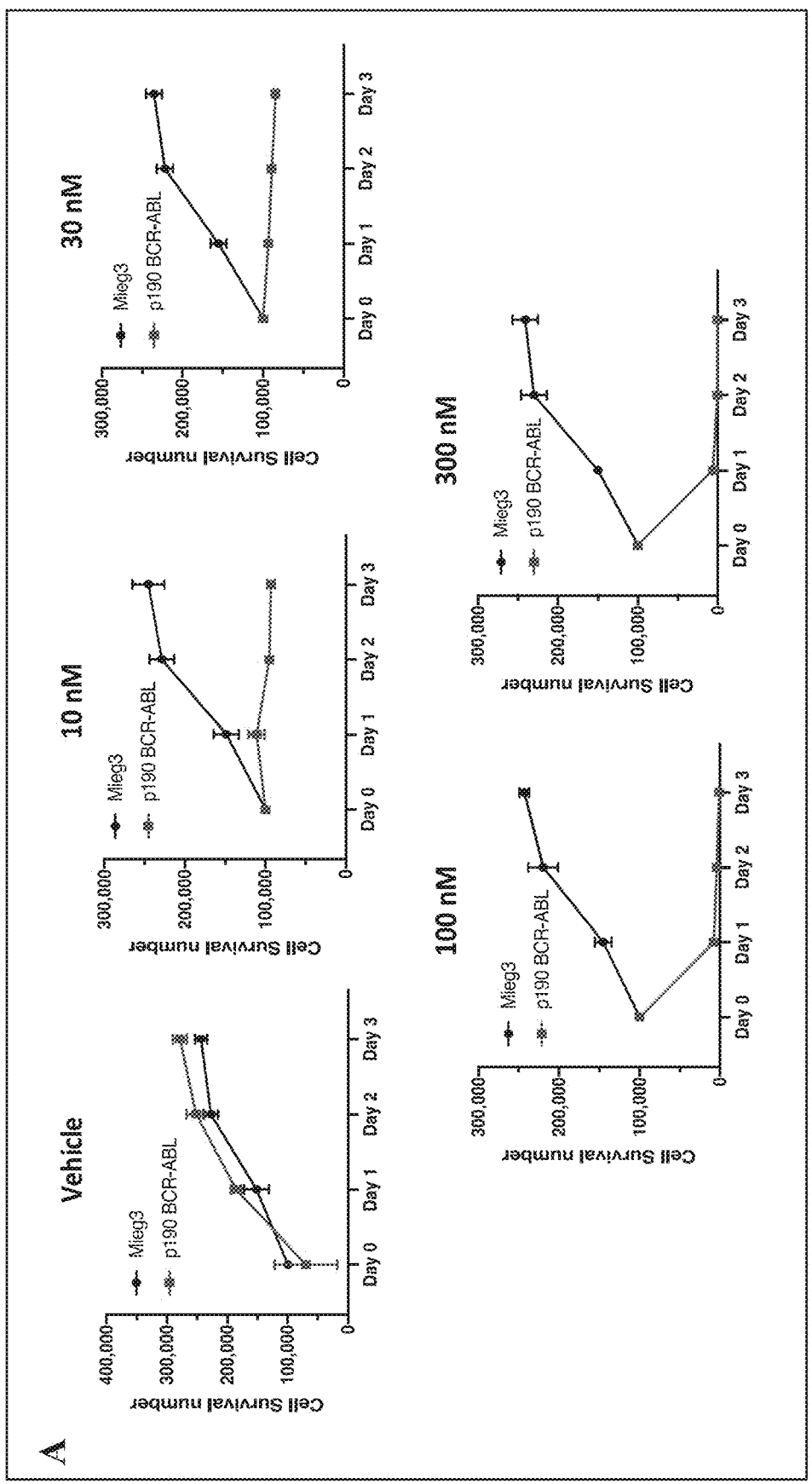
FIG. 19: NIRA2 inhibits the proliferation and survival of BCR-ABL1 expressing cells in vitro. (A) Leukemic Ba/F3 cells transduced with p190-BCR-ABL1 (red circles) or Mieg3 empty vector (black circles) were grown in the presence of vehicle control or NIRA2 at the indicated concentrations and counted daily for 3 days using trypan blue exclusion. (B) NIRA2-dependent survival plots of p190-BCR-ABL1 expressing Ba/F3 cells from (A) at the 24 h time-point yields an EC50 of 42.2 nM. Fitting of the data was done in Prism version 8.4.
Figure 19:
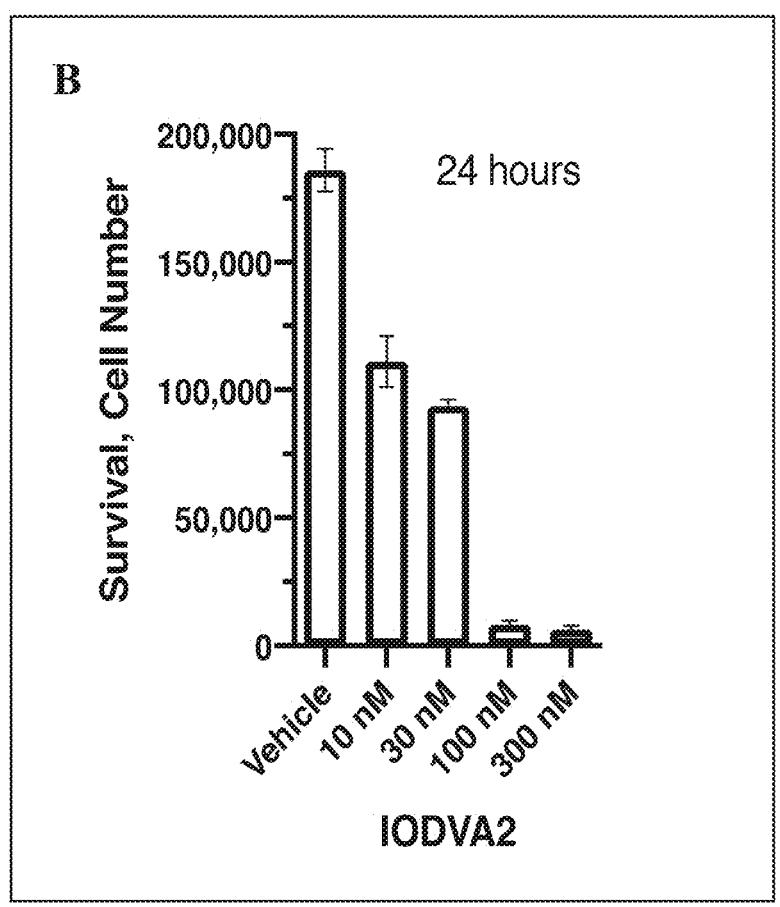

NIRA2 is a potent inhibitor of p190-BCR-ABL expressing cells in cellular assays. The efficacy of NIRA2 was tested in Ba/F3 cells transduced with p190-BCR-ABL, a commonly used Ph+ B-ALL cell model or with empty vector Mieg3. Ba/F3 cells are bone marrow-derived, interleukin-3 dependent, murine pro-B cells widely used in studying the mechanism of leukemia initiation and progression and targeted-therapy discovery. Cells were grown in suspension in the presence of IL-3 and NIRA2 (0 to 300 nM) and counted cells daily for 3 days by trypan blue exclusion (FIG. 19). At 10 and 30 nM, NIRA2 is cytostatic on BCR-ABL expressing cells. At 100 nM, NIRA2 reduced the viability of BCR-ABL expressing cells by 98±4% (SEM, N=9) at day 1; viability of Mieg3 empty vector expressing cells was not affected regardless of NIRA2 concentration. Plot of the concentration-cell survival at the 24-hour time point shows that NIRA2 inhibits survival of p190-BCR-ABL expressing Ba/F3 cells with a half maximal effective concentrations (EC50) of 42.2 nM (FIG. 19). NIRA2 is thus a potent inhibitor of p190-BCR-ABL expressing cells but does not affect the proliferation of empty vector Mieg3 expressing Ba/F3 cells suggesting that it is specific to oncogene expressing cells.

Figure 20:
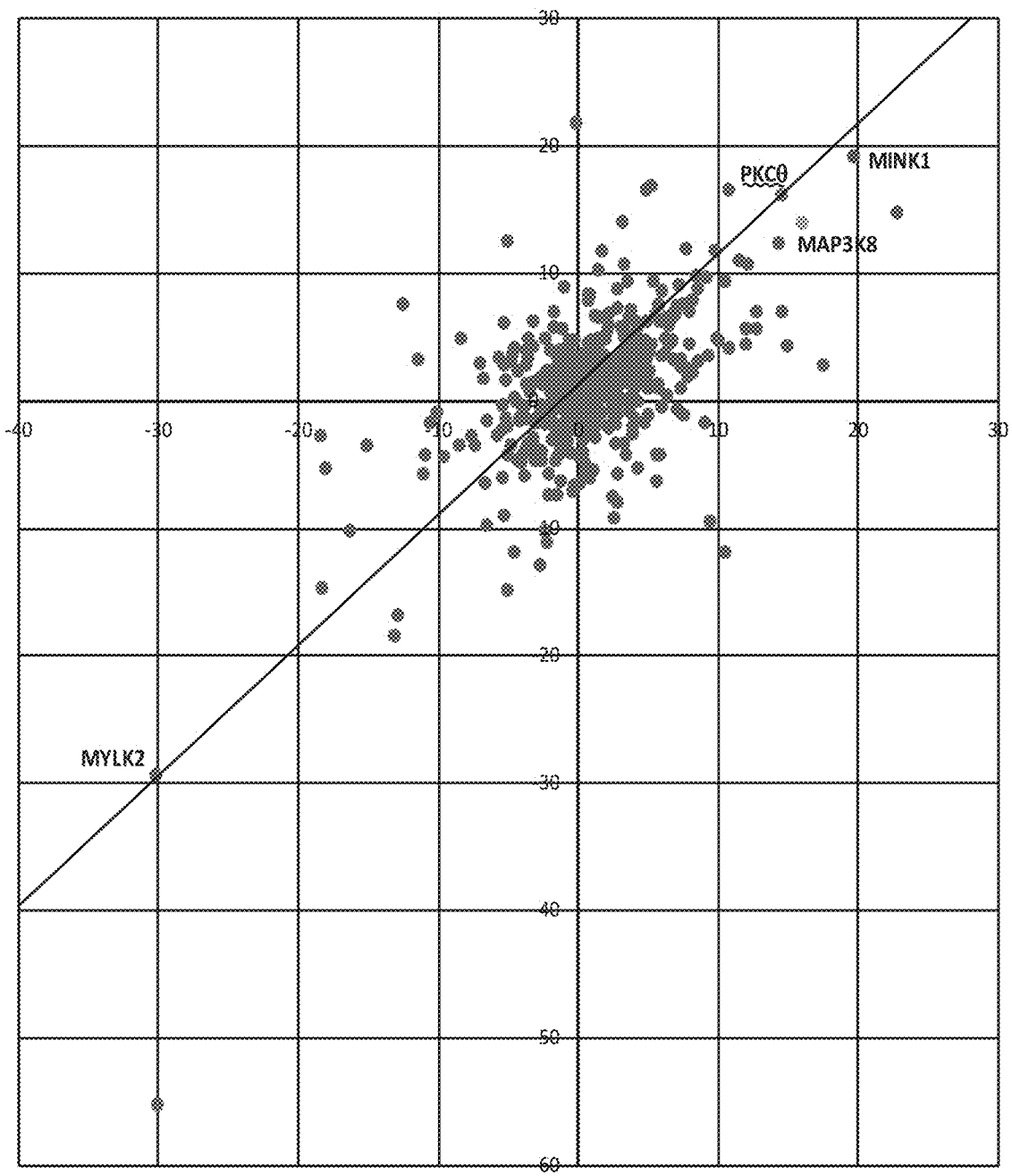
FIG. 20: NIRA2 kinome inhibitory activity. The activity of 485 kinases (ThermoFisher) was tested twice in the presence of 0.5 µM NIRA2. Plotted is the remaining activity of replicate 1 vs replicate 2 expressed as % of vehicle control set at 0% for each kinase. Kinases whose activities were decreased or increased by more than 3σ from mean are indicated.

NIRA2 is not a kinase inhibitor. To test if NIRA2 is a kinase inhibitor, its potential to interfere with the ability of 485 recombinant wild-type and mutant kinases to hydrolyze ATP was evaluated. Each kinase was tested twice at one NIRA2 concentration of 0.5 µM in the presence of ATP (at either the $K_m$ concentration or at 10 µM) and $Mg^{2+}$ (5 mM) and data were averaged and compared to vehicle DMSO control. A plot of the replicates compared to vehicle control set at 0% is shown in FIG. 20. Statistical analysis of the kinome data shows that NIRA2 is ineffective on all tested kinases in vitro. It shows an inhibition by 19 to 15% of MINK1, PKCθ, and MAP3K8 and an activation by 30% of MYLK2. However, the inhibition and stimulation effects are modest and higher NIRA2 concentrations are needed to inhibit or stimulate the aforementioned kinases to a level of 50%. Thus, NIRA2 is not a kinase inhibitor and the cellular effects previously observed with the p190-BCR-ABL expressing Ba/F3 cells cannot be explained by kinase inhibition or stimulation given that the cellular EC50 of NIRA2 (42.2 nM) is way below the concentration used for the kinase assays.

Figure 21:
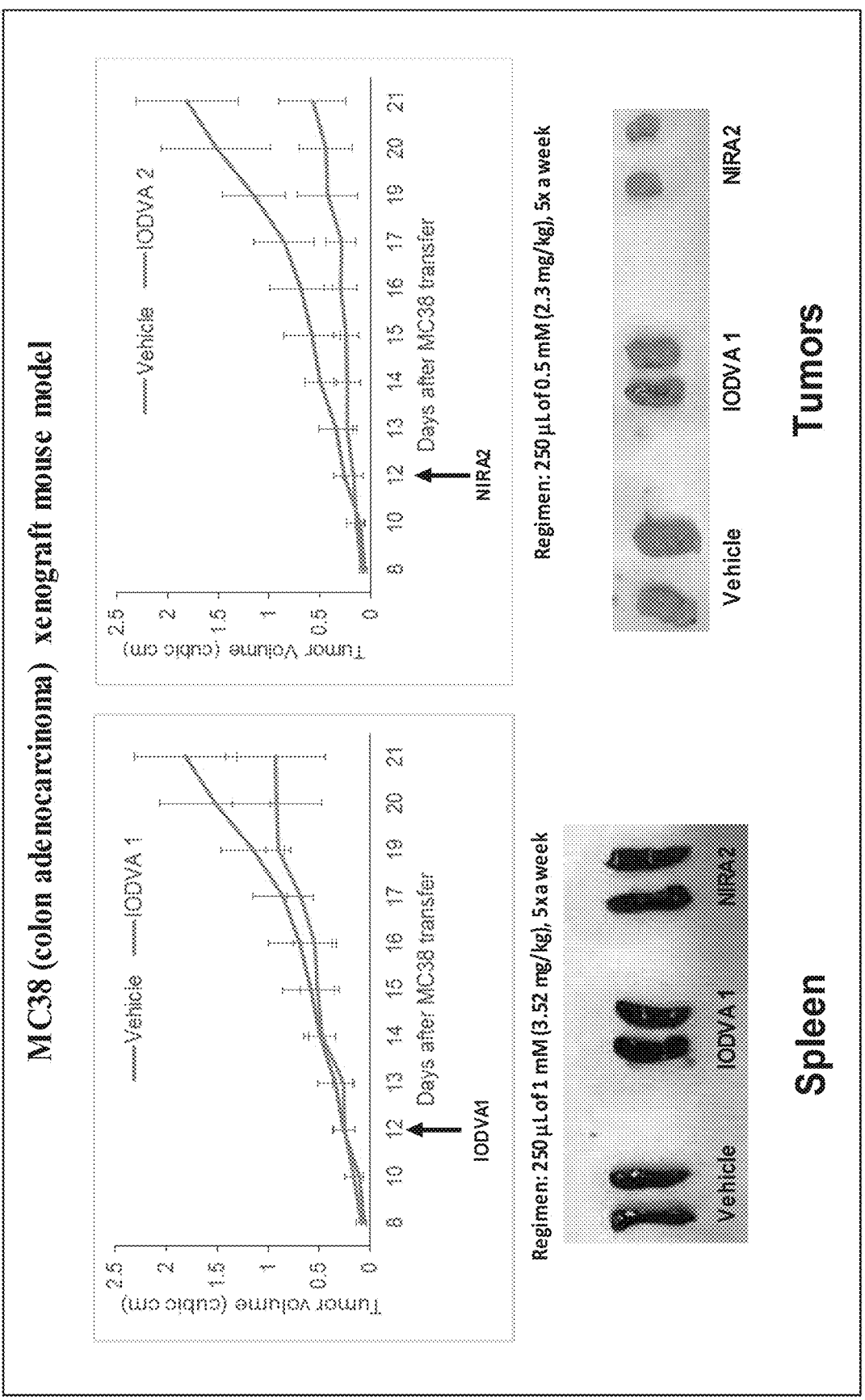
FIG. 21: NIRA2 inhibits tumor growth of murine colon adenocarcinoma xenografts. Orthotopic xenografts of MC38 colon adenocarcinoma cells demonstrated decreased tumor growth with NIRA2 treatment. Animals began treatment with vehicle, IODVA1, or NIRA2 (N=10 per group) when tumors reached 100-200 mm³ in volume (day 12 post-injection) and received treatment 5 times per week for two weeks. Representative pictures of the spleens and extracted tumors are shown.

NIRA2 inhibits tumor growth of a colon cancer mouse model. The in vivo efficacy of NIRA2 was tested against a xenograft mouse model generated with the murine colon adenocarcinoma MC38 cells. Cells were injected subcutaneously in the flank of a hind leg. Each injection contained one million cells of Matrigel+MC38 in a volume of 100 µL. Tumors were calipered until an average size of 100-200 $mm^3$ is reached. Animals were sorted in into treatment groups (N=10) and administered (5× a week) by IP 250 µL of a PBS solution containing vehicle control, IODVA1 (1 mM), or NIRA2 (0.5 mM). Treatments lasted 2 weeks. Animals were euthanized as tumor size reached 2 $cm^3$ or at the end of the study. Tumors were measured daily and mice weighed 3 times a week. As shown in FIG. 21, IODVA1 and NIRA2 significantly reduced tumor growth and tumor volumes. NIRA2 was more efficacious than IODVA1, however dose regimen of both drugs was not optimized. At the end of the study, we did not notice any effect of IODVA1 or NIRA2 on spleen.

REFERENCES

Aguilar, H. et al. VAV3 mediates resistance to breast cancer endocrine therapy. *Breast Cancer Res* 16, R53 (2014).

Anastassiadis, T., Deacon, S. W., Devarajan, K., Ma, H., and Peterson, J. R. (2011). Comprehensive assay of kinase catalytic activity reveals features of kinase inhibitor selectivity. Nat Biotechnol 29, 1039-1045.

Aoki, Y., Niihori, T., Inoue, S., and Matsubara, Y. (2016). Recent advances in RASopathies. J Hum Genet 61, 33-39.

Araki, M., Shima, F., Yoshikawa, Y., Muraoka, S., Ijiri, Y., Nagahara, Y., Shirono, T., Kataoka, T., and Tamura, A. (2011). Solution structure of the state 1 conformer of GTP-bound H-Ras protein and distinct dynamic properties between the state 1 and state 2 conformers. J Biol Chem 286, 39644-39653.

Arrigoni, E. et al. Concise Review: Chronic Myeloid Leukemia: Stem Cell Niche and Response to Pharmacologic Treatment. *Stem Cells Transl Med* 7, 305-314 (2018).

Azam, M., Latek, R. R. & Daley, G. Q. Mechanisms of autoinhibition and STI-571/imatinib resistance revealed by mutagenesis of BCR-ABL. *Cell* 112, 831-43 (2003).

Bar-Sagi D, Hall A. Ras and Rho GTPases: a family reunion. Cell. 2000; 103(2):227-38. Epub 2000/11/01. doi: 10.1016/s0092-8674(00)00115-x. PubMed PMID: 11057896.

Bassermann, F. et al. Association of Bcr-Abl with the proto-oncogene Vav is implicated in activation of the Rac-1 pathway. *J Biol Chem* 277, 12437-45 (2002).

Basu, T. N., Gutmann, D. H., Fletcher, J. A., Glover, T. W., Collins, F. S., and Downward, J. (1992). Aberrant regulation of ras proteins in malignant tumour cells from type 1 neurofibromatosis patients. Nature 356, 713-715.

Bavetsias, V., Crumpler, S., Sun, C., Avery, S., Atrash, B., Faisal, A., Moore, A S., Kosmopoulou, M., Brown, N., Sheldrake, P. W., et al. (2012). Optimization of imidazo [4,5-b]pyridine-based kinase inhibitors: identification of a dual FLT3/Aurora kinase inhibitor as an orally bioavailable preclinical development candidate for the treatment of acute myeloid leukemia. J Med Chem 55, 8721-8734.

Berridge, M. V., Herst, P. M., and Tan, A. S. (2005). Tetrazolium dyes as tools in cell biology: new insights into their cellular reduction. Biotechnol Annu Rev 11, 127-152.

Biesiada, J., Porollo, A., Velayutham, P., Kouril, M., and Meller, J. (2011). Survey of public domain software for docking simulations and virtual screening. Hum Genomics 5, 497-505.

Biswas, M. et al. MBD3/NuRD loss participates with KDM6A program to promote DOCKS/8 expression and Rac GTPase activation in human acute myeloid leukemia. *FASEB J* 33, 5268-5286 (2019).

Bixby, D. & Talpaz, M. Mechanisms of resistance to tyrosine kinase inhibitors in chronic myeloid leukemia and recent therapeutic strategies to overcome resistance. *Hematology Am Soc Hematol Educ Program*, 461-76 (2009).

Boriack-Sjodin, P. A., Margarit, S. M., Bar-Sagi, D., and Kuriyan, J. (1998). The structural basis of the activation of Ras by Sos. Nature 394, 337-343.

Bourgoin, S., Harbour, D., Desmarais, Y., Takai, Y. & Beaulieu, A. Low molecular weight GTP-binding proteins in HL-60 granulocytes. Assessment of the role of ARF and of a 50-kDa cytosolic protein in phospholipase D activation. *J Biol Chem* 270, 3172-8 (1995).

Bustelo, X. R. RHO GTPases in cancer: known facts, open questions, and therapeutic challenges. *Biochem Soc Trans* 46, 741-760 (2018).

Cardama, G. A. et al. Relevance of small GTPase Rac1 pathway in drug and radio-resistance mechanisms: Opportunities in cancer therapeutics. *Crit Rev Oncol Hematol* 124, 29-36 (2018).

Chatterjee, S. S., Biswas, M., Boila, L. D., Banerjee, D. & Sengupta, A. SMARCB1 Deficiency Integrates Epigenetic Signals to Oncogenic Gene Expression Program Maintenance in Human Acute Myeloid Leukemia. *Mol Cancer Res* 16, 791-804 (2018).

Chang, K. H. et al. Vav3 collaborates with p190-BCR-ABL in lymphoid progenitor leukemogenesis, proliferation, and survival. *Blood* 120, 800-11 (2012).

Chen, X. et al. Vav3 oncogene is upregulated and a poor prognostic factor in breast cancer patients. *Oncol Lett* 9, 2143-2148 (2015).

Cilloni, D. & Saglio, G. Molecular pathways: BCR-ABL. *Clinical cancer research: an official journal of the American Association for Cancer Research* 18, 930-7 (2012).

Citterio, C. et al. The rho exchange factors vav2 and vav3 control a lung metastasis-specific transcriptional program in breast cancer cells. *Sci Signal* 5, ra71 (2012).

Coleman, M. L., Marshall, C. J. & Olson, M. F. RAS and RHO GTPases in G1-phase cell-cycle regulation. *Nat Rev Mol Cell Biol* 5, 355-66 (2004).

Condeelis, J., Singer, R. H., and Segall, J. E. (2005). The great escape: when cancer cells hijack the genes for chemotaxis and motility. Annu Rev Cell Dev Biol 21, 695-718.

Corsello, S. M., Bittker, J. A., Liu, Z., Gould, J., McCarren, P., Hirschman, J. E., Johnston, S. E., Vrcic, A., Wong, B., Khan, M., et al. (2017). The Drug Repurposing Hub: a next-generation drug library and information resource. Nat Med 23, 405-408.

Cox, A. D., Fesik, S. W., Kimmelman, A. C., Luo, J., and Der, C. J. (2014). Drugging the undruggable RAS: Mission possible? Nat Rev Drug Discov 13, 828-851.

Denizot, F., and Lang, R. (1986). Rapid colorimetric assay for cell growth and survival. Modifications to the tetrazolium dye procedure giving improved sensitivity and reliability. J Immunol Methods 89, 271-277.

Espina C, Cespedes M V, Garcia-Cabezas M A, Gomez del Pulgar M T, Boluda A, Oroz L G, et al. A critical role for Rac1 in tumor progression of human colorectal adenocarcinoma cells. Am J Pathol. 2008; 172(1):156-66. doi: 10.2353/ajpath.2008.070561. PubMed PMID: 18165265; PubMed Central PMCID: PMCPMC2189620.

Etienne-Manneville, S. & Hall, A. Rho GTPases in cell biology. *Nature* 420, 629-35 (2002).

Euhus, D. M., Hudd, C., LaRegina, M. C., and Johnson, F. E. (1986). Tumor measurement in the nude mouse. Journal of surgical oncology 31, 229-234.

Evelyn, C. R., Biesiada, J., Duan, X., Tang, H., Shang, X., Papoian, R., Seibel, W. L., Nelson, S., Meller, J., and Zheng, Y. (2015). Combined rational design and a high throughput screening platform for identifying chemical inhibitors of a Ras-activating enzyme. J Biol Chem 290, 12879-12898.

Evelyn, C. R., Duan, X., Biesiada, J., Seibel, W. L., Meller, J., and Zheng, Y. (2014). Rational design of small molecule inhibitors targeting the Ras GEF, SOS1. Chem Biol 21, 1618-1628.

Ford, B., Skowronek, K., Boykevisch, S., Bar-Sagi, D., and Nassar, N. (2005). Structure of the G60A mutant of Ras: implications for the dominant negative effect. J Biol Chem 280, 25697-25705.

Ford, B. A., Boykevisch, S., Zhao, C., Kunzelmann, S., Bar-Sagi, D., Herrmann, C., and Nassar, N. (2009). Characterization of a Ras mutant with identical GDP- and GTP-bound structures. Biochemistry 48, 11449-11457.

Foty R. A simple hanging drop cell culture protocol for generation of 3D spheroids. J Vis Exp. 2011; (51). Epub 2011/05/19. doi: 10.3791/2720. PubMed PMID: 21587162; PubMed Central PMCID: PMCPMC3197119.

Fujikawa, K. et al. Vav1/2/3-null mice define an essential role for Vav family proteins in lymphocyte development and activation but a differential requirement in MAPK signaling in T and B cells. *J Exp Med* 198, 1595-608 (2003).

Gasilina, A. et al. IODVA1, a guanidinobenzimidazole derivative, targets Rac activity and Ras-driven cancer models. *PLoS One* 15, e0229801 (2020).

Geyer, M., Schweins, T., Herrmann, C., Prisner, T., Wittinghofer, A., and Kalbitzer, H. R. (1996). Conformational transitions in p21ras and in its complexes with the effector protein Raf-RBD and the GTPase activating protein GAP. Biochemistry 35, 10308-10320.

Gone, M. E. et al. Clinical resistance to STI-571 cancer therapy caused by BCR-ABL gene mutation or amplification. *Science* 293, 876-80 (2001).

Green, J., Cao, J., Bandarage, U. K., Gao, H., Court, J., Marhefka, C., Jacobs, M., Taslimi, P., Newsome, D., Nakayama, T., et al. (2015). Design, Synthesis, and Structure-Activity Relationships of Pyridine-Based Rho Kinase (ROCK) Inhibitors. J Med Chem 58, 5028-5037.

Hall A. Small GTP-binding proteins and the regulation of the actin cytoskeleton. Annu Rev Cell Biol. 1994; 10:31-54. Epub 1994/01/01. doi: 10.1146/annurev.cb.10.110194.000335. PubMed PMID: 7888179.

Hamilton, A. et al. Chronic myeloid leukemia stem cells are not dependent on Bcr-Abl kinase activity for their survival. *Blood* 119, 1501-10 (2012).

Harnois, T. et al. Differential interaction and activation of Rho family GTPases by p210bcr-abl and p190bcr-abl. *Oncogene* 22, 6445-54 (2003).

Hollestelle, A., Elstrodt, F., Nagel, J. H., Kallemeijn, W. W., and Schutte, M. (2007). Phosphatidylinositol-3-OH kinase or RAS pathway mutations in human breast cancer cell lines. Mol Cancer Res 5, 195-201.

Huey, R., Morris, G. M., Olson, A. J., and Goodsell, D. S. (2007). A Semiempirical Free Energy Force Field with Charge-Based Desolvation. J Computational Chemistry 28, 1145-1152.

Hwang, M. C., Sung, Y. J., and Hwang, Y. W. (1996). The differential effects of the Gly-60 to Ala mutation on the interaction of H-Ras p21 with different downstream targets. J Biol Chem 271, 8196-8202.

Jabbour, E. et al. Characteristics and outcomes of patients with chronic myeloid leukemia and T315I mutation following failure of imatinib mesylate therapy. *Blood* 112, 53-5 (2008).

Jabbour, E. et al. Frequency and clinical significance of BCR-ABL mutations in patients with chronic myeloid leukemia treated with imatinib mesylate. *Leukemia* 20, 1767-73 (2006).

Jaffe, A. B. & Hall, A. Rho GTPases: biochemistry and biology. *Annu Rev Cell Dev Biol* 21, 247-69 (2005).

Janes, M. R., Zhang, J., Li, L. S., Hansen, R., Peters, U., Guo, X., Chen, Y., Babbar, A., Firdaus, S. J., Darjania, L., et al. (2018). Targeting KRAS Mutant Cancers with a Covalent G12C-Specific Inhibitor. Cell 172, 578-589 e517.

Jerabek-Willemsen, M., Wienken, C. J., Braun, D., Baaske, P. & Duhr, S. Molecular interaction studies using microscale thermophoresis. *Assay Drug Dev Technol* 9, 342-53 (2011).

Kiosses, W. B., Shand, S. J., Pampori, N. & Schwartz, M. A. Rac recruits high-affinity integrin alphavbeta3 to lamellipodia in endothelial cell migration. *Nat Cell Biol* 3, 316-20 (2001).

Kissil J L, Walmsley M J, Hanlon L, Haigis K M, Bender Kim C F, Sweet-Cordero A, et al. Requirement for Rac1 in a K-ras induced lung cancer in the mouse. Cancer Res.

2007; 67(17):8089-94. doi: 10.1158/0008-5472.CAN-07-2300. PubMed PMID: 17804720.

Kristelly, R., Earnest, B. T., Krishnamoorthy, L. & Tesmer, J. J. Preliminary structure analysis of the DH/PH domains of leukemia-associated RhoGEF. *Acta Crystallogr D Biol Crystallogr* 59, 1859-62 (2003).

Lee, K. et al. Vav3 oncogene activates estrogen receptor and its overexpression may be involved in human breast cancer. *BMC Cancer* 8, 158 (2008).

Lee S H, Dominguez R. Regulation of actin cytoskeleton dynamics in cells. Mol Cells. 2010; 29(4):311-25. Epub 2010/05/07. doi: 10.1007/s10059-010-0053-8. PubMed PMID: 20446344; PubMed Central PMCID: PMCPMC3910092.

Lee, L. H. et al. Real-time genomic profiling of histiocytoses identifies early-kinase domain BRAF alterations while improving treatment outcomes. *JCI Insight* 2, e89473 (2017).

Loirand, G. & Pacaud, P. The role of Rho protein signaling in hypertension. *Nat Rev Cardiol* 7, 637-47 (2010).

Lorenzo-Martin, L. F. et al. Vav proteins maintain epithelial traits in breast cancer cells using miR-200c-dependent and independent mechanisms. *Oncogene* 38, 209-227 (2019).

Loveland, B. E., Johns, T. G., Mackay, I. R., Vaillant, F., Wang, Z. X., and Hertzog, P. J. (1992). Validation of the MTT dye assay for enumeration of cells in proliferative and antiproliferative assays. Biochem Int 27, 501-510.

Lugo, T. G., Pendergast, A. M., Muller, A. J. & Witte, O. N. Tyrosine kinase activity and transformation potency of bcr-abl oncogene products. *Science* 247, 1079-82 (1990).

Lyons, R. et al. The RAC specific guanine nucleotide exchange factor Asef functions downstream from TEL-AML1 to promote leukaemic transformation. *Leuk Res* 34, 109-15 (2010).

Mack, N. A., Whalley, H. J., Castillo-Lluva, S. & Malliri, A. The diverse roles of Rac signaling in tumorigenesis. *Cell Cycle* 10, 1571-81 (2011).

Mahller, Y. Y., Rangwala, F., Ratner, N., and Cripe, T. P. (2006). Malignant peripheral nerve sheath tumors with high and low Ras-GTP are permissive for oncolytic herpes simplex virus mutants. Pediatr Blood Cancer 46, 745-754.

Malliri A, van der Kammen R A, Clark K, van der Valk M, Michiels F, Collard J G. Mice deficient in the Rac activator Tiam1 are resistant to Ras-induced skin tumours. Nature. 2002; 417(6891):867-71. Epub 2002/06/21. doi: 10.1038/nature00848. PubMed PMID: 12075356.

Martin, H. et al. Pak and Rac GTPases promote oncogenic KIT-induced neoplasms. *J Clin Invest* 123, 4449-63 (2013).

Marin-Ramos, N. I., Ortega-Gutierrez, S., and Lopez-Rodriguez, M. L. (2018). Blocking Ras inhibition as an antitumor strategy. Semin Cancer Biol.

Maurer, T., Garrenton, L. S., Oh, A., Pitts, K., Anderson, D. J., Skelton, N. J., Fauber, B. P., Pan, B., Malek, S., Stokoe, D., et al. (2012). Small-molecule ligands bind to a distinct pocket in Ras and inhibit SOS-mediated nucleotide exchange activity. Proc Natl Acad Sci USA 109, 5299-5304.

McCormick, F. (2016). K-Ras protein as a drug target. J Mol Med (Berl) 94, 253-258.

Milojkovic, D. & Apperley, J. Mechanisms of Resistance to Imatinib and Second-Generation Tyrosine Inhibitors in Chronic Myeloid Leukemia. *Clin Cancer Res* 15, 7519-7527 (2009).

Minden, A., Lin, A., Claret, F. X., Abo, A. & Karin, M. Selective activation of the JNK signaling cascade and c-Jun transcriptional activity by the small GTPases Rac and Cdc42Hs. *Cell* 81, 1147-57 (1995).

Mizukawa, B. et al. Inhibition of Rac GTPase signaling and downstream prosurvival Bcl-2 proteins as combination targeted therapy in MLL-AF9 leukemia. *Blood* 118, 5235-45 (2011).

Morris, G. M., Goodsell, D. S., Halliday, R. S., Huey, R., Hart, W. E., Belew, R. K., and Olson, A. J. (1998). Automated Docking Using a Lamarckian Genetic Algorithm and an Empirical Binding Free Energy Function. J Computational Chemistry 19, 1639-1662.

Morris, G. M., Huey, R., Lindstrom, W., Sanner, M. F., Belew, R. K., Goodsell, D. S., and Olson, A. J. (2009). AutoDock4 and AutoDockTools4: Automated docking with selective receptor flexibility. Journal of computational chemistry 30, 2785-2791.

Mulloy, J. C. et al. Rho GTPases in hematopoiesis and hemopathies. *Blood* 115, 936-47 (2010).

Nicolini, F. E. et al. Mutation status and clinical outcome of 89 imatinib mesylate-resistant chronic myelogenous leukemia patients: a retrospective analysis from the French intergroup of CML (Fi(phi)-LMC GROUP). *Leukemia* 20, 1061-6 (2006).

Nieborowska-Skorska, M. et al. Rac2-MRC-cIII-generated ROS cause genomic instability in chronic myeloid leukemia stem cells and primitive progenitors. *Blood* 119, 4253-63 (2012).

Newey, S. E., Velamoor, V., Govek, E. E. & Van Aelst, L. Rho GTPases, dendritic structure, and mental retardation. *J Neurobiol* 64, 58-74 (2005).

Nouri, K. et al. IQGAP1 Interaction with RHO Family Proteins Revisited: KINETIC AND EQUILIBRIUM EVIDENCE FOR MULTIPLE DISTINCT BINDING SITES. *J Biol Chem* 291, 26364-26376 (2016).

Ostrem, J. M., and Shokat, K. M. (2016). Direct small-molecule inhibitors of KRAS: from structural insights to mechanism-based design. Nat Rev Drug Discov 15, 771-785.

Pai, E. F., Kabsch, W., Krengel, U., Holmes, K. C., John, J., and Wittinghofer, A. (1989). Structure of the guanine-nucleotide-binding domain of the Ha-ras oncogene product p21 in the triphosphate conformation. Nature 341, 209-214.

Porter, A. P., Papaioannou, A. & Malliri, A. Deregulation of Rho GTPases in cancer. *Small GTPases* 7, 123-38 (2016).

Quevedo, C. E., Cruz-Migoni, A., Bery, N., Miller, A., Tanaka, T., Petch, D., Bataille, C. J. R., Lee, L. Y. W., Fallon, P. S., Tulmin, H., et al. (2018). Small molecule inhibitors of RAS-effector protein interactions derived using an intracellular antibody fragment. Nature communications 9, 3169.

Qiu, R. G., Chen, J., Kim, D., McCormick, F. & Symons, M. An essential role for Rac in Ras transformation. *Nature* 374, 457-9 (1995).

Rauen, K. A. (2013). The RASopathies. Annual review of genomics and human genetics 14, 355-369.

Reuther, G. W. et al. Leukemia-associated Rho guanine nucleotide exchange factor, a Dbl family protein found mutated in leukemia, causes transformation by activation of RhoA. *J Biol Chem* 276, 27145-51 (2001).

Ridley, A. J. Rho GTPase signaling in cell migration. *Curr Opin Cell Biol* 36, 103-12 (2015).

Ridley A J, Hall A. The small GTP-binding protein rho regulates the assembly of focal adhesions and actin stress fibers in response to growth factors. Cell. 1992; 70(3): 389-99. Epub 1992/08/07. PubMed PMID: 1643657.

Ridley, A. J., Paterson, H. F., Johnston, C. L., Diekmann, D. & Hall, A. The small GTP-binding protein rac regulates growth factor-induced membrane ruffling. Cell 70, 401-10 (1992).

Rouard, H., Tamasdan, S., Fridman, W. H. & Teillaud, J. L. Vav and SLP-76 recruitment by cross-linking of FcgammaRIIa1 in promyelocytic HL-60 cells. Immunol Lett 68, 347-53 (1999).

Saci, A., Cantley, L. C. & Carpenter, C. L. Rac1 regulates the activity of mTORC1 and mTORC2 and controls cellular size. Mol Cell 42, 50-61 (2011).

Sahai, E. (2005). Mechanisms of cancer cell invasion. Curr Opin Genet Dev 15, 87-96.

Sahai, E. & Marshall, C. J. RHO-GTPases and cancer. Nat Rev Cancer 2, 133-42 (2002).

Sahay, S. et al. The RhoGEF domain of p210 Bcr-Abl activates RhoA and is required for transformation. Oncogene 27, 2064-71 (2008).

Schopel, M., Jockers, K. F., Duppe, P. M., Autzen, J., Potheraveedu, V. N., Ince, S., Yip, K. T., Heumann, R., Herrmann, C., Scherkenbeck, J., et al. (2013). Bisphenol A binds to Ras proteins and competes with guanine nucleotide exchange: implications for GTPase-selective antagonists. J Med Chem 56, 9664-9672.

Sengupta, A., Arnett, J., Dunn, S., Williams, D. A. & Cancelas, J. A. Rac2 GTPase deficiency depletes BCR-ABL+ leukemic stem cells and progenitors in vivo. Blood 116, 81-4 (2010).

Shima, F., Ijiri, Y., Muraoka, S., Liao, J., Ye, M., Araki, M., Matsumoto, K., Yamamoto, N., Sugimoto, T., Yoshikawa, Y., et al. (2010). Structural basis for conformational dynamics of GTP-bound Ras protein. J Biol Chem 285, 22696-22705.

Shima, F., Yoshikawa, Y., Ye, M., Araki, M., Matsumoto, S., Liao, J., Hu, L., Sugimoto, T., Ijiri, Y., Takeda, A., et al. (2013). In silico discovery of small-molecule Ras inhibitors that display antitumor activity by blocking the Ras-effector interaction. Proc Natl Acad Sci USA 110, 8182-8187.

Simanshu, D. K., Nissley, D. V., and McCormick, F. (2017). RAS Proteins and Their Regulators in Human Disease. Cell 170, 17-33.

Skorski, T. et al. BCR/ABL-mediated leukemogenesis requires the activity of the small GTP-binding protein Rac. Proc Natl Acad Sci USA 95, 11858-62 (1998).

Somervaille, T. C. & Cleary, M. L. Identification and characterization of leukemia stem cells in murine MLL-AF9 acute myeloid leukemia. Cancer Cell 10, 257-68 (2006).

Spencer-Smith, R., and O'Bryan, J. P. (2017). Direct inhibition of RAS: Quest for the Holy Grail? Semin Cancer Biol.

Spiegel, J., Cromm, P. M., Zimmermann, G., Grossmann, T. N., and Waldmann, H. (2014). Small-molecule modulation of Ras signaling. Nature chemical biology 10, 613-622.

Spoemer, M., Herrmann, C., Vetter, I. R., Kalbitzer, H. R., and Wittinghofer, A. (2001). Dynamic properties of the Ras switch I region and its importance for binding to effectors. Proc Natl Acad Sci USA 98, 4944-4949.

Spoemer, M., Hozsa, C., Poetzl, J. A., Reiss, K., Ganser, P., Geyer, M., and Kalbitzer, H. R. (2010). Conformational states of human rat sarcoma (Ras) protein complexed with its natural ligand GTP and their role for effector interaction and GTP hydrolysis. J Biol Chem 285, 39768-39778.

Spoerner, M., Nuehs, A., Herrmann, C., Steiner, G., and Kalbitzer, H. R. (2007). Slow conformational dynamics of the guanine nucleotide-binding protein Ras complexed with the GTP analogue GTPgammaS. The FEBS journal 274, 1419-1433.

Stephen, A. G., Esposito, D., Bagni, R. K., and McCormick, F. (2014). Dragging ras back in the ring. Cancer Cell 25, 272-281.

Steffen, A. et al. Rac function is crucial for cell migration but is not required for spreading and focal adhesion formation. J Cell Sci 126, 4572-88 (2013).

Studier, F. W. Protein production by auto-induction in high density shaking cultures. Protein Expr Purif 41, 207-34 (2005).

Sun, Q., Burke, J. P., Phan, J., Burns, M. C., Olejniczak, E. T., Waterson, A. G., Lee, T., Rossanese, O. W., and Fesik, S. W. (2012). Discovery of small molecules that bind to K-Ras and inhibit Sos-mediated activation. Angew Chem Int Ed Engl 51, 6140-6143.

Sundaresan, M. et al. Regulation of reactive-oxygen-species generation in fibroblasts by Rac1. Biochem J 318 (Pt 2), 379-82 (1996).

Sung, Y. J., Carter, M., Zhong, J. M., and Hwang, Y. W. (1995). Mutagenesis of the H-ras p21 at glycine-60 residue disrupts GTP-induced conformational change. Biochemistry 34, 3470-3477.

Sung, Y. J., Hwang, M. C., and Hwang, Y. W. (1996). The dominant negative effects of H-Ras harboring a Gly to Ala mutation at position 60. J Biol Chem 271, 30537-30543.

Tajan, M., Paccoud, R., Branka, S., Edouard, T., and Yart, A. (2018). The RASopathy Family: Consequences of Germline Activation of the RAS/MAPK Pathway. Endocr Rev 39, 676-700.

Thomas, E. K., Cancelas, J. A., Zheng, Y. & Williams, D. A. Rac GTPases as key regulators of p210-BCR-ABL-dependent leukemogenesis. Leukemia 22, 898-904 (2008).

Thomas, E. K. et al. Rac guanosine triphosphatases represent integrating molecular therapeutic targets for BCR-ABL-induced myeloproliferative disease. Cancer Cell 12, 467-78 (2007).

Tidyman, W. E., and Rauen, K. A. (2009a). The RASopathies: developmental syndromes of Ras/MAPK pathway dysregulation. Curr Opin Genet Dev 19, 230-236.

Tidyman, W. E., and Rauen, K. A. (2009b). The RASopathies: developmental syndromes of Ras/MAPK pathway dysregulation. Curr Opin Genet Dev 19, 230-236.

Tomayko, M. M., and Reynolds, C. P. (1989). Determination of subcutaneous tumor size in athymic (nude) mice. Cancer chemotherapy and pharmacology 24, 148-154.

Vetter, I. R., and Wittinghofer, A. (2001). The guanine nucleotide-binding switch in three dimensions. Science 294, 1299-1304.

Vigil, D., Cherfils, J., Rossman, K. L. & Der, C. J. Ras superfamily GEFs and GAPs: validated and tractable targets for cancer therapy? Nat Rev Cancer 10, 842-57 (2010).

Wang Z, Pedersen E, Basse A, Lefever T, Peyrollier K, Kapoor S, et al. Rac1 is crucial for Ras-dependent skin tumor formation by controlling Pak1-Mek-Erk hyperactivation and hyperproliferation in vivo. Oncogene. 2010; 29(23):3362-73. Epub 2010/04/13. doi: 10.1038/onc.2010.95. PubMed PMID: 20383193.

Wei, J. et al. Microenvironment determines lineage fate in a human model of MLL-AF9 leukemia. Cancer Cell 13, 483-95 (2008).

Welsch, M. E., Kaplan, A., Chambers, J. M., Stokes, M. E., Bos, P. H., Zask, A., Zhang, Y., Sanchez-Martin, M., Badgley, M. A., Huang, C. S., et al. (2017). Multivalent Small-Molecule Pan-RAS Inhibitors. Cell 168, 878-889 e829.

Williams, D. A. et al. Dominant negative mutation of the hematopoietic-specific Rho GTPase, Rac2, is associated with a human phagocyte immunodeficiency. *Blood* 96, 1646-54 (2000).

Wittinghofer, A., and Nassar, N. (1996). How Ras-related proteins talk to their effectors. Trends in biochemical sciences 21, 488-491.

Woods, K. W., Fischer, J. P., Claiborne, A., Li, T., Thomas, S. A., Zhu, G. D., Diebold, R. B., Liu, X., Shi, Y., Klinghofer, V., et al. (2006). Synthesis and SAR of indazole-pyridine based protein kinase B/Akt inhibitors. Bioorganic & medicinal chemistry 14, 6832-6846.

Xing, L., Rai, B., and Lunney, E. A. (2014). Scaffold mining of kinase hinge binders in crystal structure database. Journal of computer-aided molecular design 28, 13-23.

Yamaguchi, H., and Condeelis, J. (2007). Regulation of the actin cytoskeleton in cancer cell migration and invasion. Biochim Biophys Acta 1773, 642-652.

Yamaguchi, H., Wyckoff, J., and Condeelis, J. (2005). Cell migration in tumors. Current opinion in cell biology 17, 559-564.

Zandvakili, I., Lin, Y., Morris, J. C. & Zheng, Y. Rho GTPases: Anti- or pro-neoplastic targets? *Oncogene* 36, 3213-3222 (2017).

Zhang, S. C. et al. Liposome reconstitution and modulation of recombinant prenylated human Rac1 by GEFs, GDI1 and Pak1. *PLoS One* 9, e102425 (2014).

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A composition comprising a pharmaceutically acceptable carrier and

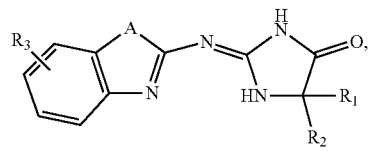

wherein A=NH, $NR_8$, S, O, C=C, N=C, C=N;

wherein $R_1$, $R_2$ are independently substituted aryl rings, furanyl, pyrimidinyl, and triazinyl rings;

wherein $R_3$=singly or multiply substituted as H, D, Halo, CN, C1-C4 Alkyl, C1-C4 alkoxy, C1-C4 alkylsulfonyl, C1-C4 Alkyl amino, or C1-C4 mercapto; and wherein $R_8$=H, Me.

2. A method of therapeutically treating leukemia in an individual in need thereof, comprising the step of administering to said individual one or more compounds selected from

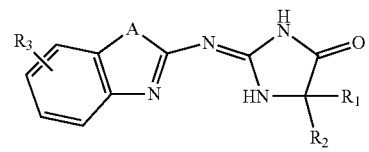

wherein A=NH, $NR_8$, S, O, C=C, N=C, C=N;

wherein $R_1$, and $R_2$ are independently substituted or unsubstituted aryl rings, furanyl, pyrimidinyl, and triazinyl rings;

wherein $R_3$=singly or multiply substituted as H, D, Halo, CN, C1-C4 Alkyl, C1-C4 alkoxy, C1-C4 alkylsulfonyl, C1-C4 Alkyl amino, or C1-C4 mercapto; and wherein $R_8$=H, Me.

3. The method of claim 2, wherein said leukemia is selected from one or more of chemotherapy-resistant leukemia, immunotherapy-resistant leukemia, relapsed leukemia, and other targeted-therapy resistant leukemias.

4. The method of claim 2, comprising the steps of:
a. determining a level of Vav3 or of Rac GTPase in a biopsy obtained from said individual; and
b. administering said one or more compounds where the level of Vav3 or of the Rac GTPase is elevated as compared to a control.

5. A method of therapeutically treating triple negative breast cancer in an individual in need thereof, comprising administering to said individual a composition comprising one or more compounds selected from

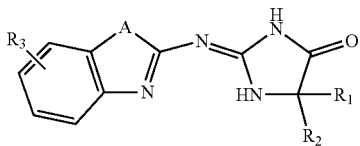

and a pharmaceutically acceptable carrier;
wherein A=NH, NR$_8$, S, O, C=C, N=C, C=N;
wherein R$_1$, and R$_2$ are independently substituted or unsubstituted aryl or heteroaryl rings, furanyl, pyrimidinyl, and triazinyl rings;
wherein R$_3$=singly or multiply substituted as H, D, Halo, CN, C1-C4 Alkyl, C1-C4 alkoxy, C1-C4 alkylsulfonyl, C1-C4 Alkyl amino, or C1-C4 mercapto; and wherein R$_8$=H, Me;
and all tautomers thereof.

6. A method of therapeutically treating non-small cell lung cancer in an individual in need thereof, comprising administering to said individual a composition comprising one or more compounds selected from

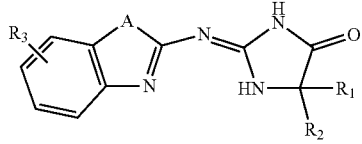

and a pharmaceutically acceptable carrier;
wherein A=NH, NR$_8$, S, O, C=C, N=C, C=N;
wherein R$_1$, and R$_2$ are independently substituted or unsubstituted aryl or heteroaryl rings, furanyl, pyrimidinyl, and triazinyl rings;
wherein R$_3$=singly or multiply substituted as H, D, Halo, CN, C1-C4 Alkyl, C1-C4 alkoxy, C1-C4 alkylsulfonyl, C1-C4 Alkyl amino, or C1-C4 mercapto; and wherein R$_8$=H, Me;
and all tautomers thereof.

7. A method of therapeutically treating colon adenocarcinoma in an individual in need thereof, comprising administering to said individual a composition comprising one or more compound selected from

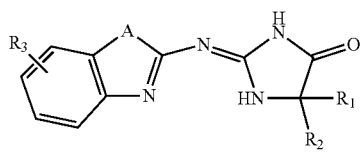

pharmaceutically acceptable salts thereof;
wherein A=NH, NR$_8$, S, O, C=C, N=C, C=N;
wherein R$_1$, and R$_2$ are independently substituted or unsubstituted aryl or heteroaryl rings, furanyl, pyrimidinyl, and triazinyl rings;
wherein R$_3$=singly or multiply substituted as H, D, Halo, CN, C1-C4 Alkyl, C1-C4 alkoxy, C1-C4 alkylsulfonyl, C1-C4 Alkyl amino, or C1-C4 mercapto; and wherein R$_8$=H, Me;
and all tautomers thereof.

* * * * *